United States Patent
Oshimura et al.

(10) Patent No.: US 9,775,331 B2
(45) Date of Patent: Oct. 3, 2017

(54) RODENT COMPRISING MOUSE ARTIFICIAL CHROMOSOME VECTOR

(71) Applicants: NATIONAL UNIVERSITY CORPORATION TOTTORI UNIVERSITY, Tottori-shi, Tottori (JP); TRANS CHROMOSOMICS, INC., Yonago, Tottori (JP)

(72) Inventors: Mitsuo Oshimura, Tottori (JP); Yasuhiro Kazuki, Tottori (JP); Masato Takiguchi, Tottori (JP); Takashi Matsuoka, Tottori (JP)

(73) Assignees: National University Corporation Tottori University, Tottori (JP); Trans Chromosomics, Inc., Tottori (JP)

(*) Notice: Subject to any disclaimer, the term of this patent is extended or adjusted under 35 U.S.C. 154(b) by 0 days.

(21) Appl. No.: 14/574,749

(22) Filed: Dec. 18, 2014

(65) Prior Publication Data
US 2015/0096063 A1    Apr. 2, 2015

Related U.S. Application Data

(62) Division of application No. 13/520,754, filed as application No. PCT/JP2011/050490 on Jan. 6, 2011, now Pat. No. 8,940,533.

(30) Foreign Application Priority Data

Jan. 6, 2010 (JP) ................. 2010-001425

(51) Int. Cl.
A01K 67/027 (2006.01)
C12N 15/10 (2006.01)
C12N 15/85 (2006.01)

(52) U.S. Cl.
CPC ...... *A01K 67/0278* (2013.01); *C12N 15/1086* (2013.01); *C12N 15/85* (2013.01); *C12N 15/8509* (2013.01); *A01K 2207/15* (2013.01); *A01K 2217/00* (2013.01); *A01K 2217/052* (2013.01); *A01K 2217/206* (2013.01); *A01K 2227/105* (2013.01); *A01K 2267/01* (2013.01); *C12N 2800/208* (2013.01); *C12N 2800/30* (2013.01)

(58) Field of Classification Search
CPC ........... C12N 15/1086; C12N 15/8509; C12N 15/85; C12N 2800/30; C12N 2800/208; A01K 2217/052; A01K 2267/01; A01K 2217/206; A01K 67/0278; A01K 2207/15; A01K 2217/00; A01K 2227/105
See application file for complete search history.

(56) References Cited

U.S. PATENT DOCUMENTS

2010/0011454 A1    1/2010  Kakeda et al.
2011/0023138 A1    1/2011  Oshimura et al.

FOREIGN PATENT DOCUMENTS

JP          2007-295860         11/2007
WO    WO 2008-013067 A1    1/2008
WO    WO 2009/063722 A1    5/2009

OTHER PUBLICATIONS

Ueda et al. "Establishment of Rat Embryonic Stem Cells and Making of Chimera Rats." PLoS ONE. 2008; 3(7): e2800.*
Carstea et al. "Germline competence of mouse ES and iPS cell lines: Chimera technologies and genetic background." World J Stem Cells. Dec. 31, 2009; 1(1): 22-29.*
Takahashi et al. "Induction of pluripotent stem cells from adult human fibroblasts by defined factors." Cell. Nov. 30, 2007;131(5):861-72.*
Tachibana et al. "Generation of chimeric rhesus monkeys." Cell. Jan. 20, 2012;148(1-2):285-95.*
Keefer et al. "Challenges and prospects for the establishment of embryonic stem cell lines of domesticated ungulates." Anim Reprod Sci. Mar. 2007;98(1-2):147-68.*
De Los Angeles et al. "Hallmarks of pluripotency." Nature. Sep. 24, 2015;525(7570):469-78.*
Men et al. "Germline Transmission of a Novel Rat Embryonic Stem Cell Line Derived from Transgenic Rats." Stem Cells Dev. Sep. 20, 2012; 21(14): 2606-2612.*
Briticannica Online. "Rodents." https://www.britannica.com/animal/rodent. accessed Dec. 19, 2016.*
Office Action issued Jul. 31, 2014, in CN 201180012643.2.
Katoh et al., "In Vivo Drug Metabolism Model for Human Cytochrome P450 Enzyme Using Chimeric Mice with Humanized Liver," Journal of Pharmaceutical Sciences, Feb. 2007, 96(2):428-437.
International Search Report PCT/JP2011/050490 dated Apr. 11, 2011.
Katoh et al., "Construction of a novel human artificial chromosome vector for gene delivery", Biochemical and Biophysical Research Communications 321 (2004) 280-290.
Telenius et al., "Stability of a functional murine satellite DNA-based artificial chromosome across mammalian species", Chromosome Research 7: 3-7, 1999.
Co et al., "Generation of transgenic mice and germline transmission of a mammalian artificial chromosome introduced into embryos by pronuclear microinjection", Chromosome Research 8: 183-191,2000.
Basu et al., "Artificial and engineered chromosomes: non-integrating vectors for gene therapy", Trends in Molecular Medicine, vol. 11, No. 5, May 2005, pp. 251-258.

(Continued)

*Primary Examiner* — Titilayo Moloye
(74) *Attorney, Agent, or Firm* — Foley & Lardner LLP

(57) ABSTRACT

Disclosed is a mouse artificial chromosome vector, comprising: a natural centromere derived from a mouse chromosome; a mouse-chromosome-derived long-arm fragment formed by deleting a long-arm distal region at a mouse chromosome long-arm site proximal to the centromere; and a telomere sequence, wherein the vector is stably retained in a cell and/or tissue of a mammal. In addition, disclosed are cells or non-human animals comprising the vector, and use of the cells or non-human animals.

24 Claims, 100 Drawing Sheets

(56) References Cited

OTHER PUBLICATIONS

Stewart et al., "Retrofitting of a satellite repeat DNA-based murine artificial chromosome (ACes) to contain loxP recombination sites", Gene Therapy (2002) 9, pp. 719-723.
Oshimura et al., "New Vectors for Gene Delivery: Human nd Mouse Artificial Chromosomes," eLS John Wiley & Sons, Ltd., 2013, 1-12.

\* cited by examiner

Fig. 39 TC (MAC1) tail fibroblast

A9(CYP3A-MAC)9

TT2F(CYP3A-MAC) 9-7

Fig. 55 Chimeric mouse retaining hChr21q-MAC

TT2F(PXR-MAC)

CHO(HPRT-; MAC4)74-30

CHO(HPRT-; MAC4, hChr4-loxP-tel) 8

CHO(UGT2-MAC, hChr4-ΔUGT2) 4

A9(UGT2-MAC)14

RODENT COMPRISING MOUSE ARTIFICIAL CHROMOSOME VECTOR

CROSS-REFERENCE TO RELATED APPLICATIONS

This application is a Divisional of U.S. application Ser. No. 13/520,754, which is the U.S. National Stage application of PCT/JP2011/050490, filed Jan. 6, 2011, which claims priority from Japanese application no. JP 2010-001425, filed Jan. 6, 2010, the entire contents of which are incorporated herein by reference.

The instant application contains a Sequence Listing which has been submitted in ASCII format via EFS-WEB and is hereby incorporated by reference in its entirety. Said ASCII copy, created on Dec. 10, 2014, is named sequence.txt and is 37 KB.

TECHNICAL FIELD

The present invention relates to mouse artificial chromosome vectors that can be stably retained in vivo in a rodent and can be transmitted to offspring.

The present invention also relates to cells comprising the above mouse artificial chromosome vector.

The present invention further relates to non-human animals, such as a mouse, comprising the above mouse artificial chromosome vector.

BACKGROUND ART

A transgenic mouse, which is produced by introducing a gene-carrying vector, has been widely used to utilize a gene of interest and its expression product. Unfortunately, in conventional transgenic mice, a transgene is introduced into any site at random, and the positional effect of the insertion site may cause reduced expression of the transgene. In addition, conventional gene transfer methods can not control the copy number of a transgene, and limit the size of a transgene to about 200 kb. Due to these problems, it was difficult to clone a gene or gene cluster of more than 200 kb which is not uncommon to mammalian genes, optionally comprising a regulatory region, into a vector. In the conventional gene transfer methods, intrinsic functions of a transgene could not thus be reconstituted and examined, which situation has set a limit.

In the presence of such a problem, the present inventors have developed a technique for producing a transchromosomic mouse by using a novel chromosomal transfer method that introduces genes at a chromosomal level (Non-Patent Literature 1). This technique has allowed a human chromosome or a fragment thereof to be introduced into a mouse embryonic stem (ES) cell, whereby chimeric mice have been produced. This study demonstrated that the human chromosome fragment has been independently retained in ES cells; a plurality of human genes have been expressed in a tissue-specific manner; and some human chromosomes have been able to be partially transmitted to offspring after having undergone meiosis. The present inventors also have introduced the entire human chromosome 21 (about 35 Mb) into a mouse, and have created a Down syndrome model mouse having a high practical value (Non-Patent Literature 2). Analysis of this mouse has revealed effectiveness of the chromosome vector because the mouse has exhibited the physiological expression pattern of the genes of the introduced human chromosome 21.

The techniques the present inventors have employed further include chromosome engineering procedures such as a chromosome deletion method using a telomere truncation technique utilizing an artificial telomere sequence and a chromosome cloning method using a Cre/loxP system. These methods have allowed for construction of a human artificial chromosome containing only a target region. As a result, the present inventors have successfully constructed a human artificial chromosome (HAC) vector containing a specific human chromosome region having a size of mega bases (Mb), and have demonstrated that the vector functions in a mouse individual (Non-Patent Literature 3). Furthermore, the above techniques have been used to construct a novel HAC vector without known genes (Non-Patent Literature 4). In addition, based on the above background, the present inventors have successfully achieved stable expression of a gene of interest by introducing into any cell a HAC vector carrying the gene of interest. Additional examples of a humanized model mouse carrying the HAC vector have been produced as follows: a drug-metabolizing enzyme CYP3A gene cluster (1 Mb) of human chromosome 7 and a human DMD gene (2.5 Mb) responsible for human X-linked muscular dystrophy have been each cloned into a HAC vector (CYP3A-HAC, DMD-HAC); and these vectors have been each introduced into a mouse ES cell to produce mice (Patent Literature 1, Non-Patent Literature 5).

A tissue retention rate and expression analysis of the mouse having the CYP3A-HAC have demonstrated that the CYP3A gene cluster on the HAC has been retained in each tissue of the mouse (FIG. 8, Patent Literature 1). Its expression pattern has been similar to that of a human tissue counterpart. That is, the expression pattern has been specific to a liver and a small intestine. In addition, a tissue retention rate and expression analysis of the mouse having the DMD-HAC have demonstrated that the DMD-HAC has been retained in each tissue of the mouse (FIG. 4A, Non-Patent Literature 5). The mouse has expressed, like a human, at least three splicing isoforms known to be expressed in a tissue-specific manner in a human. This series of results suggest usefulness of the HAC-carrying mouse as a novel gene (gene group)-transfer alternative for a conventional transgenic mouse.

Mammalian artificial chromosome vectors, including a human artificial chromosome, have advantages that conventional vector systems (e.g., a virus, a YAC, a BAC, a PAC, a cosmid, and a plasmid) do not have. Thus, the mammalian artificial chromosome vectors should be useful as a system for analyzing functions of a novel gene and for generating a humanized model animal. For example, Patent Literatures 2 and 3 disclose HAC vectors in which human chromosome 14 or 21 was modified; the chromosome was reduced in size to yield a fragment; and the fragment was relatively stably retained in cells.

Unfortunately, with regard to the human chromosome 21 transferred mouse (i.e., a Down syndrome model mouse) or the HAC vector transferred mouse, which enables the introduction of a gene of Mb units that was impossible for conventional genetically modified mice, there exist at least the following problems: that is, the human chromosome vector has a decreased retention rate; the retention rate varies among tissues and individuals; and the frequency of transmission to offspring is not stable. This facilitates the need to always consider the retention rate of the HAC vectors. Further, when the involvement with functions of a specific gene region or diseases is studied, there is a case where it may be difficult to analyze in detail and precisely a mode of expression of a gene of interest and its expression product at a tissue and/or cellular level. These things will constitute a barrier to highly reproducible, uniform analysis.

Moreover, in the case of conducting the cell fusion between a mouse cell and a human cell, a human chromosome is known to be unstable in the mouse cell. Because the human chromosome, including a human artificial chromosome vector, has thus a variable retention rate in the mouse cell, when the human artificial chromosome vector is introduced into a mouse cell to generate a transgenic mouse, the human artificial chromosome vector does not exhibit full advantages as an artificial chromosome vector. When a mouse cell having a transgene or a transgenic mouse is generated, the retention rate of the transgene should be improved and be made constant. This can promise more detailed, precise, highly reproducible gene function analysis or effective recovery of the expression product of the transgene.

PRIOR ART LITERATURES

Patent Literatures

Patent Literature 1: WO 2009/063722
Patent Literature 2: WO 2004/031385
Patent Literature 3: Japanese Patent Publication (Kokai) No. 2007-295860A Non-Patent Literatures Non-Patent Literature 1: Tomizuka et al., Nat Genet, 16, 133-143, 1997
Non-Patent Literature 2: Shinohara et al., HMG, 10, 1163-75, 2001
Non-Patent Literature 3: Kuroiwa et al., Nat Biotech, 18, 1086-1090, 2000
Non-Patent Literature 4: Katoh et al., BBRC, 321, 280-290, 2000
Non-Patent Literature 5: Hoshiya et al., Mol Ther, 17, 309-17, 2009

SUMMARY OF INVENTION

Problem to be Solved by Invention

Whereas many of previously reported mammalian artificial chromosomes are human artificial chromosomes (JP Patent Publication (Kokai) No. 2005-230020A; No. 2008-54501A; No. 2007-306928A; and No. 2007-295860A), there are a few reports on mouse artificial chromosomes, wherein these artificial chromosomes are characterized by using a sequence derived from a portion of a mouse centromere (S. Stewart et al. (2002) Gene Therapy 9, 719-723).

When a natural human chromosome fragment is transferred into a mouse cell, the human chromosome fragment is unstable in the mouse cell as previously described (e.g., Shinohara et al. (2000) Chromosome Research, 8, 713-725). This unstability is also similar even in the body and each tissue of a mouse individual. The proportion (or retention rate) of the human artificial chromosome retained in the mouse tissues and cells tends to decrease, and the retention rate in the mouse tissues and cells becomes variable. The same applies to murine individuals. That is, the retention rate of the human artificial chromosome becomes variable among murine individuals. Such a non-constant retention rate among the murine tissues and individuals causes difficulties in performing detailed, highly reproducible analysis on a transgene by using a murine cell or individual having a target gene (or a group of genes) introduced by using a human artificial chromosome.

As described above, few reports have disclosed artificial chromosomes derived from rodents including mouse and related matters. In addition, there are no artificial chromosomes that are kept stable in a rodent cell or individual. Thus, an object of the present invention is to provide a mouse artificial chromosome vector in which a transgene (a group of transgenes) of interest is/are kept stable in a rodent cell or individual, thereby enabling detailed, precise, highly reproducible analysis.

Means for Solving Problem

As a summary, the present invention includes the following features.
(1) A mouse artificial chromosome vector, comprising: an naturally occurring centromere derived from a mouse chromosome; a mouse-chromosome-derived long-arm fragment formed by deleting a long-arm distal region at a mouse chromosome long-arm site proximal to the centromere; and a telomere sequence, wherein the vector is stably retained in a cell and/or tissue of a mammal.
(2) The mouse artificial chromosome vector according to the above aspect (1), wherein the mouse chromosome is any one of chromosomes 1 to 19.
(3) The mouse artificial chromosome vector according to the above aspect (1) or (2), wherein the mouse-chromosome-derived long-arm fragment is the remainder region formed by deleting a region including at least 99.5% of all endogenous genes from a long arm of any one of mouse chromosomes 1 to 19.
(4) The mouse artificial chromosome vector according to any of the above aspects (1) to (3), wherein the vector comprises, as a basic structure, a mouse artificial chromosome contained in the deposited cell line DT40 B6bT-1 (FERM BP-11128).
(5) The mouse artificial chromosome vector according to any of the above aspects (1) to (4), wherein the mammal is a rodent.
(6) The mouse artificial chromosome vector according to the above aspect (5), wherein the rodent is a mouse, rat, or hamster.
(7) The mouse artificial chromosome vector according to any of the above aspects (1) to (6), further comprising one or more DNA sequence insertion sites.
(8) The mouse artificial chromosome vector according to the above aspect (7), wherein the DNA sequence insertion site is a recognition site for a site-specific recombinase.
(9) The mouse artificial chromosome vector according to the above aspect (7) or (8), wherein the DNA sequence insertion site is a loxP sequence, an FRT sequence, φC31 attB and φC31 attP sequences, R4 attB and R4 attP sequences, TP901-1 attB and TP901-1 attP sequences, or Bxb1 attB and Bxb1 attP sequences.
(10) The mouse artificial chromosome vector according to any of the above aspects (1) to (9), further comprising a reporter gene, a selection marker gene, or both.
(11) The mouse artificial chromosome vector according to any of the above aspects (1) to (10), further comprising an exogenous DNA sequence.
(12) The mouse artificial chromosome vector according to any of the above aspects (1) to (11), wherein the exogenous DNA sequence has a size of 200 kb or more.
(13) The mouse artificial chromosome vector according to the above aspect (11) or (12), wherein the exogenous DNA sequence is a human DNA sequence.

(14) The mouse artificial chromosome vector according to any of the above aspects (11) to (13), wherein the exogenous DNA sequence is a DNA sequence of a drug-metabolism-related gene.

(15) The mouse artificial chromosome vector according to the above aspect (14), wherein the drug-metabolism-related gene is a gene encoding an enzyme involved in a phase I reaction or a phase II reaction.

(16) The mouse artificial chromosome vector according to the above aspect (15), wherein the enzyme gene involved in a phase I reaction encodes at least one enzyme selected from the group consisting of CYPs such as CYP1A, CYP1B, CYP2A, CYP2B, CYP2C, CYP2D, CYP2E, CYP2J, CYP3A, CYP4A, CYP4B, and subfamilies thereof, and CESs.

(17) The mouse artificial chromosome vector according to the above aspect (15), wherein the enzyme gene involving the phase II reaction encodes at least one enzyme selected from the group consisting of UGT1 and UGT2.

(18) The mouse artificial chromosome vector according to the above aspect (14), wherein the drug-metabolism-related gene is a gene encoding a transporter.

(19) The mouse artificial chromosome vector according to the above aspect (18), wherein the gene encoding the transporter is at least one gene selected from the group consisting of MDR1, MDR2, MRP2, OAT, OATP, OCT, and BCRP.

(20) The mouse artificial chromosome vector according to the above aspect (14), wherein the drug-metabolism-related gene is a gene encoding a nuclear receptor.

(21) The mouse artificial chromosome vector according to the above aspect (20), wherein the gene encoding the nuclear receptor is at least one gene selected from the group consisting of PXR, AhR, CAR, and PPARα.

(22) The mouse artificial chromosome vector according to any of the above aspects (11) to (13), wherein the exogenous DNA sequence is a DNA sequence of a human-chromosome-derived long arm or short arm.

(23) The mouse artificial chromosome vector according to any of the above aspects (11) to (21), wherein the exogenous DNA sequence comprises at least two genes selected from the group consisting of genes encoding an enzyme involved in a phase I reaction, genes encoding an enzyme involved in a phase II reaction, genes encoding a transporter and genes encoding a nuclear receptor.

(24) The mouse artificial chromosome vector according to the above aspect (22), wherein the DNA sequence of the human-chromosome-derived long arm or short arm comprises a human chromosome region responsible for a disease gene.

(25) The mouse artificial chromosome vector according to any of the above aspects (11) to (13), wherein the exogenous DNA sequence is a gene or DNA sequence encoding a polypeptide such as cytokines, hormones, growth factors, nutritional factors, hematopoietic factors, coagulation or hemolysis factors, immunoglobulins, G protein-coupled receptors, or enzymes, or a gene or DNA sequence used for treatment involved in a disease such as tumor, muscular dystrophy, hemophilia, neurodegenerative disease, autoimmune disease, allergic disease, or genetic disease.

(26) The mouse artificial chromosome vector according to any of the above aspects (1) to (25), wherein the cell is a hepatocyte, enterocyte, renal cell, splenocyte, lung cell, cardiac cell, skeletal muscle cell, brain cell, bone marrow cell, lymphocyte, megakaryocyte, sperm, or ovum.

(27) The mouse artificial chromosome vector according to any of the above aspects (1) to (25), wherein the tissue is derived from a liver, intestine, kidney, spleen, lung, heart, skeletal muscle, brain, bone marrow, testis, or ovary.

(28) A cell comprising the mouse artificial chromosome vector according to any of the above aspects (1) to (27).

(29) The cell according to the above aspect (28), wherein the cell is selected from the group consisting of somatic cells, non-human germ-line cells, stem cells, and precursor cells.

(30) The cell according to the above aspect (29), wherein the stem cell is an embryonic stem (ES) cell or an induced pluripotent stem (iPS) cell.

(31) The cell according to any of the above aspects (28) to (30), wherein the cell is a primary cultured cell, subcultured cell, or cell line.

(32) The cell according to any of the above aspects (28) to (31), wherein the cell is capable of producing a human antibody.

(33) A pharmaceutical composition comprising the cell according to any of the above aspects (28) to (32), wherein the cell comprises a mouse artificial chromosome vector comprising an exogenous DNA sequence for use in treating a disease.

(34) A non-human animal comprising the mouse artificial chromosome vector according to any of the above aspects (1) to (27).

(35) The non-human animal according to the above aspect (34), wherein the animal is a disease-model animal.

(36) The non-human animal according to the above aspect (34), wherein the animal is capable of expressing an exogenous human drug-metabolism-related gene.

(37) The non-human animal according to the above aspect (34), wherein the animal is capable of producing a human antibody.

(38) The non-human animal according to any of the above aspects (34) to (37), wherein an endogenous gene corresponding to an exogenous DNA contained in the mouse artificial chromosome vector is disrupted or the endogenous gene has decreased expression.

(39) A process for producing a protein, comprising: culturing the cell according to any of the above aspects (28) to (32), the cell comprising the mouse artificial chromosome vector comprising a sequence of an exogenous DNA to produce a protein encoded by the DNA; and collecting the protein.

(40) A process for producing a human antibody, comprising: using the non-human animal according to the above aspect (37) or (38), the animal comprising the mouse artificial chromosome vector comprising a gene encoding a human antibody to produce the human antibody; and collecting the human antibody.

(41) A method for screening for a substance effective in treating a disease, comprising: administering a candidate drug to a disease-model animal of the non-human animal according to the above aspect (35) as a disease-model animal; and evaluating a therapeutic effect of the drug.

(42) A method for testing a pharmacological effect and/or metabolism and/or toxicity of a drug or food, comprising: administering a drug or food to the non-human animal according to the above aspect (36) or (38) or a cell, organ, or tissue thereof, wherein the animal, cell, organ or tissue comprises the mouse artificial chromosome vector comprising a human drug-metabolism-related gene; and determining a pharmacological effect and/or metabolism and/or toxicity of the drug or food.

(43) A method for testing toxicity of a drug or food, comprising: coculturing a drug and/or food and a culture cells or bacterium with a microsome or S9 microsome fraction as obtained from the non-human animal according to the above aspect (36) or (38), wherein the animal comprises the mouse artificial chromosome vector comprising a human drug-metabolism-related gene; and determining an effect of the drug or food on the culture cell or bacterium.

(44) A method for stabilizing a large-size DNA in a cell or individual, comprising: using the mouse artificial chromosome vector according to any of the above aspects (1) to (27) to stably keep an exogenous DNA having a large size of 200 kb or more in a rodent cell or individual at a retention rate of 90% or more.

According to the present invention, when a gene (or a group of genes) of interest is/are introduced into a rodent cell or individual, the mouse artificial chromosome vector comprising a DNA sequence insertion site can maintain the gene (or a group of genes) stably and at an identical retention rate in any cell or tissue, although it was difficult to introduce the gene or a group of genes into the cell or tissue by conventional means, and because a reporter gene can be inserted together with an exogenous DNA sequence or gene of interest, the cell carrying the vector can be visualized and detailed, precise, highly reproducible analyses or effective recovery of expression products can be achieved.

The contents described in the specification and/or drawings of Japanese Patent Application No. 2010-1425, from which the present application claims the priority, are herein incorporated by reference.

BRIEF DESCRIPTION OF DRAWINGS

FIG. 15b shows the analysis results of homologous recombinants using Southern hybridization with respect to hygromycin resistant cell lines of DT40 cell clone containing human chromosome 7 fragment which has been transfected with the linearized vector. With regard to the arrowheads of FIG. 15b, the top arrowhead indicates the non-homologous recombinant (approximately 10.9 kb) and the bottom arrowhead indicates the homologous recombinant (approximately 8.9 kb).

MODE FOR CARRYING OUT INVENTION

Figure 1:
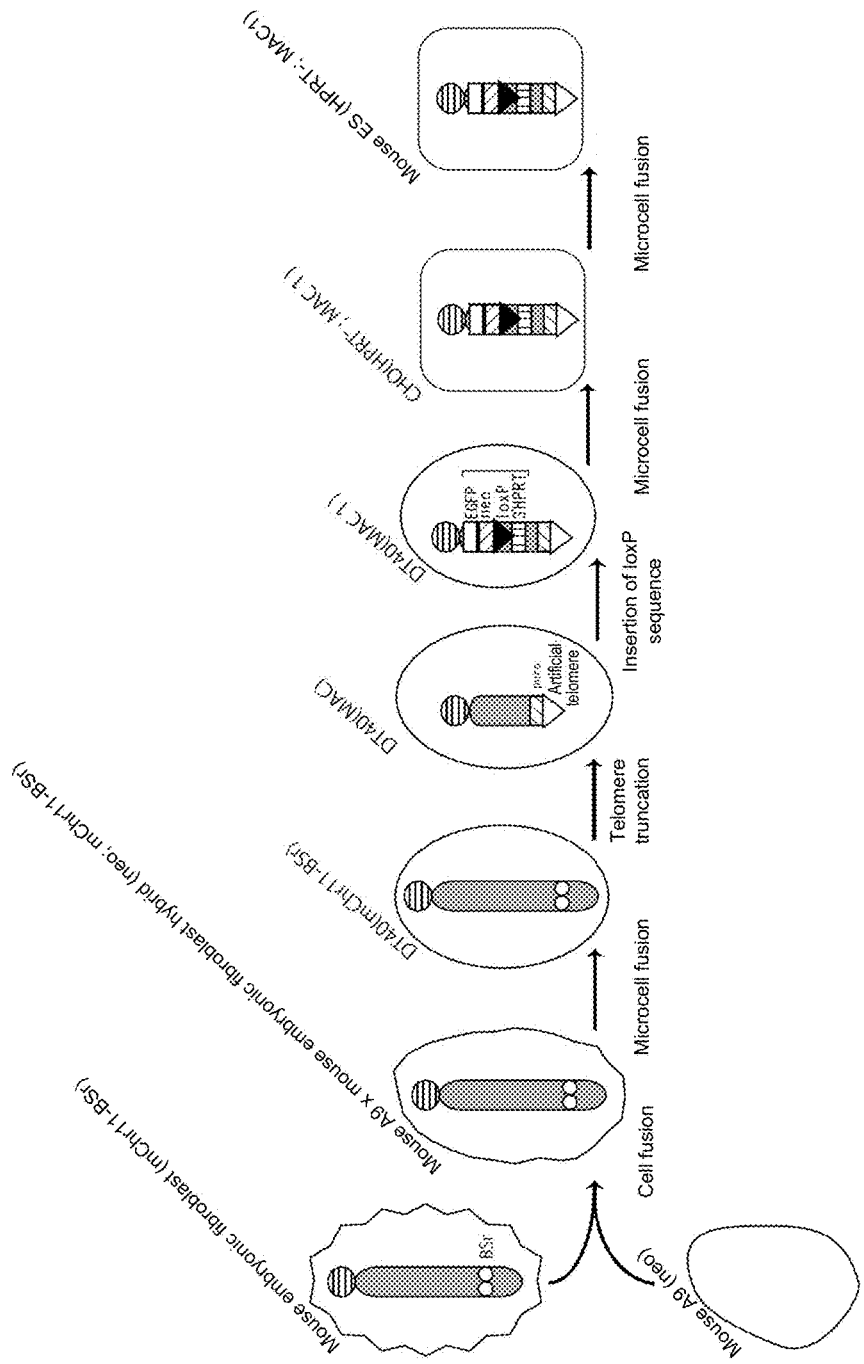
FIG. 1 is a schematic diagram illustrating the procedures of Examples 1 and 2 later. Cell names in the figure are described according to the following format. Cell name (cellular genetic modification; retained chromosome fragment name, and transgene-retaining chromosome name). Symbols given in the drawings are as follows. BSr: blasticidin (BS) resistant gene, puro: puromycin resistant gene, artificial telomere: artificial telomere (TTAGGG) repeat sequence, EGFP: gene expressing enhanced green fluorescent protein, neo: neomycin (G418) resistant gene, loxP: site specific DNA sequence insertion site, 3' HPRT: the 3rd to 9th exon sequences of HPRT gene.

The present invention will be further described in more detail.

As described above, the first embodiment of the present invention provides a mouse artificial chromosome vector comprising: an natural centromere derived from a mouse chromosome; a mouse-chromosome-derived long-arm fragment formed by deleting a long-arm distal region at a mouse chromosome long-arm site proximal to the centromere; and a telomere sequence, wherein the vector is stably retained in cells and tissues of a mammal As used herein, the term "natural centromere derived from a mouse chromosome" refers to the entire centromere (or the intact centromere) of any one of mouse chromosomes. Thus, the centromere does not include a structure having centromere function which is obtained spontaneously or synthetically by using a portion of the centromere sequence of a mouse chromosome, as well as the centromere of a chromosome derived from other animals.

As used herein, the term "mouse artificial chromosome" or "mouse artificial chromosome vector" refers to an artificial chromosome constructed by top-down approach, but it does not mean an artificial chromosome constructed by bottom-up approach. The top-down approach refers to an approach in which gene-coding regions are deleted from an intact chromosome by chromosomal modification; and a natural centromere is used to construct an artificial chromosome vector. The bottom-up approach refers to an approach in which a portion of a centromere sequence is obtained as a cloned DNA, which is then transfected into a mammalian cell to construct an artificial chromosome having centromere function.

As used herein, the "mouse-chromosome-derived long-arm fragment formed by deleting a long-arm distal region at a mouse chromosome long-arm site proximal to the centromere" refers to a long-arm fragment obtained by deleting a long arm of the mouse chromosome at a long-arm site proximal to the centromere so as to remove the endogenous genes from the long arm of the mouse chromosome. This is because it is desirable to eliminate effects of endogenous genes as possible as, so as to stably keep the vector of the present invention in a mouse cell or tissue and so as not to prevent the development of mice or the genetic transmission to offspring. This fragment means a long-arm fragment obtained by deleting at least 99.5%, preferably at least 99.7%, more preferably 99.8%, and still more preferably 99.9% to 100% of total endogenous genes (the number of genes) at the long-arm site proximal to the centromere.

As used herein, the term "DNA" can be used to represent any kind of DNA nucleic acid, including a gene or gene locus, cDNA, or chemically modified DNA.

As used herein, the term "retention rate," unless otherwise noted, refers to a rate of cells having an artificial chromosome in a culture cell or a mouse tissue cell.

The term "stably retained" regarding the chromosome vector of the present invention means that, during mitosis, the chromosome vector is not easily dropped-out, that is, even after mitosis, the chromosome vector is stably retained, thereby leading to efficient genetic transmission of the chromosome vector to a daughter cell or a descendant mouse.

The mouse chromosome may be any of mouse chromosomes 1 to 19, X, and Y. The chromosome, however, is preferably any one of chromosomes 1 to 19. Although chromosome 11 is exemplified in Examples below, the other chromosomes can be used to construct the mouse artificial chromosome vector as long as the above-mentioned characteristics are maintained.

In the case of an artificial chromosome vector derived from a fragment of mouse chromosome 11, the above long-arm fragment includes, but is not limited to, a long arm fragment formed by deleting a more distal region than, for example, AL671968, BX572640 (locating at a position closer to the centromere than AL671968), CR954170 (locating at a position closer to the centromere than AL671968 and BX572640), or AL713875 (locating at a position closer to the centromere than AL671968) of the long arm of the chromosome 11. Alternatively, the long-arm fragment may comprise, as a basic structure, the mouse artificial chromosome contained in a deposited cell line DT40 B6bT-1 (FERM BP-11128), which chromosome is herein designated as DT40 (MAC) (see FIGS. 1, 3, 4). In addition, in the case of, for example, an artificial chromosome vector derived from a fragment of mouse chromosome 15, the above long-arm fragment includes, but is not limited to, a long-arm fragment formed by deleting a more distal region than, for example, AC121307 or AC161799. In the case of an artificial chromosome vector derived from a fragment of mouse chromosome 16, the above long-arm fragment includes, but is not limited to, a long-arm fragment formed by deleting a more distal region at, for example, AC127687 or AC140982. These basic structures (e.g., MAC1, MAC2, MAC3, MAC4; see FIGS. 1, 3, 4) may further comprise a DNA sequence insertion site such as loxP to insert an exogenous DNA or gene.

The vector according to the present invention may comprise a sequence insertion site for an exogenous DNA or gene. Hence, the integration of the exogenous DNA or gene of interest at this site enables the exogenous DNA or gene of interest to be expressed at the time of introduction of the vector into a given cell. Thus, the vector (e.g., CYP3A-MAC, GFP-MAC; see FIGS. 2 and 5) is applicable to, for example, protein production, screening for a therapeutic agent, a drug metabolism test, DNA function analysis, iPS cell induction, gene therapy, or generation of a useful non-human animal For the vector of the present invention, a mouse chromosome is modified and an intact mouse-derived natural centromere is used, thereby constructing the vector. As a previously known mouse artificial chromosome vector, a satellite DNA-based mammalian artificial chromosome (referred to as Aces or SATAC) which is generated by using a portion of a centromere sequence is known; however, a mouse artificial chromosome which is generated by using the entire centromere of a mouse chromosome does not have any precedent. In addition, the above mammalian artificial chromosome, like a HAC vector, has a varied retention rate among tissues of a mouse individual and is thus unstable (Co Do et al., Chromosome Res., 2000, 8(3), 83-91).

A useful and unexpected property of the vector of the present invention is that the retention rate of the vector increases in cells or tissues of mammals including rodents such as a mouse, rat, and hamster, suggesting that the vector is stably retained in cells, i.e., a gene (a group of genes) of interest is (are) maintained in cells for a longer period. Hence, the amount of a transgene does not vary among rodent individuals or tissues, and the transgene can be expressed for an extended period. Additional examples of the properties can include increased efficiency of genetic transmission and organism development of a rodent by means of pluripotent cells (e.g., ES cells or iPS cells). Compared with a human artificial chromosome (HAC), the mouse artificial chromosome according to the present invention has intriguing properties that: a variation of the retention rate is extremely small among tissues including hematopoietic tissues in which the retention rate of a HAC is very low and is less than 20%; i.e., the retention rate is 90% or more in any tissue tested (e.g., tissues derived from the liver, intestine, kidney, spleen, lung, heart, skeletal muscle, brain, or bone marrow). The mouse artificial chromosome of the present invention can also proliferate more efficiently than the HAC and can maintain a plurality of (or multiple) copies in a cell, which is impossible for the HAC.

Definition

The definitions of terms as used herein specifically include the following meanings in addition to ordinal meanings used in the art.

As used herein, the term "mouse artificial chromosome" or "mouse artificial chromosome vector" refers to an artificial chromosome having the above-described characteristics, the artificial chromosome being constructed from the mouse-derived chromosome fragment as described above. As such, the artificial chromosome is an artificial chromosome constructed by top-down approach, not bottom-up approach. Again, the top-down approach is an approach in which gene regions are deleted from a natural chromosome by chromosomal modification techniques and a natural centromere is used to construct an artificial chromosome vector. In contrast, the bottom-up approach is an approach in which a portion of a centromere sequence is obtained as a cloned DNA, which is then transfected into a mammalian cell to construct a structure having centromere function. The artificial chromosome can stably replicate and can be distributed as a chromosome independent from the native chromosome of a host cell. The mouse-derived chromosome fragment is any of chromosome fragments of mouse chromosomes 1 to 19, X, and Y (i.e., a long-arm fragment formed by deleting at least 99.5% of all endogenous genes from a long arm). This fragment includes a long-arm fragment formed by deleting a long-arm distal region at a mouse chromosome long-arm site proximal to the centromere, as defined above. The construction of the artificial chromosome of the present invention is described in Examples below, in particular Examples 1 to 5, and in FIGS. 1 to 4. These Examples and figures illustrate how to construct an artificial chromosome from a fragment of mouse chromosome 11. The mouse artificial chromosome can also be constructed from a fragment of another chromosome in a substantially similar manner.

Sequence information of mouse chromosomes is available from DDBJ/EMBL/GenBank or chromosome databases at Santa Cruz Biotechnology, Inc. and other organizations.

As used herein, the term "long arm" of a chromosome refers to a chromosome region from the centromere side to the region containing genes in a mouse chromosome. Meanwhile, the mouse chromosome has almost no short arm.

As used herein, the term "distal region" means a region distal from the centromere (i.e., a region of the telomere side). On the other hand, the "proximal region" is referred to as a region near to the centromere (i.e., a region of the centromere side). The long-arm distal region means a region being on the telomere side from a specific site of a long arm. The long-arm proximal region means a region being on the centromere side from a specific site of the long arm. This specific site is a position at which at least 99.5%, preferably at least 99.7%, more preferably 99.8%, and still more preferably 99.9 to 100% of all endogenous genes (or the number of all endogenous genes) that are present in the long arm of a chromosome derived from a mouse are deleted.

As used herein, the term "retention rate" refers to a proportion of cells having artificial chromosome in culture cells or tissue cells of a mouse.

As used herein, the term "DNA sequence insertion site" means an insertion site for a target DNA (including a gene) sequence, for example, a recognition site for a site-specific recombinase. Examples of such a recognition site include, but are not limited to, loxP (a Cre recombinase recognition site), FRT (a Flp recombinase recognition site), φC31 attB and φC31 attP (φC31 recombinase recognition sites), R4 attB and R4 attP (R4 recombinase recognition sites), TP901-1 attB and TP901-1 attP (TP901-1 recombinase recognition sites), and Bxb1 attB and Bxb1 attP (Bxb1 recombinase recognition sites).

As used herein, the term "site-specific recombinase" refers to an enzyme that induces a specific recombination with a target DNA sequence at the recognition site of the enzyme. Examples of the enzyme include Cre integrase (also referred to as Cre recombinase), φC31 integrase, R4 integrase, TP901-1 integrase, and Bxb1 integrase.

As used herein, the term "telomere sequence" refers to a natural telomere sequence derived from same or different species, or an artificial telomere sequence. Here, the same species means the same species as the mouse from which a chromosome fragment of an artificial chromosome vector is derived, whereas the different species means a mammal (including a human) other than the mouse. In addition, the artificial telomere sequence refers to a sequence having a telomere function and prepared by synthesis, such as a (TTAGGG)n sequence (where "n" means the number of repeats). Introducing a telomere sequence into an artificial chromosome can be performed by telomere truncation (i.e., substitution by a telomere sequence) as disclosed in WO 00/10383 for example. The telomere truncation can be used to shorten a chromosome during construction of the artificial chromosome of the present invention.

As used herein, the term "exogenous gene" or "exogenous DNA" refers to a gene or DNA of interest contained in a vector, wherein the gene or DNA is inserted into a gene insertion site of the vector. The term means a gene or DNA or a sequence thereof that is originally absent in a cell and that is to be expressed in the cell.

As used herein, the term "mammal" include, but are not limited to, primates such as human, monkey, and chimpanzee, rodents such as a mouse, rat, hamster, and guinea pig, and ungulates such as a cow, pig, sheep, and goat.

As used herein, the term "embryonic stem cell" or "ES cell" refers to a semi-immortalized pluripotent stem cell that is established from an inner cell mass of a blastocyst of a fertilized egg derived from a mammal (M. J. Evans and M. H. Kaufman (1981) Nature 292, 154-156; J. A. Thomson et al. (1999) Science 282, 1145-1147; J. A. Thomson et al. (1995) Proc. Natl. Acad. Sci. USA 92, 7844-7848; J. A. Thomson et al. (1996) Biol. Reprod. 55, 254-259; J. A. Thomson and V. S. Marshall (1998) Curr. Top. Dev. Biol. 38, 133-165). The cell having characteristics equivalent to ES cell, which is artificially induced by reprogramming of a somatic cell, is an "induced pluripotent stem cell" or "iPS cell" (K. Takahashi and S. Yamanaka (2006) Cell 126, 663-676; K. Takahashi et al. (2007) Cell 131, 861-872; J. Yu et al. (2007) Science 318, 1917-1920).

Preparation and Use of Mouse Artificial Chromosome Vector:

Hereinafter, the preparation and use of the mouse artificial chromosome vector of the present invention will be described. Specifically, the procedures are described in Examples 1 to 5 (FIGS. 1 to 4) below.

(1) Preparation of Mouse Artificial Chromosome Vector

The artificial chromosome vector of the present invention can be prepared in accordance with a method comprising the following steps (a) to (c):

(a) obtaining a cell having a mouse chromosome;

(b) deleting a long-arm distal region of the mouse chromosome so as not to include a large part (i.e., from 99.5% to 100%) of endogenous genes (or the number of endogenous genes); and (c) inserting one or more DNA sequence insertion sites into a long-arm proximal region. The order of the steps (b) and (c) may be interchangeable.

Step (a):

In order to prepare the artificial chromosome vector according to the present invention, a cell having a mouse chromosome is first to be produced. For example, a mouse embryonic fibroblast (mChr11-BSr), which is a mouse fibroblast carrying a drug resistance gene (e.g., blasticidin S resistance gene (BSr))-labeled mouse chromosome, is subjected to cell infusion with a mouse A9 (neo), which is a mouse A9 cell (ATCC VA20110-2209) having a neo gene (i.e., a G418-resistant gene). Next, the mouse A9 hybrid cell having the drug resistance gene-labeled mouse chromosome, i.e. the mouse A9× mouse embryonic fibroblast (neo; mChr11-BSr), is used to transfer the chromosome into a cell having a high homologous recombination rate, thereby preparing the cell having a mouse chromosome. The mouse fibroblast is available based on procedures described in literatures. For example, the mouse fibroblast can be established from C57B6 mouse commercially available from CLEA Japan, Inc. Examples of the available cell having a high homologous recombination rate can include chicken DT40 cell (Dieken et al., Nature Genetics, 12, 1 74-182, 1996). Furthermore, the above-described transfer can be carried out using known chromosome transfer techniques, such as microcell fusion (Koi et al., Jpn. J. Cancer Res., 80, 413-418, 1973).

Figure 9:
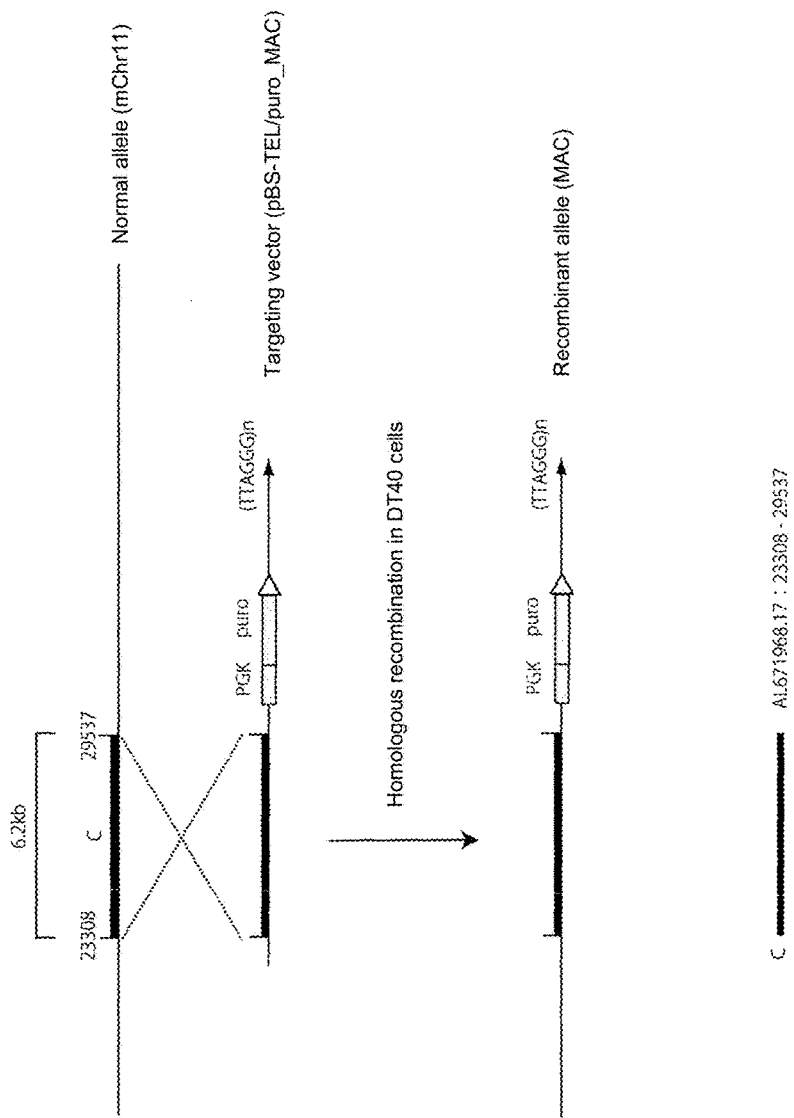
FIG. 9 shows the vector for telomere truncation in AL671968 region of mouse chromosome 11 and a partial structure of the mouse chromosome 11 allele, in which homologous recombination has been carried out by using the vector.

Step (b):

In a cell having a single mouse-derived chromosome, a long-arm distal region of the mouse chromosome is deleted. It is important to delete (or remove or cleave out) a large part of endogenous genes present in a long arm and then to construct an artificial chromosome having a mouse centromere. It is also important to determine a cleavage site in order to delete a region containing at least 99.5%, preferably at least 99.7%, more preferably at least 99.8%, and still more preferably 99.9 to 100% of all endogenous genes present in the long arm. By doing so, a cell, tissue, or individual, which has the artificial chromosome and is derived from a mammal such as rodent (preferably mouse), can stably retain the artificial chromosome at a high retention rate, and it can be used for precise analysis of a gene (a group of genes) of interest and for production of materials. The above-described endogenous genes can be deleted by telomere truncation as disclosed in, for example, WO 00/10383. Specifically, a targeting vector having an artificial telomere sequence is constructed and is used to obtain a clone in which a (artificial) telomere sequence has been inserted at a desired position on the chromosome by homologous recombination in a cell having a mouse chromosome. This makes it possible to obtain a deletion mutant via telomere truncation. That is, the desired position (or site) is a cleavage position of a long-arm distal region to be deleted. The artificial telomere sequence is inserted into this position by substitution via the homologous recombination, so that the long-arm distal region is deleted. This position can be appropriately determined depending on a target sequence design at the time of constructing a targeting vector. For example, in Examples below, a target sequence has been designed based on the DNA sequence of AL671968 (GenBank Accession Number) on the long arm of mouse chromosome 11, so that the telomere truncation occurs at a position of the telomere side from the target sequence (see FIG. 9). As a results, a fragment of mouse chromosome 11 having deletion of a large part of endogenous genes can be obtained. For other chromosomes, the telomere truncation can be carried out similarly.

Step (c):

As a DNA sequence insertion site, a recognition site for a site-specific recombinase can be preferably inserted. Specifically, the phenomenon that a certain enzyme recognizes a specific recognition site, and causes DNA recombination specifically at the recognition site is known. The mouse artificial chromosome vector according to the present invention uses a system having such an enzyme and its recognition site to insert or carry a gene or DNA sequence of interest. Examples of such a system include a system having bacteriophage P1-derived Cre enzyme and its recognition site, i.e. loxP sequence (a Cre/loxP system; B. Sauer in Methods of Enzymology, 1993, 225, 890-900), a system having budding yeast-derived Flp enzyme and its recognition site, i.e. FRT (Flp Recombination Target) sequence (a Flp/FRT system), a system having *Streptomyces* phage-derived φC31 integrase and its recognition site, i.e. φC31 attB/attP sequences, a system having R4 integrase and its recognition site, i.e. R4 attB/attP sequences, a system having TP901-1 integrase and its recognition site, TP901-1 attB/attP sequences, and a system having Bxb1 integrase and its recognition site, i.e. Bxb1 attB/attP sequences. As long as functioning as a DNA sequence insertion site, the system is not limited to the above systems.

In order to insert a recognition site for such a site-specific recombinase, known methods, such as homologous recombination, can be employed. The position and number of insertion can be appropriately determined in a long-arm proximal region and a short-arm proximal region.

Figure 11:
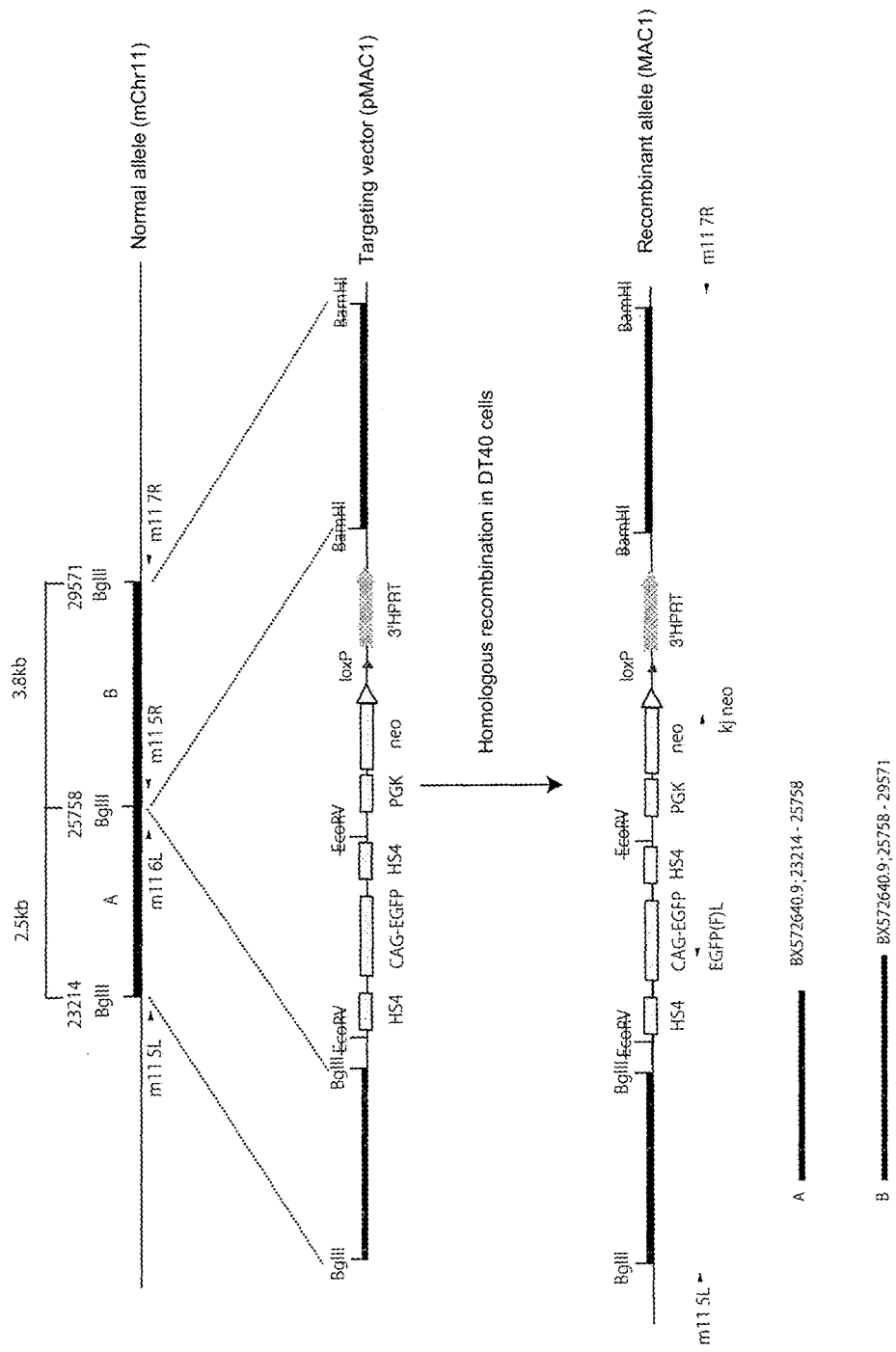
FIG. 11 shows a GFP-neo-loxP-3' HPRT type of loxP targeting vector (pMAC1) and a partial structure of allele of mouse artificial chromosome MAC in which homologous recombination has been carried out by using the vector.
Figure 20:
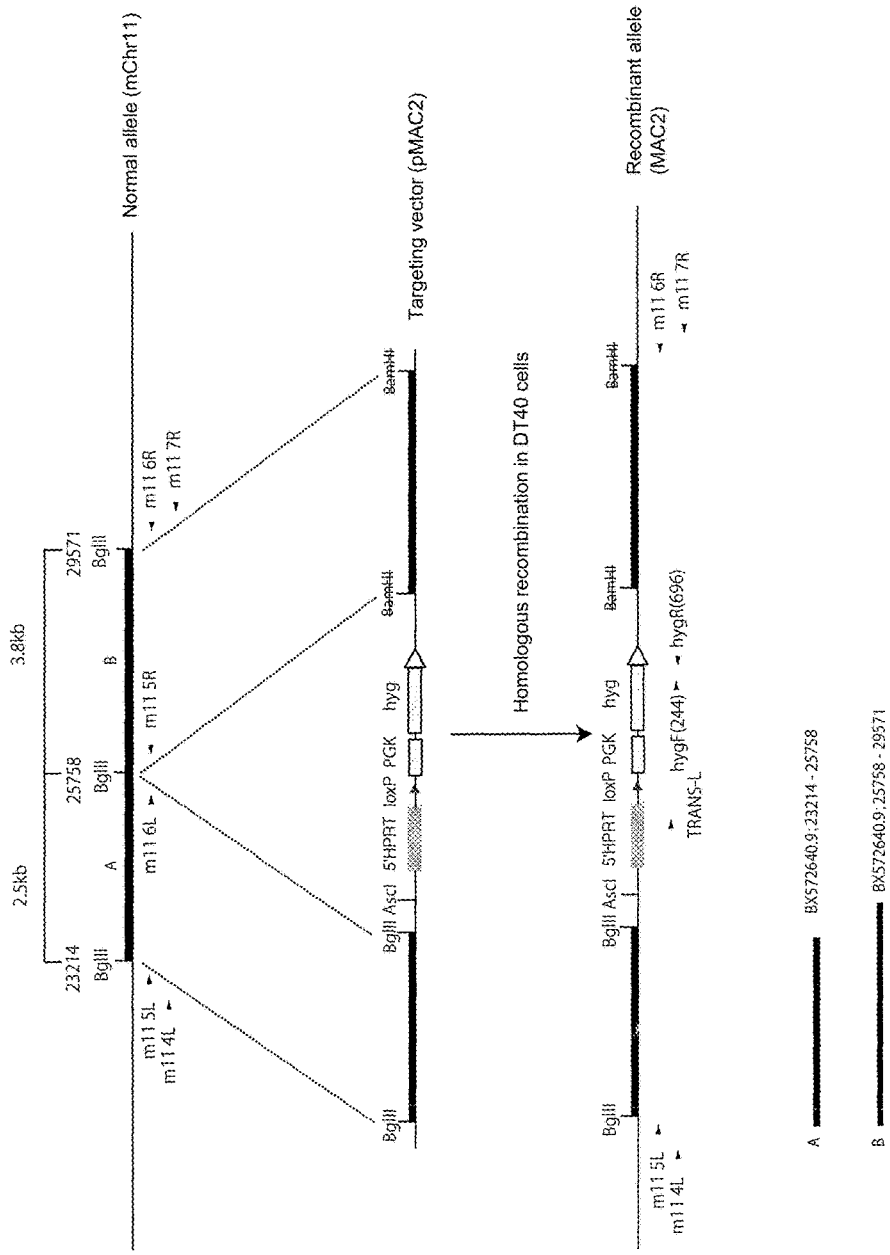
FIG. 20 shows the targeting vector (pMAC2) for constructing the mouse artificial chromosome vector MAC2, and a partial structure of allele of mouse artificial chromosome MAC in which homologous recombination has been carried out by using the vector.
Figure 24:
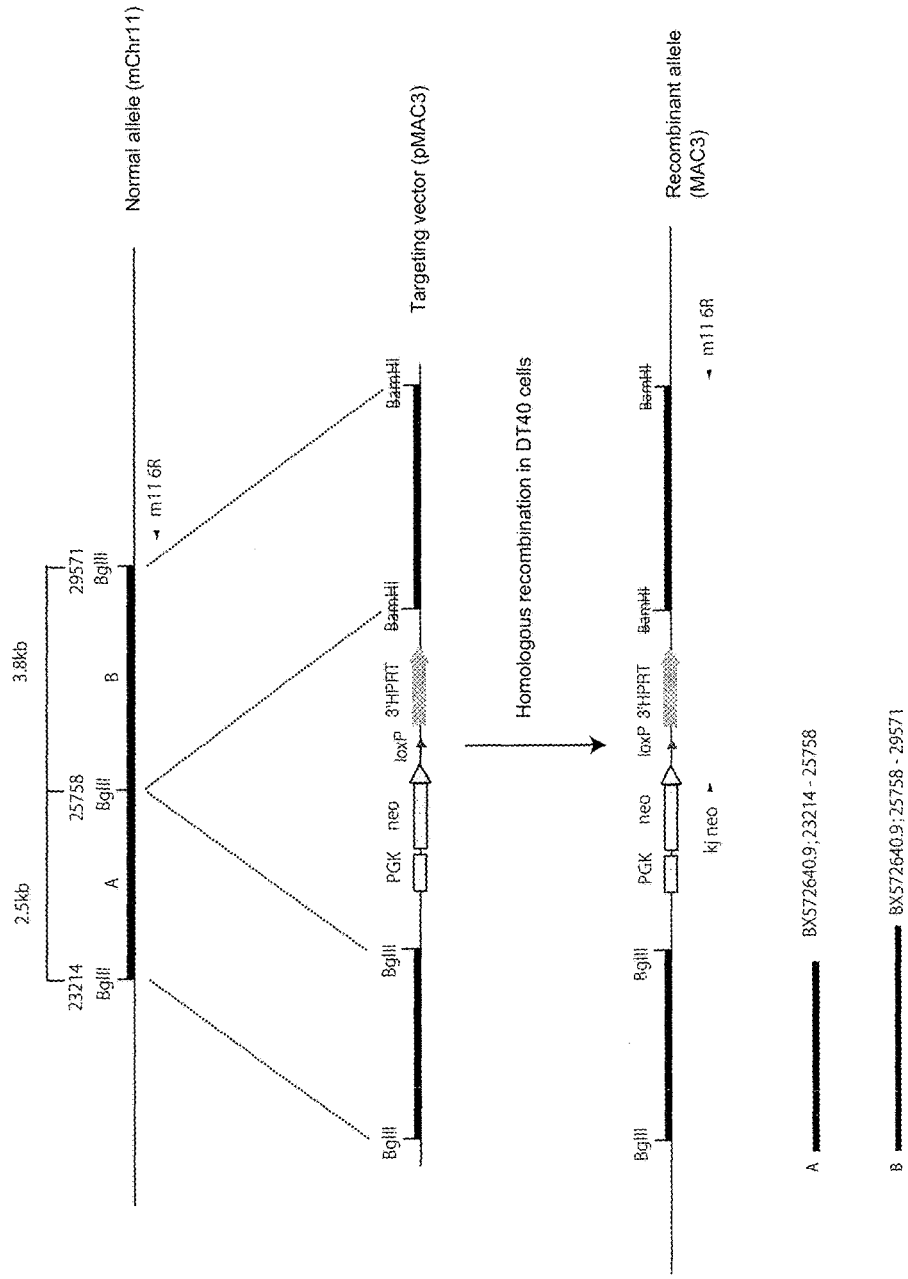
FIG. 24 shows a PGKneo-loxP-3' HPRT type of loxP targeting vector (pMAC3), and a partial structure of allele of mouse artificial chromosome MAC3 in which homologous recombination has been carried out by using the vector.

According to the present invention, one of certain recognition sites or different recognition sites can be inserted. The design of a recognition site enables specifying an insertion site for an exogenous gene or exogenous DNA, so that the insertion site is fixed and no unexpected positional effects are thus exerted. A mouse artificial chromosome as illustrated in Examples below can express, in a tissue-specific fashion, a gene inserted at a loxP sequence that is inserted into BX572640 locus on mouse chromosome 11 and that is a recognition site for a site specific recombinase (FIGS. 11, 20, and 24).

Preferably, the mouse artificial chromosome vector having a DNA sequence insertion site according to the present invention may beforehand have a reporter gene while preserving an insertion site for a target gene or DNA sequence. Examples of the reporter gene include, but are not limited to, fluorescent protein genes (e.g., green fluorescent protein (GFP or EGFP) gene, yellow fluorescent protein (YFP) gene), a tag-protein-encoding DNA, β-galactosidase gene, and luciferase gene. Preferred is GFP or EGFP.

The mouse artificial chromosome vector according to the present invention may further comprise a selection marker gene. The selection marker is effective in selecting a cell transformed by the vector. The selection marker gene is represented by either a positive selection marker gene or a negative selection marker gene, or both. Examples of the positive selection marker gene include drug resistance genes such as a neomycin-resistant gene, an ampicillin-resistant gene, a blasticidin S (BS)-resistant gene, a puromycin-resistant gene, a geneticin (G418)-resistant gene, and a hygromycin-resistant gene. In addition, examples of the negative selection marker gene include a herpes simplex thymidine kinase (HSV-TK) gene, and a diphtheria toxin A fragment (DT-A) gene. In general, the HSV-TK is used in combination with ganciclovir or ciclovir.

Homologous recombination can be preferably used as a technique for inserting a reporter gene or a target exogenous gene or DNA into the mouse artificial chromosome vector according to the present invention. The homologous recombination can be carried out using a targeting vector which is obtained by ligating an DNA cassette to be inserted between sequences (5' arm and 3' arm) homologous to nucleotide sequences of 5' and 3' regions (each having approximately 1 to 4 kb, preferably approximately 2 to 4 kb) at an insertion position of the mouse chromosome. Examples of the vector that can be used for this purpose include a plasmid, a phage, a cosmid, and a virus. Preferred is a plasmid. Examples of a basic plasmid for targeting vector construction include, but are not limited to, V907 and V913 (Lexicon Genetics). The basic vector may contain one or two or more sequences or elements that are generally inserted for the vector construction, such as a promoter, an enhancer, a selection marker gene, a replication origin, and the like.

The mouse artificial chromosome prepared using the above procedures comprises a mouse-derived chromosome fragment (which comprises a natural centromere, a long-arm fragment formed by deleting at least 99% or preferably at least 99.5% of endogenous genes, and a short arm (if present)), and an artificial telomere sequence. The above centromere also consists of an entire mouse chromosome centromere structure which is used for the artificial chromosome construction.

An example of the mouse artificial chromosome vector of the present invention is the mouse artificial chromosome vector as prepared in Examples below. This artificial chromosome is a vector produced by deleting a long-arm distal region of mouse chromosome 11 at AL671968 (FIGS. 1, 3, 4, 9, and 10). This vector comprises, as a basic structure, the mouse artificial chromosome contained in the deposited cell line DT40 B6bT-1 (FERM BP-11128), which vector is herein designated as DT40 (MAC). Because this vector has a basic structure, this DNA structure can comprise the following insertions such as a DNA sequence insertion site, a selection marker gene, and an exogenous gene (or DNA).

The above mouse artificial chromosome vector preferably comprises one or more DNA sequence insertion sites such as a recognition site for a site-specific recombinase (e.g., a loxP sequence which is a Cre enzyme recognition site) (FIGS. 1, 3, 4, 11, 20, and 24). Examples of the recognition site for the site-specific recombinase include, but are not limited to, loxP sequences of GFP-PGKneo-loxP-3' HPRT type, 5' HPRT-loxP-hyg type, PGKneo-loxP-3' HPRT type, or GFP-5' HPRT-loxP-PGKhyg type, wherein the GFP represents a green fluorescent protein gene, the PGKneo represents a phosphoglycerate kinase promoter/neomycin-resistant gene cassette, the HPRT represents a hypoxanthine guanine phosphoribosyltransferase gene, and the hyg represents a hygromycin-resistant gene.

The above-described mouse artificial chromosome vector may further comprise a reporter gene or a selection marker gene (e.g., a positive selection marker gene, or a negative selection marker gene). The vector may further comprise a target exogenous gene or DNA sequence.

The advantages of the mouse artificial chromosome vector according to the present invention include advantages of conventional artificial chromosome vectors as follows: 1) The vector is independently maintained without being inserted into a host chromosome, so that no disruption of a host gene is caused; 2) The vector is stably retained at a certain copy number (which may be a plurality of (or multiple) copies) and is exposed to the physiological expression regulation of a host cell, so that the overexpression or loss of expression of the inserted gene is not caused; 3) DNA that can be introduced has no size limitation and so it becomes possible to introduce a gene comprising expression regulatory region or a plurality of genes/isoforms. In addition, the retention rate of the vector in a rodent cell or individual increases compared with that of conventional artificial chromosomes, and a transgene can be stably expressed for a long term and the rate of genetic transmission of the vector to offspring is improved, thereby increasing the efficiency of producing a transgenic mouse. Further, 4) there is less variation among tissues after introduction of the vector, that is, the retention rate is 90% or higher in any tissue. Even a hematopoietic tissue, which usually has a retention rate of less than 20% in the case of the HAC, has a retention rate of 90% or higher.

(2) Introduction of Exogenous Gene or DNA

An exogenous gene or DNA can be introduced into the mouse artificial chromosome vector according to the present invention.

The size of the exogenous gene or DNA sequence is not particularly limited, but may be 20 kb or less or may exceed 20 kb, such as 50 kb or more, 100 kb or more, 200 kb or more, 500 kb or more, 700 kb or more, 1 Mb or more, 10 Mb or more, 20 Mb or more, 30 Mb or more, 40 Mb or more, and 50 Mb or more. The vector of the present invention can carry an exogenous DNA (chromosome fragment) of 1 Mb or more as seen in HAC vector, the size of which is difficult to be carried by artificial chromosome vectors such as BAC, PAC, and YAC vectors. Moreover, the vector of the present invention can stably retain a large-size exogenous gene or DNA of 200 kb or more, for example 1 Mb or more, at a higher retention rate (90% or more) than the HAC vector in a mammalian cell or tissue or in a non-human animal individual, preferably in a rodent cell, tissue or individual.

An embodiment of the present invention provides a vector and a method for preparing the same, wherein the vector is able to stably maintain a big-size exogenous gene or DNA of 200 kb or more in a rodent cell or individual at a retention rate of 90% or more.

The exogenous gene or DNA refers to a nucleic acid sequence that is introduced from outside of a cell of interest, but is not particularly limited. This gene or DNA may be derived from any organism, tissue or cell, preferably from a mammal, and more preferably from a human. Examples of such a gene or DNA include, but are not limited to, genes or DNAs encoding polypeptides such as cytokines, hormones, growth factors, neurotrophic factors, hematopoietic factors, immunoglobulins, G protein-coupled receptors, and enzymes, in addition to genes or DNAs used for treatment involved in various diseases such as tumor, muscular dystrophy, hemophilia, neurodegenerative diseases (e.g., Alzheimer's disease, Huntington's disease, and Parkinson's disease), autoimmune diseases, allergic diseases, and genetic diseases, genes (gene groups) or DNAs encoding (human) drug-metabolizing enzymes, (human) drug metabolism-related genes, long-arm or short-arm DNAs of human chromosomes, and (human) genomic libraries.

Examples of the cytokines include interferons (e.g., IF-α, IF-β, and IF-γ), interleukins (e.g., IL-1, IL-2, IL-4, IL-6, IL-11, and IL-12), tumor necrosis factors (e.g., TNF-α, and TNF-β), and TGF-β family proteins (e.g., bone morphogenic protein (BMP)).

Examples of the hormones include growth hormones, human chorionic gonadotropin (hCG), human placental lactogen (hPL), human pituitary gonadotropic hormone, thyroid-stimulating hormone (TSH), luteinizing hormone-releasing factor, insulin, glucagon, somatostatin, and prolactin.

Examples of the growth factors or neurotrophic factors include insulin-like growth factor, brain-derived neurotrophic factor (BDNF), albumin-fused ciliary neurotrophic factor, platelet-derived neurotrophic factor (PDNF), transforming growth factor, nerve growth factor (NGF), and TNF growth factor.

Examples of the coagulation or hemolysis factors include Factor VII, Factor VIII, Factor X, and t-PA.

Examples of the hematopoietic factors include erythropoietin, (granulocyte) colony-stimulating factor, and thrombopoietin.

Examples of the immunoglobulins include human antibodies, humanized antibodies, chimeric antibodies, and recombinant antibodies such as synthetic antibodies, which are elicited against various antigens.

Examples of the G protein-coupled receptors include adrenergic receptor, muscarinic acetylcholine receptor, adenosine receptor, GABA receptor (type B), angiotensin receptor, cholecystokinin receptor, dopamine receptor, glucagon receptor, histamine receptor, odorant receptor, opioid receptor, secretin receptor, somatostatin receptor, gastrin receptor, and P2Y receptor.

Examples of the enzymes include asparaginase, superoxide dismutase, uricase, streptokinase, dopamine synthase, and adenosine deaminase.

Examples of the genes used for treatment involved in various diseases such as tumor, muscular dystrophy, neurodegenerative diseases (e.g., Alzheimer's disease, Huntington's disease, and Parkinson's disease), autoimmune diseases, allergic diseases, and genetic diseases include dystrophin gene, IL-12 gene, TNF-α gene, tumor suppressor genes, dopamine synthase gene, and genes encoding genetically deficient enzymes.

The drug-metabolizing enzymes are involved in the metabolic reactions to degrade or excrete xenobiotics such as drugs or toxins. Examples of the enzymes include enzymes involved in the phase I reaction (e.g., oxidation, reduction, and hydrolysis) or the phase II reaction (conjugation). Examples of the enzymes involved in the phase I reaction include known enzymes such as cytochrome P450 ("CYP"), specifically, CYP1A, CYP1B, CYP2A, CYP2B, CYP2C, CYP2D, CYP2E, CYP2J, CYP3A, CYP4A, CYP4B, and subfamilies thereof, and CESs. With regard to the CYP subfamily, examples of the CYP3A subfamily include CYP3A4, CYP3A43, CYP3A5, and CYP3A7. In addition, examples of the CYP2C subfamily include CYP2C8, CYP2C9, CYP2C18, and CYP2C19. For a reference, CYP3A-MAC as described in Examples below means a CYP3A cluster, which includes CYP3A4, CYP3A43, CYP3A5, and CYP3A7. On the other hand, examples of the enzymes involved in the phase II reaction (conjugation) include UGT1 and UGT2.

Examples of the drug metabolism-related genes include genes encoding transporters and genes encoding nuclear receptors. Examples of the genes encoding transporters include MDR1, MDR2, MRP2, OAT, OATP, OCT, and BCRP. Examples of the genes encoding nuclear receptors include PXR, AhR, CAR, and PPARα.

In view of the above, a drug-metabolism-related exogenous DNA sequence that is capable of introduced into the vector of the present invention can comprise at least one gene sequence or at least two gene sequences selected from the group consisting of genes encoding enzymes involved in the phase I reaction, genes encoding enzymes involved in the phase II reaction, genes encoding transporters, and genes encoding nuclear receptors.

At least one insulator sequence may be present at a proximal region or both sides of the insertion site of an exogenous gene or DNA contained in the mouse artificial chromosome vector of the present invention. The insulator sequence exerts an enhancer blocking effect (i.e., wherein adjacent genes do not affect each other) or a chromosome boundary effect (i.e., wherein a region promoting gene expression is separated and distinguished from a region inhibiting the gene expression). Examples of such a sequence include human β-globin HS1 to HS5 and chicken β-globin HS4.

The exogenous gene or DNA can be introduced by using the above-described site-specific recombinase system which is inserted as the above-described DNA sequence insertion site. For example, a targeting vector is constructed that comprises an exogenous gene or DNA and a loxP sequence which is the recognition site for Cre enzyme, or a chromosome fragment is constructed that comprises an exogenous gene or DNA and an inserted loxP sequence which is the recognition site for Cre enzyme. Then, the Cre enzyme is expressed in a cell having the mouse artificial chromosome vector according to the present invention, thereby inducing a site-specific recombination at the loxP sequence with the targeting vector or the chromosome fragment to introduce the exogenous gene or DNA.

The mouse artificial chromosome vector according to the present invention can incorporate a circular DNA having a recognition site (e.g., a loxP sequence or an FRT sequence) for a site-specific recombinase. The DNA may be inserted that has been cloned by using known vectors such as plasmids for host *Escherichia coli* and circular YAC for host yeast. Preferable loxP sequence is a wild type sequence derived from P1 phage, and the insertion reaction of the circular insert into the loxP sequence on the artificial chromosome vector using the Cre enzyme is reversible. Once the circular insert is inserted, two loxP sequences are left on the artificial chromosome vector. Because of this, reexpression of the Cre enzyme may cause a reversible reaction that cleaves out the circular insert, and thus it becomes difficult to further modify the artificial chromosome vector so as to secondarily insert the insert. When a mutant loxP sequence with nucleotide substitution or a combination of attB/attP sequences which is the recognition site for φC31 integrase is used, the reversible reaction does not occur and so it becomes possible to construct a system into which a plurality of circular inserts are sequentially inserted.

(3) Transfer of Mouse Artificial Chromosome Vector into Cell and Creation of Non-Human Animal The mouse artificial chromosome vector of the present invention, or the mouse artificial chromosome vector comprising an exogenous gene or DNA according to the present invention, can be transferred or introduced into any cell. Examples of the method to achieve that goal include microcell fusion, lipofection, a calcium phosphate method, microinjection, and electroporation. Preferred method is the microcell fusion.

The microcell fusion is a method for transferring a mouse artificial chromosome vector into a desirable cell by microcell fusion between a first cell (e.g., mouse A9 cell) which has an ability to form micronuclei and contains the mouse artificial chromosome vector of the present invention and a second desirable cell. The first cell having an ability to form micronuclei is treated with a polyploid inducer (e.g., colcemid or colchicine) to form a multinucleated cell having micronuclei. Then, the cell is subjected to cytochalasin treatment to form microcells, which are subsequently fused with a desirable cell.

Examples of the cells capable of introducing the above vector include animal cells, preferably mammalian cells including human cells, such as germline cells (e.g., oocyte and spermatocyte), stem cells (e.g., embryonic stem (ES) cells, germline stem (GS) cells, somatic stem cells), somatic cells, embryonal cells, adult cells, normal cells, disease cells, primary cultured cells, subcultured cells, and cell lines. Examples of the stem cells include pluripotent stem cells (e.g., ES cells, embryonic germline (EG) cells, embryonic carcinoma (EC) cells, mGS cells, and human mesenchymal stem cells), induced pluripotent stem (iPS) cells, and nuclear transfer clone embryo-derived embryonic stem (ntES) cells. The preferred cells can be selected from the group consisting of mammalian (preferably a rodent including mouse) somatic cells, non-human germline cells, stem cells, and precursor cells. When the cell is derived from a mammal such as a rodent and the vector of the present invention is introduced into the cell or tissue of the mammal (e.g., a rodent such as mouse), the vector can be more stably retained. That is, drop-out of the vector from the cell significantly decreases, or the drop-out never happens.

Examples of the cells include hepatocyte, enterocyte, renal cell, splenocyte, lung cell, cardiac cell, skeletal muscle cell, brain cell, bone marrow cell, lymphocyte, megakaryocyte, spermatocyte, and oocyte.

Examples of the tissues include liver, intestine, kidney, spleen, lung, heart, skeletal muscle, brain, bone marrow, testis, and ovary.

ES cells can be established and maintained as follows: first, an inner cell mass is removed from the blastocyst of a fertilized egg of an animal of interest; the inner cell mass is then cultured using a mitomycin C-treated mouse embryonic fibroblast as a feeder, thereby establishing the ES cells which are then maintained (M. J. Evans and M. H. Kaufman (1981) Nature 292, 154-156).

iPS cells are generated by introducing specific reprogramming factors (DNAs or proteins) into a somatic cell (including a somatic stem cell), by culturing and subculturing the cell in appropriate media, thereby producing colonies after about 3 to 5 weeks. Examples of the known combination of reprogramming factors include a combination of Oct3/4, Sox2, Klf4, and c-Myc; a combination of Oct3/4, Sox2, and Klf4; a combination of Oct4, Sox2, Nanog, and Lin28; and a combination of Oct3/4, Sox2, Klf4, c-Myc, Nanog, and Lin28 (K. Takahashi and S. Yamanaka, Cell 126, 663-676 (2006); WO 2007/069666; M. Nakagawa et al., Nat. Biotechnol. 26, 101-106 (2008); K. Takahashi et al., Cell 131, 861-872 (2007); J. Yu et al., Science 318, 1917-1920 (2007); J. Liao et al., Cell Res. 18, 600-603 (2008)). Examples of the culture include: using a mitomycin C-treated mouse embryonic fibroblast cell line (e.g., STO) as a feeder cell; and culturing, at about 37° C., a somatic cell (approximately $10^4$ to $10^5$ cells/cm$^2$) with introduced vector on the feeder cell layer using a medium for ES cells. The feeder cell is not necessarily required (Takahashi, K. et al., Cell 131, 861-872 (2007)). Examples of the basic medium include Dulbecco's Modified Eagle's Medium (DMEM), Ham's F-12 medium, and a mixture thereof. Examples of the ES-cell medium that can be used include a medium for mouse ES cells and a medium for primate ES cells (Reprocell Inc.).

ES cells and iPS cells are known to contribute to the germline transmission. Hence, a non-human animal (or a transgenic animal (excluding a human)) can be generated by a method comprising: introducing into the ES cell or iPS cell, the mouse artificial chromosome vector having a gene or DNA of interest according to the present invention; injecting the cell into the blastocyst of an embryo derived from the same mammalian species as that from which the cell is derived; and transplanting the embryo into the uterus of a foster mother, which gives birth to an animal(s). Homozygous animals are created by further crossing between a male and a female of the resulting transgenic animals. In addition, their offspring can also be produced.

An exogenous gene or DNA, such as a human antibody gene, a gene for treating a disease, and a drug metabolism-related gene, is introduced into pluripotent cells such as ES cells and iPS cells or the above other cells via the mouse artificial chromosome vector of the present invention, thereby producing a cell or non-human animal that can produce a human antibody. In addition, a cell that can produce a therapeutic protein can be generated. Furthermore, a non-human animal model for a disease such as a drug metabolism-related disease can also be generated.

In some cases, it is preferable that such a non-human animal has a disrupted endogenous gene or decreased expression of the endogenous gene corresponding to the exogenous gene included in the mouse artificial chromosome vector. Gene targeting can be employed as the disruption technique. RNAi method can be used as a method for decreasing endogenous gene expression. Examples of such an exogenous gene include a drug metabolism-related gene and a human antibody gene. A non-human animal whose endogenous gene has been disrupted can be created by crossing between a non-human chimeric animal having the mouse artificial chromosome vector containing the exogenous gene or its offspring and a chimeric animal having a deletion of the entire cluster of the corresponding endogenous gene or its offspring to yield an animal having a heterozygous deletion of the endogenous gene, and by further crossing between the heterozygous animals.

The cell or transgenic non-human animal having a mouse artificial chromosome vector can be produced by the above-described techniques. Examples of the specific non-human animal include a rodent, such as mouse or rat, having the mouse artificial chromosome vector.

Thus, the present invention provides a cell or non-human animal comprising the mouse artificial chromosome vector.

Furthermore, the cell, tissue, or organ obtained from the non-human animal of the present invention can be used to generate a cell line that produces a protein expressed by the exogenous gene.

(4) Method for Producing Useful Protein

The present invention provides a method for producing a protein, comprising: culturing a cell comprising a mouse artificial chromosome vector comprising a sequence of an exogenous DNA in a situation capable of expression; and collecting a protein encoded by the DNA.

Examples of the protein include the above therapeutically, agriculturally, or industrially useful proteins and polypeptides. DNAs encoding these proteins or polypeptides are each inserted into the mouse artificial chromosome vector so that the DNA can be expressed in the presence of a promoter (and an enhancer if needed). Then, appropriate cells are transformed or transfected with the DNA. The resulting cells are cultured, and the DNA is expressed to produce the protein or peptide. After that, the protein or peptide is collected from the cells or medium.

Examples of the cells that can be used include eukaryotic cells, e.g., insect cells such as an Sf cell, bird cells, yeasts, and plant cells, in addition to mammalian cells.

Culture conditions including a medium are selected depending on cell types, and can employ known conditions as culture conditions. Examples of the media for animal cells include MEM medium, DMEM medium, Ham's F12 medium, Eagle's MEM medium, Iscove's EME medium, RPMI1640 medium, and a mixture thereof Collecting (or isolating) a protein or polypeptide can be performed by using chromatography techniques, such as gel filtration chromatography, ion exchange chromatography, affinity chromatography, chromatography, HPLC, and FPLC, salting-out, ammonium sulfate precipitation, organic solvent precipitation, ultrafiltration, and crystallization, alone or in combination.

(5) Method for Producing Human Antibody

The present invention further provides a method for producing a human antibody, comprising: using the above non-human animal carrying the mouse artificial chromosome vector comprising a human antibody gene to produce the human antibody; and collecting the human antibody.

Examples of genes encoding a human antibody include genes encoding any class of human IgG, IgM, IgA, IgD, and IgE or any subclass of human IgG1, IgG2, IgG3, IgG4, IgA1, and IgA2. The preferred human antibody gene is a gene encoding an IgG class or a subclass thereof.

A human antibody consists of two heavy (H) chains having an identical sequence and two light (L) chains having an identical sequence. Both H and L chains comprise a variable region and a constant region. The variable region of the human H or L chain has three complementarity determining regions (CDR1, CDR2, and CDR3 in the order from N-terminal side to C-terminal side) and four framework regions (FR1, FR2, FR3, and FR4 in the order from N-terminal side to C-terminal side). Three individual CDR sequences of the human H or L chain determine the specificity of an antibody.

A human IgG antibody comprises a μ chain of the heavy chain and a λ or κ chain of the light chain. These antibody chain genes are present on human chromosome 14, chromosome 22, and chromosome 2, respectively. As a human antibody gene used in the present invention, a human chromosome fragment containing each antibody gene locus is used to integrate each locus into the same or different mouse artificial chromosome. Antibody gene sequences are available from databases of NCBI (U.S.). This series of procedures are an improved version of the techniques disclosed in Japanese Patent Publication (Kokai) NO. 2005-230020A.

A non-human animal that can produce an intact human antibody can be produced by crossing between a non-human animal comprising a mouse artificial chromosome vector comprising a human μ-chain gene locus and the same non-human animal species comprising a mouse artificial chromosome vector comprising a human λ- and/or κ-chain gene loci to generate a non-human chimeric animal having both H- and L-chain gene loci and offspring thereof.

The resulting non-human animal (e.g., a rodent such as mouse) that can produce an intact human antibody is immunized with a specific antigenic peptide or polypeptide. Then, the human antibody is isolated from blood of the animal. Through the above process, the human antibody can be produced.

Alternatively, a non-human animal is immunized with a specific antigen. Next, the spleen of the non-human animal is removed. Then, cells from the spleen can be made to be fused with myeloma cells to yield hybridomas producing a monoclonal antibody.

(6) Method for Screening for Therapeutic Substance

The present invention further provides a method for screening for a substance effective in treating a disease, comprising: administering a candidate drug to a disease-model animal of the above non-human animal; and evaluating a therapeutic effect of the dug.

The disease-model non-human animal is an artificially produced animal having a disease caused by abnormalities such as abnormal biological functions due to deficiency, mutation or the like of a certain protein, abnormal drug metabolism, and abnormal chromosomes. Examples of the non-human animal model having an abnormal chromosome include, but are not limited to, animals having trisomy of human chromosome 18 or 21.

These non-human animals can be created by the method comprising: constructing a gene or a chromosome fragment having the above abnormality; incorporating the gene or chromosome fragment into the mouse artificial chromosome vector of the present invention; introducing the vector into ES cells or iPS cells; injecting the obtained cells into the blastocyst of a fertilized egg; transplanting the egg into the uterus of a foster mother; and delivering offspring.

A substance effective in treating the above disease can be screened by administering a candidate drug to a non-human animal created above and then evaluating a therapeutic effect of the drug.

Examples of the candidate drug include, but are not limited to, low-molecular-weight compounds, polymers, (glyco)proteins, peptides, (phospho or glyco)lipids, and sugars.

(7) Method for Testing Pharmacological Effect, Metabolism, or Toxicity of Drug or Food In an embodiment of the present invention, the invention also provides a method for testing a pharmacological effect and/or metabolism and/or toxicity of a drug or food, comprising: administering a drug or food to the above non-human animal or a cell, organ, or tissue thereof, wherein the animal, cell, organ, or tissue comprises the mouse artificial chromosome vector comprising a human drug metabolism-related gene; and determining a pharmacological effect and/or metabolism and/or toxicity of the drug or food.

The present invention further provides a method for testing toxicity of a drug or food, comprising: coculturing a drug and/or food and a culture cell or bacterium with a microsome or microsome fraction S9 as obtained from the above non-human animal, wherein the animal comprises the mouse artificial chromosome vector comprising a human drug-metabolism-related gene; and determining an (adverse) influence (e.g., a mutation) on the culture cell or bacterium by the drug or food.

The human drug metabolism-related gene is as exemplified above. Also, a method for creating a non-human animal is as described above.

In the above-described method using the above non-human animal comprising the mouse artificial chromosome vector comprising a human drug metabolism-related gene, for example, the animal's conditions are observed and influences on organs or chromosomes are tested, thereby being able to determine a pharmacological effect, metabolism, or toxicity of the drug or food.

In another method of the present invention, a microsome or microsome fraction S9 (i.e., the 9000×g fraction containing a large number of enzymes that catalyze hydrolysis, reduction, oxidation, or conjugation) as obtained from a non-human animal is cocultured with a culture cell (in particular, animal cell, preferably mammalian cell) or bacterial cell (preferably *salmonella*) in the presence of a drug and/or food. Toxicity of the drug or food on the cells can be detected by Ames test or a micronucleus test. The Ames test determines the toxicity based on mutations of *salmonella*. The micronucleus test determines the toxicity based on abnormalities of chromosomes in a cell nucleus. These tests have been well known, and can be used in the methods according to the present invention.

Hereinafter, the present invention will further be described in more detail by referring to Examples. The scope of the present invention, however, is not limited to the specific Examples.

EXAMPLES

Example 1

Construction of the Mouse Artificial Chromosome Vector MAC

By performing telomere truncation of a mouse chromosome, mouse artificial chromosome MAC [DT40 (B6bT)] containing no endogenous gene is constructed (FIG. 1).

[A] Establishment of Hybrid Cells of A9 Cells and Mouse Fibroblast (Neo; mChr11-BSr)

Mouse embryonic fibroblast (mChr11-BSr), which is mouse fibroblast containing mouse chromosome 11 labeled with drug resistant gene (Bsr gene), is cell-fused with mouse A9 (neo) obtained by inserting neo gene, i.e., G418 resistant gene, into known mouse A9 cells to establish mouse A9×mouse embryonic fibroblast hybrid (neo; mChr11-BSr), i.e., mouse A9 hybrid cell retaining a mouse chromosome labeled with a drug resistant gene. To introduce the mouse chromosome labeled with a drug resistant gene into chicken DT40 cells having high homologous recombination frequency by microcell fusion, a mouse chromosome labeled with a drug resistant gene is introduced into mouse A9 cell known to have a high microcell formation rate.

[A. 1] Cell Fusion and Isolation of Dual Drug Resistant Clone

Cell surfaces of mouse embryonic fibroblast (mChr11-BSr), which is mouse fibroblast established from C57B6 lineage-based mouse embryo available from CLEA Japan, Inc. and in which a drug resistant gene (Bsr gene) is inserted into the mouse chromosome and mouse A9 (neo), which is mouse A9 cell in which neo gene (i.e., G418 resistant gene) is inserted, are washed with PBS (−) separately. Cells are then dispersed by adding trypsin, suspended in culture medium (10% FBS, DMEM), and $1\times10^6$ cells of said cells are simultaneously inoculated into a culture flask (25 cm$^2$) and cultured for 1 day. The cell surfaces were washed twice with PBS (−), treated with 3 ml of PEG (1:1.4) solution [5 g, PEG1000, cat: 165-09085, Wako, is dissolved in 6 ml of serum free DMEM, and 1 ml of dimethyl sulfoxide was added thereto, and the mixture is sterilized by filtration] for 1 min, and further treated with 3 ml of PEG (1:3) solution [5 g, PEG1000, cat: 165-09085, Wako, is dissolved in 15 ml of serum free DMEM, and sterilized by filtration] for 1 min. The PEG solution was aspirated off, and the cells were washed three times with serum free DMEM, and cultured for 1 day with common culture medium (10% FBS, DMEM). Cell surfaces were washed with PBS (−) and the cells were dispersed by adding trypsin, and after suspended in a double selection culture medium containing G418 (800 µg/ml) and blasticidin S (4 µg/ml), inoculated into plastic culture dishes and then subjected to selection culture for 2 to 3 weeks. Total three resistant colonies obtained by two cell fusions were isolated, amplified, and subjected to the following analysis (clone name: mouse A9×mouse embryonic fibroblast hybrid (neo; mChr11-BSr)).

[A. 2] Selection of Hybrid Cells
[A. 2. 1] PCR

From the dual drug resistant clone, genomic DNA was extracted and PCR was carried out by using the following primers to confirm that the mouse chromosome labeled with the drug resistant gene (Bsr gene) is retained.

```
                                         (SEQ ID NO: 1)
Bsr R1: 5' CATGTGGGAGCGGCAATTC 3'

(SEQ ID NO: 2)
Bsr L1: 5' TTGAGTGGAATGAGTTCTTCAATCG 3'
```

For PCR, GeneAmp 9600 (manufactured by PerkinElmer, Inc.) was used as a thermal cycler and Ampli Taq Gold (Applied Biosystems) was used as Taq polymerase. Buffers and dNTPs (dATP, dCTP, dGTP, and dTTP) used were those included in the product and they were used under the conditions described by manufacturer's instruction. Temperature and cycle conditions were as follows: after heat denaturation at 95° C. for 10 min, 35 cycles of 94° C. for 30 sec, 60° C. for 30 sec, and 72° C. for 30 sec were carried out. As a result of PCR, all clones out of the three clones were found to be positive.

TABLE 1

| | Mouse A9 x mouse embryonic fibroblast hybrid (neo, mChr11-BSr) | | | Mouse embryonic fibroblast (mChr11-BSr) | | |
|---|---|---|---|---|---|---|
| | 5 | 6 | 7 | 1 | 2 | A9(neo) |
| Bsr R1/L1 | ○ | ○ | ○ | ○ | ○ | X |

[A. 2. 2] Quinacrine-Hoechst Double Staining

Figure 6:
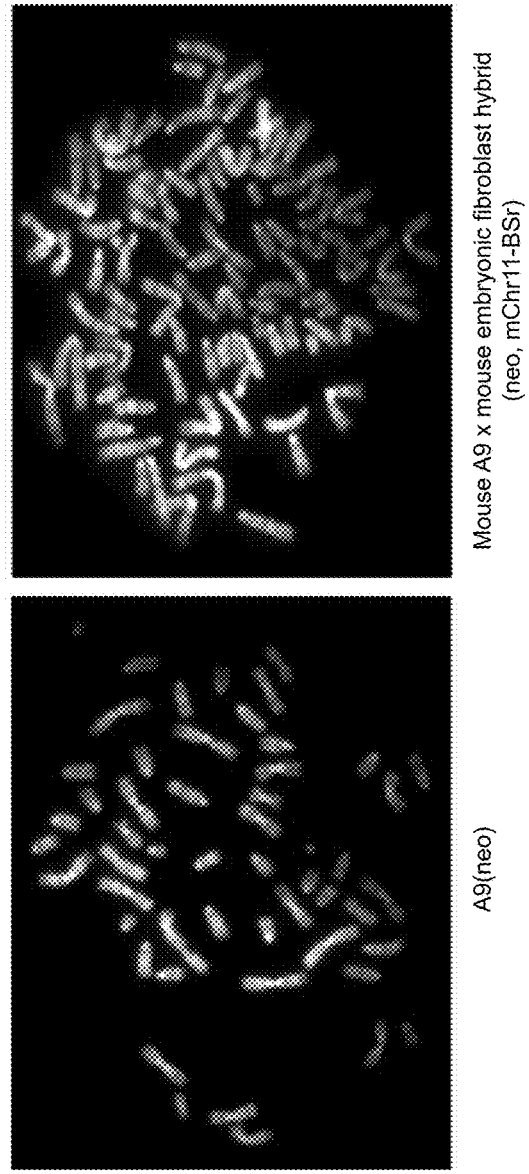
FIG. 6 shows the mouse A9 cell (mouse A9 (neo)) (left) and the cell fusion clone (mouse A9×mouse embryonic fibroblast hybrid (neo; mChr11-BSr)) between the mouse A9 cell and mouse fibroblast (mouse embryonic fibroblast (mChr11-BSr)).

Clones found to be positive by the above PCR analysis were subjected to Quinacrine-Hoechst double staining. For Quinacrine-Hoechst double staining, a chromosome slide was first immersed in 50 ml of McIlvaine solution [11.18 g of citric acid monohydrate and 13.29 g of disodium hydrogen phosphate are dissolved in 1 L of water and autoclaved], and then immersed for 20 min in 50 ml of McIlvaine solution in which Quinacrine [cat: Q2876, SIGMA] is dissolved at 60 µg/ml, and the backside of the chromosome slide was washed with tap water, immersed in McIlvaine solution, and then immersed for 15 min in 50 ml of McIlvaine solution in which Hoechst [cat: B-2883] is dissolved at 0.5 µg/ml, and the slide was covered with a cover glass. As a result of fluorescent microscopic observation, most nuclear types generally having 2n became to have 4n or more in all three clones. It was particularly found that, in clone A9 (21-B6b) 7, the mouse fibroblast retaining the mouse chromosome labeled with the drug resistant gene (Bsr gene) and mouse A9 cells into which neo gene (i.e., G418 resistant gene) was inserted, were cell-fused in one to one ratio (FIG. 6).

TABLE 2

| | Metaphase | | | |
|---|---|---|---|---|
| | 2n | 4n | 8n | Total |
| Mouse A9 x mouse embryonic fibroblast hybrid (neo, mChr11-BSr)-5 | 1 | 10 | 9 | 20 |
| Mouse A9 x mouse embryonic fibroblast hybrid (neo, mChr11-BSr)-6 | 3 | 2 | 15 | 20 |
| Mouse A9 x mouse embryonic fibroblast hybrid (neo, mChr11-BSr)-7 | 5 | 14 | 1 | 20 |
| A9(neo) | 18 | 2 | | 20 |

From these results, it was concluded that mouse A9×mouse embryonic fibroblast hybrid (neo; mChr11-BSr) had a labeled mouse chromosome.

[B] Introduction of Mouse Chromosome Labeled with Drug Resistant Gene into DT40 Cells A mouse chromosome labeled with a drug resistant gene from mouse A9×mouse embryonic fibroblast hybrid (neo; mChr11-BSr), which is a mouse A9 hybrid cell containing a mouse chromosome labeled with a drug resistant gene, was introduced into DT40, which is a chicken DT40 cell. To perform efficiently the insertion of the loxP sequence as a DNA sequence insertion site to a mouse chromosome by identification of mouse chromosome number, telomere truncation (i.e., site specific cleavage of a chromosome via insertion of an artificial telomere), and homologous recombination, a mouse chromosome labeled with a drug resistant gene is introduced into DT40, which is a chicken DT40 cell having a high homologous recombination frequency, by microcell fusion.

[B. 1] Microcell Fusion and Isolation of Drug Resistant Clone

For efficient identification of chromosome and modification of chromosome, the mouse chromosome was transferred from A9×mouse embryonic fibroblast hybrid (neo; mChr11-BSr) 7, which is a A9 hybrid cell clone, to DT40 which is a chicken DT40 cell having a high homologous recombination frequency. When the A9×mouse embryonic fibroblast hybrid (neo; mChr11-BSr) 7, which is a donor cell cultured in flask×24, reached 70% confluency in each flask, colcemid treatment (colcemid 0.05 µg/ml, 20% FCS, DMEM) was carried out for 48 hours at 37° C. under 5% $CO_2$ condition. Upon the completion of the colcemid treatment, the medium inside the flask was aspirated off, and the flask was filled up to 90% with cytochalasin B. The flask was placed in a container dedicated to a large size high-speed centrifuge (BECKMAN) and warm water (34° C.) was added to the level at which the flask was still not covered, and centrifugation was carried out (Rortor ID10.500, 8,000 rpm, 1 h, 34° C.). Upon the completion of the centrifugation, cytochalasin B was recovered, and pellets in each flask were collected in 15 ml tube each containing 2 ml of serum free culture medium DMEM. After slow filtration in the order of 8 µm→5 µm→3 µm filters, each tube was centrifuged (1,200 rpm, 5 min at R.T). The supernatant was aspirated off, and pellets from each tube were combined, recovered and suspended in 5 ml of serum free culture medium DMEM, and centrifuged (2000 rpm 5 min).

Since DT40 cells as a recipient are floating cells, they need to be in adherent state once. In order to adhere DT40 on one well of 6-well plate (Nunc), one well was incubated overnight at 37° C. with 1.5 ml of poly-L-lysine (SIGMA), which has been adjusted to 50 µg/ml, for coating. The poly-L-lysine was recovered, and the plate was washed with PBS (−), and approximately $1×10^7$ DT40 cells were gently plated onto 2 ml of serum free culture medium (DMEM).

The plate itself was set in a centrifuge (Beckman) and centrifuged at 37° C., 1200 rpm, for 3 min to obtain adhered DT40.

Purified microcells were suspended in 2 ml of serum free culture medium containing PHA-P (SIGMA), and gently plated onto the adhered DT40 from which the serum free culture medium (DMEM) were depleted. The plate was centrifuged for 3 min at 37° C., 1200 rpm. The supernatant was removed and fused exactly for 1 min with 1 ml of PEG1000 (Wako) solution [5 g of PEG1000 is completely dissolved in serum free DMEM culture medium, added with 1 ml of dimethyl sulfoxide, and sterilized by filtration]. The cells were washed four times with 4 ml of serum free culture medium (DMEM), and by pipetting with 3 ml of common culture medium for DT40, the adhered DT40 were brought back to a floating state. Thereafter, the cells were plated onto two 24-well plates at 37° C. and incubated overnight. Blasticidin S was added at 1500 µg/ml and then the cells were subjected to selection culture for 3 to 4 weeks. Total two resistant colonies obtained by one microcell fusion were isolated, amplified, and subjected to the following analysis (clone name: DT40 (mChr11-BSr)).

[B. 2] Selection of Drug Resistant Clone
[B. 2. 1] FISH Analysis

Figure 7:
FIG. 7 shows the results of FISH analysis of DT40 (mChr11-Bsr) clone in which mouse Cot-1 DNA is used as a probe.

DT40 (mChr11-BSr) clones obtained from the above were subjected to FISH analysis by using mouse Cot-1 DNA as a probe according to the method described by Shinohara et al. (Human Molecular Genetics, 10: 1163-1175, 2001). As a result, 95% of DT40 (mChr11-BSr)-1 had a single copy of mouse chromosome per normal nuclear type (2n). The following analysis was performed (FIG. 7).

mal nucleotide sequence (AL671968) of mouse chromosome 11 obtained from GenBank database, target sequence for homologous recombination was designed. Genomic DNA was extracted from DT40 (mChr11-BSr) and used as a template, and the sequences of the primers for PCR amplification of the target sequence for homologous recombination are given below.

```
m11 17L:
                                    (SEQ ID NO: 3)
5'-CGAGGATCCCACATTGGTAGTCTTTTCACTGCCATCA-3' m11 17R:
                                    (SEQ ID NO: 4)
5'-CGAGGATCCCCACTTAACTTTTCCAGGCTTACGGAGA-3'
```

For PCR, GeneAmp 9600 (manufactured by PerkinElmer, Inc.) was used as a thermal cycler and LA Taq (TAKARA) was used as Taq polymerase. Buffers and dNTPs (dATP, dCTP, dGTP, and dTTP) used were those included in the product and they were used under the conditions described in manufacturer's instruction. Temperature and cycle conditions were as follows: after heat denaturation at 94° C. for 1 min, 35 cycles of 98° C. for 10 sec and 65° C. for 8 min were carried out. The PCR product was digested with BamHI (TAKARA), separated by agarose gel, purified, and cloned into BamHI site of pBS-TEL/puro (vector name: pBS-TEL/puro_MAC). The targeting vector, target sequence, and chromosome allele obtained by homologous recombination were shown in FIG. 9.

TABLE 3

|  | Metaphase | | | | | Interphase | | | | |
|---|---|---|---|---|---|---|---|---|---|---|
|  | mChr11 x0/2n | mChr11 x1/2n | mChr11 x2/2n | mChr11 x2/4n | Total | x0 | x1 | x2 | x3 | Total |
| DT40 (mChr11-BSr)-1 | 1 | 17 |  | 2 | 20 | 2 | 95 | 3 |  | 100 |
| DT40 (mChr11-BSr)-2 |  | 2 | 18 |  | 20 | 5 | 15 | 79 | 1 | 100 |

Figure 8:
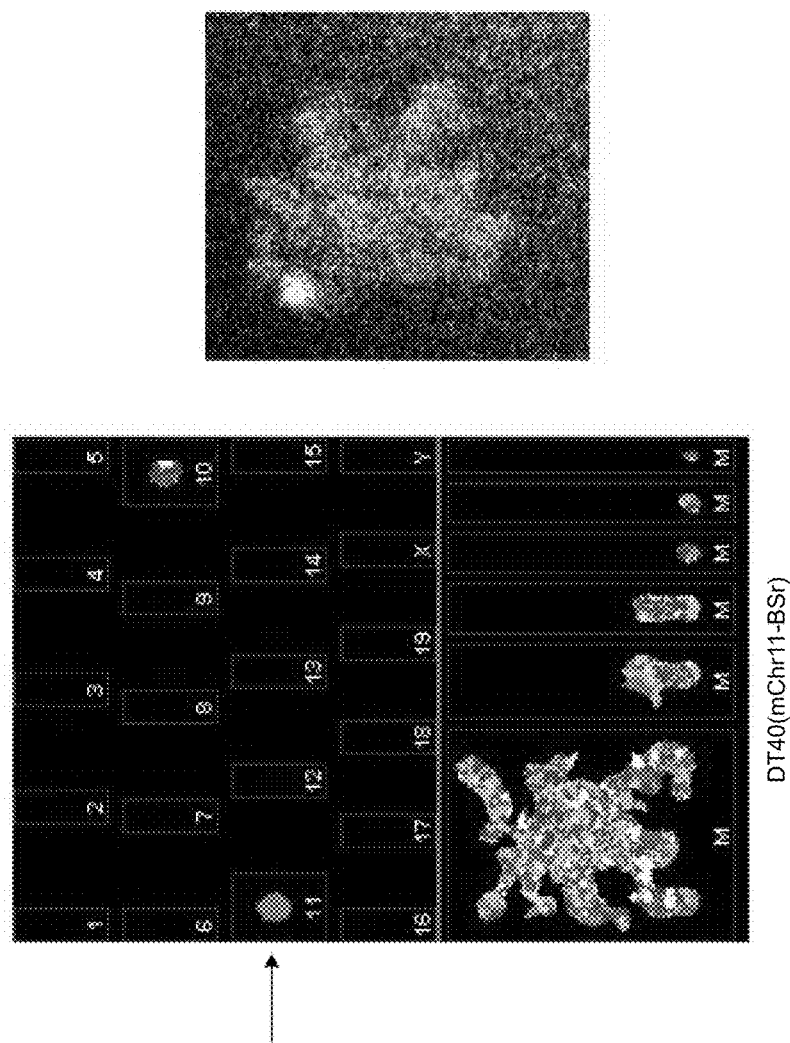
FIG. 8 shows the results of the SKY FISH analysis indicating that mouse chromosome (mChr11-BSr) introduced into the chicken DT40 cell is mouse chromosome 11 (left panel), and the SKY FISH staining image (right panel).

[B. 2. 2] Identification of Mouse Chromosome Introduced into DT40 and Labeled with Drug Resistant Gene SKY-FISH was carried out according to the method described by Kai et al. (Cell Res, 19: 247-58, 2009). As a result, it was found that the mouse chromosome introduced into the chicken DT40 cells is mouse chromosome 11 (FIG. 8).

[C] Site Specific Cleavage by Telomere Truncation of Distal Region from Mouse Chromosome 11 Region AL671968 in Chicken DT40 Cell Since less amount of endogenous genes other than a gene to be introduced in the mouse artificial chromosome vector has a less influence on an experiment system and, among endogenous genes, a gene having an influence on development of a mouse individual due to change in gene expression amount, like an imprinting gene, should be removed as much as possible, most of the mouse long arm is deleted.

[C. 1] Preparation of Telomere Truncation Vector

As for a basic vector for short arm proximal region-specific restriction, pBS-TEL/puro construct (Kuroiwa et al. Nature Biotech 2002) was used. From the long-arm proxi-

[C. 2] Selection of Homologous Recombinant

A vector, in which the site specific cleavage of the region distal from mouse chromosome 11 region AL671968 is to be carried out, was transfected by using pBS-TEL/puro_MAC described above, and puromycin resistant and blasticidin S non-resistant clones were isolated and selected for homologous recombinants. As a result, five clones in which the mouse chromosome 11 region could be cleaved were confirmed (clone name: DT40 (MAC)). The targeting vector, target sequence, and chromosome allele obtained by homologous recombination were shown in FIG. 9.

[C. 3] Selection of Drug Resistant Clone by Mono-Color FISH Analysis

Figure 10:
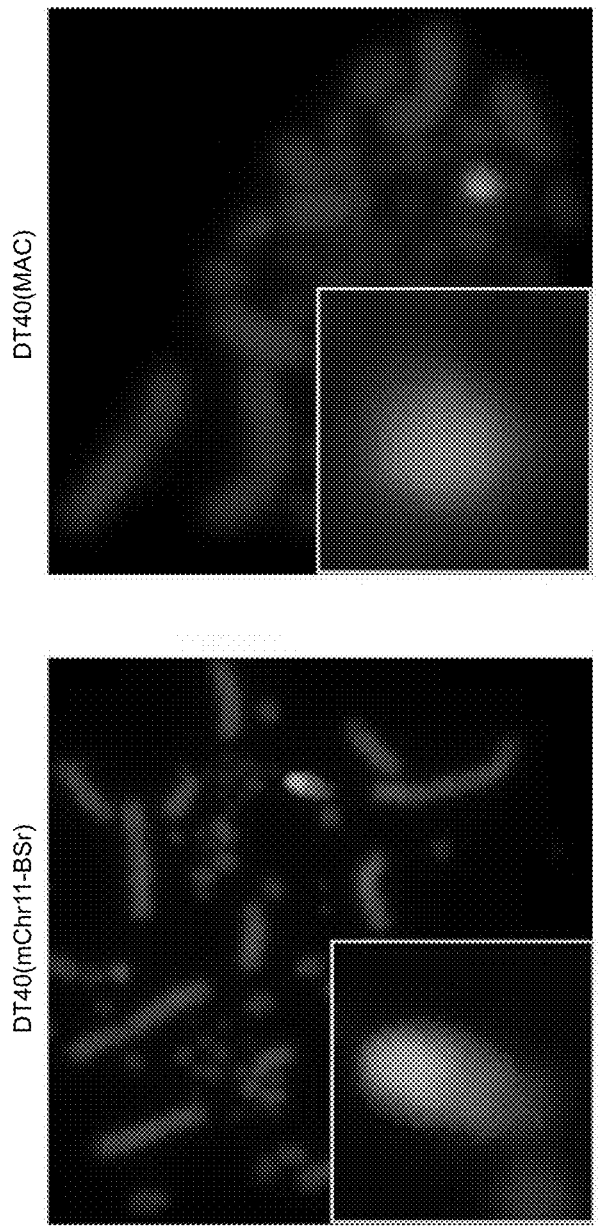
FIG. 10 shows the results of mono-color FISH analysis of DT40 (MAC) [DT40 (B6bT-1)] clone containing allele of mouse artificial chromosome MAC in which telomere truncation has occurred at AL671968 region of mouse chromosome 11 by using pBS-TEL/puro_MAC vector (right panel). DT40 (mChr11-BSr) of the left panel indicates DT40 (mChr11-BSr) clone before the telomere truncation.

Five DT40 (MAC) clones obtained from the above were subjected to FISH analysis by using mouse Cot-1 DNA as a probe according to the method described by Shinohara et al. (Human Molecular Genetics, 10: 1163-1175, 2001). As a result, it was confirmed that the long-arm part of mouse chromosome 11 was cleaved near the centromere in two clones out of the five clones (FIG. 10).

TABLE 4

| | Metaphase | | | Interphase | | | | Remaining chromosome region | Origin |
|---|---|---|---|---|---|---|---|---|---|
| | x0/2n | x1/2n | Total | x0 | x1 | x2 | Total | | |
| DT40 (MAC)-1 | 2 | 18 | 20 | | 94 | 6 | 100 | No | DT40 (mChr11-BSr)-1 |
| DT40 (MAC)-2 | 1 | 19 | 20 | 1 | 93 | 6 | 100 | No | DT40 (mChr11-BSr)-1 |
| DT40 (MAC)-3 | 1 | 19 | 20 | 1 | 94 | 5 | 100 | Yes | DT40 (mChr11-BSr)-1 |
| DT40 (MAC)-4 | | 20 | 20 | 3 | 93 | 4 | 100 | Yes | DT40 (mChr11-BSr)-1 |
| DT40 (MAC)-5 | 20 | | 20 | 100 | | | 100 | | DT40 (mChr11-BSr)-1 |
| DT40 (MAC)-6 | | 20 | 20 | 5 | 95 | | 100 | No | DT40 (mChr11-BSr)-1 |

From the results above, it was concluded that the mouse artificial chromosome MAC in which extra mouse chromosome long arm has been removed could be constructed. DT40 (MAC)-1, which is a chicken DT40 cell retaining the mouse artificial chromosome vector MAC, was internationally deposited at the National Institute of Advanced Industrial Science and Technology (AIST) (Central 6, 1-1-1 Higashi, Tsukuba, Ibaraki, Japan) on May 14, 2009 under the identification name of DT40 B6bT-1 according to the term of the Budapest Treaty. It was given the accession number FERM BP-11128.

Example 2

Construction of the Mouse Artificial Chromosome Vector MAC1

As a DNA insertion sequence, GFP-PGKneo-loxP-3' HPRT type loxP sequence was inserted into the mouse artificial chromosome MAC to construct the mouse artificial chromosome vector MAC1. Stability of MAC1 in mouse ES cells was examined and stability in each individual tissue was examined by preparing a progeny-transmitted mouse to which MAC 1 was introduced.

[A] Insertion of GFP-PGKneo-loxP-3' HPRT Type loxP Sequence into the Mouse Artificial Chromosome Vector MAC

[A. 1] Preparation of GFP-PGKneo-loxP-3' HPRT Type loxP Targeting Vector

As a basic plasmid for inserting loxP sequence into DT40 (MAC), V913 (Lexicon genetics) was used. The DNA sequence of mouse chromosome 11 as loxP insertion site was obtained from GenBank database (BX572640.9). From the drug resistant clones, genomic DNA was extracted and used as a template, and the sequences of the primers used for amplification of two target sequences for homologous recombination are shown below.

(SEQ ID NO: 5)
m11 5L: 5'-TGACAGAGAGCTTCCTCCTGCCTCTGTA-3'

(SEQ ID NO: 6)
m11 5R: 5'-CTAAAGACCCTCATGCTCCTGTGTGGAA-3'

(SEQ ID NO: 7)
m11 6L: 5'-GTTCAACCTGAGCTCCACATCATGCTC-3'

(SEQ ID NO: 8)
m11 7R: 5'-CACTCTTTACCCCTCACCGCTAACCTTG-3'

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 10 sec and 68° C. for 5 min were carried out.

Each of the PCR products was digested with BglII (TAKARA), separated by agarose gel, purified, and cloned into BglII site or BamHI site of V913 (vector name: VH21-12). For 3' HPRT-loxP, loxP sequence obtained by oligosynthesis was cloned into XbaI site of V820 (Lexicon genetics). 3' HPRT-loxP, which is the third to ninth exons of HPRT gene, was cloned between EcoRI and AscI of V907 (Lexicon genetics) (vector name: X3.1). Further, the PGKneo sequence cut out by using KpnI and NotI was cloned into KpnI site and EcoRI site of X3.1 (vector name: X4.1). PGKneo-loxP-3' HPRT cut out from X4.1 by using KpnI and AscI was cloned into KpnI site and AscI site of V913 (vector name: pVNLH). HS4-CAG-EGFP-HS4 obtained by digestion with NotI and SalI followed by blunting (provided by Dr. Okabe at Osaka University and Dr. Felsenfeld at NIH) was cloned Into the EcoRV site of pVNLH (vector name: pVGNLH). GFP-PGKneo-loxP-3' HPRT cassette cut out from pVGNLH with SalI and AscI was cloned into XhoI site and AscI site of VH21-12 (vector name: pMAC1). The targeting vector, target sequence, and chromosome allele obtained by homologous recombination are shown in FIG. 11.

[A. 2] Transfection and Isolation of G418 Resistant Clone

Cell culture of chicken DT40 cells was performed in RPMI 1640 culture medium (Gibco) supplemented with 10% fetal bovine serum (Gibco, herein below, described as FBS), 1% chicken serum (Gibco), and 10-4 M 2-mercaptoethanol (Sigma). Approximately $10^7$ DT40 (MAC)-1 cells were washed once with supplement-free RPMI 1640 culture medium, suspended in 0.5 ml of supplement-free RPMI 1640 culture medium, added with 25 μg of the targeting vector pMAC1 which has been linearized with the restriction enzyme NotI (TAKARA), transferred to a cuvette (Bio-Rad Laboratories, Inc.) for electroporation, and left to stand for 10 min at room temperature. The cuvette was set in Gene Pulser (Bio-Rad Laboratories, Inc.) and voltage was applied under the conditions of 550 V and 25 μf. After being left to stand for 10 min at room temperature, the cells were cultured for 24 hours. The culture medium was exchanged with a culture medium containing G418 (1.5 mg/ml), and dispensed into two 96-well culture plates, and then subjected to selection culture for about 2 weeks. Total 14 resistant colonies obtained after two transfections were isolated, amplified, and subjected to the following analysis (clone name: DT40 (MAC1)).

[A. 3] Selection of Homologous Recombinant
[A. 3. 1] PCR Analysis

For extracting genomic DNA from G418 resistant cell line and using it as a template for selecting a recombinant, PCR was carried out by using the following primers and it was confirmed whether or not recombination has site-specifically occurred on mouse chromosome 11. The primer sequences are given below.

```
                                          (SEQ ID NO: 9)
kj neo: 5'-CATCGCCTTCTATCGCCTTCTTGACG-3'
``` m11 7R (described above)
m11 5L (described above)

```
                                          (SEQ ID NO: 10)
EGFP-F (L) 5'-CCTGAAGTTCATCTGCACCA-3'
```

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 10 sec and 68° C. for 7 min were carried out. As a result of PCR, two clones out of the 88 clones were found to be positive for all primer sets, and therefore the following analysis was performed by using those two clones.

TABLE 5

| | Origin DT40 (MAC)-1 Clone name DT40 (MAC1) | | Negative control |
|---|---|---|---|
| Clone number | 52 | 58 | DT40 |
| kj neo/m11 7R | ○ | ○ | X |
| m11 5L/EGFP-F(L) | ○ | ○ | X |

[A. 3. 2] Two-Color FISH Analysis

Figure 12:
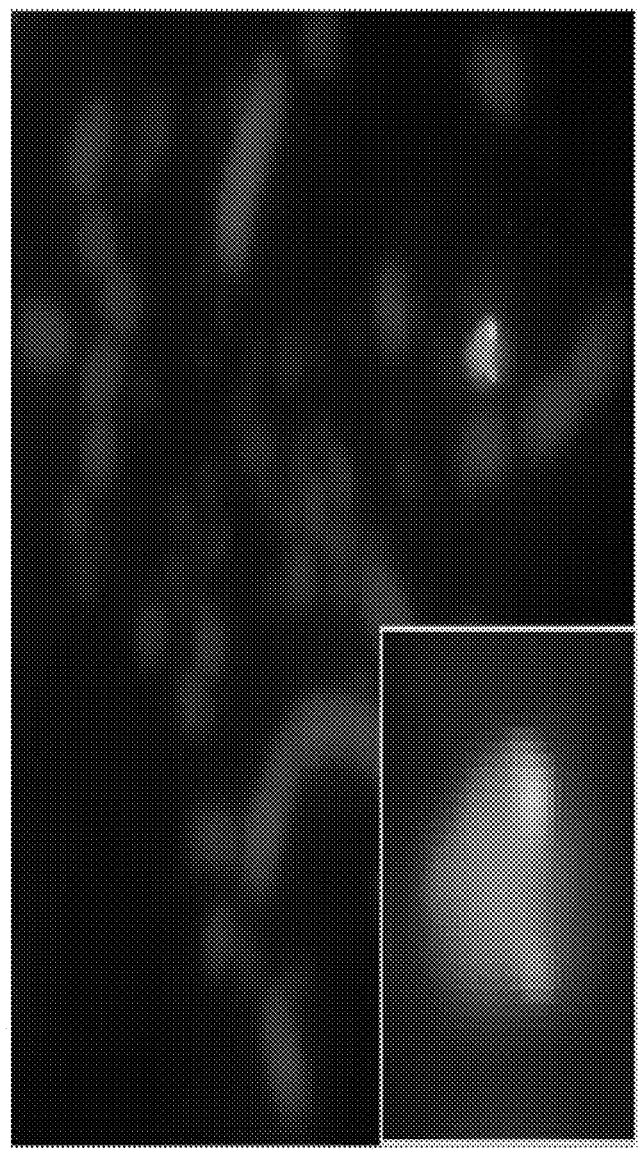
FIG. 12 shows the results of the two-color FISH analysis of DT40 (MAC1) clone in which mouse Cot-1 DNA and GFP-PGKneo-loxP-3' HPRT cassette were used as probes.

For DT40 (MAC1)-52 and DT40 (MAC1)-58 obtained from the above, two-color FISH analysis was carried out according to Matsubara et al. (FISH test protocol, Shujunsha Co., Ltd., 1994). FISH analysis was carried out by using mouse cot-1 DNA and GFP-PGKneo-loxP-3' HPRT cassette as probes. As a result, FITC signal derived from the probe was detected near the centromere of mouse chromosome 11 fragment which has been targeted with loxP sequence, and a signal not observed for the mouse chromosome 11 fragment (e.g., DT40 (MAC)-1) before targeting as a negative control was detected, therefore it was visually confirmed that recombination has site-specifically occurred (FIG. 12). From these results, it was possible to conclude that DT40 cell clones retaining the mouse artificial chromosome vector MAC1 were obtained.

TABLE 6

| | Metaphase | | | Interphase | | | | |
|---|---|---|---|---|---|---|---|---|
| | With FITC x 1/2n | Without FITC x 1/2n | Total | x0 | x1 | x2 | Total | Origin |
| DT40 (MAC)-1 | 2 | 18 | 20 | 2 | 95 | 3 | 100 | Control |
| DT40 (MAC1)-52 | 20 | | 20 | | 98 | 2 | 100 | DT40 (MAC)-1 |
| DT40 (MAC1)-58 | 19 | 1 | 20 | 1 | 95 | 4 | 100 | DT40 (MAC)-1 |

[B] Introduction of MAC1 from DT40 Cell Containing the Mouse Artificial Chromosome Vector MAC1 into CHO Cell In order to introduce the mouse artificial chromosome vector MAC1 into mouse ES cells via CHO cells, or to stably insert a target gene (group), e.g., CYP3A cluster or the like, via loxP as a DNA sequence insertion site of the mouse artificial chromosome vector MAC1 within CHO cells, introduction to CHO cells was made.

[B. 1] Microcell Fusion and Isolation of Drug Resistant Clone

By using DT40 (MAC1) 52 and 58 as recipient cells, microcell fusion was carried out with CHO (HPRT⁻), i.e., CHO hprt depleted cell (obtained from the Health Science Research Resources Bank, registration number: JCRB0218), in the same manner as above. Total 24 resistant colonies obtained by two microcell fusions were isolated, amplified, and subjected to the following analysis (clone name: CHO (HPRT⁻; MAC1)).

[B. 2] Selection of Drug Resistant Clone
[B. 2. 1] PCR Analysis

For extracting genomic DNA from G418 resistant cell line and using it as a template for selecting a recombinant, PCR was carried out by using the following primers and it was confirmed whether or not mouse artificial chromosome MAC1 has been introduced into CHO cells. The primer sequences are given below.

kj neo (described above)
m11 7R (described above)
m11 5L (described above)
EGFP F (L) (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 10 sec and 68° C. for 7 min were carried out. As a result of PCR, 20 clones out of the 24 clones were found to be positive for all primer sets, and the following analysis was performed by using those 20 clones.

TABLE 7

| | Origin | | | | | | | | | | | | | | | | |
|---|---|---|---|---|---|---|---|---|---|---|---|---|---|---|---|---|---|
| | DT40 (MAC1)-52 | | | | | | | | | | | | | DT40 (MAC1)-58 | | | |
| | Clone name | | | | | | | | | | | | | | | | |
| | CHO(HPRT⁻; MAC1) | | | | | | | | | | | | | | | | |
| | Clone number | | | | | | | | | | | | | | | | |
| | 1 | 2 | 3 | 4 | 5 | 6 | 7 | 8 | 9 | 10 | 11 | 12 | 13 | 14 | 15 | 16 | 17 |
| kj neo/m11 7R | ○ | ○ | ○ | ○ | ○ | ○ | ○ | ○ | ○ | ○ | ○ | ○ | ○ | ○ | ○ | ○ | ○ |
| m11 5L/EGFP-F(L) | X | ○ | ○ | ○ | ○ | ○ | ○ | ○ | ○ | ○ | ○ | ○ | ○ | ○ | ○ | ○ | X |

| | Origin | | | | | | | | | | |
|---|---|---|---|---|---|---|---|---|---|---|---|
| | DT40 (MAC1)-58 | | | | | | | | | | |
| | Clone name | | | | | | | | | | |
| | CHO(HPRT⁻; MAC1) | | | | | | | Positive control | | Negative control | |
| | Clone number | | | | | | | DT40(MAC1) | | CHO | |
| | 18 | 19 | 20 | 21 | 22 | 23 | 24 | 52 | 58 | DT40 | (HPRT) |
| kj neo/m11 7R | ○ | ○ | ○ | ○ | ○ | ○ | ○ | ○ | ○ | X | X |
| m11 5L/EGFP-F(L) | X | X | ○ | ○ | ○ | ○ | ○ | ○ | ○ | X | X |

Figure 13:
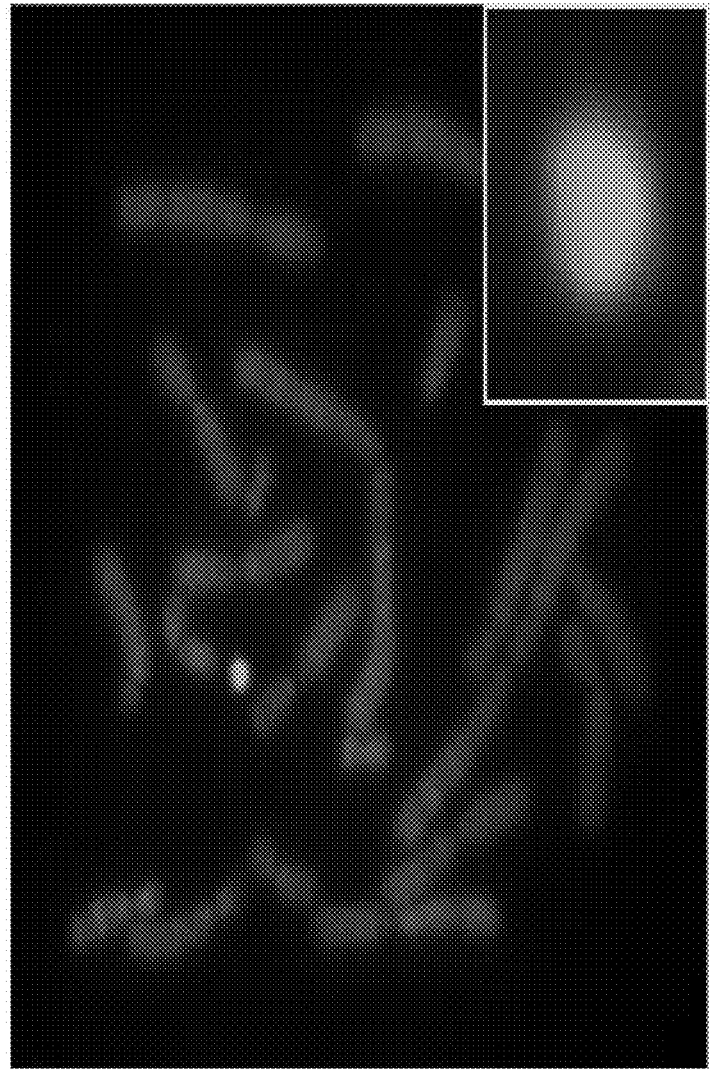
FIG. 13 shows the results of the mono-color FISH analysis of CHO (HPRT; MAC1) clone in which mouse Cot-1 DNA was used as a probe.

[B. 2. 2] Mono-Color FISH Analysis 20 clones of CHO (HPRT⁻; MAC1) obtained from the above were subjected to FISH analysis by using mouse cot-1 DNA as a probe according to the method described by Shinohara et al. (Human Molecular Genetics, 10: 1163-1175, 2001). As a result, it was confirmed that the mouse artificial chromosome vector MAC1 has been introduced into CHO cells with a rate of 95% in five clones out of the 20 clones (FIG. 13).

TABLE 8

| | Metaphase | | | | | | | | | | |
|---|---|---|---|---|---|---|---|---|---|---|---|
| | x0/2n | x1/2n | x1/4n | x2/4n | x2~/4n | Big x1/2n | Big x1/4n | Big x2/4n | Big x3~ | With translocation/ 2n, 4n | Total |
| CHO(HPRT⁻; MAC1)-2 | 1 | 13 | | 1 | | 1 | 2 | | | 2 | 20 |
| CHO(HPRT⁻; MAC1)-3 | 1 | 15 | | 4 | | | | | | | 20 |
| CHO(HPRT⁻; MAC1)-4 | | 8 | | | | 9 | | | | 3 | 20 |
| CHO(HPRT⁻; MAC1)-5 | | 17 | | 3 | | | | | | | 20 |
| CHO(HPRT⁻; MAC1)-6 | 1 | 3 | | | 1 | 10 | | 3 | 1 | 1 | 20 |
| CHO(HPRT⁻; MAC1)-7 | 2 | 12 | 2 | | | 1 | | 1 | | 2 | 20 |
| CHO(HPRT⁻; MAC1)-8 | 1 | 16 | | 3 | | | | | | | 20 |
| CHO(HPRT⁻; MAC1)-9 | | 7 | 2 | | | 6 | | 1 | | 4 | 20 |
| CHO(HPRT⁻; MAC1)-10 | 2 | 10 | | 3 | | 4 | | 1 | | | 20 |
| CHO(HPRT⁻; MAC1)-11 | | 2 | | | | | | | | 18 | 20 |
| CHO(HPRT⁻; MAC1)-12 | | 3 | | | | | | | | 17 | 20 |
| CHO(HPRT⁻; MAC1)-13 | 1 | 3 | | | | | | | | 16 | 20 |
| CHO(HPRT⁻; MAC1)-14 | | 8 | 4 | 1 | | 2 | | | | 5 | 20 |
| CHO(HPRT⁻; MAC1)-15 | 2 | 4 | | | | | 6 | 4 | 4 | | 20 |
| CHO(HPRT⁻; MAC1)-16 | 2 | 8 | | 4 | | 3 | | 3 | | | 20 |
| CHO(HPRT⁻; MAC1)-20 | | 6 | 1 | 2 | | 5 | | 5 | | 1 | 20 |
| CHO(HPRT⁻; MAC1)-21 | 2 | 4 | | | | 2 | 6 | 4 | | 2 | 20 |
| CHO(HPRT⁻; MAC1)-22 | | 18 | | 1 | | | 1 | | | | 20 |
| CHO(HPRT⁻; MAC1)-23 | | 13 | | 1 | | | | 4 | 2 | | 20 |
| CHO(HPRT⁻; MAC1)-24 | 4 | 10 | | | | 3 | | 2 | | 1 | 20 |

| | Interphase | | | | | Origin CHO(HPRT⁻; | |
|---|---|---|---|---|---|---|---|
| | x0 | x1 | x2 | x3 | Total | MAC1)- | Remarks |
| CHO(HPRT⁻; MAC1)-2 | 3 | 78 | 15 | 4 | 100 | 52 | |
| CHO(HPRT⁻; MAC1)-3 | 2 | 79 | 16 | 3 | 100 | 52 | → hChr7 was transferred |
| CHO(HPRT⁻; MAC1)-4 | 1 | 78 | 18 | 3 | 100 | 52 | |
| CHO(HPRT⁻; MAC1)-5 | 8 | 83 | 6 | 3 | 100 | 52 | → hChr7 was transferred |
| CHO(HPRT⁻; MAC1)-6 | 3 | 67 | 23 | 7 | 100 | 52 | |
| CHO(HPRT⁻; MAC1)-7 | 20 | 59 | 14 | 9 | 102 | 52 | |
| CHO(HPRT⁻; MAC1)-8 | 7 | 87 | 6 | | 100 | 52 | → hChr7 was transferred |
| CHO(HPRT⁻; MAC1)-9 | 6 | 79 | 7 | 8 | 100 | 52 | |
| CHO(HPRT⁻; MAC1)-10 | 3 | 84 | 9 | 4 | 100 | 52 | |
| CHO(HPRT⁻; MAC1)-11 | 5 | 39 | 45 | 11 | 100 | 52 | |
| CHO(HPRT⁻; MAC1)-12 | 9 | 72 | 12 | 7 | 100 | 52 | |

TABLE 8-continued

| | | | | | | | |
|---|---|---|---|---|---|---|---|
| CHO(HPRT⁻; MAC1)-13 | 5 | 78 | 9 | 8 | 100 | 58 | |
| CHO(HPRT⁻; MAC1)-14 | 1 | 83 | 11 | 5 | 100 | 58 | |
| CHO(HPRT⁻; MAC1)-15 | 4 | 75 | 13 | 8 | 100 | 58 | |
| CHO(HPRT⁻; MAC1)-16 | 8 | 70 | 21 | 1 | 100 | 58 | |
| CHO(HPRT⁻; MAC1)-20 | 2 | 62 | 31 | 5 | 100 | 58 | |
| CHO(HPRT⁻; MAC1)-21 | 4 | 72 | 18 | 6 | 100 | 58 | |
| CHO(HPRT⁻; MAC1)-22 | 1 | 91 | 8 | | 100 | 58 | → hChr7 was transferred |
| CHO(HPRT⁻; MAC1)-23 | 1 | 68 | 29 | 2 | 100 | 58 | |
| CHO(HPRT⁻; MAC1)-24 | 21 | 67 | 10 | 2 | 100 | 58 | |

From the results above, it was concluded that the mouse artificial chromosome vector MAC1 could be introduced into CHO cells.

[C] Introduction of the Mouse Artificial Chromosome Vector MAC1 from CHO Cell Containing the Mouse Artificial Chromosome Vector MAC1 into Mouse ES Cells In order to examine the stability of the mouse artificial chromosome vector MAC1 in mouse ES cells and individual mouse, the mouse artificial chromosome MAC1 was introduced into mouse ES cells to prepare chimeric mouse and a progeny-transmitted mouse containing the mouse artificial chromosome vector MAC1.

[C. 1] Microcell Fusion and Isolation of Drug Resistant Clone

CHO (HPRT⁻; MAC1)-3, 5, 8, and 22 as recipient cells were cultured on cell culture dishes. At the time of reaching confluency, the culture medium was exchanged with F12 culture medium supplemented with 20% FBS and 0.1 µg/ml colcemid. After further culturing for 48 hours, the culture medium was again exchanged with F12 culture medium supplemented with 20% FBS and 0.1 µg/ml colcemid followed by incubation overnight to form microcells. The culture medium was removed and cytochalasin B (10 µg/ml, Sigma) solution which has been previously kept warm at 37° C. was filled in a flask for centrifugation. The centrifugation was performed for 1 hour at 34° C., at 8000 rpm. The microcells were suspended in serum free DMEM culture medium and purified with filters of 8 µm, 5 µm, and 3 µm. After the purification, the cells were centrifuged for 10 min at 2000 rpm, and suspended in 5 ml of serum free DMEM culture medium. The microcells were suspended in 5 ml of serum free DMEM culture medium and purified with filters of 8 µm, 5 µm, and 3 µm. After the purification, the cells were centrifuged for 10 min at 2000 rpm.

As a donor cell, B6-ES, which is a C57B6 line-based mouse ES cell, B6 (HPRT⁻), which is a HPRT depleted cell line obtained by treating B6-ES cell with 6TG, TT2F, which is a C57B6×CBA lineage-based F1 mouse ES cell, and KO56 (HPRT), which is a HPRT depleted cell line obtained by treating TT2F cell with 6TG, were used. For cell culture, to DMEM (Dulbecco's Modified Eagle's Medium-high glucose: SIGMA), 10% FCS, LIF (Muerin Leukemia Inhibitory Factor), $1 \times 10^{-5}$ M 2-ME (2-mercaptoethanol: SIGMA), L-glutamine (3.5 g/ml: GIBCO), sodium pyruvate solution (3.5 g/ml: GIBCO), and MEM nonessential amino acids (0.125 mM: GIBCO) were added, and culture was performed under 5% $CO_2$, at 37° C. After washing twice the cell surface of mouse ES cells with PBS (−), the cells were dispersed with trypsin treatment and recovered with a culture medium in which 10% FBS was added to DMEM culture medium. Centrifugation was carried out at 1500 rpm, the supernatant was removed, re-suspended in 5 ml of serum free culture medium, and gently added to the serum free culture medium containing microcell pellets after centrifugation. It was further centrifuged at 1200 rpm. The supernatant was removed and fused with 0.5 ml of PEG1000 (Wako) solution [5 g of PEG1000 is dissolved completely in serum free DMEM culture medium, added with 1 ml of dimethyl sulfoxide, and sterilized by filtration] precisely for 1 min and 30 sec. 13 ml of serum free culture medium (DMEM) was gently added and centrifuged at 1200 rpm. The supernatant was removed, common culture medium for mouse ES cells was added, and using G418 resistant mouse embryonic fibroblast treated with mitomycin as a feeder cell, the cells were plated onto two culture dishes with a diameter of 10 cm followed by incubation overnight. G418 was added to 250 µg/ml and subjected to selection culture for 3 to 4 weeks (clone name: B6-ES (MAC1) and B6 (HPRT⁻; MAC1) and KO56 (HPRT⁻; MAC1)). For B6-ES (MAC1), B6 (HPRT⁻; MAC1) and KO56 (HPRT⁻; MAC1), total 32 resistant colonies obtained by two microcell fusions were isolated, amplified, and subjected to the following analysis. For TT2F (MAC1), total 30 resistant colonies obtained by four microcell fusions were isolated, amplified, and subjected to the analysis after FISH analysis.

[C. 2] Selection of Drug Resistant Clone

[C. 2. 1] PCR Analysis

For extracting genomic DNA from G418 resistant cell line and using it as a template for selecting a recombinant, PCR was carried out by using the following primers and it was confirmed whether or not mouse artificial chromosome MAC1 can be introduced into mouse ES cells. The primer sequences are given below.

m11 5L (described above)

EGFP F (L) (described above)

kj neo (described above)

m11 7R (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 10 min were carried out. As a result of PCR, 30 clones out of the 32 clones were found to be positive for all primer sets, and the following analysis was performed by using 14 clones among them.

TABLE 9

| | Origin | | | | | | | |
|---|---|---|---|---|---|---|---|---|
| | CHO(HPRT-; MAC1)-3 | CHO(HPRT-; MAC1)-3 | CHO(HPRT-; MAC1)-5 | CHO(HPRT-; MAC1)-22 | CHO(HPRT-; MAC1)-3 | CHO(HPRT-; MAC1)-22 | CHO(HPRT-; MAC1)-3 | CHO(HPRT-; MAC1)-7 |
| | | | | Clone name | | | | |
| | B6 (HPRT-; MAC1) | | | B6-ES(MAC1) | | | | |
| | | | | Clone number | | | | |
| | 1 | 2 | 4 | 2 | 3 | 4 | 5 | 6 | 7 | 8 | 9 | 10 | 11 |
| m11 5L/ EGFP-F(L) | X | ○ | ○ | ○ | ○ | ○ | ○ | ○ | ○ | ○ | ○ | X | ○ |
| kj neo/ m11 7R | ○ | ○ | ○ | ○ | ○ | ○ | ○ | ○ | ○ | ○ | ○ | ○ | ○ |

| | Origin | | | | | | | |
|---|---|---|---|---|---|---|---|---|
| | CHO(HPRT-; MAC1)-22 | CHO(HPRT-; MAC1)-3 | CHO(HPRT-; MAC1)-5 | CHO(HPRT-; MAC1)-7 | CHO(HPRT-; MAC1)-22 | CHO(HPRT-; MAC1)-3 | CHO(HPRT-; MAC1)-7 |
| | | | | Clone name | | | |
| | B6-ES(MAC1) | | | KO56(HPRT-; MAC1) | | | |
| | | | | Clone number | | | |
| | 12 | 13 | 14 | 1 | 3 | 4 | 5 | 6 | 7 | 8 | 9 | 10 | 11 | 12 |
| m11 5L/ EGFP-F(L) | ○ | ○ | ○ | ○ | ○ | ○ | ○ | ○ | ○ | ○ | ○ | ○ | ○ | ○ |
| kj neo/ m11 7R | ○ | ○ | ○ | ○ | ○ | ○ | ○ | ○ | ○ | ○ | ○ | ○ | ○ | ○ |

| | | Origin | | | | | |
|---|---|---|---|---|---|---|---|
| | | CHO(HPRT-; MAC1)-22 | CHO(HPRT-; MAC1)-3 | CHO(HPRT-; MAC1)-22 | | | |
| | | | Clone name | | | | |
| | | KO56(HPRT-; MAC1) | | | | | |
| | | | Clone number | | CHO(HPRT-; | | |
| | | 13 | 14 | 15 | 16 | 17 | MAC1)-22 | CHO(HPRT-) | B6-ES | TT2F |
| | m11 5L/ EGFP-F(L) | ○ | ○ | ○ | ○ | ○ | ○ | X | X | X |
| | kj neo/ m11 7R | ○ | ○ | ○ | ○ | ○ | ○ | X | X | X |

[C. 2. 2] Mono-Color FISH Analysis

B6-ES (MAC1) and B6 (HPRT−; MAC1) and KO56 (HPRT−; MAC1) clones obtained from the above were subjected to FISH analysis by using mouse minor satellite DNA as a probe according to the method described by Shinohara et al. (Human Molecular Genetics, 10: 1163-1175, 2001). As a result, it was confirmed that MAC1 has been introduced into mouse ES cells at a rate of 85% or more in all 14 clones. Further, the number of endogenous mouse chromosomes with normal nuclear type was confirmed to be 40 for B6-ES and 39 for KO56. In case of B6 (HPRT−; MAC1), clones with 40 nuclear type were not obtained. Similarly, for TT2F (MAC1), analysis was carried out with seven clones. As a result, in all seven clones, it was confirmed that the introduction has been made with a rate of 90% or more. In addition, the number of endogenous mouse chromosomes with normal nuclear type was confirmed to be 39 for three clones out of the seven clones.

Figure 14:
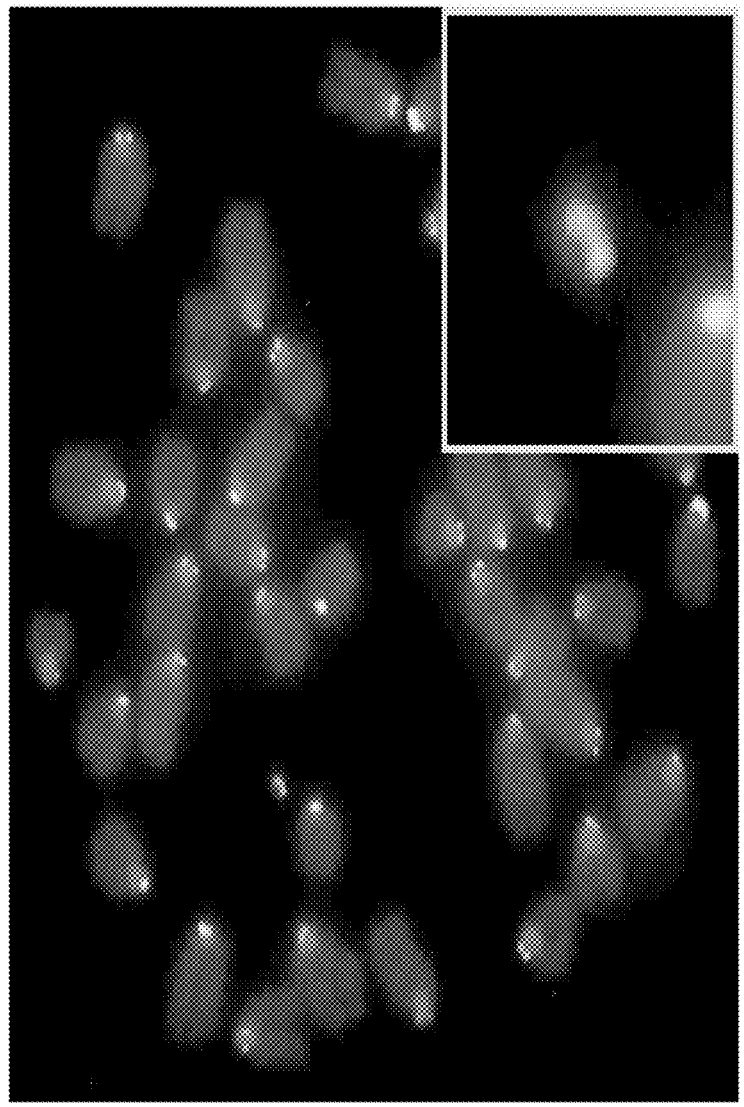
FIG. 14 shows the results of the mono-color FISH analysis of mouse ES (MAC1) clone in which mouse minor satellite DNA was used as a probe.

From the results above, it was concluded that the mouse artificial chromosome vector MAC1 can be introduced into mouse ES cells (FIG. 14).

TABLE 10

| | Number of mouse endogenous chromosomes | | | | | | | | Origin |
|---|---|---|---|---|---|---|---|---|---|
| | 38 | 39 | | 40 | | | 41 | Total | CHO MAC1− |
| | | | MAC copy number | | | | | | |
| | x1 | x0 | x1 | x2 | x0 | x1 | x2 | x1 | | |
| B6 HPRT−/− MAC1-2 | | | 16 | 1 | 1 | 2 | | | 20 | 22 |
| B6ES MAC1 3 | | | 1 | | | 15 | 4 | | 20 | 22 |
| B6ES MAC1 8 | | | 3 | | | 16 | 1 | | 20 | 3 |
| B6ES MAC1 9 | | | 1 | | 1 | 17 | 1 | | 20 | 22 |
| KO56 MAC1-1 | | | 18 | | | 2 | | | 20 | 5 |
| KO56 MAC1-3 | | 1 | 19 | | | | | | 20 | 7 |
| KO56 MAC1-5 | 1 | 2 | 16 | | | 1 | | | 20 | 22 |
| KO56 MAC1-6 | | | 18 | | | 2 | | | 20 | 22 |
| KO56 MAC1-7 | | | 19 | 1 | | | | | 20 | 22 |
| KO56 MAC1-8 | 1 | | 19 | | | | | | 20 | 22 |
| KO56 MAC1-9 | | 3 | 16 | | | 1 | | | 20 | 22 |
| KO56 MAC1 10 | | 1 | 18 | | | 1 | | | 20 | 22 |
| KO56 MAC1 12 | 1 | 1 | 14 | 2 | | 2 | | | 20 | 7 |
| KO56 MAC1 15 | | | 20 | | | | | | 20 | 3 |

Example 3

Construction of the Mouse Artificial Chromosome Vector CYP3A-MAC

Figure 2:
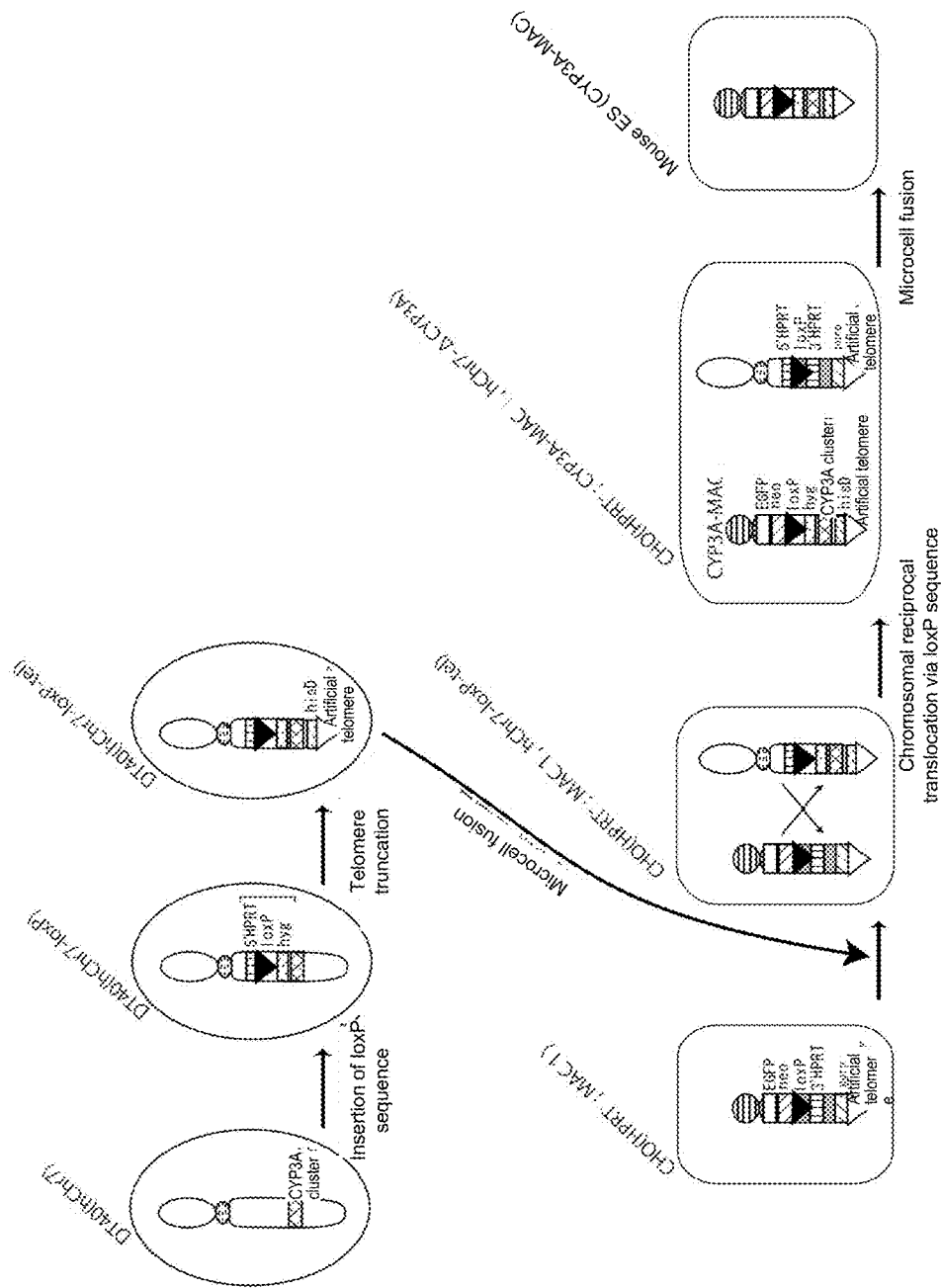
FIG. 2 is a schematic diagram illustrating the procedures of Example 3. Cell names in the drawings are described according to the following format. Cell name (cellular genetic modification; retained chromosome fragment name, and transgene-retaining chromosome name). Symbols given in the figure are as follows. hChr7: human chromosome 7, CYP3A cluster: human CYP3A gene cluster, 5' HPRT: theist to 2nd exon sequences of HPRT gene, loxP: site specific DNA sequence insertion site, hyg: hygromycin resistant gene, hisD: histidinol resistant gene, artificial telomere: artificial telomere (TTAGGG) repeat sequence, EGFP: gene expressing enhanced green fluorescent protein, neo: neomycin (G418) resistant gene, 3' HPRT: the 3rd to 9th exon sequences of HPRT gene, puro: puromycin resistant gene.

Translocation cloning of CYP3A cluster, which is a group of human drug metabolizing enzyme-related genes, is carried out for the mouse artificial chromosome vector MAC1 by using Cre/loxP system to construct CYP3A-MAC. Further, stability of CYP3A-MAC in mouse ES cells is examined and stability in tissues of each individual is examined by preparing a genetically transmitted progeny mouse into which CYP3A-MAC has been introduced. Further, in the genetically transmitted progeny mouse, tissue specific gene expression of CYP3A gene is examined (FIG. 2).

[A] Site Specific Insertion of loxP Sequence into Human Chromosome 7 AC004922

For translocation insertion into the mouse artificial chromosome vector MAC1 via loxP sequence, the loxP sequence is inserted into AC004922 proximal to CYP3A gene cluster of human chromosome 7 (hChr7) in DT40 cells.

[A. 1] Preparation of Targeting Vector pMPloxPHyg

Targeting vector pMPloxPHyg for inserting loxP, which is a recognition sequence for Cre recombinase, into AC004922 region, which is located extremely close to CYP3A gene locus of human chromosome 7 and on the centromere side (i.e., locating on the centromere side by approximately 300 Kb from CYP3A gene locus), was prepared as follows. First, the AC004922 genome region was amplified by PCR using the following primers.

```
                                         (SEQ ID NO: 11)
p45oloxP7L;  5'-GGCCTAGAGCCTGGACTCATTCATTCAA-3'

(SEQ ID NO: 12)
p45oloxP7R;  5'-GACAGATGTCATGCCCCAGGTAGGTATG-3'
```

Figure 15:
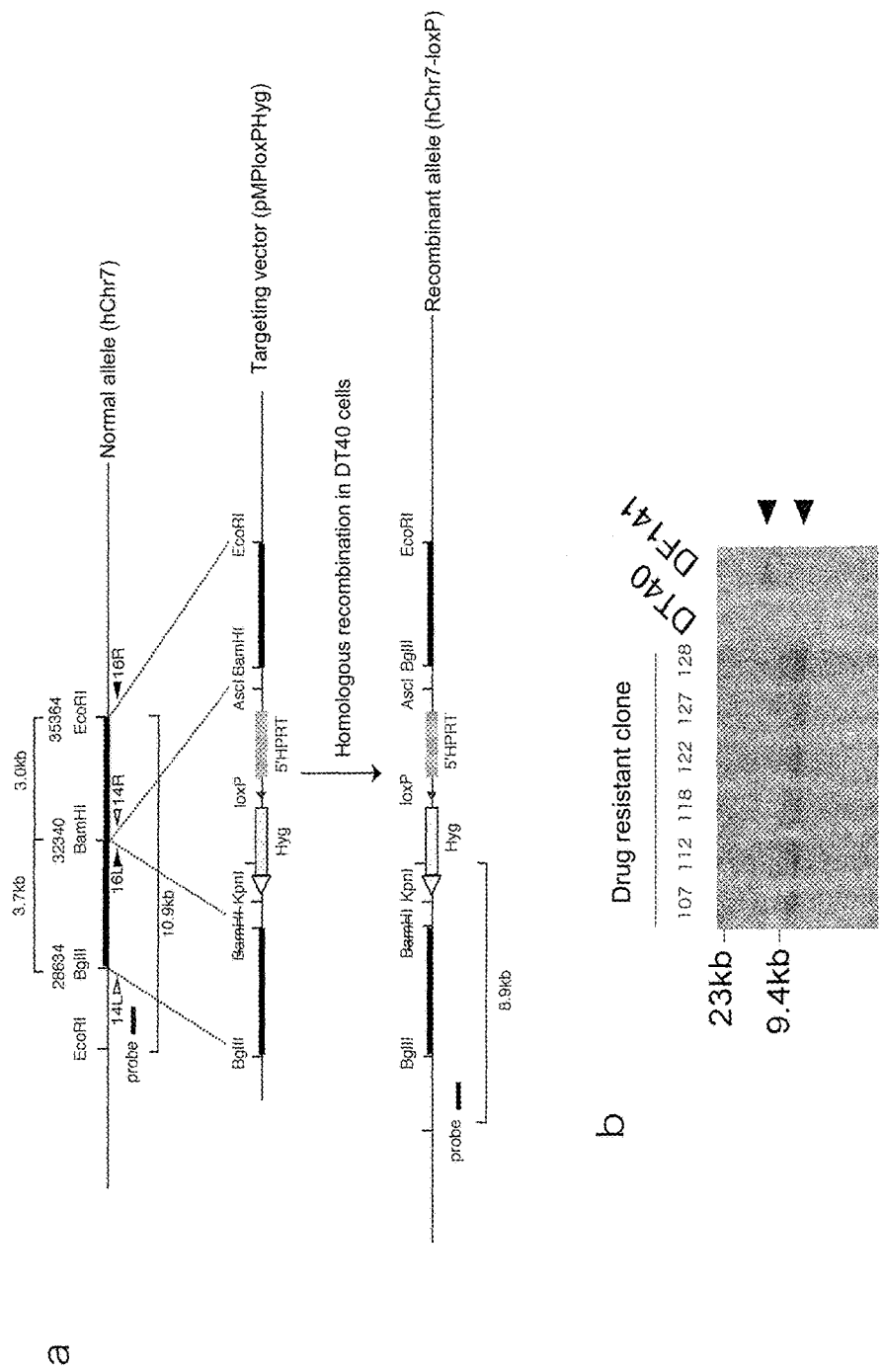
FIG. 15 shows the targeting vector (pMPloxPHyg) for inserting loxP into the AC004922 region, which locates extremely close to CYP3A gene locus of human chromosome 7 and on the centromere side (i.e., locating on the centromere side by approximately 300 Kb from CYP3A gene locus), and a partial structure of the human chromosome 7 allele in which homologous recombination has been carried out by using the vector (FIG. 15a).

As a basic plasmid for inserting loxP sequence, V901 (Lexicon genetics) was used. For PCR, GeneAmp 9600 manufactured by PerkinElmer, Inc. was used as a thermal cycler and LA Taq (TAKARA SHUZO CO., LTD.) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 7 min were carried out. PCR product was treated with proteinase K (Gibco) and subjected to gel filtration by using CHROMASPIN-TE400 (Clontech). After that, the product was cleaved with the restriction enzymes BamHI (Boehringer Ingelheim GmbH) and EcoRI (NIPPON GENE CO., LTD.) and BglII (NIPPON GENE CO., LTD.) and subjected to gel filtration by using CHROMASPIN-TE1000 (Clontech). The PCR fragments (3.7 kb and 3.0 kb) were cloned into the EcoRI and BamHI or BglII sites of V901 plasmid (vector name: V901-NP21). Next, the V901-NP21 was cleaved with the restriction enzymes AscI (NEB) and KpnI, and from cassette vector 5' HPRT-loxP-Hyg-TK (Kazuki et al., Gene Therapy: PMID: 21085194, 2010), the DNA fragment containing loxP was cut out by using the restriction enzymes AscI and KpnI before ligation. The resultant product in which the loxP sequence is in the same direction as the cloned AC004922 genome fragment was taken as targeting vector pMPloxPHyg. Size of the final construct inserted with loxP is 12 kb. The targeting vector, target sequence, and chromosome allele obtained by homologous recombination are shown (FIG. 15a).

[A. 2] Transfection and Isolation of Drug Resistant Clone

As described above, targeting vector pMPloxPHyg prepared above was linearized with the restriction enzyme NotI (TAKARA), and used for transfection of chicken DT40 cells (clone DF141) retaining human chromosome 7 fragment (in which the site specific cleavage was made at AF006752 locus) which is prepared by the method described in WO01/011951. After exchanging the culture medium with a culture medium containing hygromycin B (1.5 mg/ml), the cells were dispensed into three 96-well culture plates and then subjected to selection culture for about 2 weeks. Total 96 resistant colonies obtained from five transfections were isolated, amplified, and subjected to the following analysis (clone name: DT40 (hChr7-loxP)).

[A. 3] Selection of Homologous Recombinant

[A. 3. 1] PCR Analysis

Genomic DNA was extracted from the hygromycin resistant clone by using Puregene DNA Isolation Kit (Gentra Systems, Inc.) and identification of homologous recombinant was performed by PCR using the following two sets of primer.

Identification of homologous recombinant was performed by PCR using the following two sets of primer.

```
                                         (SEQ ID NO: 13)
p45oloxP14L;  5'-AGTTCTTTTGAGGGCCTAGAGCCTGGAC-3'

(SEQ ID NO: 14)
p45oloxP14R;  5'-AAAGGACAGAAGGAGGGAGCAACAGGAT-3'

(SEQ ID NO: 15)
p45oloxP16L;  5'-TCTGGGCATCAGTGTCCTCTCCAGTAAA-3'

(SEQ ID NO: 16)
p45oloxP16R;  5'-TTGGCGACATCCAATGCTAGTGCTATTC-3'
```

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 10 sec and 68° C. for 4 min were carried out. As a result of screening 96 clones, 36 clones were identified as a homologous recombinant.

[A. 3. 2] Southern Blot Analysis

For the 6 clones which have been confirmed to have recombination by PCR analysis above, Southern blot analysis was carried out as follows. The genomic DNA was treated with the restriction enzyme EcoRI (TAKARA), electrophoresed on 0.8% agarose gel, and subjected to alkali blotting using a GeneScreen Plus™ hybridization transfer membrane (NEN™ Life Science Products, Inc.). The filter was then subjected to Southern hybridization by using MPp probe, which has been obtained by amplification of the gene sequence in AC004922 by PCR, to identify the homologous recombinant. For preparing MPp probe, PCR was carried out by using as a template genomic DNA of DF141 using the primers described below, and $^{32}$P labeled DNA probe was prepared by random priming using the PCR product as a template (according to Amersham's attached protocols). Primers for preparing MPp probe:

```
                                          (SEQ ID NO: 17)
MPp6L; 5'-TGGAGACGTTGTTTAGCCTCTCCTCCTC-3'

(SEQ ID NO: 18)
MPp6R; 5'-CACAGCTTAGAGGCCATTCCCATAGTCC-3'
```

For PCR, GeneAmp 9600 manufactured by PerkinElmer, Inc. was used as a thermal cycler and EX Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 93° C. for 5 min, 35 cycles of 93° C. for 1 min, 54° C. for 1 min, and 72° C. for 1 min as one cycle were carried out. Based on Southern hybridization, it was expected that a band at approximately 10.9 kb is detected from the non-homologous recombinant while a band at approximately 8.9 kb is detected from the homologous recombinant (FIG. 15b). As a result of Southern hybridization, it was found that all 6 clones are the desired homologous recombinant.

[A. 3. 3] Two-Color FISH Analysis

FISH analysis was carried out according to Matsubara et al. (FISH test protocol, Shujunsha Co., Ltd., 1994). FISH analysis was carried out for six clones out of the clones which have been confirmed to have recombination in the above by using human cot-1 DNA and hygromycin as probes. As a result, it was confirmed that human chromosome 7 was not translocated to the host chromosome in any clone, and based on the fact that hygromycin-derived signal was detected near 7q22, recombination has site-specifically occurred. From these results, it was concluded that the loxP sequence as a gene insertion site was site-specifically inserted into human chromosome 7 fragment.

[B] Site Specific Cleavage at Human Chromosome 7 Region AC073842 in hChr7-loxP

As disclosed in WO2009/063722 (PCT/JP2008/068928), in order to delete the genes which are strongly involved with the development of a mouse individual and exist on the distal side of the CYP3A gene cluster of human chromosome 7, telomere truncation, which is site specific deletion of a chromosome, is performed.

[B. 1] Preparation of Targeting Vector pTELhisD-PT

Targeting vector pTELhisD-PT for inserting human telomere sequence into AC073842 region, which is located extremely close to CYP3A gene locus of human chromosome 7 and on the telomere side (i.e., locating on the telomere side by approximately 150 Kb from CYP3A gene locus), was prepared as follows. First, the AC073842 genome region was amplified by PCR using the following primers.

```
                                          (SEQ ID NO: 19)
PT1L; 5'-TGCGGTGAAGGTCCAAGGAGATAGATTT-3'

(SEQ ID NO: 20)
PT2R; 5'-TCTAGCAGAGAGATGGTGGCAGGATTCA-3'
```

Figure 16:
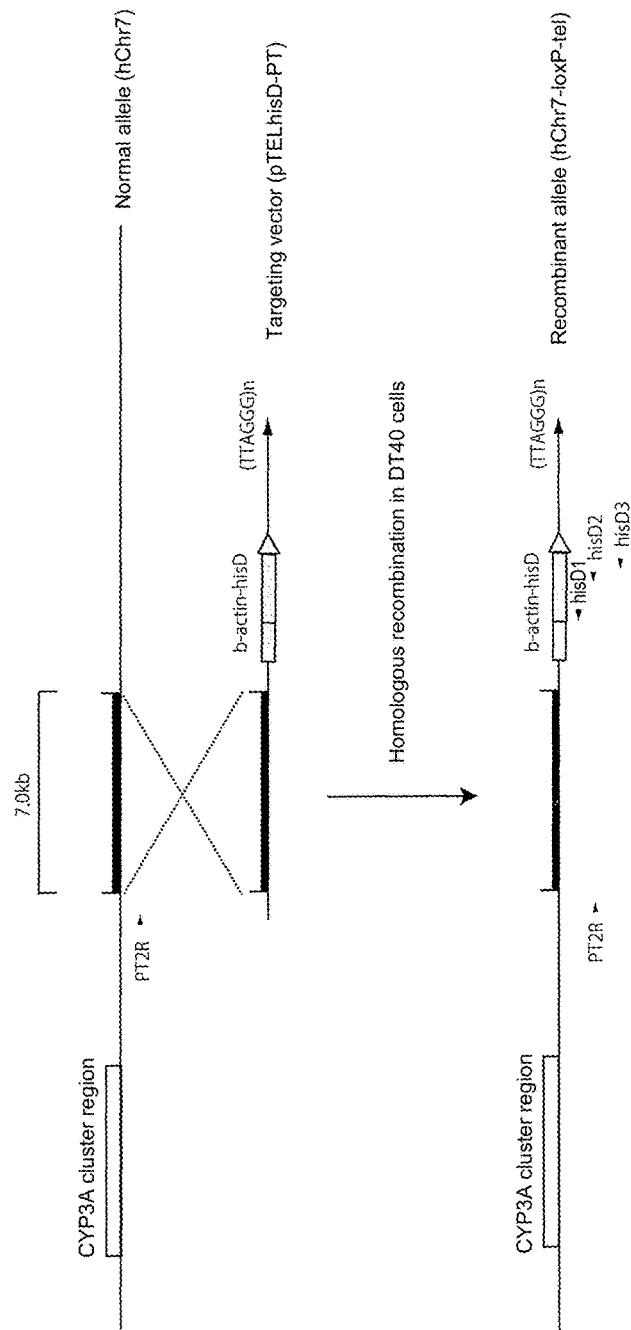
FIG. 16 shows the targeting vector (pTELhisD-PT) for inserting the human telomere sequence into the AC073842 region, which is located extremely close to CYP3A gene locus of human chromosome 7 and at the telomere side (i.e., locating on the telomere side by approximately 150 Kb from CYP3A gene locus), and a partial structure of the human chromosome 7 allele in which homologous recombination has been carried out by using the vector.

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 8 min were carried out. PCR product was treated with proteinase K (Gibco) and subjected to gel filtration by using CHROMASPIN-TE400 (Clontech). After that, the product was cleaved with the restriction enzymes BamHI (Boehringer Ingelheim GmbH) and BglII (NIPPON GENE CO., LTD.) and subjected to gel filtration by using CHROMASPIN-TE1000 (Clontech). The PCR fragment was cloned into the BamHI site of plasmid pTELhisD (Kuroiwa et al., Nature Biotech., 20: 88, 2002). Since the genome sequence direction of AC073842 is telomere→centromere, the resultant product in which cloned genome fragment of AC073842 was in the same direction as the human telomere sequence was taken as desired targeting vector pTELhisD-PT. Size of the final construct for long-arm proximal region specific restriction was 14.4 kb. The targeting vector, target sequence, and chromosome allele obtained by homologous recombination are shown in FIG. 16.

[B. 2] Transfection and Isolation of Histidinol Resistant Clone

As described above, targeting vector pTELhisD-PT prepared above was linearized with the restriction enzyme SrfI (TOYOBO CO., LTD.), and used for transfection of clone DT40 (hChr7-loxP) 122 prepared above. After exchanging the culture medium with a culture medium containing histidinol (0.5 mg/ml), the cells were dispensed into ten 96-well culture plates and then subjected to selection culture for about 2 weeks. Total 335 resistant colonies obtained from five transfections were isolated, amplified, and subjected to the following analysis (clone name: DT40 (hChr7-loxP-tel)).

[B. 3] Selection of Homologous Recombinant

[B. 3. 1] PCR Analysis

In order to select the recombinant by using genomic DNA of histidinol resistant cell line as a template, as a primary screening, PCR was carried out by using the following primers that are located closer to the telomere side than the restriction sites, and it was confirmed whether or not site specific cleavage has occurred. The primer sequences are given below.

```
                                          (SEQ ID NO: 21)
COPS6-1L; 5'-TGAGGGTACTTGAAGGGCTGATG-3'

(SEQ ID NO: 22)
COPS6-1R; 5'-CAGGGGCTGCTCCCCTTTTATTA-3'

(SEQ ID NO: 23)
AP4M1-1L: 5'-CCTAACATCGTGTCCCAGCTCA-3'
```

-continued (SEQ ID NO: 24)
AP4M1-1R: 5'-TCCTTTCAGACCCCTTCATCTTAG-3'

(SEQ ID NO: 25)
LRCH4-2L: 5'-TTCAGCCCCAACCAAAGACACTA-3'

(SEQ ID NO: 26)
LRCH4-1R: 5'-GCCCCGAACCCCTACAAATATAGA-3'

(SEQ ID NO: 27)
STAG3-1L: 5'-GGGCCTCCAATAAGTGTCCCATA-3'

(SEQ ID NO: 28)
STAG3-1R: 5'-TTGCTGACTTAGTTGCAGCAGGA-3'

(SEQ ID NO: 29)
PILRB-2L: 5'-CCCATTGGCAAGATACATGGAGA-3'

(SEQ ID NO: 30)
PILRB-2R: 5'-AGTGTGGATGCTCCTGGATGAAG-3'

For PCR, GeneAmp 9600 manufactured by PerkinElmer, Inc. was used as a thermal cycler and Ampli Taq Gold (Applied Biosystems) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 95° C. for 10 min, 30 cycles of 95° C. for 20 sec, 55° C. for 30 sec, and 72° C. for 30 sec were carried out. As a result of PCR, two clones out of the 433 clones were found to be positive.

Among the 433 clones, two clones that are not detected with the above primers were confirmed whether site specific homologous recombination has occurred by PCR using the following primers. Sequences are as follows. PT2R; (described above)

(SEQ ID NO: 31)
hisD2: 5'-GTAAACGCCCTCAAGGAGCAAGCATGA-3'

(SEQ ID NO: 32)
hisD3: 5'-TGTGACCAAAGATTTAGCGCAGTGCGT-3'

For PCR, LA Taq (TAKARA SHUZO CO., LTD.) was used with the above primers. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 8 min were carried out. Only in two clones having site specific recombination, a band at approximately 8 kb was detected. In DT40, DT40 (hChr7-loxP) as a negative control, no band was detected.

TABLE 11

| Clone number | Clone name | | | | |
|---|---|---|---|---|---|
| | DT40(hChr7-loxP-tel) | | | DT40(hChr7-loxP) | |
| | 548 | 608 | 748 | 122 | DT40 |
| CYP 3A4 R/F | ○ | ○ | ○ | ○ | X |
| 3A4 4L/3R | ○ | ○ | ○ | ○ | X |
| CYP 3A7 R/F | ○ | ○ | ○ | ○ | X |
| 3A7 3L/3R | ○ | ○ | ○ | ○ | X |
| COPS6 1L/1R | ○ | X | X | ○ | X |

TABLE 11-continued

| Clone number | Clone name | | | | |
|---|---|---|---|---|---|
| | DT40(hChr7-loxP-tel) | | | DT40(hChr7-loxP) | |
| | 548 | 608 | 748 | 122 | DT40 |
| AP4M 1L/1R | ○ | X | X | ○ | X |
| LRCH4 1L/1R | ○ | X | X | ○ | X |
| STAG3 1L/1R | ○ | X | X | ○ | X |
| PILRB 2L/1R | ○ | X | X | ○ | X |
| PILRB 2L/2R | ○ | X | X | ○ | X |
| PT2R/hisD2 | X | ○ | ○ | X | X |
| PT2R/hisD3 | X | ○ | ○ | X | X |

[B. 3. 2] Two-color FISH analysis

FISH analysis was carried out according to Matsubara et al. (FISH test protocol, Shujunsha Co., Ltd., 1994). FISH analysis was carried out for two clones out of the clones which have been confirmed to have recombination in the above by using human cot-1 DNA and histidinol as probes. As a result, it was confirmed that human chromosome 7 into which loxP sequence has been inserted was not translocated to the host chromosome in any clone, and based on the fact that histidinol-derived signal was detected at terminal of human chromosome 7 fragment, recombination has site-specifically occurred.

From these results, it was concluded that, in clone DT40 (hChr7-loxP-tel) 608 and 748, cleavage can be made at distal region from AC073842 which is closer to the telomere side than CYP3A gene cluster region.

TABLE 12

| | Metaphase | | | hisD-FITC-stpot | |
|---|---|---|---|---|---|
| | x0/2n | x1/2n | Total | + | − |
| DT40(hChr7-loxP-tel)-608 | 3 | 17 | 20 | 17 | 3 |
| DT40(hChr7-loxP-tel)-748 | 2 | 18 | 20 | 14 | 6 |

[C] Introduction of hChr7-loxP-Tel from DT40 Containing hChr7-loxP-Tel into CHO Cell Containing MAC1

For translocation insertion of human CYP3A gene cluster region into the mouse artificial chromosome vector MAC1 via loxP sequence in CHO cells, hChr7-loxP-tel is introduced into CHO cells containing the mouse artificial chromosome vector MAC1.

[C. 1] Microcell Fusion and Isolation of Drug Resistant Clone

By using DT40 (hChr7-loxP-tel) 608 and 748 as recipient cells, microcell fusion was carried out for CHO (HPRT⁻; MAC1), i.e., a CHO hprt depleted cell containing MAC1 (obtained from the Health Science Research Resources Bank, registration number: JCRB0218), in the same manner as above. Total 48 resistant colonies obtained by five microcell fusions were isolated, amplified, and subjected to the following analysis (clone name: CHO (HPRT⁻; MAC1, hChr7-loxP-tel)).

[C. 2] Selection of Drug Resistant Clone

[C. 2. 1] PCR Analysis

For extracting genomic DNA from hygromycin resistant cell line and using it as a template for selecting a recombi nant, PCR was carried out by using the following primers and it was confirmed whether human chromosome 7 fragment has been introduced into CHO cells containing MAC1. The primer sequences are given below.

m11 5L (described above)
EGFP (F) L (described above)
kj neo (described above)

```
                             (SEQ ID NO: 33)
m11 6R:  5'-CCCAGGAATCAGTCAGGAAGGCTGTAA-3'
```

P450 loxP 14L: (described above)

```
                             (SEQ ID NO: 34)
hyg F (244):  5'-GAATTCAGCGAGAGCCTGAC-3'

(SEQ ID NO: 35)
hyg R (696):  5'-GATGTTGGCGACCTCGTATT-3'
```

P450 loxP 16R: (described above)

```
                             (SEQ ID NO: 36)
CYP3A4 R:     5'-GGCTGCATCAGCATCATCTA-3'

(SEQ ID NO: 37)
CYP3A4 F:     5'-GCAAGACTGTGAGCCAGTGA-3'

(SEQ ID NO: 38)
CYP3A5 R:     5'-TCAGCTGTGTGCTGTTGTTTGC-3'

(SEQ ID NO: 39)
CYP3A5 F:     5'-ATAGAAGGGTCTGTCTGGCTGG-3'

(SEQ ID NO: 40)
CYP3A7 R:     5'-GAGTTAATGGTGCTAACTGGGG-3'

(SEQ ID NO: 41)
CYP3A7 F:     5'-ACCCTGAAATGAAGACGGGC-3'

(SEQ ID NO: 42)
3A4 4L:       5'-TCCCCCTGAAATTAAGCTTA-3'

(SEQ ID NO: 43)
3A4 3R:       5'-TGAGGTCTCTGGTGTTCTCA-3'

(SEQ ID NO: 44)
3A7 3L:       5'-TCCCCCTGAAATTACGCTTT-3'

(SEQ ID NO: 45)
3A7 3R:       5'-CATTTCAGGGTTCTATTTGT-3'
```

PT2R: (described above)

```
                             (SEQ ID NO: 46)
hisD1:  5'-GTATTGGTCACCACGGCCGAGTTTCCGC-3'
``` hisD2: (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, DGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, 19 clones out of the 48 clones were found to be positive for all primer sets, and the following analysis was performed by using 20 clones including 1 negative clone among them.

TABLE 13A

| Clone origin type | | | | | | | | | | | | | | | | | | | | | | | | |
|---|---|---|---|---|---|---|---|---|---|---|---|---|---|---|---|---|---|---|---|---|---|---|---|---|
| A | | | | | E | | | | | C | | D | | | | | | | B | | | C | | |
| Clone name CHO(HPRT⁻; MAC1, hChr7-loxP-tel) | | | | | | | | | | | | | | | | | | | | | | | Positive control | Negative control |
| Clone number | | | | | | | | | | | | | | | | | | | | | | | | |
| 1 | 2 | 3 | 4 | 5 | 6 | 7 | 8 | 9 | 10 | 11 | 12 | 13 | 14 | 15 | 16 | 17 | 18 | 19 | 20 | 21 | 35 | 47 | | |
| m11 5L/EGFP(F)L | | | | | | | | | | | | | | | | | | | | | | | | |
| ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | X |
| kj neo/m11 6R | | | | | | | | | | | | | | | | | | | | | | | | |
| ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | X |
| P450 loxP 14L/hyg F(244) | | | | | | | | | | | | | | | | | | | | | | | | |
| ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | X |
| hyg F(696)/P450 loxP 16R | | | | | | | | | | | | | | | | | | | | | | | | |
| ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | X |
| CYP3A4 R/F | | | | | | | | | | | | | | | | | | | | | | | | |
| ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | X |
| CYP3A5 R/F | | | | | | | | | | | | | | | | | | | | | | | | |
| ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | X |
| CYP3A7 R/F | | | | | | | | | | | | | | | | | | | | | | | | |
| ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | X |
| 3A4 4L/3R | | | | | | | | | | | | | | | | | | | | | | | | |
| ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | X |
| 3A7 3L/3R | | | | | | | | | | | | | | | | | | | | | | | | |
| ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ | X |
| PT2R/hisD1 | | | | | | | | | | | | | | | | | | | | | | | | |
| ○ | ○ | ○ | ○ | ○ | ○ | ○ | ○ | ○ | ○ | ○ | ○ | ○ | ○ | ○ | ○ | ○ | ○ | ○ | X | X | X | X | ○ | X |
| PT2R/hisD2 | | | | | | | | | | | | | | | | | | | | | | | | |
| ○ | ○ | ○ | ○ | ○ | ○ | ○ | ○ | ○ | ○ | ○ | ○ | ○ | ○ | ○ | ○ | ○ | ○ | ○ | X | X | X | X | ○ | X |

TABLE 13B

| | Donor cell line | | Recipient cell line |
|---|---|---|---|
| Origin type for each clone | A  DT40(hChr7-loxP-tel)-608 | → | CHO(HPRT⁻; MAC1)-5 |
| | B  DT40(hChr7-loxP-tel)-608 | → | CHO(HPRT⁻; MAC1)-22 |
| | C  DT40(hChr7-loxP-tel)-748 | → | CHO(HPRT⁻; MAC1)-3 |
| | D  DT40(hChr7-loxP-tel)-748 | → | CHO(HPRT⁻; MAC1)-5 |
| | E  DT40(hChr7-loxP-tel)-748 | → | CHO(HPRT⁻; MAC1)-22 |

Figure 17:
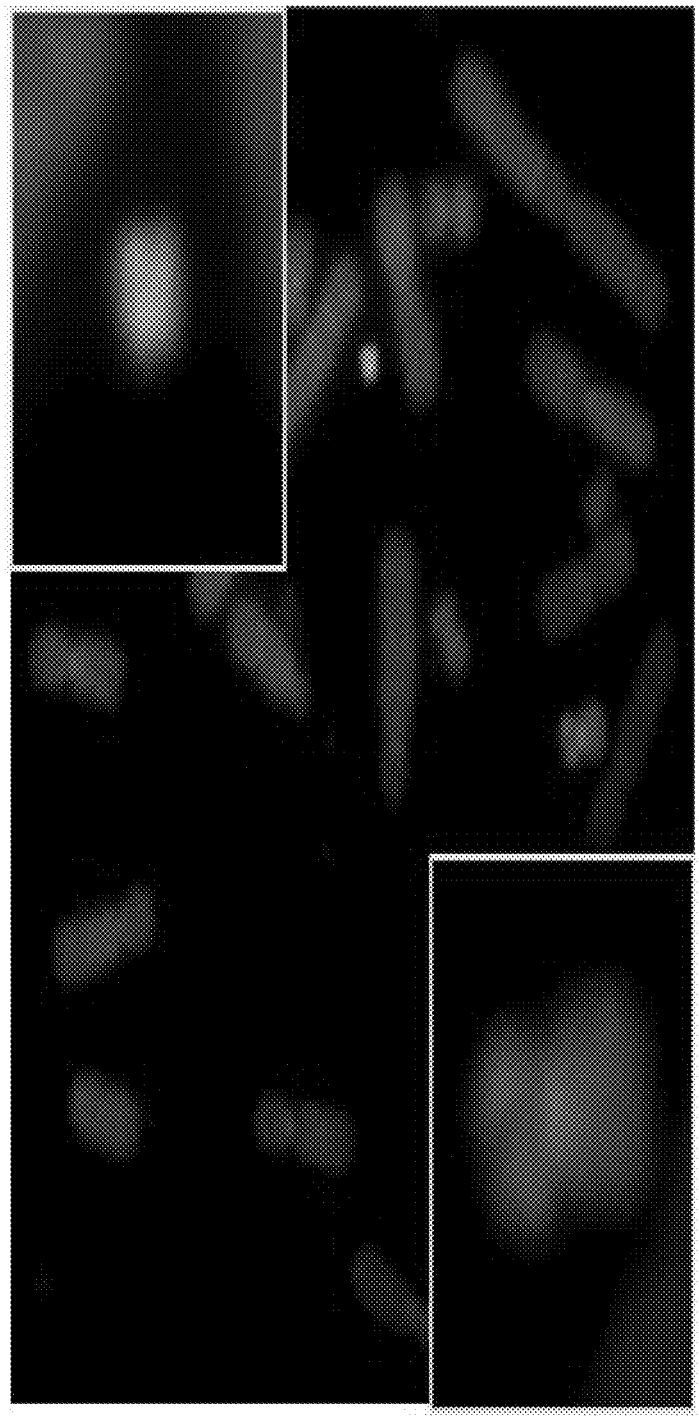
FIG. 17 shows the results of the two-color FISH analysis of CHO (HPRT-, MAC1+hChr7-loxP-tel) clone in which mouse Cot-1 DNA and human Cot-1 DNA were used as probes.

[C. 2. 2] Two-Color FISH Analysis 19 clones of CHO (HPRT⁻; MAC1, hChr7-loxP-tel) obtained from the above were subjected to FISH analysis by using mouse Cot-1 DNA and human Cot-1 DNA as probes according to the method described by Shinohara et al. (Human Molecular Genetics, 10: 1163-1175, 2001). As a result, it was confirmed that 18 clones except negative clones contain one or two copies of MAC1 and hChr7-loxP-tel in CHO cells (FIG. 17).

TABLE 14

| | Metaphase Human copy number | | | | | | | | |
|---|---|---|---|---|---|---|---|---|---|
| | hx1 | hx2 | hx3 | hx2 (x1 fragment) | hx2 | | | | |
| | | | | MAC copy number | | | | | |
| | mx 1/2n | mx 1/2n | mx 1/4n | mx 1/2n | mx 2/4n | h only | m only | Other abnormality including trans-location | Total |
| CHO(HPRT−; MAC1, hChr7-loxP-tel)-1 | 9 | 2 | | | | 8 | 1 | | 20 |
| CHO(HPRT−; MAC1, hChr7-loxP-tel)-2 | 8 | 1 | | 7 | | 4 | | | 20 |
| CHO(HPRT−; MAC1, hChr7-loxP-tel)-3 | 8 | | | 5 | | 4 | | 3 | 20 |
| CHO(HPRT−; MAC1, hChr7-loxP-tel)-4 | 8 | 2 | | 6 | | 4 | | | 20 |
| CHO(HPRT−; MAC1, hChr7-loxP-tel)-5 | 12 | 2 | | 2 | 1 | 1 | | 2 | 20 |
| CHO(HPRT−; MAC1, hChr7-loxP-tel)-6 | 11 | | 1 | 8 | | | | | 20 |
| CHO(HPRT−; MAC1, hChr7-loxP-tel)-7 | 8 | 5 | 2 | 3 | 2 | | | | 20 |
| CHO(HPRT−; MAC1, hChr7-loxP-tel)-8 | 7 | 2 | | 9 | | 1 | | 1 | 20 |
| CHO(HPRT−; MAC1, hChr7-loxP-tel)-9 | 10 | 4 | | 3 | | | | 3 | 20 |
| CHO(HPRT−; MAC1, hChr7-loxP-tel)-10 | 8 | 5 | | 5 | | | | 2 | 20 |
| CHO(HPRT−; MAC1, hChr7-loxP-tel)-11 | 13 | 4 | | | 1 | 1 | | 1 | 20 |
| CHO(HPRT−; MAC1, hChr7-loxP-tel)-12 | 5 | 4 | 9 | | | 2 | | | 20 |
| CHO(HPRT−; MAC1, hChr7-loxP-tel)-13 | | | | | | | 20 | | 20 |
| CHO(HPRT−; MAC1, hChr7-loxP-tel)-14 | 3 | | 1 | | | 6 | | 10 | 20 |
| CHO(HPRT−; MAC1, hChr7-loxP-tel)-15 | | | | | | 3 | | 17 | 20 |
| CHO(HPRT−; MAC1, hChr7-loxP-tel)-16 | | | | | | 5 | | 15 | 20 |
| CHO(HPRT−; MAC1, hChr7-loxP-tel)-17 | | | | | | 5 | | 15 | 20 |
| CHO(HPRT−; MAC1, hChr7-loxP-tel)-18 | 2 | | | | | 8 | | 10 | 20 |
| CHO(HPRT−; MAC1, hChr7-loxP-tel)-40 | 2 | | | 1 | | | 17 | | 20 |
| CHO(HPRT−; MAC1, hChr7-loxP-tel)47 | 3 | 10 | 4 | | | 2 | | | 19 |

| | Interphase Human copy number | | | | | | |
|---|---|---|---|---|---|---|---|
| | hx1 | hx2 | hx2 | | | | |
| | | | MAC copy number | | | | |
| | mx1 | mx1 | mx2 | h only | m only | Total | Origin |
| CHO(HPRT−; MAC1, hChr7-loxP-tel)-1 | 61 | | | 39 | | 100 | DT40(hChr7-loxP-tel)-608 → CHO(HPRT−; MAC1)-5 |
| CHO(HPRT−; MAC1, hChr7-loxP-tel)-2 | 75 | 6 | | 19 | | 100 | DT40(hChr7-loxP-tel)-608 → CHO(HPRT−; MAC1)-5 |
| CHO(HPRT−; MAC1, hChr7-loxP-tel)-3 | 90 | | 4 | 6 | | 100 | DT40(hChr7-loxP-tel)-608 → CHO(HPRT−; MAC1)-5 |
| CHO(HPRT−; MAC1, hChr7-loxP-tel)-4 | 59 | 32 | | 9 | | 100 | DT40(hChr7-loxP-tel)-608 → CHO(HPRT−; MAC1)-5 |
| CHO(HPRT−; MAC1, hChr7-loxP-tel)-5 | 75 | 13 | | 12 | | 100 | DT40(hChr7-loxP-tel)-608 → CHO(HPRT−; MAC1)-5 |
| CHO(HPRT−; MAC1, hChr7-loxP-tel)-6 | 60 | 32 | | 8 | | 100 | DT40(hChr7-loxP-tel)-608 → CHO(HPRT−; MAC1)-5 |
| CHO(HPRT−; MAC1, hChr7-loxP-tel)-7 | 63 | 30 | 7 | | | 100 | DT40(hChr7-loxP-tel)-608 → CHO(HPRT−; MAC1)-5 |
| CHO(HPRT−; MAC1, hChr7-loxP-tel)-8 | 39 | 55 | | 6 | | 100 | DT40(hChr7-loxP-tel)-608 → CHO(HPRT−; MAC1)-5 |
| CHO(HPRT−; MAC1, hChr7-loxP-tel)-9 | 82 | 17 | | 1 | | 100 | DT40(hChr7-loxP-tel)-608 → CHO(HPRT−; MAC1)-5 |
| CHO(HPRT−; MAC1, hChr7-loxP-tel)-10 | 43 | 53 | | 4 | | 100 | DT40(hChr7-loxP-tel)-608 → CHO(HPRT−; MAC1)-5 |
| CHO(HPRT−; MAC1, hChr7-loxP-tel)-11 | 82 | 15 | 3 | | | 100 | DT40(hChr7-loxP-tel)-748 → CHO(HPRT−; MAC1)-22 |
| CHO(HPRT−; MAC1, hChr7-loxP-tel)-12 | 33 | 64 | | 3 | | 100 | DT40(hChr7-loxP-tel)-748 → CHO(HPRT−; MAC1)-3 |
| CHO(HPRT−; MAC1, hChr7-loxP-tel)-13 | 57 | 34 | | 9 | | 100 | DT40(hChr7-loxP-tel)-748 → CHO(HPRT−; MAC1)-5 |
| CHO(HPRT−; MAC1, hChr7-loxP-tel)-14 | 42 | 43 | | 15 | | 100 | DT40(hChr7-loxP-tel)-748 → CHO(HPRT−; MAC1)-5 |
| CHO(HPRT−; MAC1, hChr7-loxP-tel)-15 | 33 | 47 | 20 | | | 100 | DT40(hChr7-loxP-tel)-748 → CHO(HPRT−; MAC1)-5 |
| CHO(HPRT−; MAC1, hChr7-loxP-tel)-16 | 43 | 36 | 21 | | | 100 | DT40(hChr7-loxP-tel)-748 → CHO(HPRT−; MAC1)-5 |

TABLE 14-continued

| | | | | | |
|---|---|---|---|---|---|
| CHO(HPRT⁻; MAC1, hChr7-loxP-tel)-17 | 35 | 49 | 16 | | 100 DT40(hChr7-loxP-tel)-748 → CHO(HPRT⁻; MAC1)-5 |
| CHO(HPRT⁻; MAC1, hChr7-loxP-tel)-18 | 32 | 53 | 15 | | 100 DT40(hChr7-loxP-tel)-748 → CHO(HPRT⁻; MAC1)-5 |
| CHO(HPRT⁻; MAC1, hChr7-loxP-tel)-40 | 23 | | | 77 | 100 DT40(hChr7-loxP-tel)-748 → CHO(HPRT⁻; MAC1)-3 |
| CHO(HPRT⁻; MAC1, hChr7-loxP-tel)47 | 44 | 42 | 14 | | 100 DT40(hChr7-loxP-tel)-748 → CHO(HPRT⁻; MAC1)-3 |

From the results above, it was concluded that hChr7-loxP-tel could be introduced into CHO cells containing the mouse artificial chromosome vector MAC1.

Figure 18:
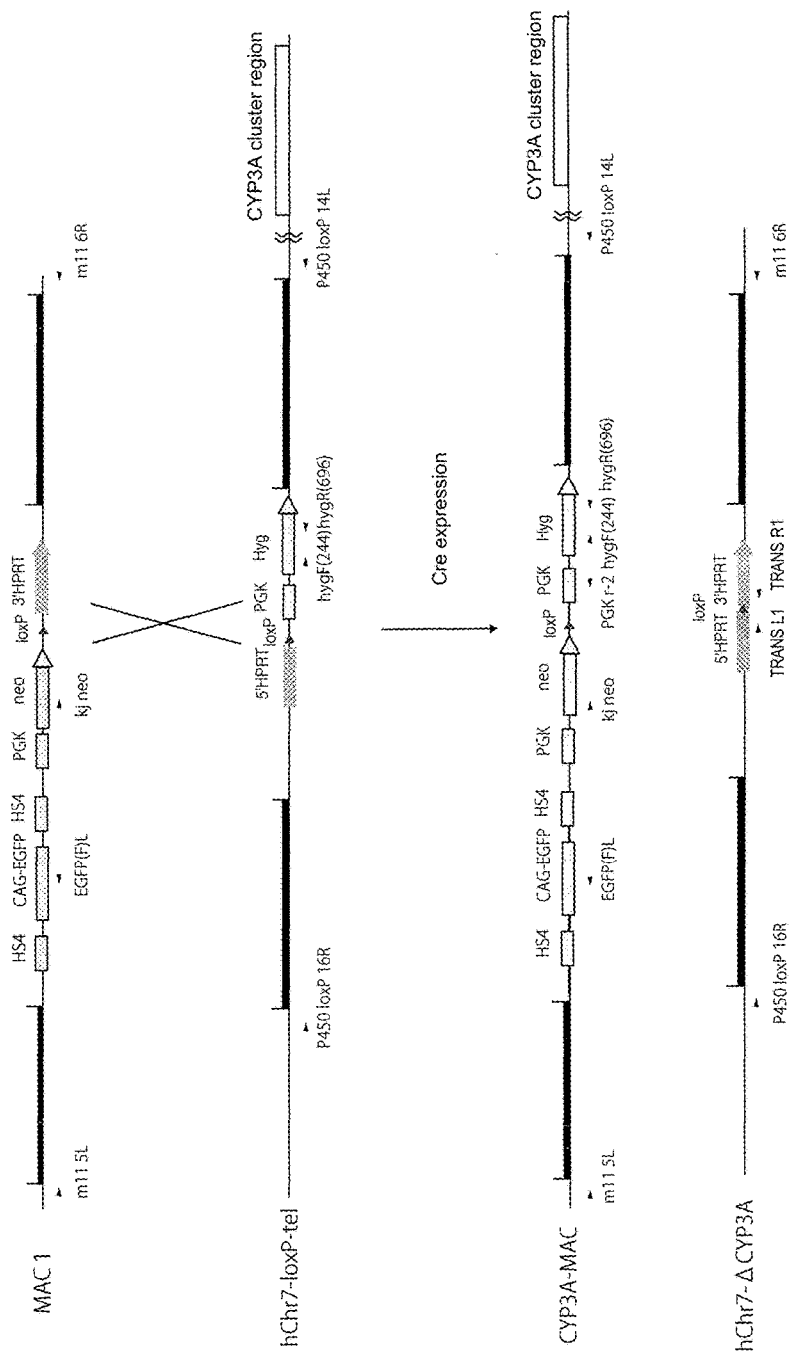
FIG. 18 shows the construction of mouse artificial chromosome CYP3A-MAC by translocation-cloning approximately 1 Mb human CYP3A gene cluster region (i.e., AC004922-human CYP3A gene cluster-AC073842) into MAC1.

[D] Site Specific Translocation of 1 Mb Human CYP3A Gene Cluster Region (i.e., AC004922-Human CYP3A Gene Cluster-AC073842) to MAC1 Vector in CHO (HPRT⁻; MAC1, hChr7-loxP-Tel) Clone To stably keep the human CYP3A gene cluster, which is a DNA with 1 Mb size, in an mouse individual, translocation insertion into the mouse artificial chromosome vector MAC1 was performed (FIG. 18).

[D. 1] Transfection and Isolation of HAT Resistant Clone

Gene introduction was carried out by lipofection for CHO (HPRT⁻; MAC1, hChr7-loxP-tel)-6, 9, 12, and 47 obtained from the above. To cells in 6 wells with 90% confluency, 3 µg of Cre was introduced according to the commercially available protocol (Invitrogen). After culture for 2 weeks under HAT selection culture, a resistant colony was generated and total 42 colonies obtained by four introductions were isolated, amplified, and subjected to the following analysis (clone name: CHO (CYP3A-MAC1, hChr7-ΔCYP3A)).

[D. 2] Selection of Drug Resistant Clone

[D. 2. 1] PCR Analysis

For extracting genomic DNA from HAT resistant cell line and using it as a template for selecting a clone with reciprocal translocation, PCR was carried out by using the following primers and it wad confirmed whether or not reciprocal chromosomal translocation has occurred on human chromosome 7 fragment and MAC1. The primer sequences are given below.

P450 loxP 16R (described above)
hyg R (696) (described above)
kj neo (described above)
P450 loxP 14L (described above)
m11 5L (described above)
m11 6R (described above)
CYP3A4 R (described above)
CYP3A4 F (described above)
CYP3A5 R (described above)
CYP3A5 F (described above)
CYP3A7 R (described above)
CYP3A7 F (described above)
3A4 4L (described above)
3A4 3R (described above)
3A7 3L (described above)
3A7 3R (described above)

```
                                           (SEQ ID NO: 47)
TRANS L1: 5'-TGGAGGCCATAAACAAGAAGAC-3'

(SEQ ID NO: 48)
TRANS R1: 5'-CCCCTTGACCCAGAAATTCCA-3'
```

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, 27 clones out of the 42 clones were found to be positive for all primer sets, and therefore the following analysis was performed by using those 27 clones.

TABLE 15

| | Cell origin | | | | | | | | | | | | | | | | | |
|---|---|---|---|---|---|---|---|---|---|---|---|---|---|---|---|---|---|---|
| | 9 | 6 | 12 | | | | | 47 | | | | | | | | | 12 | |
| | Clone name | | | | | | | | | | | | | | | | | |
| | CHO(CYP3A-MAC1 + hChr7-ΔCYP3A) | | | | | | | | | | | | | | | | | |
| | Clone number | | | | | | | | | | | | | | | | | |
| | 3 | 10 | 11 | 12 | 13 | 14 | 15 | 16 | 18 | 19 | 20 | 22 | 23 | 24 | 25 | 26 | 27 | 28 |
| P450 loxP16R/hygR(696) | ◯ | ◯ | ◯ | ◯ | ◯ | ◯ | ◯ | ◯ | ◯ | ◯ | ◯ | ◯ | ◯ | ◯ | ◯ | ◯ | ◯ | ◯ |
| kj neo/P450 loxP 14L | ◯ | ◯ | ◯ | ◯ | ◯ | ◯ | ◯ | ◯ | ◯ | ◯ | ◯ | ◯ | ◯ | ◯ | ◯ | ◯ | ◯ | ◯ |
| m11 5L/hyg R(696) | ◯ | ◯ | ◯ | ◯ | ◯ | ◯ | ◯ | ◯ | ◯ | ◯ | ◯ | ◯ | ◯ | ◯ | ◯ | ◯ | ◯ | ◯ |
| P450 loxP16R/TRANS-R1 | ◯ | ◯ | ◯ | ◯ | ◯ | ◯ | ◯ | ◯ | ◯ | ◯ | ◯ | ◯ | ◯ | ◯ | ◯ | ◯ | ◯ | ◯ |
| Trans L1/m11 6R | ◯ | ◯ | ◯ | ◯ | ◯ | ◯ | ◯ | ◯ | ◯ | ◯ | ◯ | ◯ | ◯ | ◯ | ◯ | ◯ | ◯ | ◯ |
| Trans L1/R1 | ◯ | ◯ | ◯ | ◯ | ◯ | ◯ | ◯ | ◯ | ◯ | ◯ | ◯ | ◯ | ◯ | ◯ | ◯ | ◯ | ◯ | ◯ |
| CYP3A4 R/F | ◯ | ◯ | ◯ | ◯ | ◯ | ◯ | ◯ | ◯ | ◯ | ◯ | ◯ | ◯ | ◯ | ◯ | ◯ | ◯ | ◯ | ◯ |
| CYP3A5 R/F | ◯ | ◯ | ◯ | ◯ | ◯ | ◯ | ◯ | ◯ | ◯ | ◯ | ◯ | ◯ | ◯ | ◯ | ◯ | ◯ | ◯ | ◯ |
| CYP3A7 R/F | ◯ | ◯ | ◯ | ◯ | ◯ | ◯ | ◯ | ◯ | ◯ | ◯ | ◯ | ◯ | ◯ | ◯ | ◯ | ◯ | ◯ | ◯ |
| 3A4 4L/3R | ◯ | ◯ | ◯ | ◯ | ◯ | ◯ | ◯ | ◯ | ◯ | ◯ | ◯ | ◯ | ◯ | ◯ | ◯ | ◯ | ◯ | ◯ |
| 3A7 3L/3R | ◯ | ◯ | ◯ | ◯ | ◯ | ◯ | ◯ | ◯ | ◯ | ◯ | ◯ | ◯ | ◯ | ◯ | ◯ | ◯ | ◯ | ◯ |

TABLE 15-continued

| | Cell origin | | | | | | | | | Control | |
|---|---|---|---|---|---|---|---|---|---|---|---|
| | 12 | | 47 | 12 | | | 12 | | | | |
| | Clone name | | | | | | | | | | |
| | CHO(CYP3A-MAC1 + hChr7-ΔCYP3A) Clone number | | | | | | | | | CHO (HPRT⁻; MAC1, | CHO |
| | 31 | 32 | 33 | 34 | 35 | 37 | 40 | 41 | 42 | hChr7-loxP-tel)12 | (HPRT⁻) |
| P450 loxP16R/hygR(696) | ◯ | ◯ | ◯ | ◯ | ◯ | ◯ | ◯ | ◯ | ◯ | ◯ | X |
| kj neo/P450 loxP 14L | ◯ | ◯ | ◯ | ◯ | ◯ | ◯ | ◯ | ◯ | ◯ | X | X |
| m11 5L/hyg R(696) | ◯ | ◯ | ◯ | ◯ | ◯ | ◯ | ◯ | ◯ | ◯ | X | NT |
| P450 loxP16R/TRANS-R1 | ◯ | ◯ | ◯ | ◯ | ◯ | ◯ | ◯ | ◯ | ◯ | X | NT |
| Trans L1/m11 6R | ◯ | ◯ | ◯ | ◯ | ◯ | ◯ | ◯ | ◯ | ◯ | X | X |
| Trans L1/R1 | ◯ | ◯ | ◯ | ◯ | ◯ | ◯ | ◯ | ◯ | ◯ | X | X |
| CYP3A4 R/F | ◯ | ◯ | ◯ | ◯ | ◯ | ◯ | ◯ | ◯ | ◯ | ◯ | X |
| CYP3A5 R/F | ◯ | ◯ | ◯ | ◯ | ◯ | ◯ | ◯ | ◯ | ◯ | ◯ | X |
| CYP3A7 R/F | ◯ | ◯ | ◯ | ◯ | ◯ | ◯ | ◯ | ◯ | ◯ | ◯ | X |
| 3A4 4L/3R | ◯ | ◯ | ◯ | ◯ | ◯ | ◯ | ◯ | ◯ | ◯ | ◯ | X |
| 3A7 3L/3R | ◯ | ◯ | ◯ | ◯ | ◯ | ◯ | ◯ | ◯ | ◯ | ◯ | X |

Figure 19:
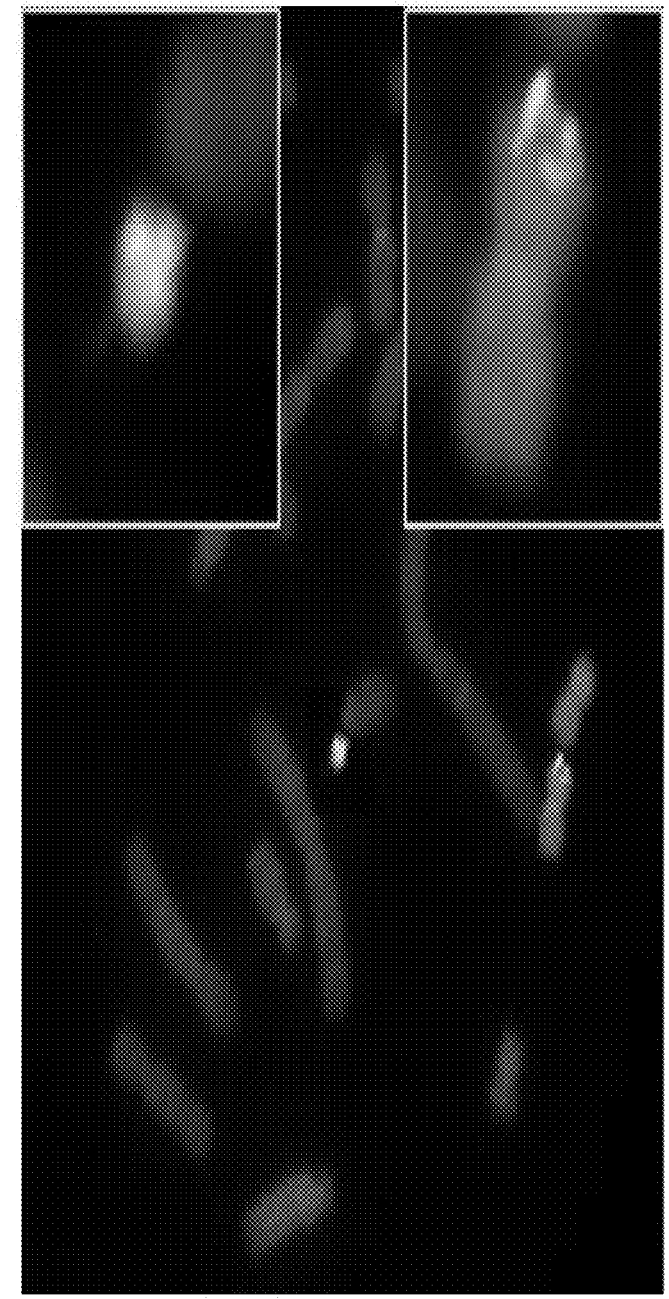
FIG. 19 shows the results of the two-color FISH analysis of CHO (CYP3A-MAC, hChr7-ΔCYP3A) clone in which human Cot-1 DNA and mouse Cot-1 DNA were used as probes.

[D. 2. 2] Two-Color FISH Analysis 27 clones of CHO (CYP3A-MAC1, hChr7-ΔCYP3A) obtained from the above were subjected to FISH analysis by using mouse Cot-1 DNA and human Cot-1 DNA as probes according to the method described by Shinohara et al. (Human Molecular Genetics, 10: 1163-1175, 2001). As a result, it was confirmed that 25 clones out of the 27 clones are observed at a rate of 50% or more with the signal derived from human chromosome 7 on MAC1 which consists of mouse chromosome 11 fragment containing loxP sequence (FIG. 19).

TABLE 16

| | With MAC | | | | | | Without MAC | | | | | | |
|---|---|---|---|---|---|---|---|---|---|---|---|---|---|
| | \multicolumn{6}{c}{Total number of human chromosome} | | | | | | | |
| | One | Two | | Three | Three | Six | One | Two | Three | Abnormal translocation | No translocation | Total | Origin CHO (HPRT-; MAC1, hChr7-IoxP-tel) |
| | | | Human region-retaining MAC | Human region-retaining hChr7f | MAC region-retaining hChr7f | | | | | | | | |
| | MAC(+Rho spot) x1 | MAC(+Rho spot) x2 | MAC(+Rho spot) x1 | MAC(+Rho spot) x1 | MAC (weak or no Rho) x1 | MAC(+Rho spot) x2 | | | | | | | |
| | +h7(+FITC spot) x1 /2n | +h7(+FITC spot) x2 /4n | +h7(+FITC spot) x1 +h7(noFITC) x1/2n | +h7(+FITC spot) x1 +h7(noFITC) x2/2n | +h7(+FITC spot) x1 +h7(noFITC) x2/2n | +h7(+FITC spot) x2 +h7(no FITC) x4/4n | h7 (+FITC spot) x 1 only | h7(+FITC spot)x1 + h7 (without FITC spot)x1 | h7(+FITC spot)x1 + h7 (without FITC spot)x2 | | | | |
| CHO(CYP3A-MAC + hChr7-Δ CYP3A)-3 | | | | | | | | | | 19 | 1 | 20 | 9 |
| CHO (CYP3A-MAC + hChr7-Δ CYP3A)-10 | | | | | | | | | | 19 | 1 | 20 | 6 |
| CHO(CYP3A-MAC + hChr7-Δ CYP3A)-11 | | 14 | | | | | | 6 | | | | 20 | 12 |
| CHO(CYP3A-MAC + hChr7-Δ CYP3A)-12 | | | | 13 | | | | | 7 | | | 20 | 12 |
| CHO(CYP3A-MAC + hChr7-Δ CYP3A)-13 | | | | 17 | | | | | 3 | | | 20 | 47 |
| CHO(CYP3A-MAC + hChr7-Δ CYP3A)-14 | | | | 12 | | | | | 8 | | | 20 | 47 |
| CHO(CYP3A-MAC + hChr7-Δ CYP3A)-15 | | | | 17 | | 3 | | | | | | 20 | 47 |
| CHO(CYP3A-MAC + hChr7-Δ CYP3A)-16 | | | | 14 | 3 | | | | 3 | | | 20 | 47 |
| CHO(CYP3A-MAC + hChr7-Δ CYP3A)-18 | | | | 17 | 3 | | | | | | | 20 | 47 |
| CHO(CYP3A-MAC + hChr7-Δ CYP3A)-19 | | | | 11 | 5 | 4 | | | | | | 20 | 47 |
| CHO(CYP3A-MAC + hChr7-Δ CYP3A)-20 | | | | 20 | | | | | | | | 20 | 12 |
| CHO(CYP3A-MAC + hChr7-Δ CYP3A)-22 | | 16 | | 2 | | | | 2 | | | | 20 | 12 |
| CHO(CYP3A-MAC + hChr7-Δ CYP3A)-23 | | 4 | | 14 | | 1 | | | 1 | | | 20 | 12 |
| CHO(CYP3A-MAC + hChr7-Δ CYP3A)-24 | | 7 | | 8 | | 2 | | 3 | | | | 20 | 12 |
| CHO(CYP3A-MAC + hChr7-Δ CYP3A)-25 | | 16 | | 2 | | 1 | | 1 | | | | 20 | 12 |
| CHO(CYP3A-MAC + hChr7-Δ CYP3A)-26 | | 10 | | 9 | | 1 | | | | | | 20 | 12 |
| CHO(CYP3A-MAC + hChr7-Δ CYP3A)-27 | | | | | | | | | | | | 20 | 12 |

TABLE 16-continued

| | With MAC — Total number of human chromosome | | | | | | | Without MAC | | | Abnormal translocation | No translocation | Total | Origin CHO (HPRT-; MAC1, hChr7-loxP-tel) |
|---|---|---|---|---|---|---|---|---|---|---|---|---|---|---|
| | One | Two | | Three | | | Six | One | Two | Three | | | | |
| | MAC(+Rho spot) x1 | MAC(+Rho spot) x2 | Human region-retaining MAC: MAC(+Rho spot) x1 | MAC(+Rho spot) x1 | MAC (weak or no Rho) x1 MAC region-retaining hChr7f | | MAC(+Rho spot) x2 | | | | | | | |
| | +h7(+FITC spot) x1 /2n | +h7(+FITC spot) x2 /4n | +h7(+FITC spot) x1 +h7(noFITC) x1/2n | +h7(+FITC spot) x1 +h7(noFITC) x2/2n | +h7(+FITC spot) x1 +h7(no FITC) x2/2n | +h7(+FITC spot) x2 +h7(no FITC) x4/4n | | h7 (+FITC spot) x 1 only | h7(+FITC spot)x1+ h7 (without FITC spot)x1 | h7(+FITC spot)x1+ h7 (without FITC spot)x2 | | | | |
| CHO(CYP3A-MAC + hChr7-Δ CYP3A)-28 | 17 | | | | | | | | | | | | 20 | 12 |
| CHO(CYP3A-MAC + hChr7-Δ CYP3A)-31 | 12 | | 3 | 12 | | | | | | | | | 20 | 12 |
| CHO(CYP3A-MAC + hChr7-Δ CYP3A)-32 | | | 11 | | 5 | | | | 4 | | | | 20 | 12 |
| CHO(CYP3A-MAC + hChr7-Δ CYP3A)-33 | | | 13 | | 1 | | | | | 6 | | | 20 | 12 |
| CHO (CYP3A-MAC + hChr7-Δ CYP3A)-34 | | 1 | | | | | | 3 | | | | | 20 | 47 |
| CHO(CYP3A-MAC + hChr7-Δ CYP3A)-35 | | | 3 | 16 | 1 | | 1 | 3 | | | | | 20 | 47 |
| CHO(CYP3A-MAC + hChr7-Δ CYP3A)-37 | | | | 14 | | | | | | 3 | | | 20 | 12 |
| CHO(CYP3A-MAC + hChr7-Δ CYP3A)-40 | | | 10 | | 2 | | 1 | | 7 | 6 | | | 20 | 12 |
| CHO(CYP3A-MAC + hChr7-Δ CYP3A)-41 | | | | | | | | | | | | | 20 | 12 |
| CHO(CYP3A-MAC + hChr7-Δ CYP3A)-42 | | | 13 | | | | | | | 7 | | | 20 | 12 |

From these results, it was concluded that 1 Mb of CYP3A cluster on human chromosome 7 fragment into which loxP sequence has been inserted could be cloned into the mouse artificial chromosome vector MAC1 by reciprocal translocation.

Example 4

Construction of the Mouse Artificial Chromosome Vector MAC2

Figure 3:
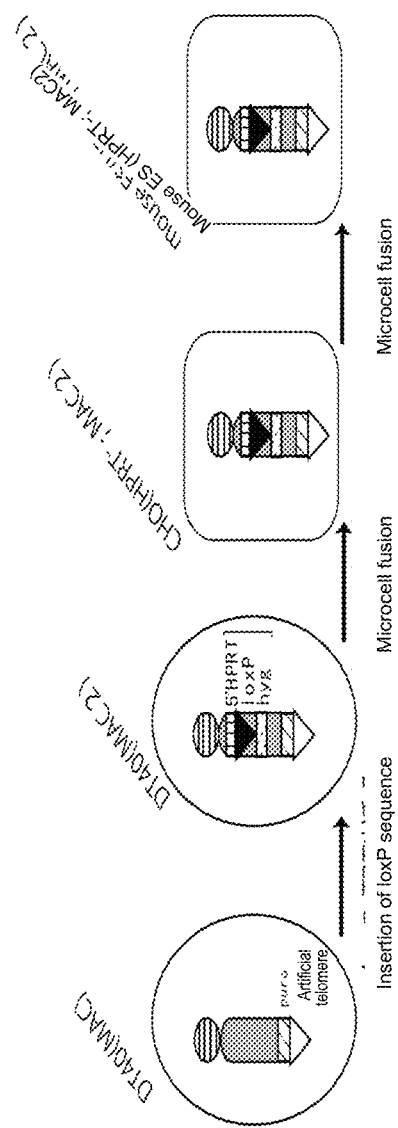
FIG. 3 is a schematic diagram showing the procedures of Example 4. Cell names in the drawings are described according to the following format. Cell name (cellular genetic modification; retained chromosome fragment name, and transgene-retaining chromosome name). Symbols given in the drawings are as follows. puro: puromycin resistant gene, artificial telomere: artificial telomere (TTAGGG) repeat sequence, 5' HPRT: the 1st to 2nd exon sequences of HPRT gene, hyg: hygromycin resistant gene, loxP: site specific DNA sequence insertion site.

The mouse artificial chromosome vector MAC2 is constructed in which 5' HPRT-loxP-PGKhyg type loxP sequence, which is a DNA insertion sequence, is inserted into the mouse artificial chromosome vector MAC (FIG. 3). As the 5' HPRT-loxP-PGK hyg type loxP sequence is inserted to HAC vector carrying GFP (21HAC2) derived from chromosome 21 described in a report by Kazuki et al. (Gene Therapy: PMID: 21085194, 2010), gene expression of HAC and MAC can be compared to each other in the same vector. Further, the gene introduction vector for insertion into 21HAC2 can be used as it is without undergoing the step of preparing a vector.
[A] Insertion of 5' HPRT-loxP-PGKhyg Type loxP Sequence into Mouse Artificial Chromosome MAC
[A. 1] Preparation of 5' HPRT-loxP-PGKhyg Type loxP Targeting Vector As a basic plasmid for inserting loxP sequence, VH21-12 prepared above was used. The 5' HPRT-loxP-PGKhygro cassette cut out from the X6.1 by using KpnI and AscI was cloned into KpnI and AscI sites of V907 (Lexicon genetics) (vector name: p V907-AML). Further, 5' HPRT-loxP-PGK hygro cassette was cut out from p V907-AML by using XhoI and SalI and cloned into XhoI site of VH21-12 (vector name: pMAC2). The targeting vector, target sequence, and chromosome allele obtained by homologous recombination are shown in FIG. 20.
[A. 2] Transfection and Isolation of Drug Resistant Clone As described above, targeting vector pMAC2 prepared above was linearized with the restriction enzyme NotI (TAKARA), and used for transfection of clone DT40 (MAC) prepared above. After exchanging the culture medium with a culture medium containing hygromycin (1.5 mg/ml), the cells were dispensed into two 96-well culture plates and then subjected to selection culture for about 2 weeks. Total 45 resistant colonies obtained from one transfection were isolated, amplified, and subjected to the following analysis (clone name: DT40 (MAC2)).
[A. 3] Selection of Homologous Recombinant
[A. 3. 1] PCR Analysis For extracting genomic DNA from hygromycin resistant cells and using it as a template for selecting a recombinant, PCR was carried out by using the following primers and it was confirmed whether or not recombination has site-specifically occurred on the mouse artificial chromosome vector MAC. The primer sequences are given below.
TRANS-L (described above)
m11 6R (described above)
m11 7R (described above)

(SEQ ID NO: 49)
m11 4L: 5'-ACTCCTAAGGGAGTTGGTGCTGTTGGTG-3' m11 5L (described above)
hygF (244): (described above)
hygR (696): (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 10 sec and 68° C. for 7 min were carried out. As a result of PCR, eight clones out of the 45 clones were found to be positive for all primer sets. Six clones randomly selected from those eight clones were subjected to the following analysis.

TABLE 17

| | TRANS-L1/ m116R | TRANS-L1/ m117R | hygF(244)/ m116R | hygF(244)/ m117R | m114L/ hygR(696) | m115L/ hygR(696) | Cell origin |
|---|---|---|---|---|---|---|---|
| DT40(MAC2)-1 | X | NT | NT | NT | NT | NT | DT40 (MAC)-1 |
| DT40(MAC2)-2 | X | NT | NT | NT | NT | NT | DT40 (MAC)-1 |
| DT40(MAC2)-3 | X | NT | NT | NT | NT | NT | DT40 (MAC)-1 |
| DT40(MAC2)-4 | O | O | O | O | O | O | DT40 (MAC)-1 |
| DT40(MAC2)-5 | O | O | O | O | O | O | DT40 (MAC)-1 |
| DT40(MAC2)-6 | X | NT | NT | NT | NT | NT | DT40 (MAC)-1 |
| DT40(MAC2)-7 | X | NT | NT | NT | NT | NT | DT40 (MAC)-1 |
| DT40(MAC2)-8 | X | NT | NT | NT | NT | NT | DT40 (MAC)-1 |
| DT40(MAC2)-9 | X | NT | NT | NT | NT | NT | DT40 (MAC)-1 |
| DT40(MAC2)-10 | O | O | O | O | O | O | DT40 (MAC)-1 |
| DT40(MAC2)-11 | X | NT | NT | NT | NT | NT | DT40 (MAC)-1 |
| DT40(MAC2)-12 | X | NT | NT | NT | NT | NT | DT40 (MAC)-1 |
| DT40(MAC2)-13 | O | O | O | O | O | O | DT40 (MAC)-1 |
| DT40(MAC2)-14 | X | NT | NT | NT | NT | NT | DT40 (MAC)-1 |
| DT40(MAC2)-15 | O | O | O | O | O | O | DT40 (MAC)-1 |
| DT40(MAC2)-16 | X | NT | NT | NT | NT | NT | DT40 (MAC)-1 |
| DT40(MAC2)-17 | O | O | O | O | O | O | DT40 (MAC)-1 |
| DT40(MAC2)-18 | X | NT | NT | NT | NT | NT | DT40 (MAC)-1 |
| DT40(MAC2)-19 | X | NT | NT | NT | NT | NT | DT40 (MAC)-1 |
| DT40(MAC2)-20 | X | NT | NT | NT | NT | NT | DT40 (MAC)-1 |
| DT40(MAC2)-21 | X | NT | NT | NT | NT | NT | DT40 (MAC)-1 |
| DT40(MAC2)-22 | X | NT | NT | NT | NT | NT | DT40 (MAC)-1 |
| DT40(MAC2)-23 | X | NT | NT | NT | NT | NT | DT40 (MAC)-1 |
| DT40(MAC2)-24 | X | NT | NT | NT | NT | NT | DT40 (MAC)-1 |
| DT40(MAC2)-25 | X | NT | NT | NT | NT | NT | DT40 (MAC)-1 |
| DT40(MAC2)-26 | X | NT | NT | NT | NT | NT | DT40 (MAC)-1 |

TABLE 17-continued

| | TRANS-L1/ m116R | TRANS-L1/ m117R | hygF(244)/ m116R | hygF(244)/ m117R | m114L/ hygR(696) | m115L/ hygR(696) | Cell origin |
|---|---|---|---|---|---|---|---|
| DT40(MAC2)-27 | X | NT | NT | NT | NT | NT | DT40 (MAC)-1 |
| DT40(MAC2)-28 | X | NT | NT | NT | NT | NT | DT40 (MAC)-1 |
| DT40(MAC2)-29 | X | NT | NT | NT | NT | NT | DT40 (MAC)-1 |
| DT40(MAC2)-30 | X | NT | NT | NT | NT | NT | DT40 (MAC)-1 |
| DT40(MAC2)-31 | X | NT | NT | NT | NT | NT | DT40 (MAC)-1 |
| DT40(MAC2)-32 | X | NT | NT | NT | NT | NT | DT40 (MAC)-1 |
| DT40(MAC2)-33 | X | NT | NT | NT | NT | NT | DT40 (MAC)-1 |
| DT40(MAC2)-34 | X | NT | NT | NT | NT | NT | DT40 (MAC)-1 |
| DT40(MAC2)-35 | X | NT | NT | NT | NT | NT | DT40 (MAC)-1 |
| DT40(MAC2)-36 | X | NT | NT | NT | NT | NT | DT40 (MAC)-1 |
| DT40(MAC2)-37 | X | NT | NT | NT | NT | NT | DT40 (MAC)-1 |
| DT40(MAC2)-38 | X | NT | NT | NT | NT | NT | DT40 (MAC)-1 |
| DT40(MAC2)-39 | X | NT | NT | NT | NT | NT | DT40 (MAC)-1 |
| DT40(MAC2)-40 | X | NT | NT | NT | NT | NT | DT40 (MAC)-1 |
| DT40(MAC2)-41 | X | NT | NT | NT | NT | NT | DT40 (MAC)-1 |
| DT40(MAC2)-42 | X | NT | NT | NT | NT | NT | DT40 (MAC)-1 |
| DT40(MAC2)-43 | X | NT | NT | NT | NT | NT | DT40 (MAC)-1 |
| DT40(MAC2)-44 | ◯ | ◯ | ◯ | ◯ | ◯ | ◯ | DT40 (MAC)-1 |
| DT40(MAC2)-45 | ◯ | ◯ | ◯ | ◯ | ◯ | ◯ | DT40 (MAC)-1 |
| Positive control | ◯ | NT | NT | NT | NT | NT | |
| Negative control | X | X | X | X | X | X | |

[A. 3. 2] Two-Color FISH Analysis

Figure 21:
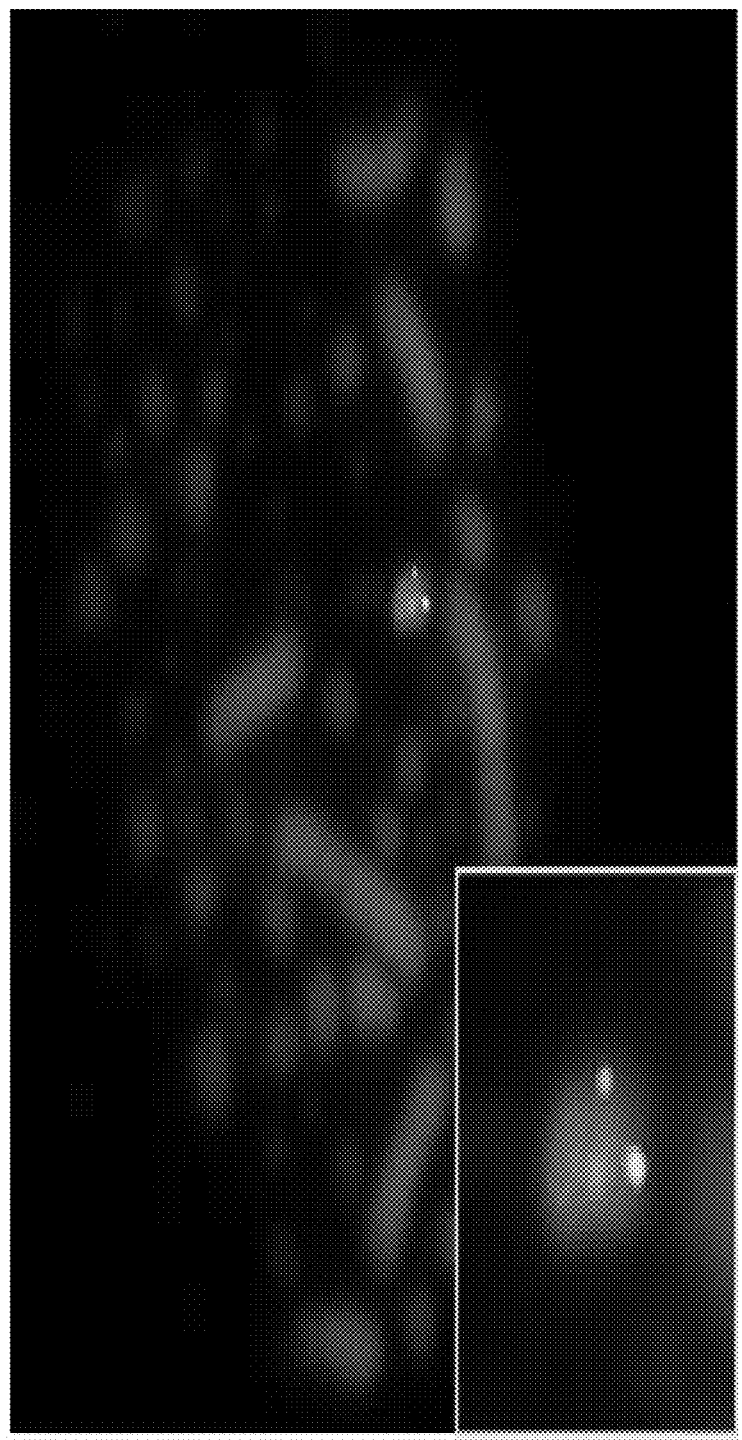
FIG. 21 shows the results of the two-color FISH analysis of DT40 (MAC2) clone in which mouse Cot-1 DNA and 5' HPRT-loxP-PGK hygro cassette were used as probes.

For the 6 clones of DT40 (MAC2) obtained from the above, two-color FISH analysis was carried out according to Matsubara et al. (FISH test protocol, Shujunsha Co., Ltd., 1994). FISH analysis was carried out by using mouse cot-1 DNA and 5' HPRT-loxP-PGK hygro cassette as probes. As a result, it was found that the detection rate of a signal clearly derived from probe is 10% in the mouse artificial chromosome vector MAC, which is a mouse chromosome 11 fragment before targeting as negative control, while it is detected with a rate of 50% or more a signal derived from probe in the six clones of DT40 (MAC2). Thus, site specific recombination occurring in the six clones was visually confirmed (FIG. 21). From these results, it was possible to conclude that DT40 cell clones retaining the mouse artificial chromosome vector MAC2 are obtained.

TABLE 18

| | Metaphase | | | | | Interphase | | | |
|---|---|---|---|---|---|---|---|---|---|
| | MACx1 F−/2n | MACx1 F+/2n | MACx1 F weak+/2n | MACx2/4n | Total | x0 | x1 | x2 | Total |
| DT40 (MAC)-1 | 12 | 2 | 5 | 1 | 20 | | 100 | | 100 |
| DT40 (MAC2)-2 | 1 | 15 | 3 | 1 | 20 | | 98 | 2 | 100 |
| DT40 (MAC2)-5 | | 18 | 2 | | 20 | | 97 | 3 | 100 |
| DT40 (MAC2)-17 | 1 | 18 | 1 | | 20 | 2 | 96 | 2 | 100 |
| DT40 (MAC2)-10 | 4 | 16 | | | 20 | 3 | 94 | 3 | 100 |
| DT40 (MAC2)-13 | 2 | 14 | 4 | | 20 | 2 | 98 | | 100 |
| DT40 (MAC2)-15 | 6 | 10 | 4 | | 20 | 5 | 92 | 3 | 100 |

[B] Introduction of MAC2 from Chicken DT40 Cell Containing the Mouse Artificial Chromosome Vector MAC2 into CHO Cells In order to stably introduce the mouse artificial chromosome vector MAC2 into mouse ES cells, introduction to CHO cells is carried out. Further, in order to stably insert a target gene (for example, GFP gene) via loxP, which is a DNA insertion site of the mouse artificial chromosome vector MAC2, introduction to CHO cells is carried out.

[B. 1] Microcell Fusion and Isolation of Drug Resistant Clone

By using DT40 (MAC2)-5 and 17 as a recipient cell, microcell fusion was carried out for CHO (HPRT), which is CHO hprt depleted cells (obtained from the Health Science Research Resources Bank, registration number: JCRB0218), in the same manner as above. Total 44 resistant colonies obtained by two microcell fusions were isolated, amplified, and subjected to the following analysis (clone name: CHO (HPRT; MAC2)).

[B. 2] Selection of Drug Resistant Clone

[B. 2. 1] PCR Analysis

For extracting genomic DNA from hygromycin resistant cell line and using it as a template for selecting a recombinant, PCR was carried out by using the following primers and it was confirmed whether or not mouse artificial chromosome MAC2 can be introduced into CHO cells. The primer sequences are given below.

TRANS-L (described above)
m11 6R (described above)
m11 7R (described above)
m11 4L (described above)
m11 5L (described above)
hygF (244): (described above)
hygR (696): (described above))

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, 14 clones out of the 44 clones were found to be positive for all primer sets, and the following analysis was performed by using clones randomly selected from those 14 clones.

lowed by incubation overnight to form microcells. The culture medium was removed, and cytochalasin B (10 μg/ml,

TABLE 19

| | Cell origin | | | | | | | | | | | | | | | |
|---|---|---|---|---|---|---|---|---|---|---|---|---|---|---|---|---|
| | DT40 (MAC2)-17 | DT40 (MAC2)-5 | | | | | | DT40 (MAC2)-17 | | | | | | | | |
| | | | | | Clone name | | | | | | | | | | | |
| | | | | | CHO (HPRT; MAC2) | | | | | | | | | | | |
| | | | | | Clone number | | | | | | | | | | | |
| | 11 | 12 | 13 | 14 | 15 | 16 | 17 | 18 | 19 | 20 | 21 | 22 | 23 | 24 | Positive control | Negative control |
| TRANS-L1/m11 6R | ○ | ○ | ○ | ○ | ○ | ○ | ○ | ○ | ○ | ○ | ○ | ○ | ○ | ○ | ○ | X |
| TRANS-L1/m11 7R | ○ | ○ | ○ | ○ | ○ | ○ | ○ | ○ | ○ | ○ | ○ | ○ | ○ | ○ | ○ | X |
| hyg F (244)/m11 6R | ○ | ○ | ○ | ○ | ○ | ○ | ○ | ○ | ○ | ○ | ○ | ○ | ○ | ○ | ○ | X |
| hyg F (244)/m11 7R | ○ | ○ | ○ | ○ | ○ | ○ | ○ | ○ | ○ | ○ | ○ | ○ | ○ | ○ | ○ | X |
| m11 4L/hygR (696) | ○ | ○ | ○ | ○ | ○ | ○ | ○ | ○ | ○ | ○ | ○ | ○ | ○ | ○ | ○ | X |
| m11 5L/hygR (696) | ○ | ○ | ○ | ○ | ○ | ○ | ○ | ○ | ○ | ○ | ○ | ○ | ○ | ○ | ○ | X |

[B. 2. 2] Two-Color FISH Analysis

Figure 22:
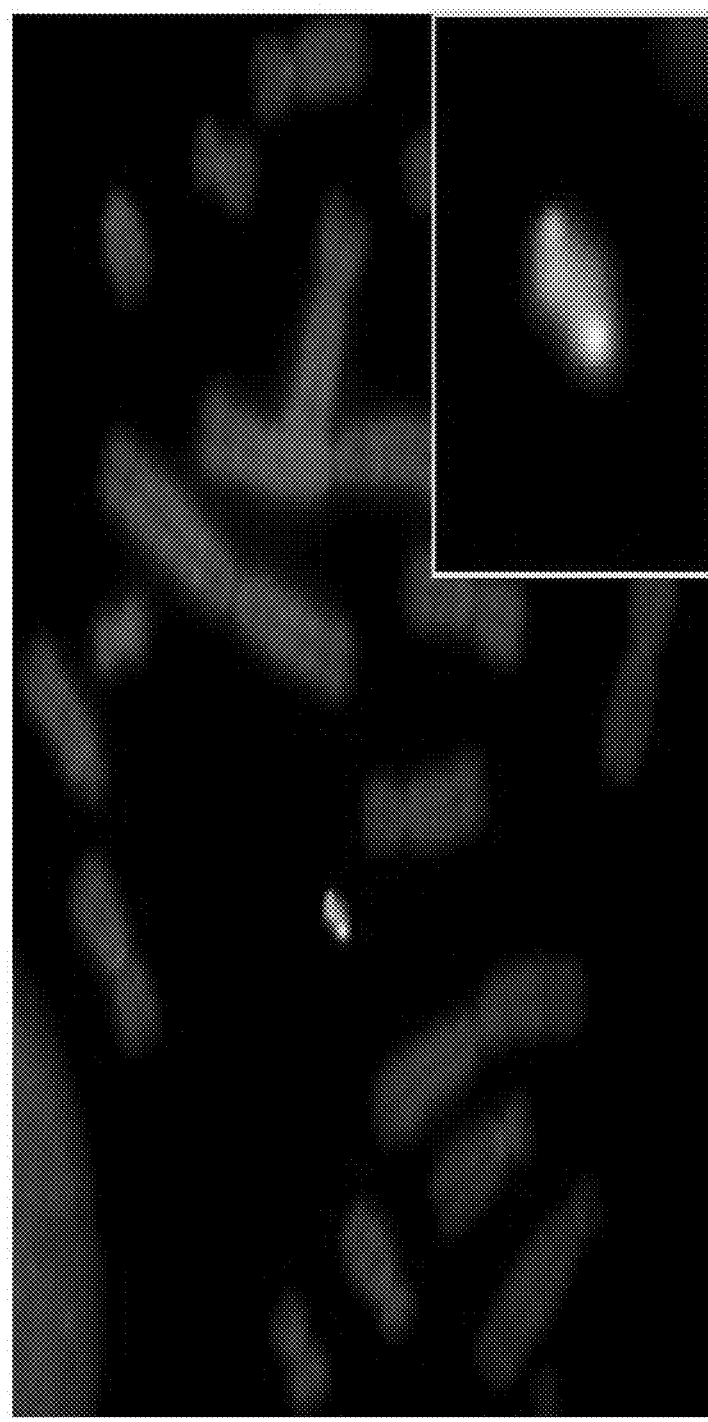
FIG. 22 shows the results of the two-color FISH analysis of CHO (HPRT⁻; MAC2) clone in which mouse Cot-1 DNA and 5' HPRT-loxP-PGK hygro cassette were used as probes.

With nine clones randomly selected from the 14 clones of CHO (HPRT$^-$; MAC2) obtained from the above, FISH analysis was carried out by using mouse Cot-1 DNA and 5' HPRT-loxP-PGK hygro cassette as probes by the method according to Matsubara et al. (FISH test protocol, Shujunsha Co., Ltd., 1994). As a result, it was confirmed that MAC2 was introduced into CHO cells with a rate of 95% in eight clones out of the nine clones (FIG. 22).

Sigma) solution which has been previously kept warm at 37° C. was filled in a flask for centrifugation. The centrifugation was performed for 1 hour at 34° C., at 8000 rpm. The microcells were suspended in serum free DMEM culture medium and purified with filters of 8 μm, 5 μm, and 3 μm. After the purification, the cells were centrifuged for 10 min at 2000 rpm, and suspended in 5 ml of serum free DMEM culture medium. The microcells were suspended in 5 ml of serum free DMEM culture medium and purified with filters

TABLE 20

| | Metaphase CHO nuclear type | | | | | | | | | Interphase | | | | | | | |
|---|---|---|---|---|---|---|---|---|---|---|---|---|---|---|---|---|---|
| | 2n | | | | | | | | | | | | | | | | |
| | MAC copy number | | | | | | | | | | | | | | | | |
| | 0 | 1 | 2 | 3 | 4 | 1 | 2 | 3 | Total | x0 | x1 | x2 | x3 | x4 | x5 | Total | Origin |
| DT40 (MAC)-6 | | 20 | | | | | | | 20 | | | | | | | | |
| CHO (HPRT$^-$; MAC2)-12 | | 19 | | | | | | | 19 | 2 | 88 | 10 | | | | 100 | DT40 (MAC2)-5 |
| CHO (HPRT$^-$; MAC2)-13 | | 20 | | | | | | | 20 | 0 | 91 | 9 | | | | 100 | DT40 (MAC2)-5 |
| CHO (HPRT$^-$; MAC2)-14 | 1 | 12 | 4 | 2 | | | | 1 | 20 | 12 | 46 | 35 | 7 | | | 100 | DT40 (MAC2)-5 |
| CHO (HPRT$^-$; MAC2)-15 | 1 | 17 | 1 | 1 | | | | | 20 | 3 | 79 | 16 | 2 | | | 100 | DT40 (MAC2)-5 |
| CHO (HPRT$^-$; MAC2)-16 | 1 | 2 | 4 | 12 | 1 | | | | 20 | 1 | 15 | 55 | 23 | 4 | 2 | 100 | DT40 (MAC2)-5 |
| CHO (HPRT$^-$; MAC2)-17 | | 13 | 4 | 1 | | | 1 | | 19 | 1 | 70 | 27 | 2 | | | 100 | DT40 (MAC2)-17 |
| CHO (HPRT$^-$; MAC2)-18 | 1 | 17 | | | | | 2 | | 20 | 14 | 72 | 13 | 1 | | | 100 | DT40 (MAC2)-17 |
| CHO (HPRT$^-$; MAC2)-22 | 1 | 13 | 5 | | | 1 | | | 20 | 7 | 69 | 17 | 6 | | 1 | 100 | DT40 (MAC2)-17 |
| CHO (HPRT$^-$; MAC2)-23 | 4 | 15 | | | | 1 | | | 20 | 26 | 64 | 9 | 1 | | | 100 | DT40 (MAC2)-17 |

From these results, it was concluded that the mouse artificial chromosome vector MAC2 in which loxP sequence as a gene insertion site is inserted into mouse artificial chromosome MAC, which is a chromosome fragment derived from mouse chromosome 11, could be introduced into CHO cells.

[C] Introduction of the Mouse Artificial Chromosome Vector MAC2 from CHO Cell Containing the Mouse Artificial Chromosome Vector MAC2 into Mouse ES Cell.

[C. 1] Microcell Fusion and Isolation of Drug Resistant Clone

CHO (HPRT$^-$; MAC2)-13 and -18 as recipient cells were cultured on cell culture dishes. At the time of reaching confluency, the culture medium was exchanged with F12 culture medium supplemented with 20% FBS and 0.1 μg/ml colcemid. After further culturing for 48 hours, the culture medium was again exchanged with F12 culture medium supplemented with 20% FBS and 0.1 μg/ml colcemid folof 8 μm, 5 μm, and 3 μm. After the purification, the cells were centrifuged for 10 min at 2000 rpm.

As a donor cell, B6-ES, which is a C57B6 line-based mouse ES cell obtained from CLEA Japan, Inc., B6 (HPRT$^-$), which is a HPRT depleted cell line obtained by treating the ES cell with 6TG, and KO56 (HPRT$^-$), which is a HPRT depleted cell line of TT2F cell, were used. For cell culture, to DMEM (Dulbecco's Modified Eagle's Medium-high glucose: SIGMA), 10% FCS, LIF (Muerin Leukemia Inhibitory Factor), $1 \times 10^{-5}$ M 2-ME (2-mercapto-ethanol: SIGMA), L-glutamine (3.5 g/ml: GIBCO), sodium pyruvate solution (3.5 g/ml: GIBCO), and MEM nonessential amino acid (0.125 mM: GIBCO) were added and culture was performed at 5% $CO_2$, 37° C. After washing twice the cell surface of mouse ES cells with PBS (–), the cells were dispersed with trypsin treatment and recovered with culture medium in which 10% FBS was added to DMEM culture medium. Centrifugation was carried out at 1500 rpm, the supernatant was removed and re-suspended in 5 ml of serum free culture medium and gently added to the serum free culture medium containing pellets of microcells after centrifugation. It was further centrifuged at 1200 rpm. The supernatant was removed and fused with 0.5 ml of PEG1000 (Wako) solution [5 g of PEG1000 is dissolved completely in serum free DMEM culture medium, 1 ml of dimethyl sulfoxide is added thereto, and the mixture is sterilized by filtration] precisely for 1 min and 30 sec. 13 ml of serum free culture medium (DMEM) was gently added and centrifuged at 1200 rpm. The supernatant was removed, common culture medium for mouse ES cells was added, and by using G418 resistant mouse embryonic fibroblast treated with mitomycin as a feeder cell, the cells were plated onto two cell culture dishes with a diameter of 10 cm followed by incubation overnight. Hygromycin was added so as to be 250 μg/ml and selection culture was carried out for 3 to 4 weeks. Total 28 resistant colonies obtained by two microcell fusions were isolated, amplified, and subjected to the following analysis (clone name: B6-ES (MAC2), B6 (HPRT−; MAC2), and KO56 (HPRT−; MAC2)).

[C. 2] Selection of Drug Resistant Clone
[C. 2. 1] PCR Analysis

For extracting genomic DNA from hygromycin resistant cell line and using it as a template for selecting a recombinant, PCR was carried out by using the following primers and it was confirmed whether or not mouse artificial chromosome MAC2 can be introduced into mouse ES cells. The primer sequences are given below.
TRANS L (described above)
m11 6R (described above)
m11 4L (described above)
hyg R (696) (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 10 min were carried out. As a result of PCR, 27 clones out of the 28 clones were found to be positive for all primer sets, and the following analysis was performed by using three clones randomly selected from those 27 clones.

TABLE 21

| | Origin CHO(HPRT−; MAC2)-13 | | | | |
|---|---|---|---|---|---|
| | Clone name | | | | |
| | KO56(HPRT−; MAC2) | | | CHO(HPRT−; MAC2)-13 | KO56 (HPRT−) |
| Clone number | 1 | 2 | 3 | + | − |
| TRANS-L1/ m11 6R | ○ | ○ | ○ | ○ | X |
| hyg F(244)/ m11 6R | ○ | ○ | ○ | ○ | X |
| m11 4L/ hygR(696) | ○ | ○ | ○ | ○ | X |

[C. 2. 2] Mono-Color FISH Analysis

With the mouse ES (MAC2) clones obtained from the above, FISH analysis was carried out according to the method described by Shinohara et al. (Human Molecular Genetics, 10: 1163-1175, 2001) by using mouse minor satellite DNA as a probe. As a result, it was confirmed that, in one clone out of the three clones, one copy of MAC2 is introduced into mouse ES cells at a rate of 80% or more and the number of endogenous mouse chromosomes that are normal nuclear type of KO56 cells was 39.

Figure 23:
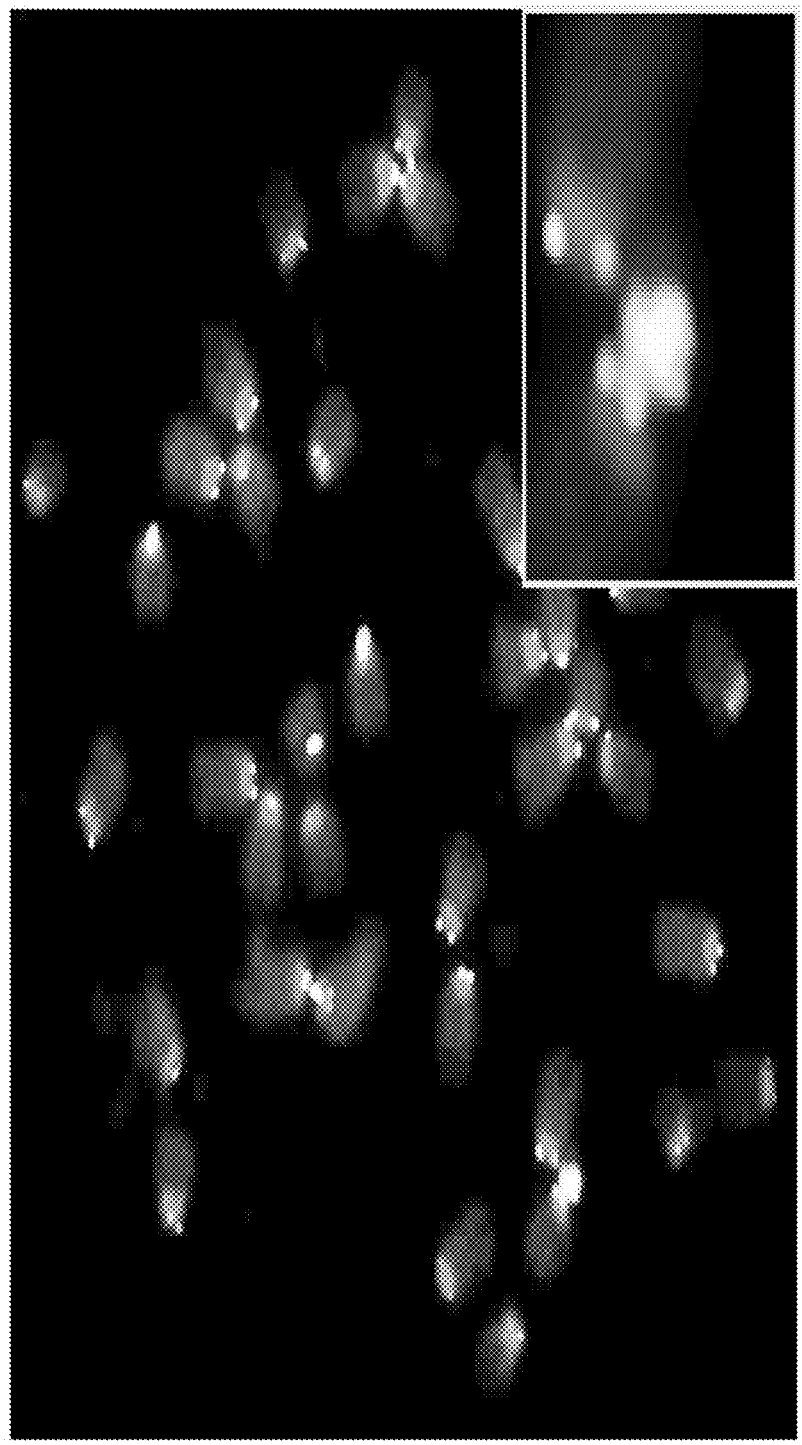
FIG. 23 shows the results of the mono-color FISH analysis of mouse ES (HPRT-, MAC2) clone in which mouse minor satellite DNA was used as a probe.

From these results, it was concluded that the mouse artificial chromosome vector MAC2 in which loxP sequence, which is a gene insertion site, was inserted into mouse artificial chromosome MAC, which is a chromosome fragment derived from mouse chromosome 11, could be introduced into mouse ES cells (FIG. 23).

TABLE 22

| Mouse chromosome | 36 | 37 | 38 | 39 | 40 | Total |
|---|---|---|---|---|---|---|
| +MAC copy number | x0 | x1 | x1 | x1 | x0 | x1 |
| KO56(HPRT−; MAC2)-2 | 1 | 1 | 3 | 14 | | 1 | 20 |

[D] As described in Example 8, in vitro stability can be examined by using mouse ES cell retaining the mouse artificial chromosome vector MAC2. Further, by preparing a chimeric mouse using the ES cells, the mouse lineage-based TC (MAC2) in which MAC2 is genetically transmitted to a progeny can be prepared. Still further, by using the TC (MAC2) mouse line, stability of MAC2 in somatic cells can be examined.

Example 5

Construction of the Mouse Artificial Chromosome Vector MAC3

Figure 4:
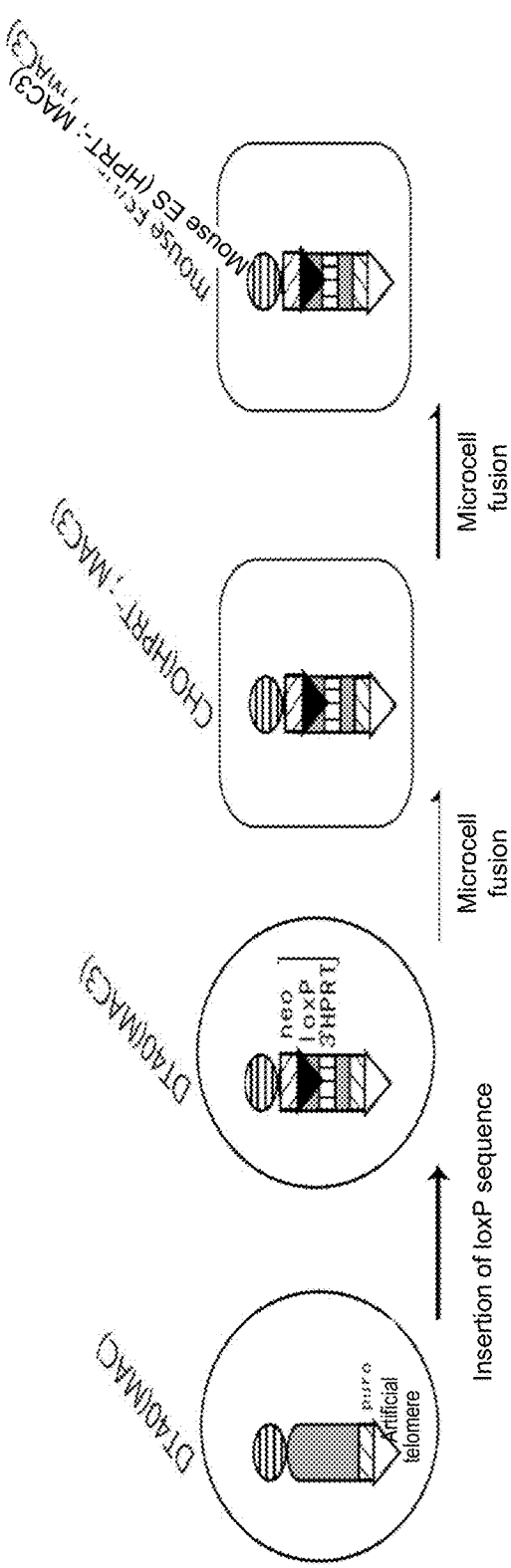
FIG. 4 is a schematic diagram illustrating the procedures of Example 5. Cell names in the drawings are described according to the following format. Cell name (cellular genetic modification; retained chromosome fragment name, and transgene-retaining chromosome name). Symbols given in the drawings are as follows. puro: puromycin resistant gene, artificial telomere: artificial telomere (TTAGGG) repeat sequence, neo: neomycin (G418) resistant gene, loxP: site specific DNA sequence insertion site, 3' HPRT: the 3rd to 9th exon sequences of HPRT gene.

The mouse artificial chromosome vector MAC3 is constructed in which the PGKneo-loxP-3' HPRT type loxP sequence as a DNA insertion sequence is inserted into mouse artificial chromosome MAC (FIG. 4). Stability of the mouse artificial chromosome vector MAC3 in mouse ES cells is examined, and by preparing a genetically transmitted progeny mouse to which MAC3 has been introduced, stability in individual tissue is examined.

[A] Insertion of PGKneo-loxP-3' HPRT Type loxP Sequence into Mouse Artificial Chromosome MAC
[A. 1] Preparation of PGKneo-loxP-3' HPRT Type loxP Targeting Vector As a basic plasmid for inserting loxP sequence, VH21-12 prepared above was used. The PGKneo-loxP-3' HPRT cassette cut out from pVNLH by using SalI and AscI was cloned into XhoI and AscI sites of VH21-12 (vector name: pMAC3). The targeting vector, target sequence, and chromosome allele obtained by homologous recombination are shown in FIG. 24.

[A. 2] Transfection and Isolation of G418 Resistant Clone

Cell culture of chicken DT40 cells was performed in RPMI 1640 culture medium (Gibco) supplemented with 10% fetal bovine serum (Gibco, herein below, described as FBS), 1% chicken serum (Gibco), and 10-4 M 2-mercaptoethanol (Sigma). Approximately $10^7$ DT40 (MAC)-1 cells were washed once with supplement-free RPMI 1640 culture medium, suspended in 0.5 ml of supplement-free RPMI 1640 culture medium, added with 25 μg of the targeting vector pMAC3 which has been linearized with the restriction enzyme NotI (TAKARA), transferred to a cuvette (Bio-Rad Laboratories, Inc.) for electroporation, and left to stand for 10 min at room temperature. The cuvette was set in Gene Pulser (Bio-Rad Laboratories, Inc.) and applied with voltage under the conditions of 550 V and 25 μF. After left to stand for 10 min at room temperature, the cells were cultured for 24 hours. The culture medium was exchanged with a culture medium containing G418 (1.5 mg/ml), and dispensed into two 96-well culture plates, and then subjected to selection culture for about 2 weeks. Total 14 resistant colonies obtained after two transfections were isolated, amplified and subjected to the following analysis (clone name: DT40 (MAC3)).

[A. 3] Selection of Homologous Recombinant

[A. 3. 1] PCR Analysis

For extracting genomic DNA from G418 resistant cell line and using it as a template for selecting a recombinant, PCR was carried out by using the following primers and it was confirmed whether or not recombination has site-specifically occurred on mouse chromosome 11. The primer sequences are given below.

m11 17L (described above)

```
                                              (SEQ ID NO: 50)
    Puro-1: 5'-GAGCTGCAAGAACTCTTCCTCACG-3'
``` kj neo (described above)
m11 6R (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they are used under the conditions described by manufacturer's instruction. Temperature and cycle conditions were as follows: after heat denaturation at 94° C. for 1 min, 35 cycles of 98° C. for 10 sec and 68° C. for 9 min were carried out. As a result of PCR, 16 clones out of the 17 clones were found to be positive for all primer sets, and therefore, the following analysis was performed by using two clones randomly selected from those 16 clones.

[A. 3. 3] Two-Color FISH Analysis

Figure 25:
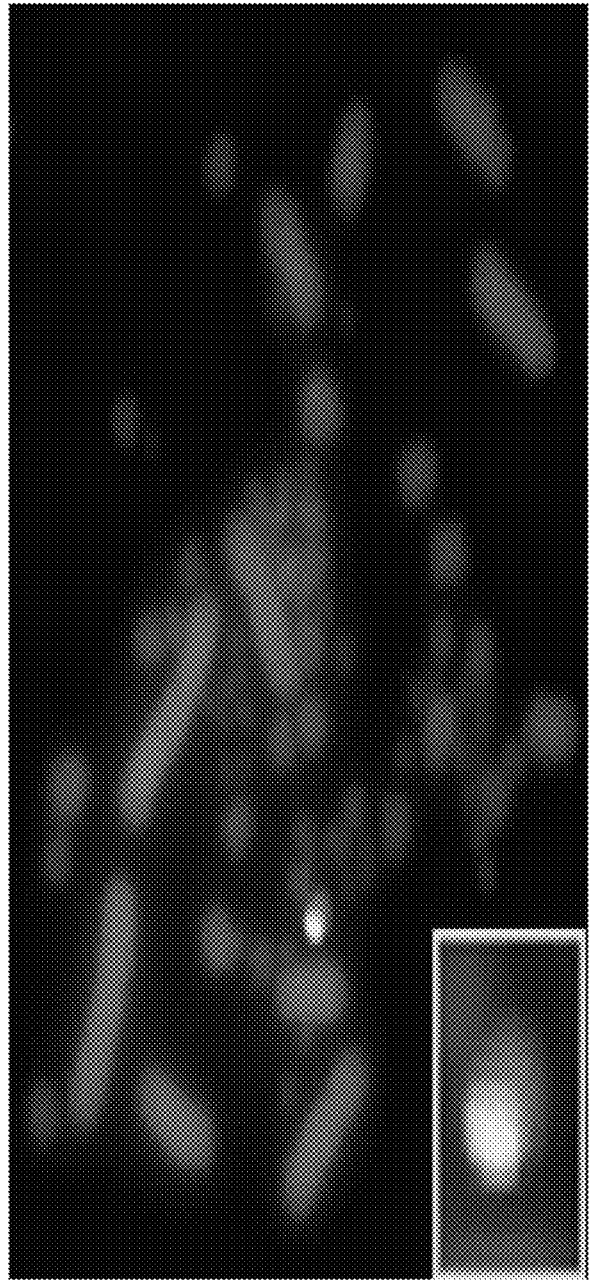
FIG. 25 shows the results of the two-color FISH analysis of DT40 (MAC3) clone in which mouse Cot-1 DNA and mouse minor satellite DNA were used as probes.
Figure 26:
FIG. 26 shows the results of the mono-color FISH analysis of CHO (HPRT⁻; MAC3) clone in which mouse Cot-1 DNA was used as a probe.

With the randomly selected DT40 (MAC3)-160 and 187, two-color FISH analysis was carried out according to Matsubara et al. (FISH test protocol, Shujunsha Co., Ltd., 1994). FISH analysis was carried out by using mouse cot-1 DNA and mouse minor satellite DNA as probes. As a result, it was found that mouse artificial chromosome MAC3 was independently present in single copy (FIG. 25).

From these results, it was concluded that DT40 cell clones retaining the mouse artificial chromosome vector MAC3 in which loxP sequence as a DNA insertion sequence was inserted near the mouse centromere were obtained.

[B] Introduction of MAC3 from Chicken DT40 Cell Containing the Mouse Artificial Chromosome Vector MAC3 into CHO Cell In order to stably insert a target gene (for example, GFP gene) via loxP as a DNA sequence insertion site of the mouse artificial chromosome vector MAC3, introduction to CHO cells was carried out.

[B. 1] Microcell Fusion and Isolation of Drug Resistant Clone

DT40 (MAC3)-160 as a recipient cell was cultured on a cell culture dish. At the time of reaching confluency, the culture medium was exchanged with RPMI 1640 culture medium supplemented with 20% FBS, 1% chicken serum, 10-4 M 2-mercaptoethanol, and 0.05 μg/ml colcemid and cultured further for 12 hours to form microcells. The culture medium was replaced with 24 ml of serum free DMEM culture medium, and 2 ml of them was dispensed into 12 25 cm² flasks for centrifugation which has been coated in advance with 100 μ/ml poly L-lysine and cultured for 30 min at 37° C. to adhere the cells at the bottom of the flask. The supernatant was removed and cytochalasin B (10 μg/ml,

TABLE 23

| | DT40 (MAC3) | | | | | | | | | | | | | | | | | Telomere vector | DT40 | |
|---|---|---|---|---|---|---|---|---|---|---|---|---|---|---|---|---|---|---|---|---|
| | 33 | 49 | 56 | 75 | 100 | 109 | 111 | 130 | 157 | 160 | 184 | 187 | 197 | 308 | 330 | 331 | 407 | | MAC1 | DT40 |
| m11 17L/ Puro-1 | ○ | ○ | ○ | ○ | ○ | ○ | ○ | ○ | ○ | ○ | ○ | ○ | ○ | ○ | ○ | ○ | ○ | ○ | NT | X |
| kj neo/ m11 6R | ○ | ○ | ○ | ○ | ○ | ○ | ○ | ○ | ○ | ○ | ○ | ○ | ○ | X | ○ | ○ | ○ | NT | ○ | X |

[A. 3. 2] Mono-Color FISH Analysis

With the two clones of DT40 (MAC3) obtained from the above, FISH analysis was carried out by using mouse Cot-1 DNA as a probe according to the method described by Shinohara et al. (Human Molecular Genetics, 10: 1163-1175, 2001). As a result, it was found that no chromosome translocation or the like occurred in any clone and it was retained independently with a rate of 90% or more.

Sigma) solution which has been previously kept warm at 37° C. was filled in a flask for centrifugation followed by centrifugation for 1 hour at 34° C., 8000 rpm. The microcells were suspended in serum free DMEM culture medium and purified with filters of 8 μm, 5 μm, and 3 μm. After the purification, cells were centrifuged for 10 min at 1700 rpm and then suspended in 5 ml of serum free DMEM culture medium.

TABLE 24

| | Metaphase | | Interphase | | | | |
|---|---|---|---|---|---|---|---|
| | MACx1/2n | Total | x0 | x1 | x2 | Total | Remarks |
| DT40 (MAC3)-160 | 20 | 20 | 4 | 96 | | 100 | →MMCT into CHO |
| DT40 (MAC3)-187 | 20 | 20 | 2 | 98 | | 100 | →MMCT into CHO |

As a donor cell, CHO (HPRT⁻), which is CHO hprt depleted cells (obtained from the Health Science Research Resources Bank, registration number: JCRB0218) was used. Purified micronuclei were re-suspended in 2 ml of serum free culture medium containing PHA-P (SIGMA), and gently plated onto CHO cells from which culture supernatant [F12 culture medium supplemented with 10% FBS (Invitrogen)] was removed. The plate was incubated for 15 min at 37° C. The supernatant was removed and fused with 1 ml of PEG1000 (Wako) solution [5 g of PEG1000 is completely dissolved in serum free DMEM culture medium, added with 1 ml of dimethyl sulfoxide, and sterilized by filtration] precisely for 1 min. The cells were washed four times with 4 ml of serum free culture medium (DMEM), added with 5 ml of common culture medium for CHO cells, and incubated overnight. Cell surfaces were washed twice with PBS (−) and the cells were dispersed by trypsin treatment, and plated onto five cell culture dishes with a diameter of 10 cm. After adding G418 so as to be 800 µg/ml, cells were subjected to selection culture for 3 to 4 weeks. Total 12 resistant colonies obtained by two microcell fusions were isolated, amplified, and subjected to the following analysis (clone name: CHO (HPRT⁻; MAC3)).

[B. 2] Selection of Drug Resistant Clone

[B. 2. 1] PCR Analysis

For extracting genomic DNA from G418 resistant cell line and using it as a template for selecting a recombinant, PCR was carried out by using the following primers and it was confirmed whether or not the mouse artificial chromosome vector MAC3 can be introduced into CHO cells. The primer sequences are given below.

kj neo (described above)
m11 6R (described above)
m11 17L (described above)
Puro-1 (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 10 min were carried out. As a result of PCR, six clones out of the seven clones were found to be positive for all primer sets, and the following analysis was performed by using those six clones.

TABLE 25

| | Derived from DT40 (MAC3)-160 CHO (HPRT−; MAC3) | | | | | | | Positive control DT40 (MAC3)-160 | Negative control DT40 (MAC)-1 | Negative control CHO HPRT−/− |
|---|---|---|---|---|---|---|---|---|---|---|
| | 1 | 3 | 5 | 6 | 7 | 9 | 11 | | | |
| kj-neo/m11 6R | ○ | X | ○ | ○ | ○ | ○ | ○ | ○ | X | X |
| m11 17L/Puro-1 | ○ | ○ | ○ | ○ | ○ | ○ | ○ | ○ | X | X |

[B. 2. 2] Mono-Color FISH Analysis

With the six clones of CHO (HPRT⁻; MAC3) obtained from the above, FISH analysis was carried out by using mouse Cot-1 DNA as a probe according to the method described by Shinohara et al. (Human Molecular Genetics, 10: 1163-1175, 2001). As a result, it was confirmed that MAC3 was introduced into CHO cells with a rate of 90% or more in three clones out of the six clones.

TABLE 26

| | Metaphase | | | | | | | | | Interphase | | | | | Origin |
|---|---|---|---|---|---|---|---|---|---|---|---|---|---|---|---|
| | x0/2n | x1/2n | x1/4n | x2/2n | x2/4n | x2/8n | x3/4n | With translocation | Total | x0 | x1 | x2 | x3 | Total | |
| CHO (HPRT−; MAC3)-1 | 4 | 12 | 2 | 1 | | | | 1 | 20 | 25 | 64 | 9 | 2 | 100 | DT40 (MAC3)-160 |
| CHO (HPRT−; MAC3)-5 | 2 | 17 | | | 1 | | | | 20 | 27 | 60 | 10 | 3 | 100 | DT40 (MAC3)-160 |
| CHO (HPRT−; MAC3)-6 | 6 | 8 | 1 | 1 | 1 | | 1 | 2 | 20 | 29 | 56 | 11 | 4 | 100 | DT40 (MAC3)-160 |
| CHO (HPRT−; MAC3)-7 | 2 | 16 | | | 1 | | | 1 | 20 | 16 | 66 | 13 | 5 | 100 | DT40 (MAC3)-160 |
| CHO (HPRT−; MAC3)-9 | 2 | 8 | 1 | 5 | 1 | | | 3 | 20 | 12 | 58 | 20 | 10 | 100 | DT40 (MAC3)-160 |
| CHO (HPRT−; MAC3)-11 | | 5 | 5 | | 2 | | 3 | 5 | 20 | 12 | 54 | 26 | 8 | 100 | DT40 (MAC3)-160 |

From these results, it was concluded that the mouse artificial chromosome vector MAC3 could be introduced into CHO cells.

[C] Introduction of MAC3 from CHO Cell Containing the Mouse Artificial Chromosome Vector MAC3 into Mouse ES Cell To examine stability of the mouse artificial chromosome vector MAC3 in mouse ES cells and a mouse individual, mouse artificial chromosome MAC3 is introduced into mouse ES cells, and the chimeric mouse and genetically transmitted progeny mouse containing mouse artificial chromosome vector MAC3 are prepared.

[C. 1] Microcell Fusion and Isolation of Drug Resistant Clone

CHO (HPRT$^-$; MAC3)-1 and -6 as recipient cells were cultured on cell culture dishes. At the time of reaching confluency, the culture medium was exchanged with F12 culture medium supplemented with 20% FBS and 0.1 µg/ml colcemid. After further culturing for 48 hours, the medium culture was exchanged with F12 culture medium supplemented with 20% FBS and 0.1 µg/ml colcemid followed by incubation overnight to form microcells. The culture medium was removed and cytochalasin B (10 µg/ml, Sigma) solution which has been previously kept warm at 37° C. was filled in a flask for centrifugation. The centrifugation was performed for 1 hour at 34° C., at 8000 rpm. The microcells were suspended in serum free DMEM culture medium and purified with filters of 8 µm, 5 µm, and 3 µm. After the purification, the microcells were centrifuged for 10 min at 2000 rpm, and suspended in 5 ml of serum free DMEM culture medium. The microcells were suspended in 5 ml of serum free DMEM culture medium and purified with filters of 8 µm, 5 µm, and 3 µm. After the purification, the cells were centrifuged for 10 min at 2000 rpm.

As a donor cell, B6 (HPRT$^-$), which is HPRT depleted cell line obtained by treating ES cells derived from a mouse C57B6 lineage obtained from CLEA Japan, Inc. with 6TG, was used. For cell culture, to DMEM (Dulbecco's Modified Eagle's Medium-high glucose: SIGMA), 10% FCS, LIF (Muerin Leukemia Inhibitory Factor), 1×10$^{-5}$ M 2-ME (2-mercaptoethanol: SIGMA), L-glutamine (3.5 g/ml: GIBCO), sodium pyruvate solution (3.5 g/ml: GIBCO), and MEM nonessential amino acid (0.125 mM: GIBCO) were added and culture was performed at 5% CO$_2$, 37° C. After washing twice the cell surface of mouse ES cells with PBS (−), the cells were dispersed with trypsin treatment and recovered with culture medium in which 10% FBS was added to DMEM culture medium. Centrifugation was carried out at 1500 rpm, the supernatant was removed and re-suspended in 5 ml of serum free culture medium and gently added to the serum free culture medium containing pellets of microcells after centrifugation. It was further centrifuged at 1200 rpm. The supernatant was removed and fused with 0.5 ml of PEG1000 (Wako) solution [5 g of PEG1000 is dissolved completely in serum free DMEM culture medium, added with 1 ml of dimethyl sulfoxide, and sterilized by filtration] precisely for 1 min and 30 sec. 13 ml of serum free culture medium (DMEM) was gently added and centrifuged at 1200 rpm. The supernatant was removed, common culture medium for mouse ES cells was added, and by using G418 resistant mouse embryonic fibroblast treated with mitomycin as a feeder cell, the cells were plated onto two cell culture dishes with a diameter of 10 cm followed by incubation overnight. G418 was added so as to be 250 µg/ml and selection culture was carried out for 3 to 4 weeks. Total 28 resistant colonies obtained by two microcell fusions were isolated, amplified, and subjected to the following analysis (clone name: B6 (HPRT$^-$; MAC3)).

[C. 2] Selection of Drug Resistant Clone

[C. 2. 1] PCR Analysis

For extracting genomic DNA from the G418 resistant cell line and using it as a template for selecting a recombinant, PCR was carried out by using the following primers, and it was confirmed whether or not site specific cleavage has occurred on mouse chromosome 11. The primer sequences are given below.

kj neo (described above)
m11 6R (described above)
m11 17L (described above)
Puro-1 (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 10 min were carried out. As a result of PCR, 27 clones out of the 28 clones were found to be positive for all primer sets, and the following analysis was performed by using those 27 clones.

TABLE 27

| | Origin | | | | | | | | | | | | | | | | | |
|---|---|---|---|---|---|---|---|---|---|---|---|---|---|---|---|---|---|---|
| | CHO (HPRT−; MAC3)-6 | CHO (HPRT−; MAC3)5 | | | | | | CHO(HPRT−; MAC3)-1 | | | | | | | | | | |
| | | | | | | | | Clone name | | | | | | | | | | |
| | B6 (HPRT−; MAC3) | | | | | | | B6(HPRT−; MAC3) | | | | | | | | | | |
| | | | | | | | | Clone number | | | | | | | | | | |
| | 1 | 2 | 3 | 4 | 5 | 6 | 7 | 8 | s1 | s2 | s3 | s4 | s5 | s6 | s7 | s8 | s9 | s10 |
| kj neo/m11 6R | ○ | ○ | ○ | ○ | ○ | ○ | ○ | ○ | ○ | ○ | ○ | ○ | ○ | ○ | ○ | ○ | ○ | ○ |
| m11 17L/Puro-1 | ○ | ○ | ○ | ○ | ○ | X | ○ | ○ | ○ | ○ | ○ | ○ | ○ | ○ | ○ | ○ | ○ | ○ |

| | Origin CHO(HPRT−; MAC3)-1 Clone name B6(HPRT−; MAC3) Clone number | | | | | | | | | | Positive control | Negative control |
|---|---|---|---|---|---|---|---|---|---|---|---|---|
| | s11 | s12 | s13 | s14 | s15 | s16 | s17 | s18 | s19 | s20 | CHO H−/− | B6-ES |
| kj neo/m11 6R | ○ | ○ | ○ | ○ | ○ | ○ | ○ | ○ | ○ | ○ | (MAC3)-5 | HPRT−/− |
| m11 17L/Puro-1 | ○ | ○ | ○ | ○ | ○ | ○ | ○ | ○ | ○ | ○ | ○ | X |

[C. 2. 2] Mono-Color FISH Analysis

For the 16 clones of B6 (HPRT−; MAC3) obtained from the above, FISH analysis was carried out by using mouse minor satellite DNA as a probe according to the method described by Shinohara et al. (Human Molecular Genetics, 10: 1163-1175, 2001). As a result, it was confirmed that MAC3 was introduced into the mouse ES cells with a rate of 95% or more in five clones out of the 16 clones.

Figure 27:
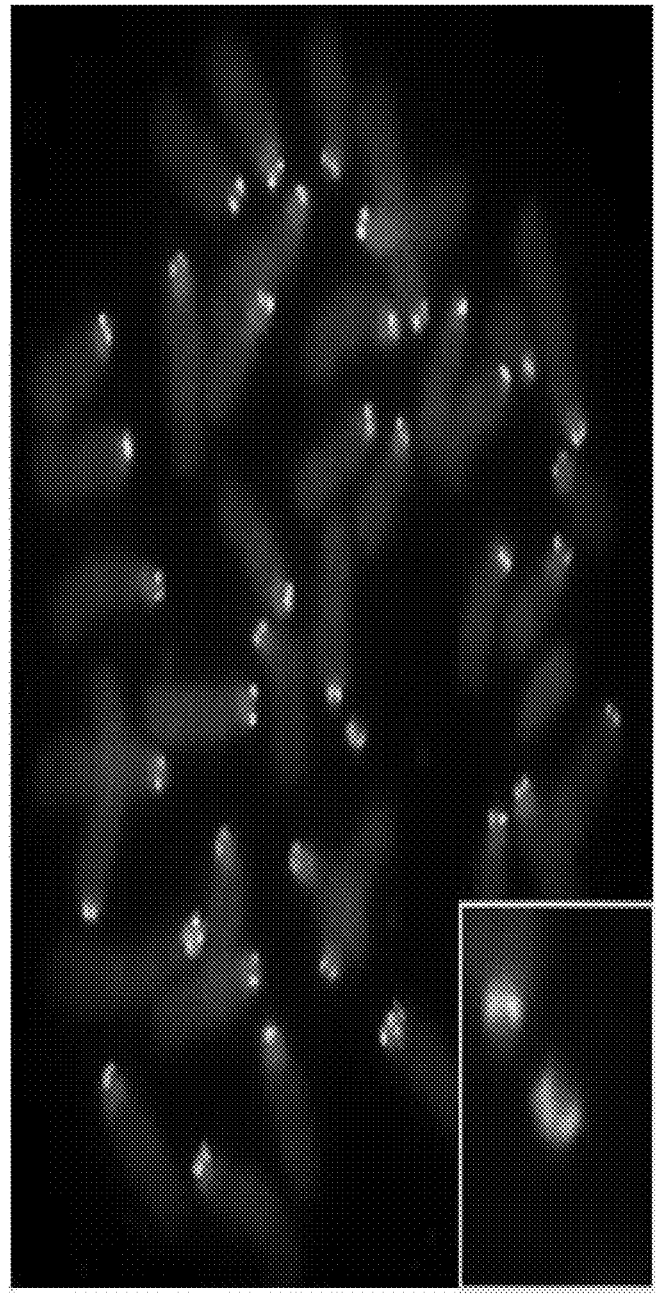
FIG. 27 shows the results of the mono-color FISH analysis of drug resistant clone B6 (HPRT⁻; MAC3) in which mouse minor satellite DNA was used as a probe.

From these results, it was concluded that the mouse artificial chromosome vector MAC3 could be introduced into mouse ES cells (FIG. 27).

From these results, it was confirmed that the mouse artificial chromosome vector MAC3 is very stably maintained at a rate of 95% or more in mouse ES cells (in vitro).

[E] Preparation of Chimeric Mouse Retaining the Artificial Chromosome Vector MAC3

By using the ES cell clones obtained from the above, a chimeric mouse was prepared according to the technique in (Gene Targeting, Experimental Medicine, 1995). As a host cell, the morula obtained by sexual crossbreeding of MCH (ICR) (white, purchased from CLEA Japan, Inc.) was used. Injected embryo is transplanted into a foster mother, and

TABLE 28

| | Metaphase | | | | | | | | | | | |
|---|---|---|---|---|---|---|---|---|---|---|---|---|
| | 38 + MACx1 | 39 + 0 | 39 + MACx1 | 40 + 0 | 40 + MACx1 | 40 + MAC fragmentx1 | 40 + MACx2 | 41 + MACx1 | 41 + MACx2 | 41 + 0 | MACx1/ 4n | Total | Origin |
| B6 (HPRT−; MAC3)-1 | 3 | 1 | | | 1 | | | 2 | | | | 7 | CHO (HPRT−; MAC3)-6 |
| B6 (HPRT−; MAC3)-2 | | | 2 | | | 16 | 2 | | | | | 20 | CHO (HPRT−; MAC3)-6 |
| B6 (HPRT−; MAC3)-3 | 1 | | 1 | 1 | 16 | 1 | | | | | | 20 | CHO (HPRT−; MAC3)-6 |
| B6 (HPRT−; MAC3)-4 | | | | 3 | | | | | | 17 | | 20 | CHO (HPRT−; MAC3)-5 |
| B6 (HPRT−; MAC3)-5 | | | | 6 | | | 2 | 4 | 4 | 4 | | 20 | CHO (HPRT−; MAC3)-5 |
| B6 (HPRT−; MAC3)-7 | | 1 | | 16 | | | 2 | 1 | | | | 20 | CHO (HPRT−; MAC3)-5 |
| B6 (HPRT−; MAC3)-s1 | | | 1 | 2 | 16 | | 1 | | | | | 20 | CHO (HPRT−; MAC3)--1 |
| B6 (HPRT−; MAC3)-s2 | | | | | 8 | | 12 | | | | | 20 | CHO (HPRT−; MAC3)--1 |
| B6 (HPRT−; MAC3)-s3 | | | | | | | | | | | 20 | 20 | CHO (HPRT−; MAC3)--1 |
| B6 (HPRT−; MAC3)-s4 | | | | 1 | 19 | | | | | | | 20 | CHO (HPRT−; MAC3)--1 |
| B6 (HPRT−; MAC3)-s5 | | 2 | | 6 | 10 | | 2 | | | | | 20 | CHO (HPRT−; MAC3)--1 |
| B6 (HPRT−; MAC3)-s6 | 1 | | 1 | | 17 | | 1 | | | | | 20 | CHO (HPRT−; MAC3)--1 |
| B6 (HPRT−; MAC3)-s7 | | | | 4 | 8 | | | 8 | | | | 20 | CHO (HPRT−; MAC3)--1 |
| B6 (HPRT−; MAC3)-s8 | | | | | | | | | | | 20 | 20 | CHO (HPRT−; MAC3)--1 |
| B6 (HPRT−; MAC3)-s9 | | 1 | | 1 | 8 | | 2 | | | | 8 | 20 | CHO (HPRT−; MAC3)--1 |
| B6 (HPRT−; MAC3)-s10 | 1 | | | 2 | 17 | | | | | | | 20 | CHO (HPRT−; MAC3)--1 |

[D] Stability of the Mouse Artificial Chromosome Vector MAC3 in Mouse ES Cells

Figure 28:
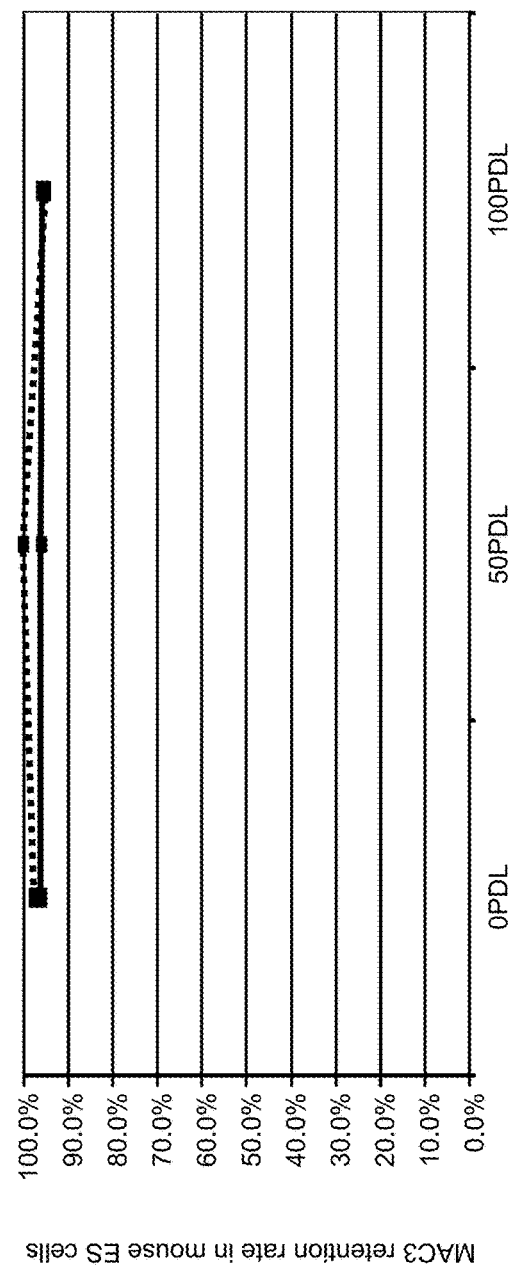
FIG. 28 shows the results of the analysis of retention rate during long-term culture of B6 (HPRT⁻; MAC3) clone. The solid line and the dashed line indicate the MAC vector retention rates in B6 (HPRT⁻: MAC3)-3 and B6 (HPRT⁻: MAC3)-s6, respectively.

Under non-selection culture of 0 to 100 PDL for the mouse ES clones obtained from the above (for example, B6 (HPRT−; MAC3)-3, -s6, obtained from the above [C]), the rate of cells retaining MAC1 after long term culture was measured by FISH analysis. As a result, the retention rate of 95% or more was obtained even for 100 PDL (FIG. 28).

coat color of the new-born mouse is examined to see whether or not it is a chimera. Further, the chimeric rate can be determined from the intracellular contribution of ES cells for forming an individual in ICR embryonic cells.

As a result of transplanting 60 embryos injected with B6 (HPRT; MAC3) clone (for example, B6 (HPRT; MAC3)-ES (MAC3)-s6 obtained from the above) into a foster mother, eight chimeric mice (dark brown color area is observed in coat color) were born. Among eight animals, two were males in which one was 10% chimeric mouse and the other one was 5% chimeric mouse and six were females in which four were 10% chimeric mouse and the remaining two were 5% chimeric mouse. In other words, it was shown that ES cell line (B6 HPRT−/− cell line) retaining mouse artificial chromosome MAC3 retains a chimera forming ability, that is, an ability of differentiating into normal tissues of a mouse individual.

[F] As described in Example 8, mouse line-based TC (MAC3) in which MAC3 is transmitted to a progeny can be prepared by crossbreeding a chimeric mouse retaining the mouse artificial chromosome vector MAC3 and a wild type mouse. Further, by using TC (MAC3) mouse line, stability of MAC3 in somatic cells can be examined.

Example 6

Construction of the Mouse Artificial Chromosome Vector GFP-MAC

Figure 5:
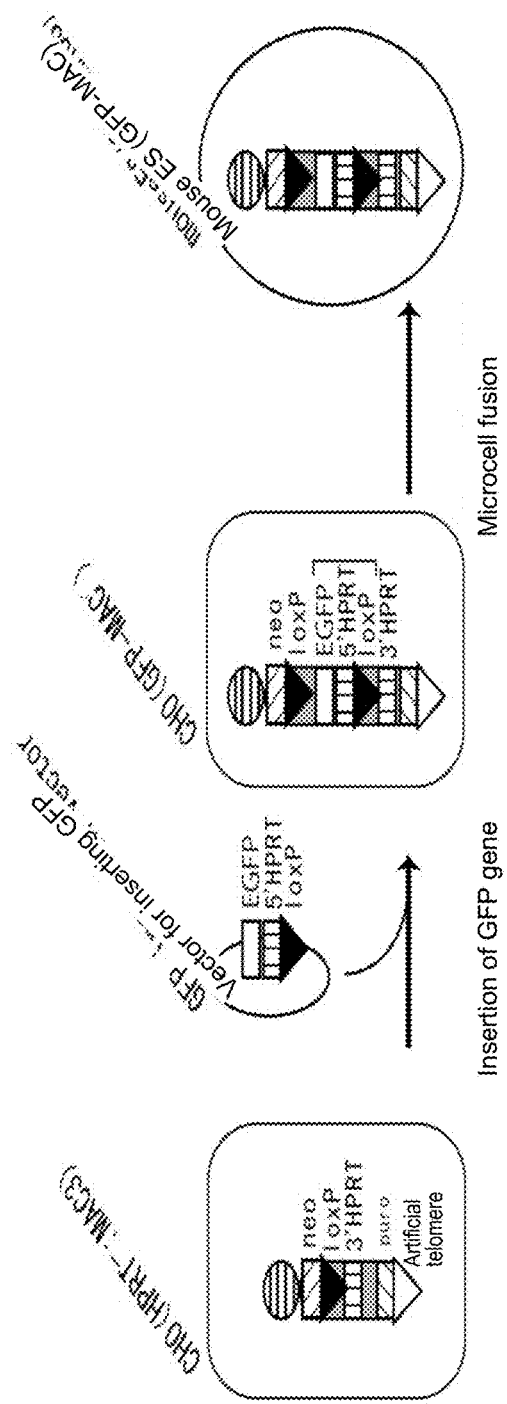
FIG. 5 is a schematic diagram illustrating the procedures of Example 6. Cell names in the drawings are described according to the following format. Cell name (cellular genetic modification; retained chromosome fragment name, and transgene-retaining chromosome name). Symbols given in the drawings are as follows. neo: neomycin (G418) resistant gene, loxP: site specific DNA sequence insertion site, 3' HPRT: the 3rd to 9th exon sequences of HPRT gene, puro: puromycin resistant gene, artificial telomere: artificial telomere (TTAGGG) repeat sequence, EGFP: gene expressing enhanced green fluorescent protein, 5' HPRT: the 1st to 2nd exon sequences of HPRT gene.

As an example of a gene encoding useful proteins, EGFP as a fluorescence gene is inserted into the mouse artificial chromosome vector MAC3 by using Cre/loxP system and expression of functional protein and long-term stability are examined (FIG. 5).

[A] Insertion of Specific Gene (for Example, GFP) into the Mouse Artificial Chromosome Vector MAC3 by Using Cre/loxP System in CHO Cell Containing Mouse Artificial Chromosome Vector MAC3

It is examined whether or not loxP is operated and plasmid DNA can be site-specifically inserted for the mouse artificial chromosome vector MAC3 obtained by inserting PGKneo-loxP-3' HPRT type loxP sequence as a DNA insertion sequence into mouse artificial chromosome MAC.

[A. 1] Preparation of EGFP Insertion Vector

Figure 29:
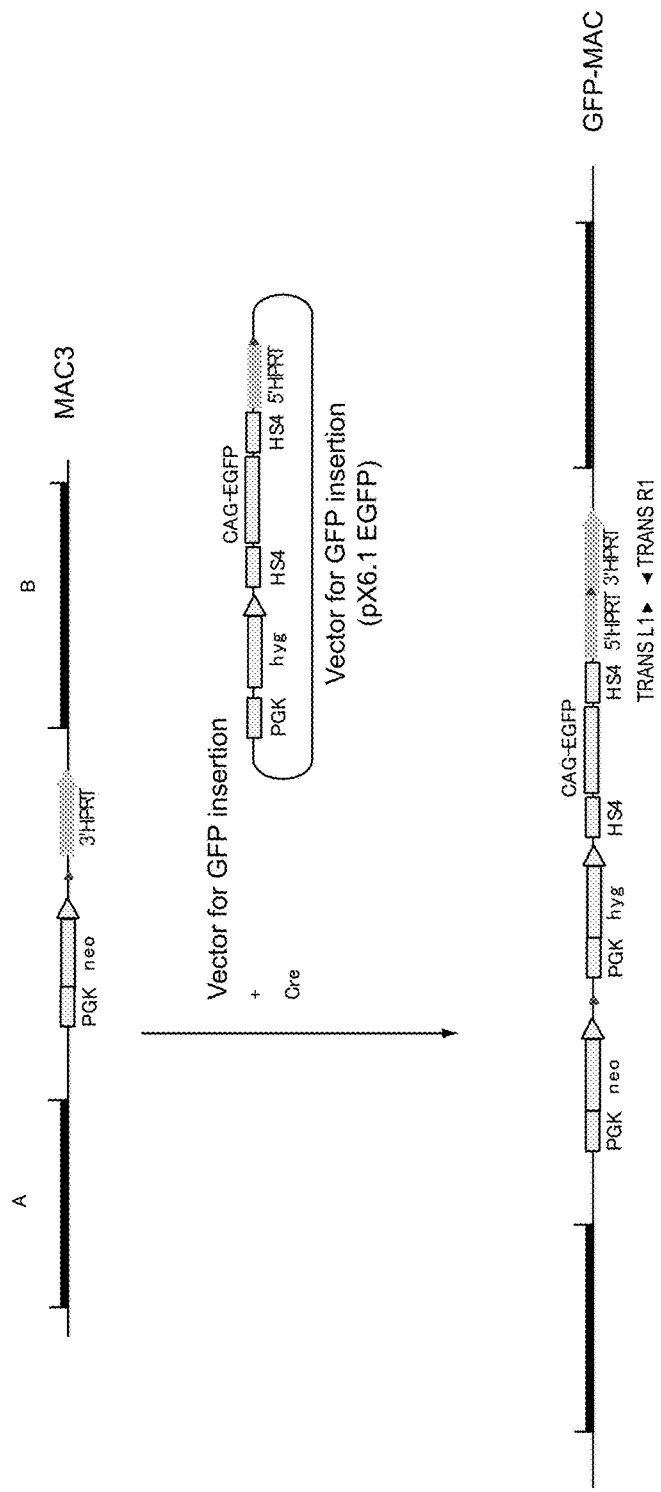
FIG. 29 shows the procedure for performing the site-specific gene insertion of a certain gene (for example, GFP) into the mouse artificial chromosome vector MAC3 by Cre-loxP method, a vector for inserting GFP, and a partial structure of the mouse chromosome 11 allele in which homologous recombination was carried out by using the vector.

As a basic plasmid for inserting loxP sequence, V913 (Lexicon genetics) was used. In 5' HPRT-loxP, loxP sequence obtained by oligo synthesis was cloned into XbaI site of V820 (Lexicon genetics). 5' HPRT-loxP was cloned into ClaI and AscI of V907 (Lexicon genetics), and PGKhygro was cloned into ClaI and KpnI sites (vector name: pX6.1). Further, into the NotI site and SalI site of X6.1, HS4-CAG-EGFP-HS4 cut out by using NotI and SalI (provided by Dr. Okabe at Osaka University and Dr. Felsenfeld at NIH) was cloned to give a GFP-inserted construct for HPRT reconstruction system (vector name: pX6.1 EGFP). Chromosome site specific DNA insertion obtained by GFP insertion in HPRT reconstruction system based on Cre/loxP system is given in FIG. 29.

[A. 2] Transfection and Isolation of HAT Resistant Clone

Gene introduction was carried out by lipofection. To cells in 6 wells with 90% confluency, 1 µg of Cre and 2 µg of GFP insertion vector were introduced according to the commercially available protocol (Invitrogen). After culture for 2 weeks under HAT selection culture, a resistant colony was generated and total 22 colonies obtained by two introductions were isolated, amplified, and subjected to the following analysis (clone name: CHO (GFP-MAC)).

[A. 3] Selection of Drug Resistant Clone

[A. 3. 1] Confirmation of GFP Insert According to Fluorescence Microscope Observation 22 cloned colonies were observed under a fluorescence microscope, and as a result, all clones were observed to have GFP positive cells, and the positive rate was almost 100%.

[A. 3. 2] PCR Analysis

In order to select a recombinant by using genomic DNA of HAT resistant cell line as a template, PCR was carried out by using the following primers, and it was confirmed whether or not site specific insertion of GFP gene has occurred. The primer sequences are given below.

TRANS L1 (described above)

TRANS R1 (described above)

For PCR, GeneAmp 9600 manufactured by PerkinElmer, Inc. was used as a thermal cycler and Ampli Taq Gold (Applied Biosystems) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 10 min, 35 cycles of 94° C. for 30 sec, 60° C. for 30 sec, and 72° C. for 30 sec were carried out. As a result of PCR, all 22 clones were found to be positive and, the following analysis was performed by using those 22 clones.

TABLE 29

| | Origin | | | | | | | | | | | | | | | | | | | | | | |
|---|---|---|---|---|---|---|---|---|---|---|---|---|---|---|---|---|---|---|---|---|---|---|---|
| | CHO (HPRT⁻; MAC3)-5 | | | | | | | | | CHO (HPRT⁻; MAC3)-6 | | | | | | | | | | | | | Negative control CHO |
| | Clone name CHO (GFP-MAC) Clone number | | | | | | | | | | | | | | | | | | | | | | |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | (HPRT) |
| TRANS L1/R1 | ○ | ○ | ○ | ○ | ○ | ○ | ○ | ○ | ○ | ○ | ○ | ○ | ○ | ○ | ○ | ○ | ○ | ○ | ○ | ○ | ○ | ○ | X |

[A. 3. 3] Two-Color FISH Analysis

Figure 30:
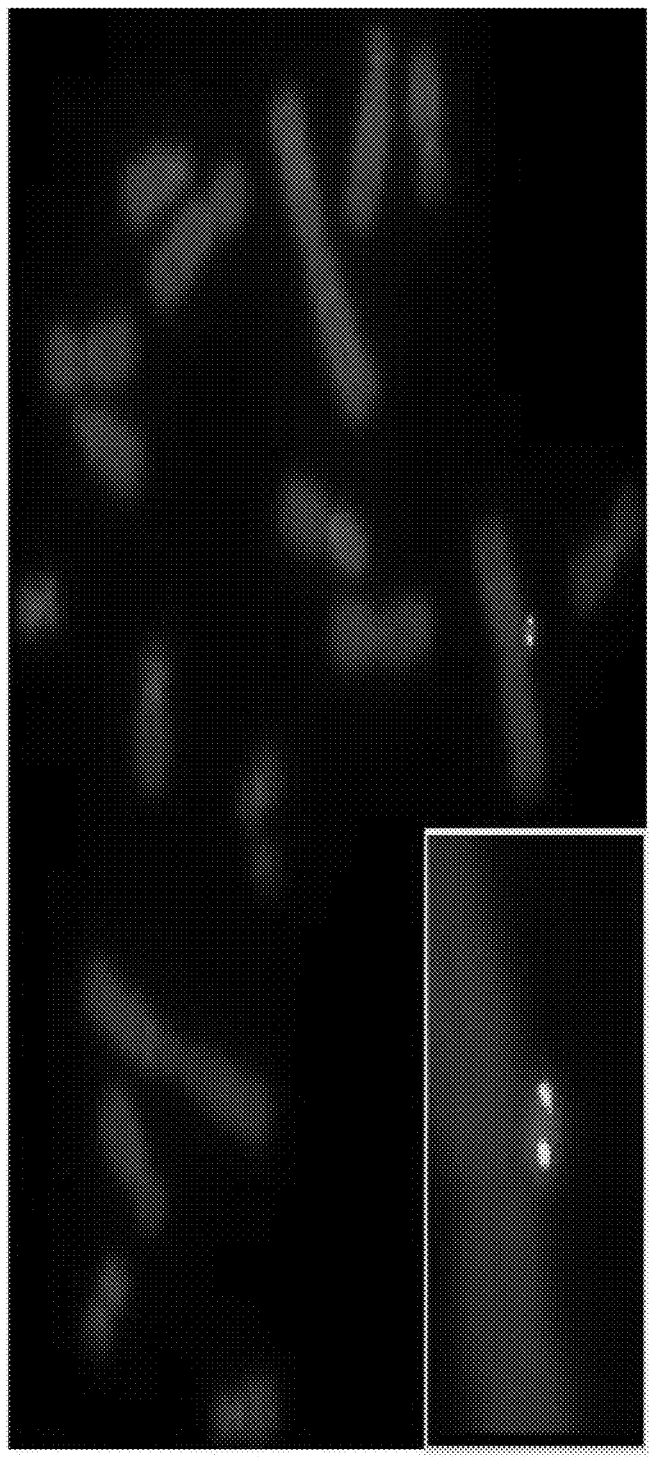
FIG. 30 shows the results of the two-color FISH analysis of CHO (GFP-MAC) clone, which is a CHO cell retaining the mouse artificial chromosome GFP-MAC, in which mouse Cot-1 DNA and X6.1 EGFP were used as probes.

For the randomly selected six clones, two-color FISH analysis was carried out according to Matsubara et al. (FISH test protocol, Shujunsha Co., Ltd., 1994). FISH analysis was carried out by using mouse cot-1 DNA and X6.1EGFP as probes. As a result, it was found that, in three clones out of the six clones, a single copy of GFP-MAC was retained at a rate of 50% or more and signal derived from X6.1EGFP was generated. Since no signal was detected from MAC3 before site specific insertion of EGFP as a negative control, it was confirmed that EGFP was site-specifically inserted (FIG. 30).

TABLE 30

| | Metaphase | | | | | | | | | | | Interphase | | | | | |
|---|---|---|---|---|---|---|---|---|---|---|---|---|---|---|---|---|---|
| | X1 F(−)/ x0/2n | X1 F(+)/ 2n | x2 F(+, +) 2n | x2 F(+, −) 4n | x2 F(−, −) 4n | x2 F(+, −)/ 4n | x3 (+, +) 2n | x3 (+, +) +)/2n | With trans- location +)/4n | Total | x0 | x1 | x2 | x3 | Total | Origin |
|---|---|---|---|---|---|---|---|---|---|---|---|---|---|---|---|---|
| CHO (HPRT−; MAC)-5 | 5 | 13 | 1 | | 1 | | | | | | 20 | 22 | 63 | 13 | 2 | 100 | |
| CHO (GFP-MAC)-2 | 2 | 7 | 9 | | | 2 | | | | | 20 | 22 | 71 | 2 | 5 | 100 | CHO (HPRT−; MAC3)-5 |
| CHO (GFP-MAC)-4 | 2 | 1 | 10 | | | | | | | 7 | 20 | 7 | 79 | 10 | 4 | 100 | CHO (HPRT−; MAC3)-5 |
| CHO (GFP-MAC)-5 | 2 | | 5 | | | 1 | | | | 12 | 20 | 9 | 81 | 5 | 5 | 100 | CHO (HPRT−; MAC3)-5 |
| CHO (GFP-MAC)-8 | | | 1 | | | | | | | 19 | 20 | 4 | 32 | 42 | 22 | 100 | CHO (HPRT−; MAC3)-5 |
| CHO (GFP-MAC)-10 | | 3 | 13 | 1 | | 1 | 1 | | | 1 | 20 | 32 | 63 | 3 | 2 | 100 | CHO (HPRT−; MAC3)-5 |
| CHO (GFP-MAC)-12 | 3 | 13 | 2 | | | | | | 1 | 1 | 20 | 8 | 76 | 14 | 2 | 100 | CHO (HPRT−; MAC3)-5 |

From the above experiments, it was confirmed that GFP expression was observed based on the fact that the mouse artificial chromosome MAC3 carried the GFP gene, and as a result, CHO cells retaining the mouse artificial chromosome vector GFP-MAC were obtained.

[B] Introduction of GFP-MAC from CHO Cell Containing the Mouse Artificial Chromosome Vector GFP-MAC to Mouse ES Cell

[B. 1] Microcell Fusion and Isolation of Drug Resistant Clone

CHO (GFP-MAC)-4, -10, and -12 as recipient cells were cultured on cell culture dishes. At the time of reaching confluency, the culture medium was exchanged with F12 culture medium supplemented with 20% FBS and 0.05 µg/ml colcemid. After further culturing for 48 hours, the culture medium was exchanged with F12 culture medium supplemented with 20% FBS and 0.05 µg/ml colcemid followed by incubation overnight to form microcells. The culture medium was removed and cytochalasin B (10 µg/ml, Sigma) solution which has been previously kept warm at 37° C. was filled in a flask for centrifugation. The centrifugation was performed for 1 hour at 34° C., 8000 rpm. The microcells were suspended in serum free DMEM culture medium and purified with filters of 8 µm, 5 µm, and 3 µm. After the purification, the cells were centrifuged for 10 min at 2000 rpm, and suspended in 5 ml of serum free DMEM culture medium.

The microcells were suspended in 5 ml of serum free DMEM culture medium and purified with filters of 8 µm, 5 µm, and 3 µm. After the purification, the cells were centrifuged for 10 min at 2000 rpm.

As a donor cell, wild type B6 cells, which were established from ES cells derived from a mouse C57B6 lineage obtained from CLEA Japan, Inc. and mouse ES cells of wild type TT2F cell, were used. For cell culture, DMEM (Dulbecco's Modified Eagle's Medium-high glucose: SIGMA) supplemented with 10% FCS, LIF (Muerin Leukemia Inhibitory Factor), $1 \times 10^{-5}$ M 2-ME (2-mercaptoethanol: SIGMA), L-glutamine (3.5 g/ml: GIBCO), sodium pyruvate solution (3.5 g/ml: GIBCO), and MEM nonessential amino acid (0.125 mM: GIBCO) and culture was performed in the presence of 5% $CO_2$ at 37° C. After washing twice the cell surface of mouse ES cells with PBS (−), the cells were dispersed with trypsin treatment, and recovered with culture medium in which 10% FBS was added to DMEM culture medium. Centrifugation was carried out at 1500 rpm, the supernatant was removed, re-suspended in 5 ml of serum free culture medium, and gently added to the serum free culture medium containing pellets of microcells after centrifugation. It was further centrifuged at 1200 rpm. The supernatant was removed and fused with 0.5 ml of PEG1000 (Wako) solution [5 g of PEG1000 is dissolved completely in serum free DMEM culture medium, added with 1 ml of dimethyl sulfoxide, and sterilized by filtration] precisely for 1 min and 30 sec. 13 ml of serum free culture medium (DMEM) was gently added and centrifuged at 1200 rpm. The supernatant was removed, common culture medium for mouse ES cells was added, and by using G418 resistant mouse embryonic fibroblast treated with mitomycin as a feeder cell, the cells were plated onto two cell culture dishes with a diameter of 10 cm followed by incubation overnight. G418 was added to 250 µg/ml and selection culture was carried out for 3 to 4 weeks. Total 36 resistant colonies obtained by two microcell fusions were isolated, amplified, and subjected to the following analysis (clone name: TT2F (GFP-MAC) and B6-ES (GFP-MAC)).

[B. 2] Selection of Drug Resistant Clone
[B. 2. 1] PCR Analysis

For extracting genomic DNA from G418 resistant cell line and using it as a template for selecting a recombinant, PCR was carried out by using the following primers, and it was confirmed whether or not site specific cleavage has occurred on mouse chromosome 11. The primer sequences are given below.

TRANS L1: (described above)
TRANS R1: (described above)
m11 6R (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions for TRANS L1/R1 were as follows: after heat denaturation at 94° C. for 1 min, 35 cycles of 98° C. for 10 sec and 68° C. for 1 min were carried out. Temperature and cycle conditions for TRANS L1/m11 6R were as follows: after heat denaturation at 94° C. for 1 min, 35 cycles of 98° C. for 10 sec and 68° C. for 7 min were carried out. As a result of PCR, 34 clones out of the 36 clones were found to be positive for all primer sets, and the following analysis was performed by using 24 clones randomly selected from the positive clones.

TABLE 31

| Clone name • Number | CHO (GFP-MAC)-derived clone | TRANS L1/R1 | TRANS L1/m11 6R |
|---|---|---|---|
| TT2F(GFP-MAC)-1 | 4 | ○ | ○ |
| TT2F(GFP-MAC) -2 | 4 | ○ | ○ |
| TT2F(GFP-MAC) -3 | 4 | ○ | ○ |
| TT2F (GFP-MAC) -4 | 4 | ○ | ○ |
| TT2F (GFP-MAC) -5 | 4 | ○ | ○ |
| TT2F (GFP-MAC) -6 | 4 | ○ | ○ |
| TT2F (GFP-MAC) -7 | 4 | ○ | ○ |
| TT2F (GFP-MAC) -8 | 4 | ○ | ○ |
| TT2F (GFP-MAC) -9 | 4 | ○ | ○ |
| TT2F (GFP-MAC) -10 | 10 | ○ | ○ |
| TT2F (GFP-MAC) -11 | 4 | ○ | ○ |
| TT2F (GFP-MAC) -12 | 4 | ○ | ○ |
| TT2F (GFP-MAC) -13 | 4 | ○ | ○ |
| TT2F (GFP-MAC) -14 | 4 | ○ | ○ |
| TT2F (GFP-MAC) -15 | 10 | Δ | ○ |
| TT2F (GFP-MAC) -16 | 10 | ○ | ○ |
| TT2F (GFP-MAC) -17 | 10 | ○ | ○ |
| TT2F (GFP-MAC) -18 | 10 | ○ | ○ |
| TT2F (GFP-MAC) -19 | 10 | ○ | ○ |
| TT2F (GFP-MAC) -20 | 10 | ○ | ○ |
| TT2F (GFP-MAC) -21 | 10 | ○ | ○ |
| TT2F (GFP-MAC) -22 | 12 | ○ | ○ |
| B6-ES (GFP-MAC) -1 | 4 | ○ | ○ |
| B6-ES (GFP-MAC) -2 | 4 | ○ | ○ |
| B6-ES (GFP-MAC) -3 | 4 | ○ | ○ |
| B6-ES (GFP-MAC) -4 | 4 | ○ | ○ |
| B6-ES (GFP-MAC) -5 | 4 | ○ | ○ |
| B6-ES (GFP-MAC) -6 | 4 | ○ | ○ |
| B6-ES (GFP-MAC) -7 | 10 | ○ | X |
| B6-ES (GFP-MAC) -8 | 10 | ○ | ○ |
| B6-ES (GFP-MAC) -9 | 10 | ○ | ○ |
| B6-ES (GFP-MAC) -10 | 10 | ○ | ○ |
| B6-ES (GFP-MAC)-11 | 10 | ○ | ○ |
| B6-ES (GFP-MAC) -12 | 4 | ○ | ○ |
| B6-ES (GFP-MAC) -14 | 12 | ○ | X |
| CHO (GFP-MAC)-10 | Positive control | ○ | ○ |
| TT2F | Negative control | X | X |
| B6-ES | Negative control | X | X |

[B. 2. 2] Quinacrine-Hoechst Double Staining

Clones found to be positive by the above PCR analysis were subjected to Quinacrine-Hoechst double staining by the same method described above. Chromosome images of the clone obtained after Quinacrine-Hoechst double staining were fluorescence-microscopically observed, and as a result it was found that 18 clones out of the 24 clones retained the mouse artificial chromosome GFP-MAC at a rate of 100%.

TABLE 32

| | Without MAC Metaphase | | With MAC Metaphase | | | | | | | | | | |
|---|---|---|---|---|---|---|---|---|---|---|---|---|---|
| | 39 + 0 | 40 + 0 | 35 + Mx1 | 38 + Mx1 | 38 + Mx2 | 39 + Mx1 | 39 + Mx2 | 39 + Mx3 | 40 + Mx1 | 40 + Mx2 | 41 + Mx1 | 42 + Mx1 | 43 + Mx1 | Total |
| TT2F (GFP-MAC)-1 | 1 | 1 | | | | 7 | | 1 | | | | | | 10 |
| TT2F (GFP-MAC)-2 | 2 | | | 1 | | 6 | | | | | | 1 | | 10 |
| TT2F (GFP-MAC)-3 | 2 | 1 | | 1 | | 6 | | | | | | | | 10 |
| TT2F (GFP-MAC)-5 | | 1 | | | | | 9 | | | | | | | 10 |
| TT2F (GFP-MAC)-6 | | | | | | | | | 4 | 6 | | | | 10 |
| TT2F (GFP-MAC)-7 | | | | | | | | | 2 | 3 | 5 | | | 10 |
| TT2F (GFP-MAC)-10 | | | | | | | | | 4 | 6 | | | | 10 |
| TT2F (GFP-MAC)-11 | | | | | | 7 | 3 | | | | | | | 10 |
| TT2F (GFP-MAC)-12 | | | | | | 10 | | | | | | | | 10 |
| TT2F (GFP-MAC)-13 | 1 | | | 2 | | 5 | 1 | | 1 | | | | | 10 |
| TT2F (GFP-MAC)-15 | | | | | | | | | 3 | | 7 | | | 10 |
| TT2F (GFP-MAC)-16 | 2 | 4 | | | | | 2 | | 2 | | | | | 10 |
| TT2F (GFP-MAC)-17 | | | | 1 | 3 | 6 | | | | | | | | 10 |
| B6-ES (GFP-MAC)-1 | | | | | | | | | | | 5 | 5 | | 10 |
| B6-ES (GFP-MAC)-2 | | | | | | 1 | | | | 9 | | | | 10 |
| B6-ES (GFP-MAC)-3 | | | | | | 1 | | | | | | 8 | 1 | 10 |
| B6-ES (GFP-MAC)-4 | | 3 | | | | | | | 7 | | | | | 10 |
| B6-ES (GFP-MAC)-5 | | | | | | 1 | | | 9 | | | | | 10 |
| B6-ES (GFP-MAC)-6 | | | | | | | | | 1 | | 7 | 2 | | 10 |
| B6-ES (GFP-MAC)-8 | | | | | | | | | 10 | | | | | 10 |
| B6-ES (GFP-MAC)-9 | | | | | | | | | 10 | | | | | 10 |
| B6-ES (GFP-MAC)-10 | | | 2 | | 3 | | | | 5 | | | | | 10 |
| B6-ES (GFP-MAC)-11 | | | | | | | | 10 | | | | | | 10 |
| B6-ES (GFP-MAC)-12 | | | | | | | | | 6 | 4 | | | | 10 |

From these results, it was concluded that the mouse ES cells to which mouse artificial chromosome GFP-MAC has been introduced had a normal nuclear type and could be used for long-term culture and preparation of a chimeric mouse.

[B. 2. 3] Two-Color FISH Analysis

With mouse ES (GFP-MAC) clones obtained from the above, FISH analysis was carried out by using mouse minor satellite DNA and pX6.1E as probes according to the method described by Shinohara et al. (Human Molecular Genetics, 10: 1163-1175, 2001). As a result, it was confirmed that GFP-MAC has been introduced into mouse ES cells at a rate of 95% or more in six clones out of the 12 clones.

From these results, it was concluded that the mouse artificial chromosome vector GFP-MAC could be introduced into mouse ES cells.

Figure 31:
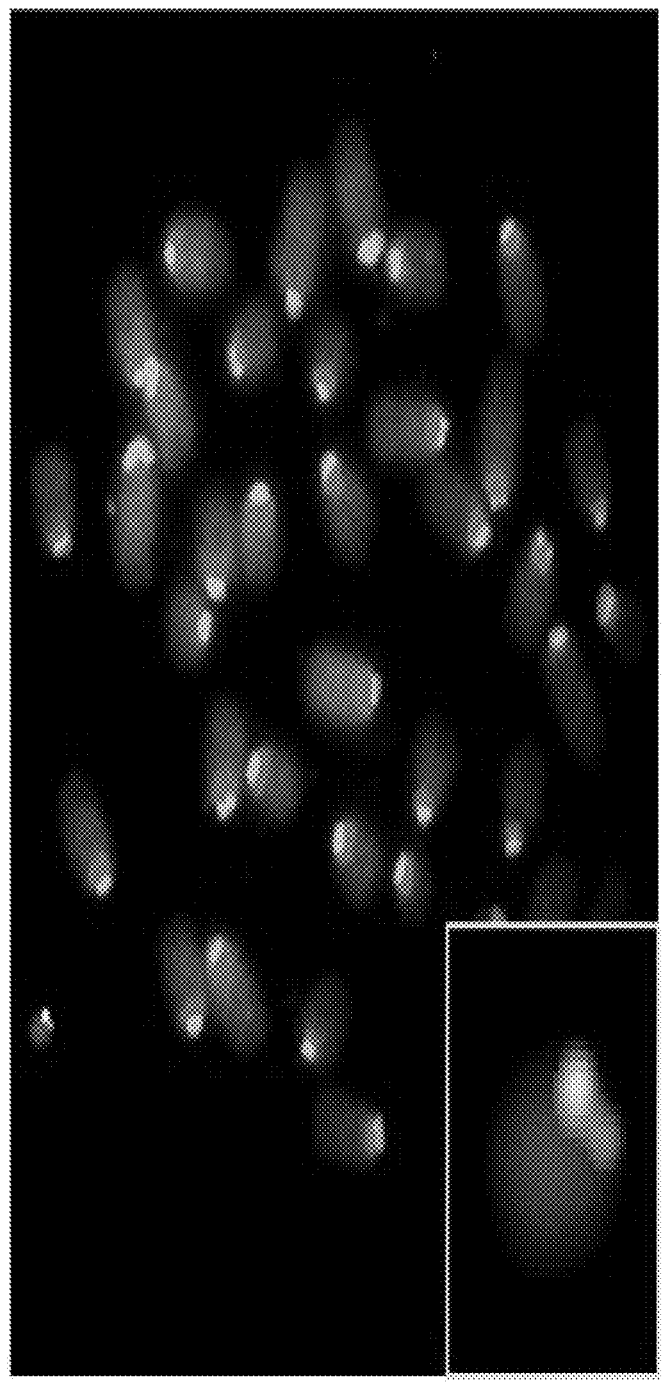
FIG. 31 shows the results of the FISH analysis of the mouse artificial chromosome GFP-MAC after long-term culture of mouse ES cells (B6-ES cell line), in which mouse minor satellite DNA and GFP were used as probes.
Figure 32:
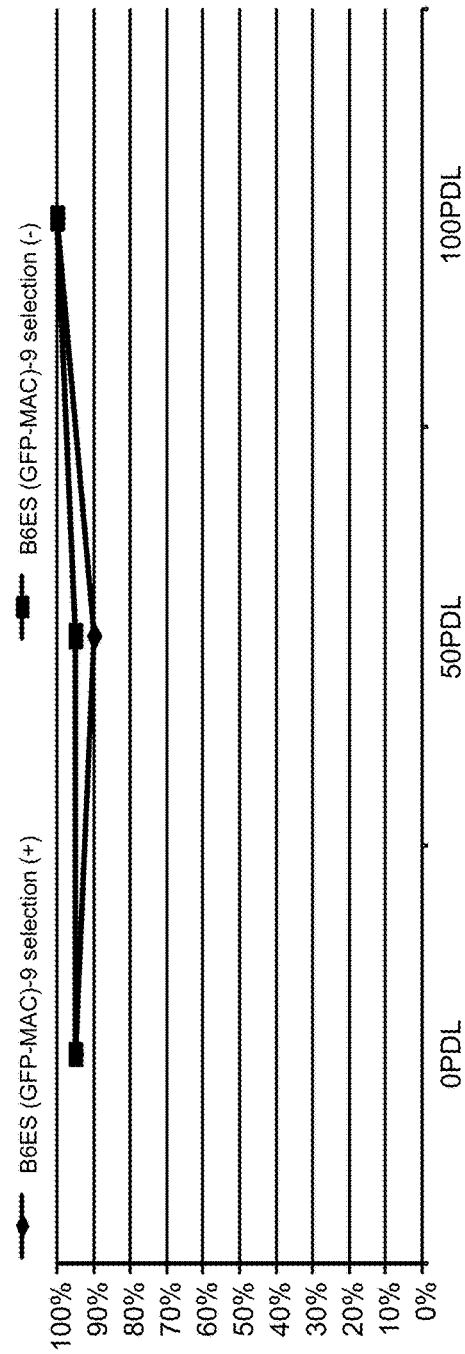
FIG. 32 shows the results of the analysis of retention rate during long-term culture of B6 (GFP-MAC) clone. The diamond represents the retention rate for the long-term culture in which drug selection was performed, while the square represents the retention rate for the long term culture in which no drug selection was performed.

[C] Stability of the Mouse Artificial Chromosome Vector GFP-MAC in Mouse ES Cells Under non-selection culture of 0 to 100 PDL for the mouse ES clones obtained from the above (for example, B6-ES (MAC3)-9, obtained from the above [B]), the rate of cells retaining GFP-MAC3 after long-term culture was measured by FISH analysis. As a result, the retention rate of 95% or more was obtained even for 100 PDL (FIG. 31 and FIG. 32). The colonies were also observed under fluorescence microscope and all clones were observed to have GFP positive cells, and the positive rate was almost 100%.

TABLE 33

| | Metaphase Number of mouse chromosomes | | | | | | | | | | | |
|---|---|---|---|---|---|---|---|---|---|---|---|---|
| | 35 | 36 | 37 | | | 38 | | | | 39 | | |
| | | | | | | MAC copy number | | | | | | |
| | Mx4 | Mx1 | Mx0 | Mx1 | Mx2 | Mx4 | Mx0 | Mx1 | Mx2 | Mx4 | Mx0 | Mx1 | Mx2 |
| B6ES (GFP-MAC)-4 | | | | | | | | | | | 1 | | |
| B6ES (GFP-MAC)-5 | | | | | | | | | | | | 3 | |
| B6ES (GFP-MAC)-8 | 1 | | | | 1 | | | | 2 | | | | |
| B6ES (GFP-MAC)-9 | | | | | | | 2 | | | | | 2 | |
| B6ES (GFP-MAC)-11 | | | | 1 | | | | 1 | | | | | 16 |
| B6ES (GFP-MAC)-12 | | | | | | | | | | | | 1 | 3 |
| TT2F (GFP-MAC)-1 | | 1 | | | | 2 | 2 | | | | 1 | 12 | |
| TT2F (GFP-MAC)-2 | | | 2 | | | | 2 | | | | 2 | 13 | |
| TT2F (GFP-MAC)-3 | | | 3 | | | | 5 | | | | 1 | 9 | |
| TT2F (GFP-MAC)-11 | | | | | | | 2 | | | | 1 | 7 | 9 |
| TT2F (GFP-MAC)-12 | | 1 | | | | | 1 | | | | 2 | 16 | |
| TT2F (GFP-MAC)-13 | | | 2 | 1 | | 1 | 2 | | | | | 8 | 3 |

| | Metaphase Number of mouse chromosomes | | | | | | | | | |
|---|---|---|---|---|---|---|---|---|---|---|
| | 40 | | | | 41 | 44 | 45 | 78 | | |
| | MAC copy number | | | | | | | | | |
| | Mx0 | Mx1 | Mx2 | Mx3 | Mx4 | Mx4 | Mx4 | Mx1 | Mx2 | Total | Origin |
| B6ES (GFP-MAC)-4 | 5 | 13 | 1 | | | | | | | 20 | CHO (GFP-MAC)-4 |
| B6ES (GFP-MAC)-5 | 2 | 15 | | | | | | | | 20 | CHO (GFP-MAC)-4 |
| B6ES (GFP-MAC)-8 | | | | | 14 | 1 | 1 | | | 20 | CHO (GFP-MAC)-10 |
| B6ES (GFP-MAC)-9 | | 16 | | | | | | | | 20 | CHO (GFP-MAC)-10 |
| B6ES (GFP-MAC)-11 | | | 2 | | | | | | | 20 | CHO (GFP-MAC)-10 |
| B6ES (GFP-MAC)-12 | | 6 | 8 | 2 | | | | | | 20 | CHO (GFP-MAC)-4 |
| TT2F (GFP-MAC)-1 | 1 | 1 | | | | | | | | 20 | CHO (GFP-MAC)-4 |
| TT2F (GFP-MAC)-2 | | | | | | | | 1 | | 20 | CHO (GFP-MAC)-4 |
| TT2F (GFP-MAC)-3 | | 1 | | | | | | 1 | | 20 | CHO (GFP-MAC)-4 |
| TT2F (GFP-MAC)-11 | | 1 | | | | | | | | 20 | CHO (GFP-MAC)-4 |
| TT2F (GFP-MAC)-12 | | | | | | | | | | 20 | CHO (GFP-MAC)-4 |
| TT2F (GFP-MAC)-13 | | 1 | | | | | | | | 18 | CHO (GFP-MAC)-4 |

TABLE 34

| | | Number of mouse chromosomes | | | | | | | | | |
|---|---|---|---|---|---|---|---|---|---|---|---|
| | | 38 | | 39 | | | 40 | | 41 | 42 | |
| | | MAC copy number | | | | | | | | | |
| | | x0 | x1 | x0 | x1 | x2 | x0 | x1 | x0 | x1 | x1 | Total | MAC retention rate |
| B6ES(GFP-MAC)-9 0PDL | | 1 | | | | | 1 | 18 | | | | 20 | 95% |
| B6ES(GFP-MAC)-9 50PDL | With drug selection | | | 1 | | | | 17 | 2 | | | 20 | 90% |
| | Without drug selection | | | 1 | | | | 14 | 1 | 4 | | 20 | 95% |
| B6ES(GFP-MAC)-9 100PDL | With drug selection | | | | 3 | | | 7 | | | | 10 | 100% |
| | Without drug selection | 1 | | | 3 | | | 12 | | 3 | 1 | 20 | 100% |

From these results, it was concluded that an exogenous gene having 20 kb or less (for example, EGFP gene) could be site-specifically and efficiently inserted into the mouse artificial chromosome vector MAC3 by using Cre/loxP system, and the MAC3 carrying the exogenous gene was very stable in mouse ES cells and the expression of the exogenous gene on MAC3 was stable for a long period of time.

[D] Preparation of Chimeric Mouse Retaining Artificial Chromosome Vector GFP-MAC By using the ES cell clones obtained from the above [B], a chimeric mouse was prepared according to the known techniques (Gene Targeting, Experimental Medicine, 1995). As a host cell, the morula and eight-cell stage embryo obtained by sexual crossbreeding of MCH (ICR) (white, purchased from CLEA Japan, Inc.) were used. Injected embryo was transplanted into a foster mother, and coat color of the new-born mouse could be examined to see whether or not it is a chimera.

As the result that embryos (260 wild type male B6 (GFP-MAC) clones and 180 wild type female TT2F (GFP-MAC) clones) injected with wild type male B6 (GFP-MAC) clone and wild type (GFP-MAC) TT2F female clone (for example, B6-ES (GFP-MAC) 4 and 18, TT2F (GFP-MAC)-12, which are obtained from the above) were transplanted into foster mothers, chimeric mice (dark brown color area was observed in coat color) were born. 42 chimeric mice derived from male wild type B6 (GFP-MAC) clone were born, and 20 of them were male mice, in which one was GFP-positive 50% chimeric mouse, five were 40% chimeric mouse, one was 30% chimeric mouse, seven were 20% chimeric mouse, three were 10% chimeric mouse, and three were 5% chimeric mouse. Further, 14 chimeric mice derived from wild type TT2F (GFP-MAC) clone were born, and one of them was a GFP-positive individual having a chimeric rate of about 100% from which almost no white color area was observed.

From the above results, it was shown that ES cell line (B6 and TT2F) retaining the mouse artificial chromosome vector GFP-MAC had a chimera forming ability, that is, an ability of differentiating into normal tissues of a mouse individual.

Figure 33:
FIG. 33 shows a progeny transfer individual that was born from a chimeric mouse retaining the mouse artificial chromosome vector (GFP-MAC).

[E] Transmission to Progeny of Mouse Artificial Chromosome from Chimeric Mouse Retaining the Mouse Artificial Chromosome Vector GFP-MAC Among four new-born mice born from a chimeric mouse obtained by crossbreeding between the female chimeric mouse (chimeric rate of about 100%) prepared from the above [D] and the C57B6 (black, purchased from CLEA Japan, Inc.) male mouse, three were observed with fluorescence of GFP, which is a dominant genetic trait of GFP-MAC derived from the ES cells. Further, one new-born mouse among the three animals was observed with fluorescence of GFP from the entire body, and therefore it was found that the mouse artificial chromosome is stable in individual mouse (FIG. 33). The mouse line in which GFP-MAC has been transmitted to a progeny is referred to as TC (GFP-MAC). As described in Example 8, stability of GFP-MAC in somatic cells could be examined by using the TC (GFP-MAC) mouse line.

Example 7

Stability of the Mouse Artificial Chromosome Vector MAC1

[A. 1] Stability of the Mouse Artificial Chromosome Vector MAC1 in CHO Cell

Figure 34:
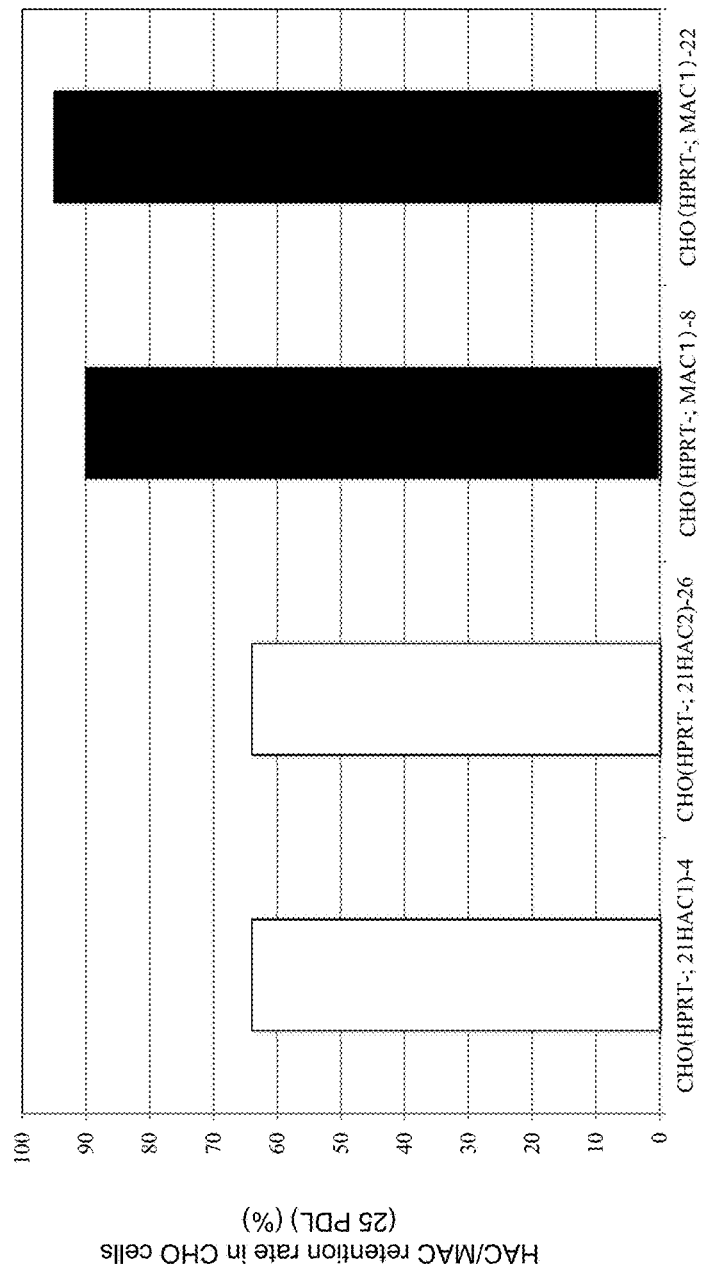
FIG. 34 shows the retention rate of 21HAC1 or 21HAC2 and MAC1 in CHO cells after long-term culture (25 PDL).

Under non-selection culture of 0 to 25 PDL for the CHO clones (for example, CHO (HPRT$^-$; MAC1)-8 and -22, obtained from Example 2 above) obtained from the above, the rate of cells retaining MAC1 after long-term culture was measured by FISH analysis. As a result, the retention rate of 90% or more was obtained even for 25 PDL. Meanwhile, in the CHO cells retaining HAC vector (21HAC2) carrying GFP derived from chromosome 21 described by Kazuki et al. (Gene Therapy: PMID: 21085194, 2010), the retention rate was 70% or less for 25 PDL. The representative results are given in FIG. 34.

Figure 35:
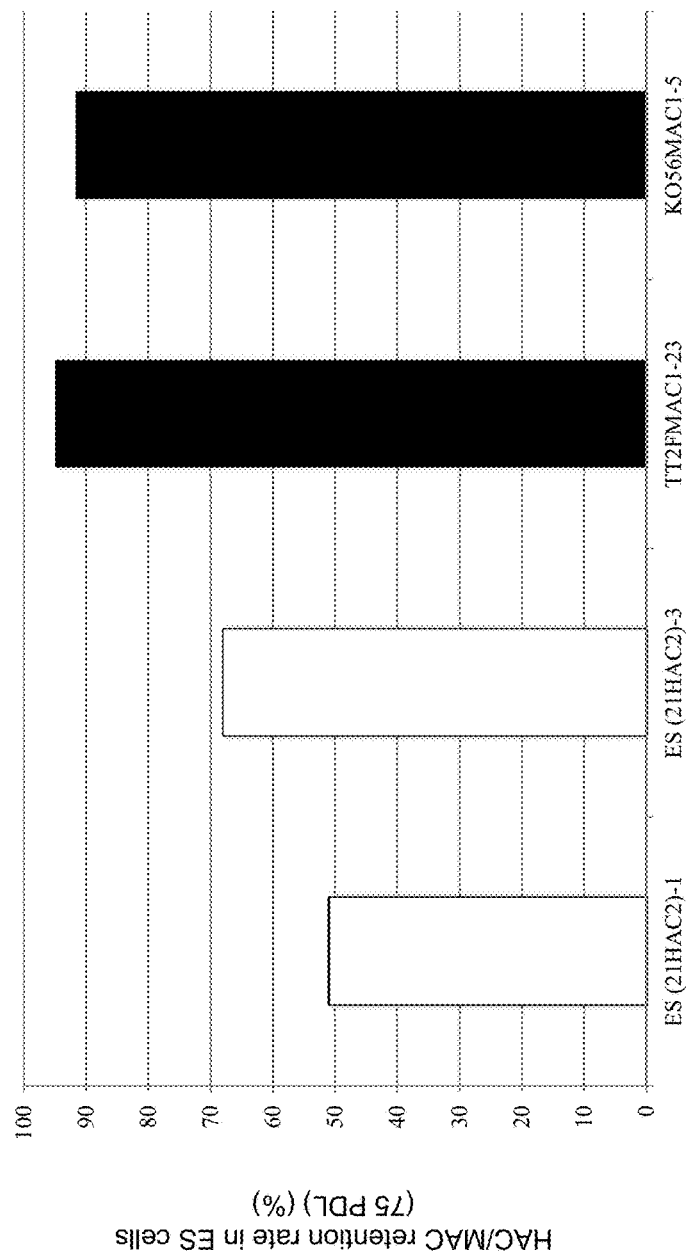
FIG. 35 shows the retention rate of 21HAC2 or MAC1 in ES cells after long-term culture (75 PDL).

[A. 2] Stability of the Mouse Artificial Chromosome Vector MAC1 in Mouse ES Cell Under non-selection culture of 0 to 75 PDL for the mouse ES clones (for example, KO56 (MAC1)-5 and TT2F (MAC1)-23, obtained from Example 2 above) obtained from the above, the rate of cells retaining MAC1 after long-term culture was measured by FISH analysis. As a result, the retention rate of 90% or more was obtained even for 75 PDL. On the other hand, in the mouse ES cells retaining HAC vector (21HAC2) carrying GFP derived from chromosome 21 described by Kazuki et al. (Gene Therapy: PMID: 21085194, 2010), the retention rate was 70% or less for 75 PDL. The representative results are given in FIG. 35.

[A. 3] Preparation of Chimeric Mouse Retaining Artificial Chromosome Vector MAC1

By using the ES cell clones obtained from Example 2 above, a chimeric mouse was prepared according to the method described by Tomizuka et al. (Nature Genet. 16: 133, 1997). As a host cell, an eight-cell stage embryo obtained by sexual crossbreeding of MCH (ICR) (white, purchased from CLEA Japan, Inc.) was used. Injected embryo is transplanted into a foster mother, and coat color of the new-born mouse could be examined in order to see whether or not it is a chimera. As the result that 1620 embryos injected with ES clones retaining MAC1 (for example, KO56MAC1-5 and TT2FMAC1-4, obtained from Example 2 above) were transplanted into foster mothers, 56 chimeric mice (in which dark brown color area was observed in coat color) were born. Among them, 13 animals were individuals having a chimeric rate of about 100% from which almost no white color area was observed. In other words, it was shown that ES cell line (KO56 and TT2F) retaining the mouse artificial chromosome vector MAC1 retained a chimera forming ability, that is, an ability of differentiating into normal tissue of a mouse individual.

[A. 4] Transmission to Progeny of MAC1 from Chimeric Mouse Retaining the Mouse Artificial Chromosome Vector MAC1

Two female chimeric mice (chimeric rate: about 100%) prepared from the above [A. 3] were mated with male mice MCH (ICR) (white, purchased from CLEA Japan, Inc.). Among 18 new-born mice born from chimeric mice, 13 were a dark brown color, which indicated the retention of a dominant genetic trait derived from the ES cells. Thus, the ES cell line retaining MAC1 was proven to be differentiated into a functional egg cell in a female chimeric mouse. Further, the retention of MAC1 was examined based on GFP fluorescence. As a result, six animals out of the 13 (46%) were GFP positive and thus it was confirmed that the progeny of the chimeric mice have retained MAC1. Specifically, according to the Mendel's genetics law, it was confirmed that the MAC1 trait appeared with frequency of about 50%, and therefore it was shown that the retention rate of MAC1 is close to 100% in an ovum. The mouse lineage in which MAC1 was transmitted to progeny is referred to as TC (MAC1).

[A.5] Stability of MAC1 in Somatic Cells of TC (MAC1) Mouse Lineage

[A. 5. 1] Observation with Stereo Fluorescence Microscope

Figure 36:
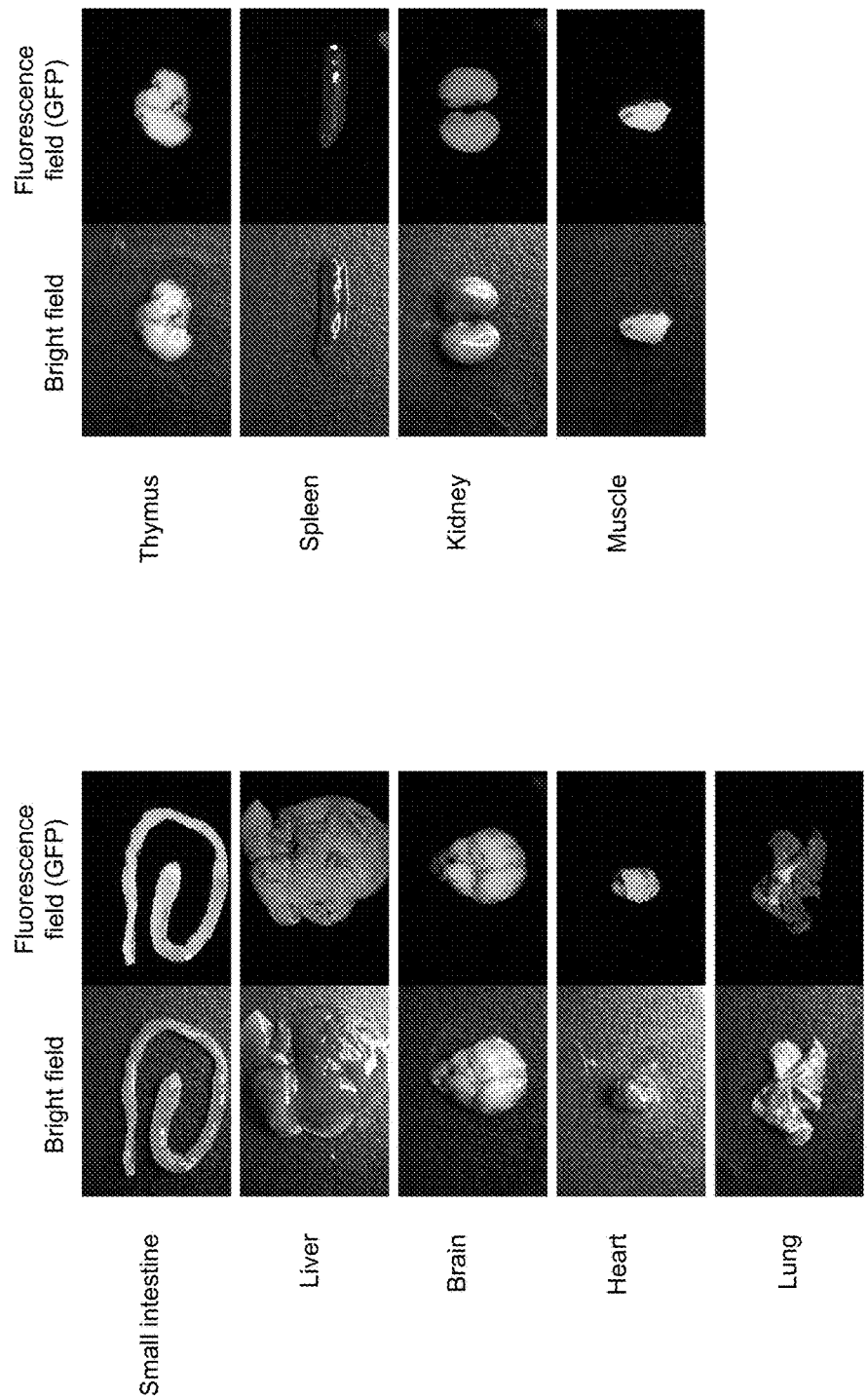
FIG. 36 shows the stereo fluorescent microscopic images of TC (MAC1) mouse (female) tissues.

For each one of the male (5) and female (2) TC (MAC1) mice obtained from the above, the brain, *thymus*, heart, lung, liver, kidney, spleen, small intestine, muscle, and testis (or ovary) were observed under stereo fluorescence microscope. As a result, all tissues were observed to be GFP positive, and therefore the positive rate was 100%. Representative results of the female (5) are given in FIG. 36.

[A. 5. 2] FACS Analysis of Hematopoietic Cells

Figure 37:
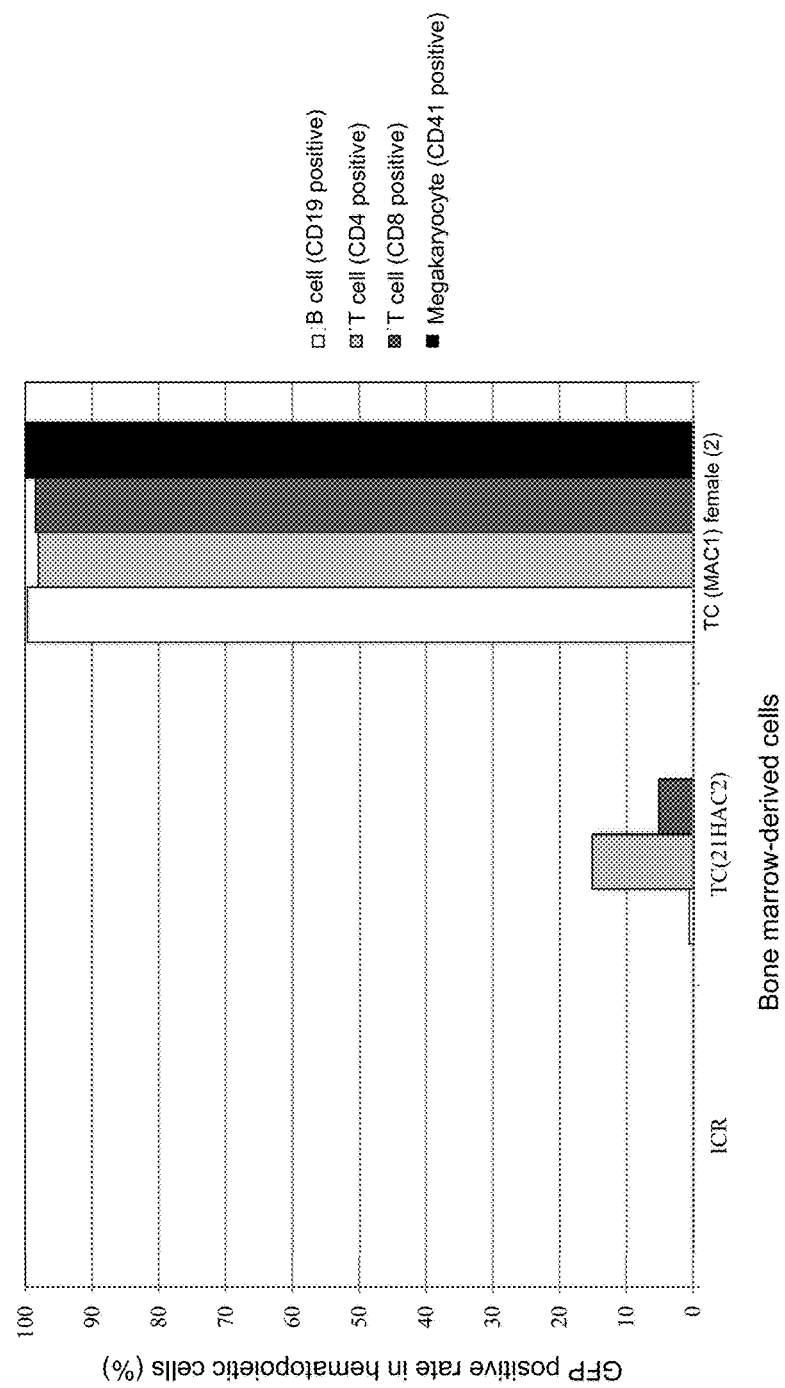
FIG. 37 shows the GFP positive rate in hematopoietic cells of bone marrow-derived cells of TC (MAC1) mouse or TC (21HAC2) mouse.
Figure 38:
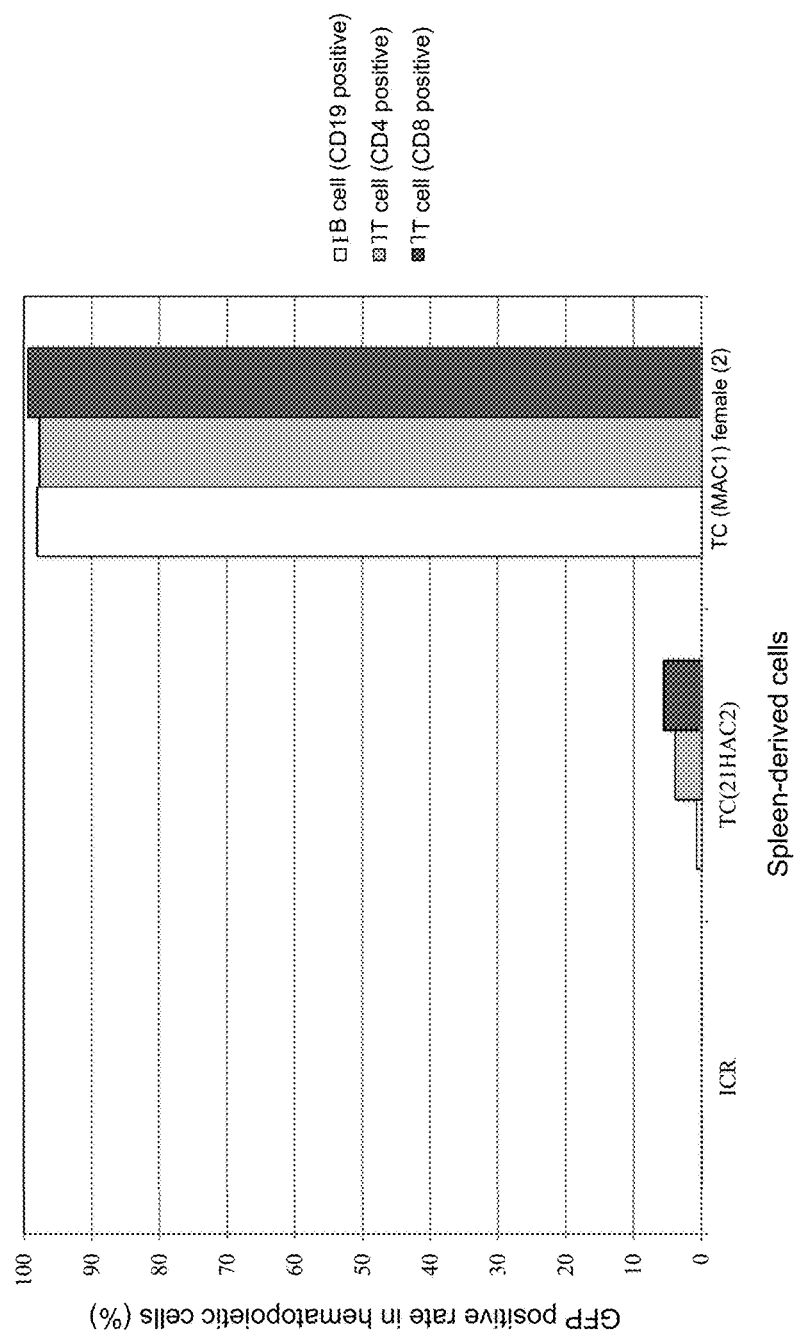
FIG. 38 shows the GFP positive rate in hematopoietic cells of spleen-derived cells of TC (MAC1) mouse or TC (21HAC2) mouse.

By using an antibody (Becton, Dickinson and Company) specific for B cells (CD19), T cells (CD4 and CD8), and megakaryocyte (CD41), GFP positive rate was studied for bone marrow and spleen cells. As a result, the positive rate was 95% or more in all tissues. On the other hand, in the mouse retaining HAC vector (21HAC2) carrying GFP derived from chromosome 21 described by Kazuki et al. (Gene Therapy: PMID: 21085194, 2010), the positive rate was 15% or less in all tissues. The representative results are given in FIG. 37 and FIG. 38.

[A. 5. 3] Fluorescence In Situ Hybridization (FISH) Analysis

Figure 39:
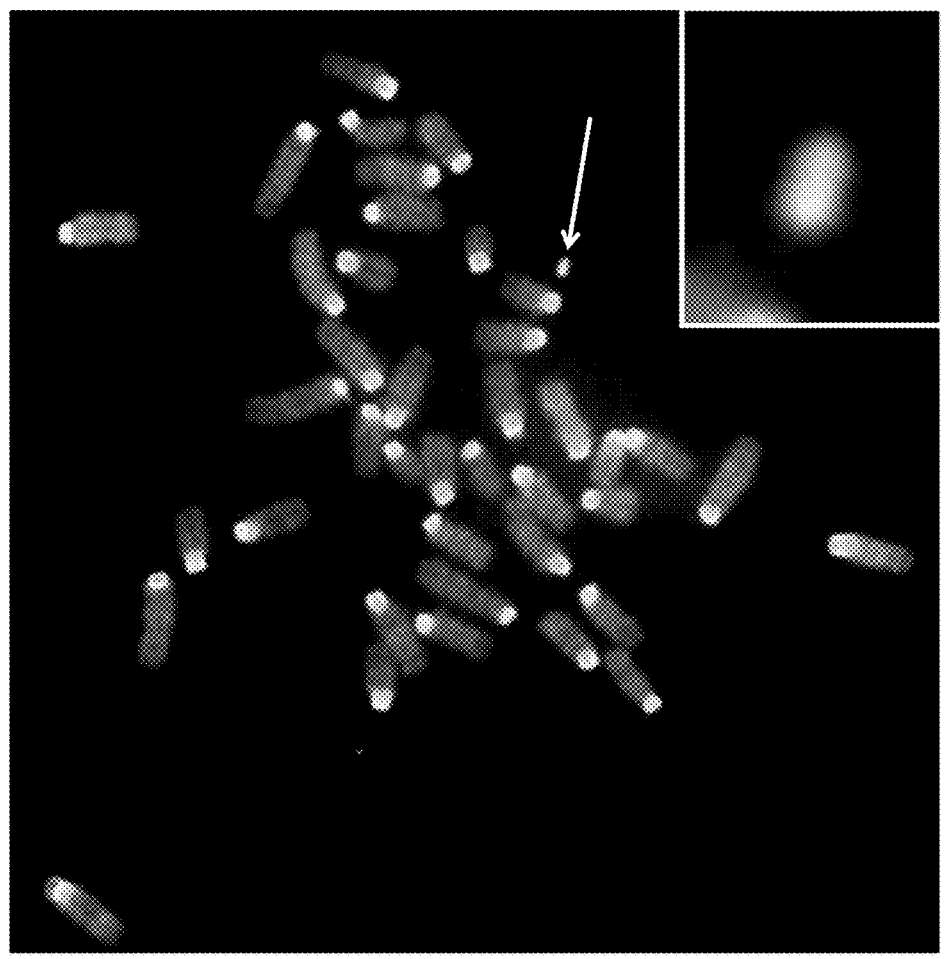
FIG. 39 shows the results of the mono-color FISH analysis of tail fibroblasts derived from TC (MAC1) mouse in which mouse minor satellite DNA probe was used.

By using the tail fibroblast prepared from the same individual as above, FISH analysis was carried out by using mouse minor satellite DNA as a probe according to the method described by Shinohara et al. (Human Molecular Genetics, 10: 1163-1175, 2001). As a result, the presence of MAC1 was visually confirmed and it was confirmed that MAC1 was present separate from the mouse chromosome in 95% or more cells (FIG. 39).

From these results, it was confirmed that the mouse artificial chromosome vector MAC1 was very stably maintained at a rate of 90% or more in the mouse ES cells (in vitro) and mouse tissues (in vivo).

Example 8

Preparation and Stability of Mouse Retaining the Mouse Artificial Chromosome Vector CYP3A-MAC

[A] Transfer of CYP3A-MAC from CHO Cell to Mouse A9 Cell

Figure 40:
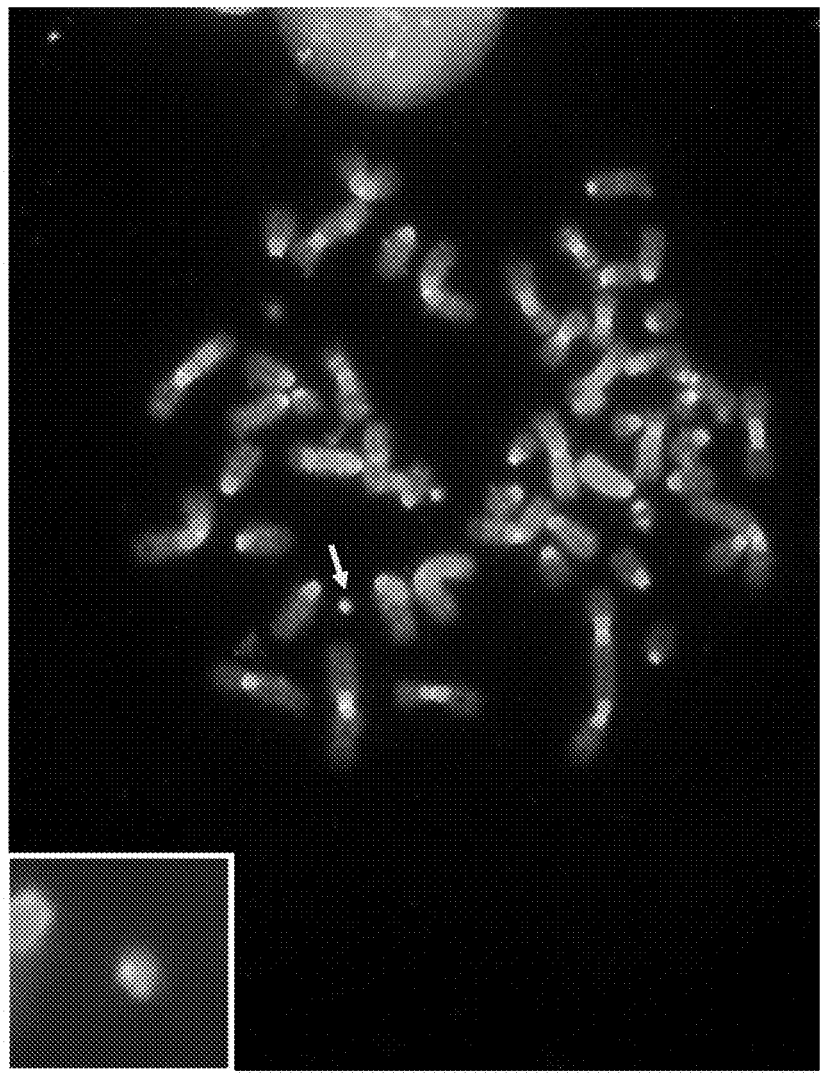
FIG. 40 shows the results of the two-color FISH analysis of A9 (CYP3A-MAC) in which CYP3A-BAC (RP11-757A13) and mouse minor satellite DNA probes were used.

To prepare mouse ES cells retaining CYP3A-MAC, introduction was carried out from CHO cells (CHO (CYP3A-MAC, hChr7-ΔCYP3A) 22, 26, 34, 35, or the like) retaining CYP3A-MAC obtained from Example 3 above, to, as a mouse A9 cell, mouse A9 cells having high microcell forming ability by microcell fusion. Total 25 resistant colonies obtained by eight microcell fusions were isolated, amplified, and subjected to the following analysis (clone name: A9 (CYP3A-MAC)). As a result, there were six clones which were determined to be positive by PCR using the primers described above for detecting the CYP3A-MAC region only. In addition, FISH analysis (Tomizuka et al., Nature Genet. 16: 133, 1997) was carried out by using CYP3A-BAC (RP11757A13) (CHORI) and mouse minor satellite DNA as probes, and as a result, the presence of CYP3A-MAC, which was specifically detected with the probes, was confirmed in three clones out of the six clones (Figure. 40). From the above results, it was concluded that three clones of A9 cells retaining CYP3A-MAC were obtained.

[B] Transfer of CYP3A-MAC from A9 Cell to Mouse ES Cell

Figure 41:
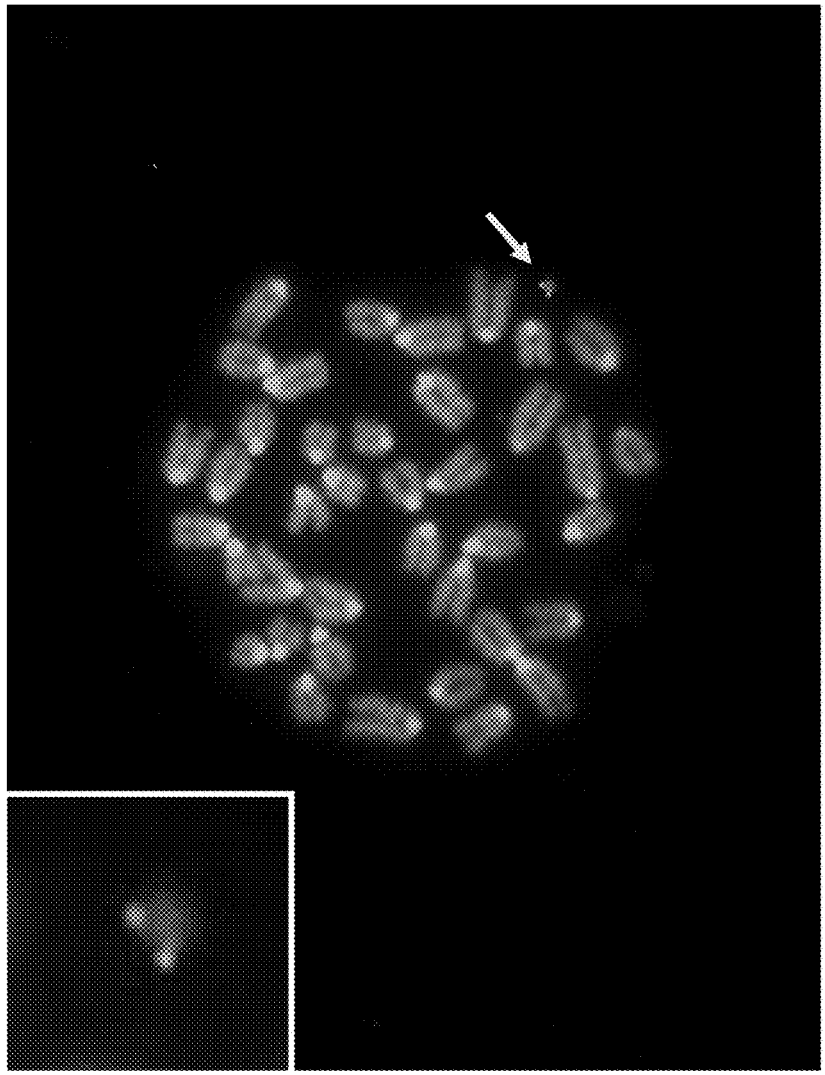
FIG. 41 shows the results of the mono-color FISH analysis of TT2F (CYP3A-MAC) in which CYP3A-BAC (RP11-757A13) DNA probe was used.

To prepare a chimeric mouse retaining CYP3A-MAC, introduction was carried out from A9 cells retaining CYP3A-MAC obtained from the above [A] to mouse ES cells (wild type TT2F) by microcell fusion. According to the method of Tomizuka et al. (Nature Genet. 16: 133, 1997), microcells were purified from approximately $10^8$ A9 cells retainingCYP3A-MAC (A9 (CYP3A-MAC) 8, 9, or the like) and suspended in 5 ml of DMEM. Approximately $10^7$ mouse ES cells of TT2F were detached by trypsin treatment, washed three times with DMEM, suspended in 5 ml of DMEM, and added to microcells obtained by centrifugation. After centrifugation for 10 min at 1250 rpm, the supernatant was completely removed. The precipitates were resolved fully by tapping, added with 0.5 ml of 1:1.4 PEG solution [5 g of PEG1000 (Wako Pure Chemical Industries, Ltd.) and 1 ml of DMSO (Sigma) are dissolved in 6 ml of DMEM], and fully stirred for about 1 min and 30 sec. After that, 10 ml of DMEM was slowly added, centrifuged for 10 min at 1250 rpm, and suspended in 30 ml of ES culture medium. Thereafter, the cells were dispensed into three petri dishes with a diameter of 100 mm (Corning Incorporated) onto which feeder cells were previously plated and then cultured. 24 hours later, the culture medium was exchanged with culture medium containing 300 μg/ml of G418 and then subjected to selection culture for about 1 week. As a result, total 34 colonies were isolated, amplified, and subjected to the following analysis. 14 clones from A9 (CYP3A-MAC) 8 and seven clones from A9 (CYP3A-MAC) 9 were determined to be positive by PCR using the primers described above for detecting the CYP3A-MAC region only. In addition, for 20 clones among the above, FISH analysis (Tomizuka et al., Nature Genet. 16: 133, 1997) was carried out by using DNA derived from CYP3A-BAC (RP11-757A13) (CHORI). As a result, the clones that were specifically detected with the probes and had normal mouse nuclear type, were found to be eight clones (FIG. 41). From the above results, it was concluded that eight clones of TT2F cells retaining CYP3A-MAC were obtained.

[C] Stability of CYP3A-MAC in Mouse ES Cell

Figure 42:
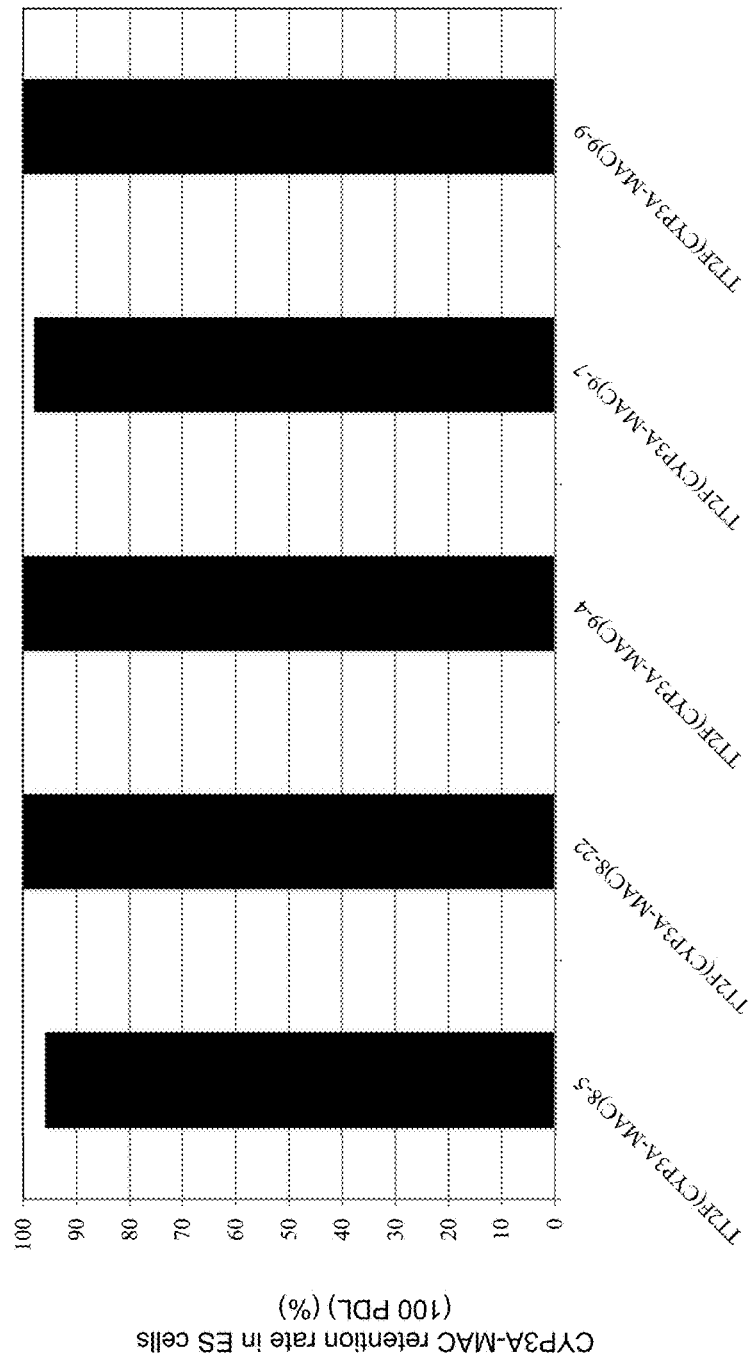
FIG. 42 shows the retention rate of CYP3A-MAC in ES cells after long-term culture (100 PDL).

Under non-selection culture of 0 to 100 PDL for the mouse ES clones obtained from the above (for example, TT2F (CYP3A-MAC) 8-5, 8-22, 9-4, 9-7, and 9-9, obtained from the above [B]), the rate of cells retaining CYP3A-MAC after long-term culture was measured by FISH analysis. As a result, the retention rate of 95% or more was obtained even for 100 PDL (FIG. 42).

[D] Preparation of Chimeric Mouse Retaining CYP3A-MAC

By using the ES cell clones retaining CYP3A-MAC obtained from the above [B], chimeric mice were prepared according to the method of Tomizuka et al. (Nature Genet. 16: 133, 1997). As a host cell, eight-cell stage embryos obtained by sexual crossbreeding of MCH (ICR) (white, purchased from CLEA Japan, Inc.) were used. Injected embryo was transplanted into a foster mother, and coat color of the new-born mouse was examined to see whether or not it is a chimera. As the result that 840 embryos injected with ES clones retaining MAC1 (for example, TT2F (CYP3A-MAC) 8-5, 8-16, 8-22, 9-4, 9-7, 9-9, 9-10, or the like, obtained from the above [B]) were transplanted into a foster mother, 28 chimeric mice (in which dark brown color area was observed in coat color) were born. Among them, five were individuals having a chimeric rate of about 100% from which almost no white area was observed. In other words, it was shown that ES cell line (TT2F) retaining the mouse artificial chromosome vector CYP3A-MAC retains a chimera forming ability, that is, an ability of differentiating into normal tissue of a mouse individual.

[E] Transmission to Progeny of CYP3A-MAC from Chimeric Mouse Retaining CYP3A-MAC Five female chimeric mice (chimeric rate: about 100%) prepared from the above [D] were mated with male mice MCH (ICR) (white, purchased from CLEA Japan, Inc.). Among 60 new-born mice born from a chimeric mouse, 50 were dark brown color, which indicated retention of a dominant genetic trait derived from the ES cells. Thus, the ES cell line retaining CYP3A-MAC was proven to be differentiated into a functional egg cell in a female chimeric mouse. Further, the retention of CYP3A-MAC was examined based on GFP fluorescence. As a result, 29 animals out of the 50 (58%) were found to be GFP positive and it was confirmed that CYP3A-MAC was retained in the progenies of a chimeric mouse. Specifically, according to the Mendel's genetics law, it was confirmed that CYP3A-MAC trait appeared with frequency of about 50%, and therefore the retention rate of CYP3A-MAC was close to 100% in an ovum. The mouse lineage in which CYP3A-MAC was transmitted to a progeny is referred to as TC (CYP3A-MAC).

[F] Stability of CYP3A-MAC in Somatic Cells of TC (CYP3A-MAC) Mouse Lineage

[F. 1] Observation with Stereo Fluorescence Microscope

Figure 43:
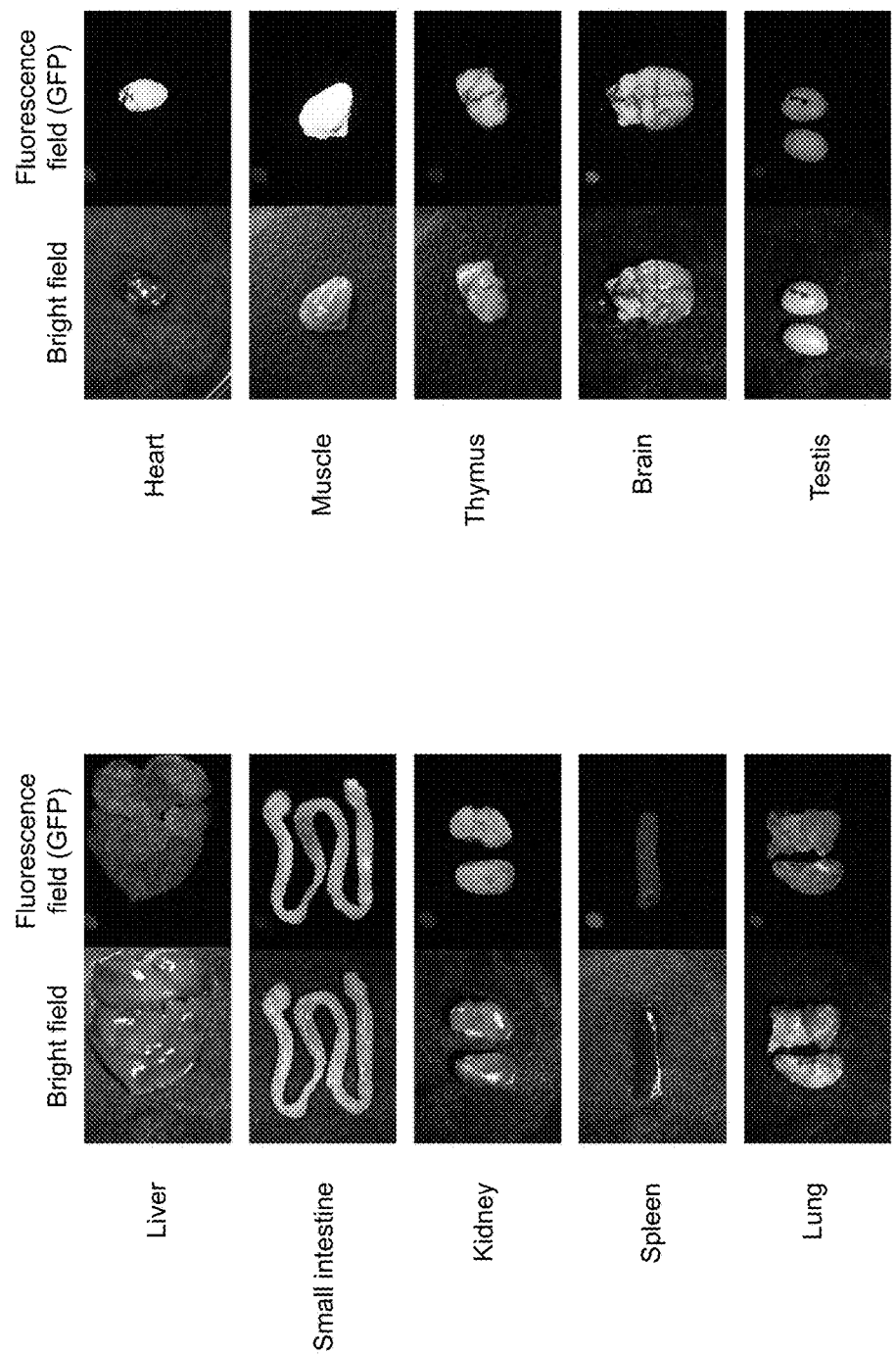
FIG. 43 shows stereo fluorescence microscopic images of TC (CYP3A-MAC) mouse (male) tissues.

For each one of the male (2) and female (14) TC (CYP3A-MAC) mice obtained from the above, the brain, *thymus*, heart, lung, liver, kidney, spleen, small intestine, muscle, and testis were observed under stereo fluorescence microscope. As a result, all tissues were observed to be GFP positive, and the positive rate was 100%. Representative results of the male (2) are given in FIG. 43.

[F. 2] FACS Analysis of Hematopoietic Cells

Figure 44:
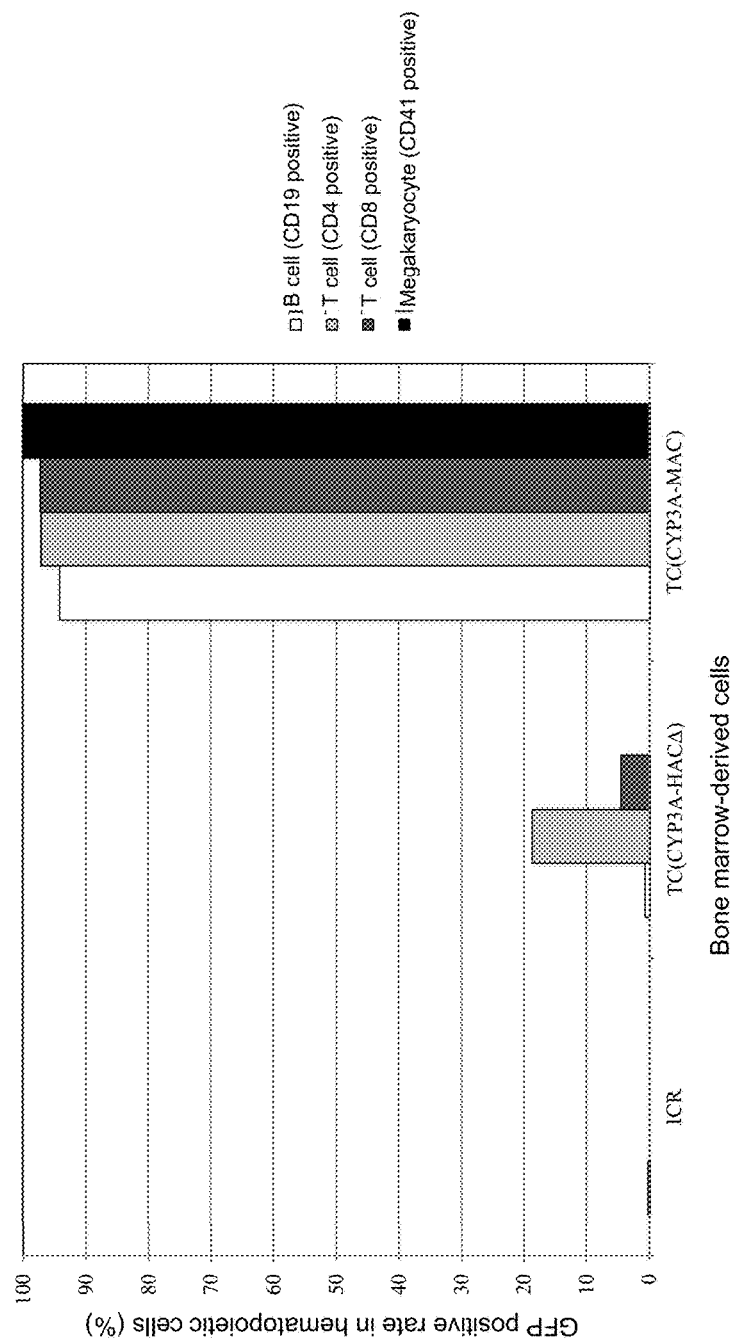
FIG. 44 shows the GFP positive rate in hematopoietic cells of bone marrow-derived cells of TC (CYP3A-MAC) mouse or TC (CYP3A-HACΔ) mouse.

By using an antibody (Becton, Dickinson and Company) specific for B cells (CD19), T cells (CD4 and CD8), and megakaryocyte (CD41), GFP positive rate was examined for bone marrow. As a result, the positive rate was 94% or more in all tissues. In contrast, in the mouse retaining HAC vector (CYP3A-HACΔ) derived from chromosome 14 described in WO 2009/063722 (PCT/JP2008/068928), the positive rate was 20% or less in all tissues. The representative results are given in FIG. 44.

[F. 3] Fluorescence In Situ Hybridization (FISH) Analysis

Figure 45:
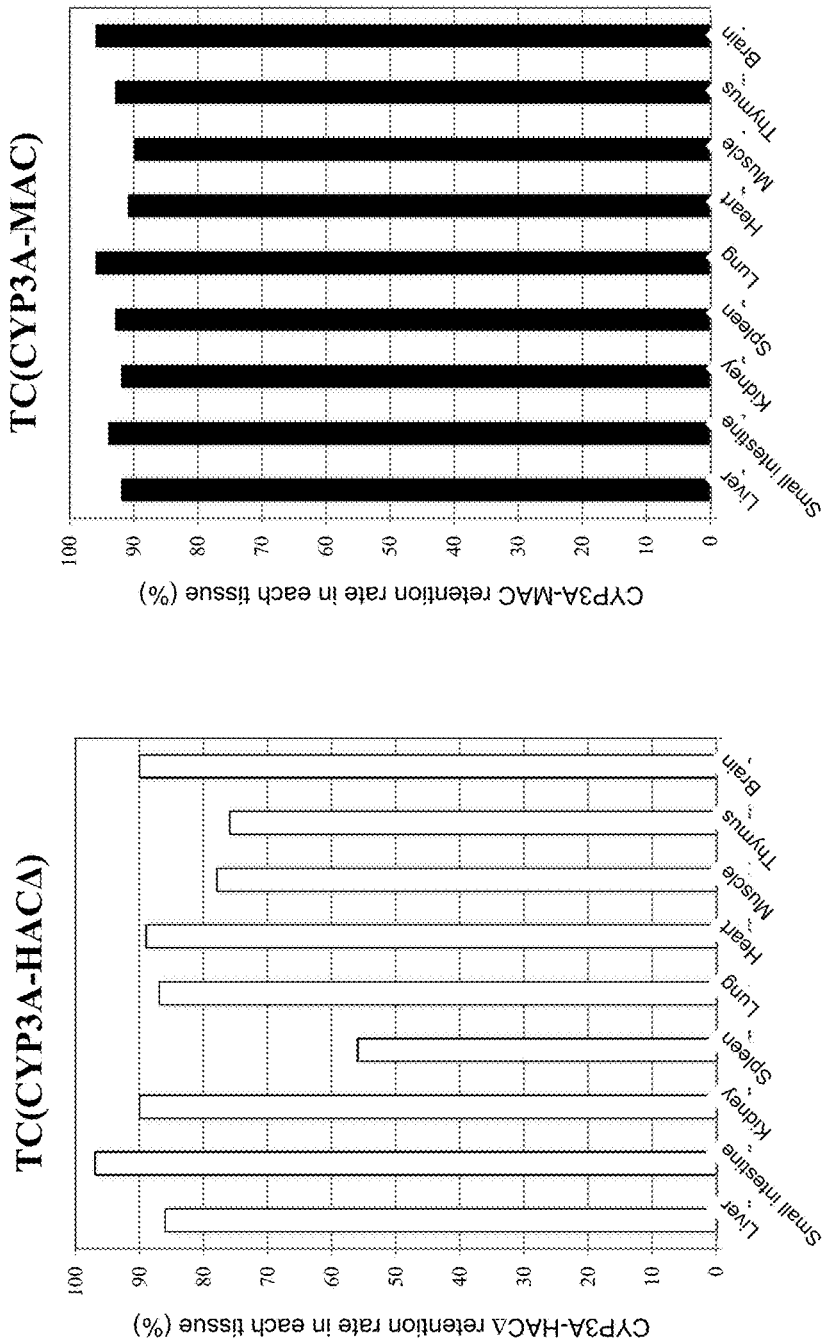
FIG. 45 shows the retention rate of CYP3A-MAC or CYP3A-HACΔ in each tissue of TC (CYP3A-MAC) mouse or TC (CYP3A-HACΔ) mouse.

For the same individual or tissues as described above, FISH analysis was carried out by using CYP3A-BAC (RP11-757A13) DNA as a probe according to the method described by Shinohara et al. (Human Molecular Genetics, 10: 1163-1175, 2001). As a result, the presence of CYP3A-MAC was visually confirmed and it was confirmed that CYP3A-MAC was present in 90 to 98% or more of the cells. In contrast, in the mouse retaining HAC vector (CYP3A-HACΔ) derived from chromosome 14 described in WO 2009/063722 (PCT/JP2008/068928), the positive rate was 56 to 97% in all tissues. The representative results are given in FIG. 45.

[F. 4] Transmission Rate of TC (CYP3A-MAC) Line

Eight TC (CYP3A-MAC) female mice were mated with eight male mice MCH (ICR) (white, purchased from CLEA Japan, Inc.) to examine the transfer rate. Among 81 new-born mice obtained, 38 animals were GFP negative individuals and 42 animals were GFP positive individuals (transmission rate: 53%). Thus, the transmission rate matched the Mendel's genetics law, and it was confirmed that CYP3A-MAC trait appeared with frequency of about 50%, and therefore it was shown that the retention rate of CYP3A-MAC was close to 100% in an ovum.

Figure 46:
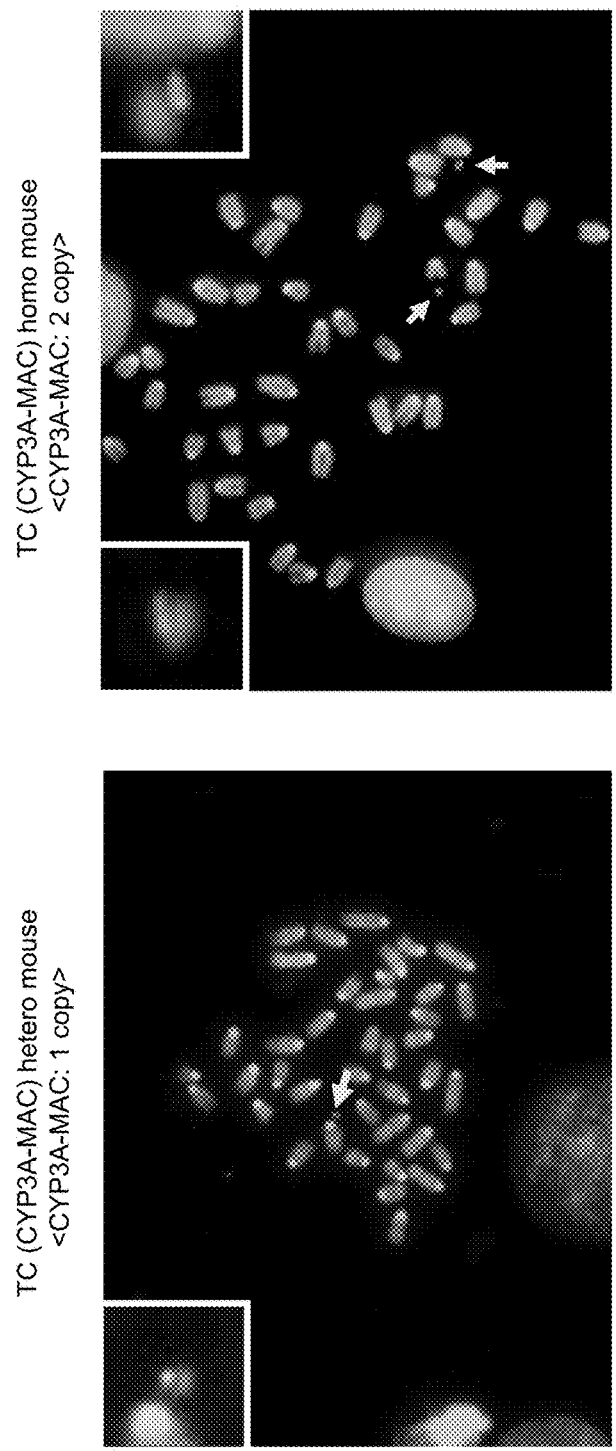
FIG. 46 shows the results of the mono-color FISH analysis of TC (CYP3A-MAC) heterozygous mouse or TC (CYP3A-MAC) homozygous mouse in which CYP3A-BAC (RP11-757A13) DNA probe was used.

[F. 5] Preparation of TC (CYP3A-MAC) Homozygous Line Retaining Two CYP3A-MAC and Transmission Rate The TC (CYP3A-MAC) male mouse and TC (CYP3A-MAC) female mouse obtained from the above were mated with each other to attempt the establishment of TC (CYP3A-MAC) homozygous line retaining two CYP3A-MAC. By using tail fibroblast of 18 new-born mice, FISH analysis was carried out by using CYP3A-BAC (RP11757A13) DNA as a probe according to the method described by Shinohara et al. (Human Molecular Genetics, 10: 1163-1175, 2001). As a result, the presence of CYP3A-MAC was visually confirmed. In 4×36 lines, three had two copies, five had one copy, and four had zero copy among 12 new-born mice. In 24×37 lines, one had two copies, three had one copy, and two had zero copy among six new-born mice. Total 18 animals were obtained, and the rate of CYP3A-MAC having two copies (four animals), one copy (eight animals), and zero copy (six animals) was 1:2:1.5, which almost matched the Mendel's genetics law. The representative results are given in FIG. 46.

From these results, it was confirmed that CYP3A-MAC was very stably maintained for a long period of time at a rate of 95% or more in the mouse ES cells (in vitro) and, as a homozygous line, it was also very stably maintained at a rate of 90% or more in the mouse tissues (in vivo).

[G] Tissue Specific Gene Expression of CYP3A Gene Cluster in TC (CYP3A-MAC) Mouse Lines For each one of the male (2) and female (14) TC (CYP3A-MAC) mice obtained from the above, total RNA was extracted from the brain, *thymus*, heart, lung, liver, kidney, spleen, small intestine, and muscle of the animals according to the commercially available protocol (QIAGEN), and cDNA was synthesized according to the commercially available protocol (invitrogen). Consequently, PCR was performed by using the cDNA as a template and expression of human CYP3A gene cluster and mouse Cyp3a gene cluster was detected. The primer sequences are given below.

Primers for Detecting Expression of Human CYP3A Gene Cluster are:

```
3A4-1L:    5'-gtatggaaaagtgtggggct-3'    (SEQ ID NO: 51)

3A4-1R:    5'-atacttcaagaattgggatg-3'    (SEQ ID NO: 52)

3A4-2L:    5'-ccaagctatgctcttcaccg-3'    (SEQ ID NO: 53)

3A4-2R:    5'-tgaagaagtcctcctaagct-3'    (SEQ ID NO: 54)

3A5-1L:    5'-ctctgtttccaaaagatacc-3'    (SEQ ID NO: 55)

3A5-1R:    5'-tcaacatctttcttgcaagt-3'    (SEQ ID NO: 56)

3A7-1L:    5'-agcttttaagatttaatcca-3'    (SEQ ID NO: 57)

3A7-1R:    5'-gagctttgtgggtctcagag-3'    (SEQ ID NO: 58)

3A7-2L:    5'-ctctcagaattcaaaagact-3'    (SEQ ID NO: 59)

3A7-2R:    5'-agaagaagtcctccaaagcg-3'    (SEQ ID NO: 60)

3A43-2L:   5'-tatgacacaactagcaccac-3'    (SEQ ID NO: 61)

3A43-2R:   5'-agtgtctagtgttctgggat-3'    (SEQ ID NO: 62)
```

Primers for Detecting Expression of Mouse Cyp3a Gene Cluster are:

```
3a11-1L:   5'-tcaaacgcctctccttgctg-3'    (SEQ ID NO: 63)

3a11-1R:   5'-gcttgcctttctttgccttc-3'    (SEQ ID NO: 64)

3a11-2L:   5'-ggtaaagtacttgaggcaga-3'    (SEQ ID NO: 65)

3a11-2R:   5'-agaaagggctttatgagaga-3'    (SEQ ID NO: 66)

3a13-1L:   5'-agaaacatgaggcagggatt-3'    (SEQ ID NO: 67)

3a13-1R:   5'-acaaggagacatttagtgca-3'    (SEQ ID NO: 68)

3a13-2L:   5'-taccccagtatttgatgcac-3'    (SEQ ID NO: 69)

3a13-2R:   5'-agataactgactgagccaca-3'    (SEQ ID NO: 70)
```

Primers for Detecting Expression of Control Gene are:

```
GAPDH-F:   5'-CCATCTTCCAGGAGCGAGA-3'     (SEQ ID NO: 71)

GAPDH-R:   5'-TGTCATACCAGGAAATGAGC-3'    (SEQ ID NO: 72)
```

For PCR, GeneAmp 9600 manufactured by PerkinElmer, Inc. was used as a thermal cycler and EX Taq (TAKARA SHUZO CO., LTD.) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 93° C. for 5 min, 35 cycles of 93° C. for 1 min, 56° C. for 1 min, and 72° C. for 1 min as one cycle were carried out.

Figure 47:
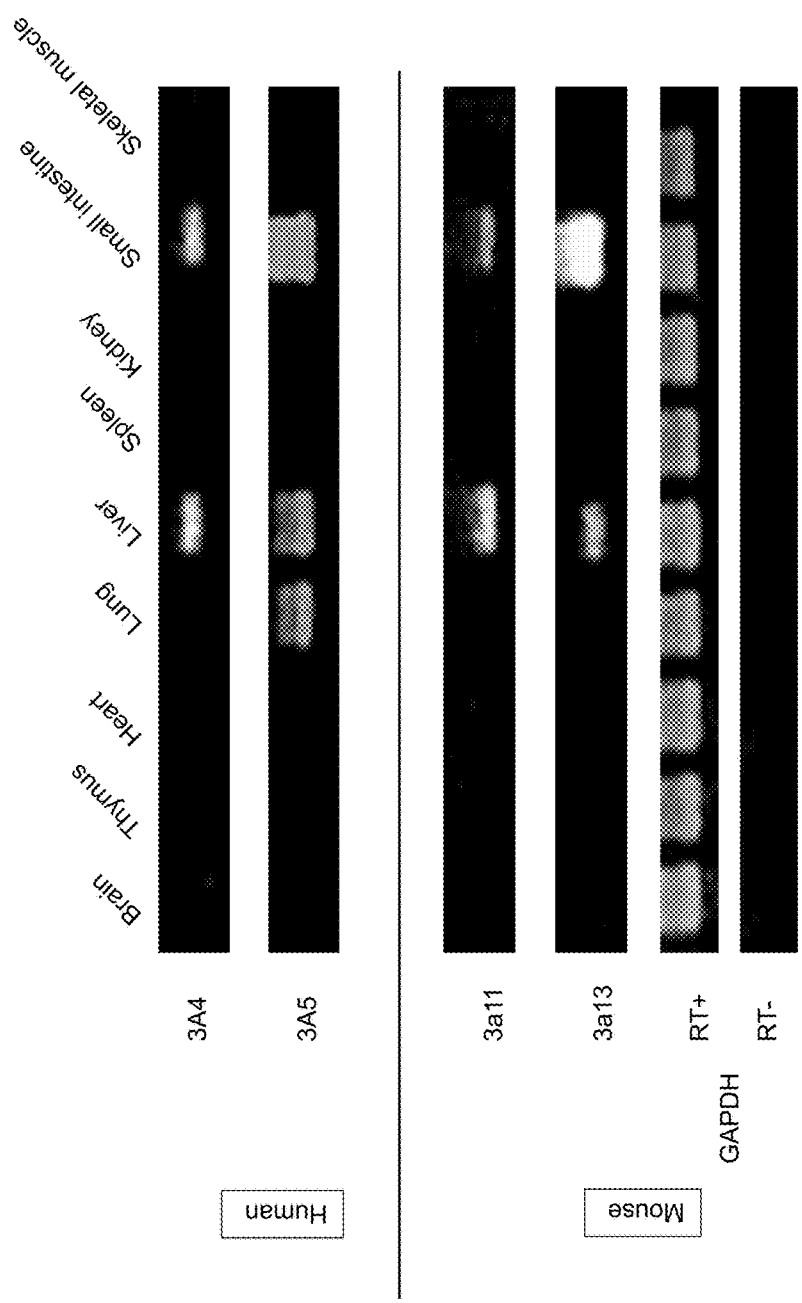
FIG. 47 shows the results of the analysis of tissue specific gene expression of CYP3A gene cluster in each tissue of TC (CYP3A-MAC) mouse. GAPDH represents glyceraldehyde 3-phosphate dehydrogenase.

As a result, in the mouse retaining TC (CYP3A-MAC), expression of CYP3A4 was able to be detected only in the liver and small intestine, expression of CYP3A5 was able to be detected only in the liver, small intestine, and lung, expression of CYP3A7 was able to be detected only in the liver, small intestine, kidney, and lung, expression of CYP3A43 was able to be detected only in the liver, small intestine, and kidney, expression of Cyp3a11 was able to be detected only in the liver and small intestine, and expression of Cyp3a13 was able to be detected only in the liver and small intestine. On the other hand, GAPDH as a control was detected in all tissues. The representative results of the female (14) are given in FIG. 47. Tissue specific expression was thus observed as seen in human, indicating the humanization.

[H] Time Specific Gene Expression of CYP3A Gene Cluster in TC (CYP3A-MAC) Mouse Lines From the male and female TC (CYP3A-MAC) mice which were GFP positive, total RNA was extracted from the liver at the fetal age of 14.5 days, fetal age of 16.5 days, fetal age of 18.5 days, day 0 after birth, 4 weeks old, 6 weeks old, 12 weeks old, and 24 weeks old according to the commercially available protocol (QIAGEN) and cDNA was synthesized according to the commercially available protocol (invitrogen). PCR was performed by using the cDNA as a template and expression was detected by using the primers for detecting the expression of human CYP3A gene cluster and mouse Cyp3a gene cluster described above.

Figure 48:
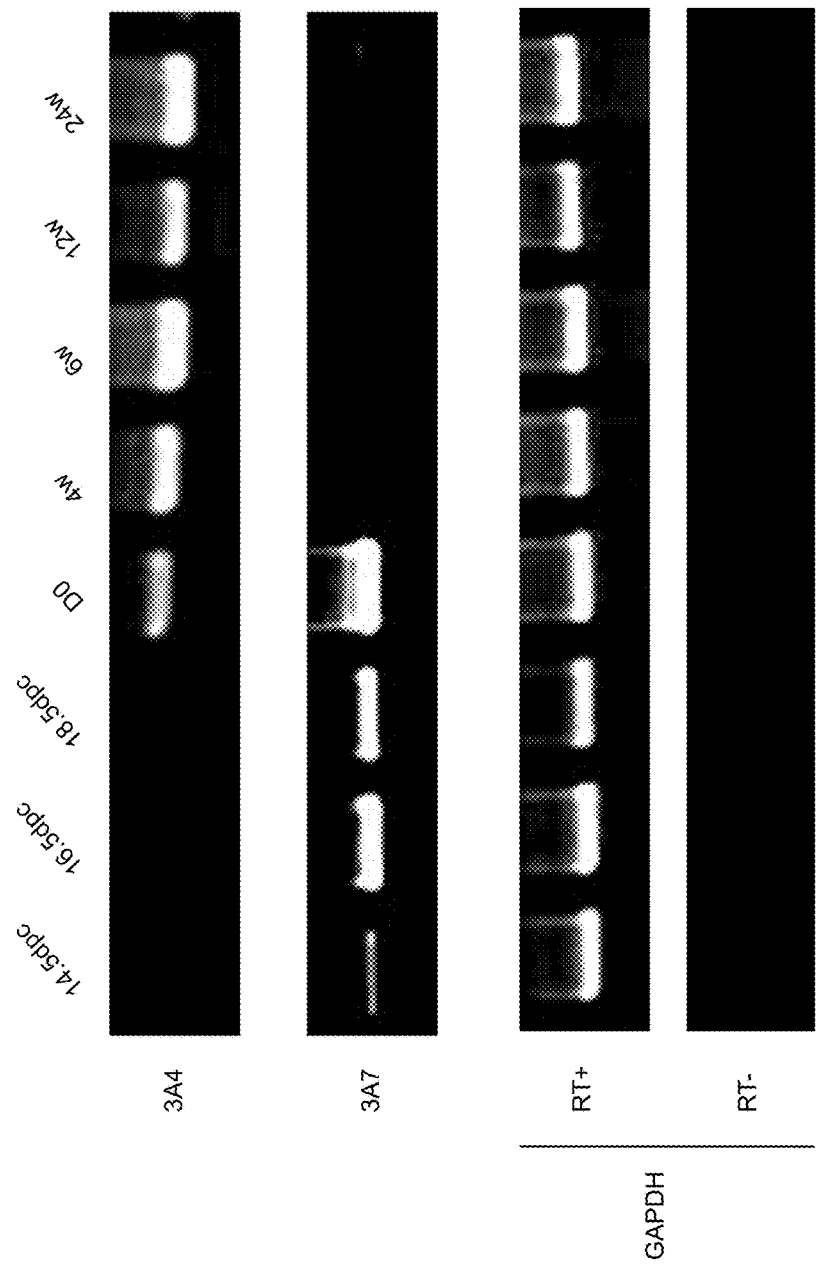
FIG. 48 shows the results of the analysis of time specific gene expression of CYP3A gene cluster in TC (CYP3A-MAC) mouse liver.

As a result, it was confirmed that the adult-expression type human CYP3A4, human CYP3A5, mouse cyp3a11, and mouse Cyp3a13 are strongly expressed in an adult period and the fetal type CYP3A7 was strongly expressed in a fetal. In addition, the expression level of GAPDH as a control was detected equally in all animals of any fetal age or week age. The representative results are given in FIG. 48. Time specific expression was thus observed as in human, indicating the humanization.

Example 9

Preparation of TC (CYP3A-MAC)/Δcyp Mouse Lines

[A] Construction of Mouse Lines Retaining CYP3A-MAC and Having Disrupted Two Alleles of Endogenous Cyp3a Gene Group TC (CYP3A-MAC) prepared in Example 8 above was subjected to back cross with Δcyp line that was prepared in Example 7 of WO 2009/063722 (PCT/JP2008/068928) to yield GFP-positive mouse individuals. Genotype analysis was performed for the mice using the PCR method described above. Tail of the 51 new-born mice obtained by crossbreeding was partially cut off, and genomic DNA was prepared from the tail sample. For the obtained DNA, PCR was carried out by using the primers for detecting CYP3A-MAC and the primers described in Table 1 of WO 2009/063722 (PCT/JP2008/068928) in the same manner as above in order to examine the retention of CYP3A-MAC and the KO of Cyp3a gene cluster. As a result, it was confirmed that 24 animals were (heterozygous KO) mouse lines in which CYP3A-MAC was retained and one allele of the endogenous Cyp3a gene cluster was disrupted. Further, the mouse in which CYP3A-MAC was retained and a group of Cyp3a genes was heterozygously disrupted, was subjected to back cross with Δcyp line. Tail of the 38 GFP-positive mice obtained was partially cut off, and genomic DNA was prepared from the tail sample. Genotype analysis was performed by the same PCR method as described above. As a result, it was confirmed that 18 animals were (homozygous KO) mouse lines in which CYP3A-MAC was retained and both alleles of the endogenous Cyp3a gene group were disrupted (hereinbelow, described as TC (CYP3A-MAC)/Δcyp).

[B] Metabolism Analysis of TC (CYP3A-MAC)/Δcyp Mouse Line

According to Omura et al. (J. Biol. Chem., 239, 2370, 1964), the liver microsome of TC (CYP3A-MAC)/Δcyp mouse and Δcyp mouse individual is mixed with triazolam (200 μM), which is known to be metabolized into CYP3A4. As a result, α-OH-triazolam and 4-OH-triazolam can be measured as metabolites. As described in WO 2009/063722 (PCT/JP2008/068928), in TC (CYP3A-MACΔ)/Δcyp mouse, it is possible to confirm that it has the same activity as the mouse of the same line or human (HLM: human liver microsome). From the above, it is able to confirm that, in TC (CYP3A-MAC)/Δcyp mouse line, the human CYP3A gene on CYP3A-MAC is functional and also equivalent to the human gene.

[C] Thus, the liver microsome derived from TC (CYP3A-MAC)/Δcyp mouse line can be used as a sample for testing a pharmacological effect and toxicity in the phase I reaction for development of a pharmaceutical product. Further, because human drug metabolism can be reproduced in TC (CYP3A-MAC)/Δcyp mouse line, it can be also used as a model mouse for in vivo test that is used for testing a pharmacological effect and toxicity in the phase I reaction for development of a pharmaceutical product.

Example 10

Preparation of Rat Retaining the Mouse Artificial Chromosome Vector CYP3A-MAC

[A] Transfer of CYP3A-MAC from A9 Cell to Rat ES Cell

Figure 49:
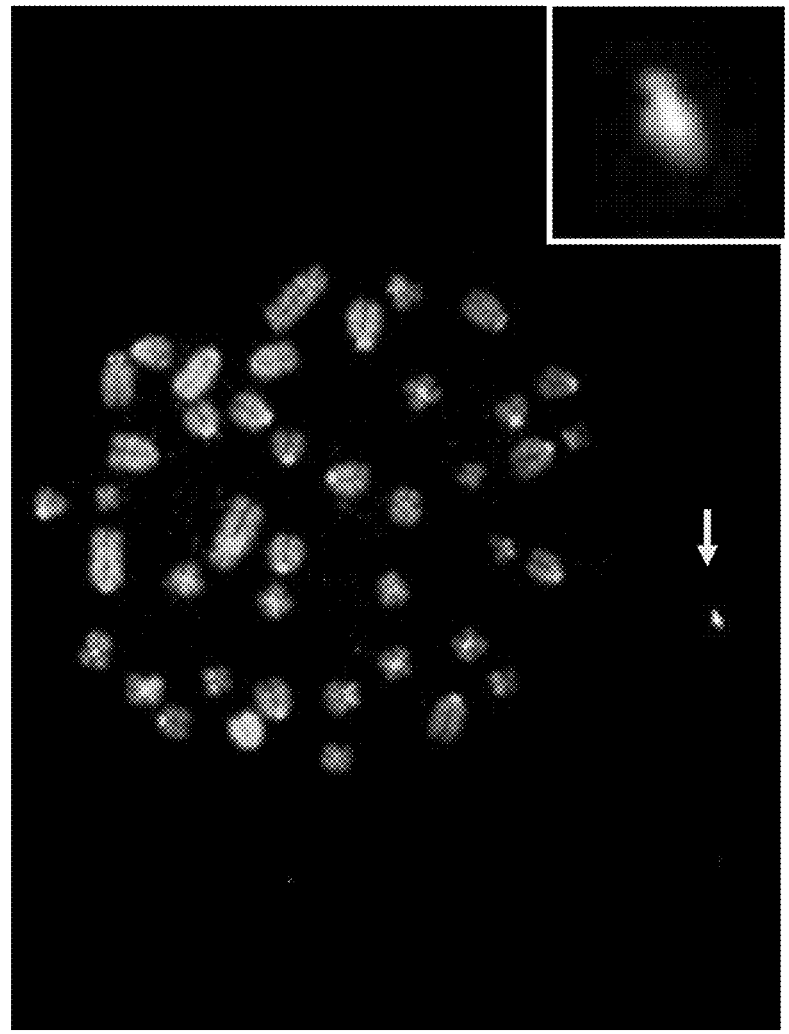
FIG. 49 shows the results of the two-color FISH analysis of rat ES (CYP3A-MAC) in which CYP3A-BAC (RP11-757A13) and mouse Cot-1 DNA probes were used.

To prepare a chimeric rat retaining CYP3A-MAC, introduction was carried out from A9 cells retaining CYP3A-MAC obtained from Example 8 above to rESWIv3i-1 (Hirabayashi et al., Mol Reprod Dev. 2010 February; 77 (2): 94), which was a rat ES cell capable of transmission to progeny, by microcell fusion. According to the method of Tomizuka et al. (Nature Genet. 16: 133, 1997), microcells were purified from approximately $10^8$ A9 cells retaining CYP3A-MAC (A9 (CYP3A-MAC) 8, 9, or the like) and suspended in 5 ml of DMEM. Approximately $10^7$ rat ES cells of rESWIv3i-1 were detached by trypsin treatment, washed three times with DMEM, suspended in 5 ml of DMEM, and added to the microcells obtained by centrifugation. After centrifugation for 10 min at 1250 rpm, the supernatant was completely removed. The precipitates were resolved fully by tapping and added with 0.5 ml of 1:1.4 PEG solution [5 g of PEG1000 (Wako Pure Chemical Industries, Ltd.), and 1 ml of DMSO (Sigma) are dissolved in 6 ml of DMEM], and fully stirred for about 1 min and 30 sec. After that, 10 ml of DMEM was slowly added, centrifuged for 10 min at 1250 rpm, and suspended in 30 ml of ES culture medium. Thereafter, the cells were dispensed into three petri dishes with a diameter of 100 mm (Corning Incorporated) onto which feeder cells were previously plated and then cultured. 24 hours later, the culture medium was exchanged with culture medium containing 300 μg/ml G418 and then subjected to selection culture for about 1 week. As a result, total 10 colonies were isolated, amplified, and subjected to the following analysis. Two clones from A9 (CYP3A-MAC) 8 and three clones from A9 (CYP3A-MAC) 8 were determined to be positive by PCR using the primers described above for detecting the CYP3A-MAC region only. In addition, for the five clones, FISH analysis (Tomizuka et al., Nature Genet. 16: 133, 1997) was carried out by using CYP3A-BAC (RP11-757A13) (CHORI) and mouse Cot-1 DNA. As a result, the clones that were specifically detected with the probes and had normal rat nuclear type, were found to be three clones (FIG. 49). From the above, it was concluded that 3 clones of rat ES cells retaining CYP3A-MAC were obtained.

[B] As described in Example 8, in vitro stability can be examined by using rat ES cells retaining the mouse artificial chromosome vector CYP3A-MAC. Further, by preparing a chimeric rat using the ES cells, rat line rTC (CYP3A-MAC) in which the vector has been transmitted to a rat progeny can be prepared. Further, by using the rTC (CYP3A-MAC) rat line, stability of CYP3A-MAC in somatic cells can be examined Still further, the liver microsome derived from rTC (CYP3A-MAC) rat line can be used as a sample for testing a pharmacological effect and toxicity in the phase I reaction for development of a pharmaceutical product. Further, because human drug metabolism can be reproduced in rTC (CYP3A-MAC) rat line, it can be also used as a model rat for in vivo test that is used for testing a pharmacological effect and toxicity in the phase I reaction for development of a pharmaceutical product.

Example 11

Construction of the Mouse Artificial Chromosome Vector hChr21q-MAC

In order to prepare a model mouse for Down's syndrome, translocation cloning of DNA sequence containing 33 Mb region distal from AP001657 of long arm of human chromosome 21 into the mouse artificial chromosome vector MAC1 is performed by using Cre/loxP system to construct hChr21q-MAC in the same manner as in Example 3.

[A] Introduction of hChr21-loxP from DT40 Containing hChr21-loxP to CHO Cell Containing MAC1

For translocation insertion of a region distal from AP001657 of long arm of human chromosome 21 into the mouse artificial chromosome vector MAC1 via loxP sequence in CHO cells, hChr21-loxP which is obtained by inserting loxP sequence into AP001657 in human chromosome 21 is introduced into CHO cells containing the mouse artificial chromosome vector MAC1.

[A. 1] Microcell Fusion and Isolation of Drug Resistant Clone

By using DT40 cells containing hChr21-loxP and DT40 (kk139) (Japanese Patent Publication (Kokai) 2007-295860 A) as a recipient cell, microcell fusion was carried out for CHO (HPRT−; MAC1), which is CHO hprt depleted cells containing MAC1 (obtained from the Health Science Research Resources Bank, registration number: JCRB0218), in the same manner as above. Total 114 resistant colonies obtained by 14 microcell fusions were isolated, amplified, and subjected to the following analysis (clone name: CHO (HPRT⁻; MAC1, hChr21-loxP)).

[A. 2] Selection of Drug Resistant Clone

[A. 2. 1] PCR Analysis

For extracting genomic DNA from hygromycin resistant cell line and using it as a template for selecting a recombinant, PCR was carried out for 60 clones out of the 114 clones by using the following primers, and it was confirmed whether or not human chromosome 21 fragment has been introduced into the CHO cells retaining MAC1. The primer sequences are given below.

m11 5L (described above)
EGFP (F) L (described above)
kj neo (described above)
m11 6R (described above)

```
#21CEN<1>2L:
                                  (SEQ ID NO: 73)
5'-aaatgcatcaccattctcccagttaccc-3'

PGKr1:
                                  (SEQ ID NO: 74)
5'-ggagatgaggaagaggagaaca-3'

D21S265-L:
                                  (SEQ ID NO: 75)
5'-gggtaagaaggtgcttaatgctc-3'

D21S265-R:
                                  (SEQ ID NO: 76)
5'-tgaatatgggttctggatgtagtg-3'

D21S261-L:
                                  (SEQ ID NO: 77)
5'-gaggggggactgggacaagccctttgctggaagaga-3'

D21S261-R:
                                  (SEQ ID NO: 78)
5'-acattaggaaaaatcaaaaggtccaattattaagg-3'

D21S268-L:
                                  (SEQ ID NO: 79)
5'-CAACAGAGTGAGACAGGCTC-3'

D21S268-R:
                                  (SEQ ID NO: 80)
5'-TTCCAGGAACCACTACACTG-3'

D21S266-L:
                                  (SEQ ID NO: 81)
5'-ggcttggggacattgagtcatcacaatgtagatgt-3'

D21S266-R:
                                  (SEQ ID NO: 82)
5'-gaagaaaggcaaatgaagacctgaacatgtaagtt-3'

D21S1259-L:
                                  (SEQ ID NO: 83)
5'-GGGACTGTAATAAATATTCTGTTGG-3'

D21S1259-R:
                                  (SEQ ID NO: 84)
5'-CACTGGCTCTCCTGACC-3'

CBR-L:
                                  (SEQ ID NO: 85)
5'-gatcctcctgaatgcctg-3'

CBR-R:
                                  (SEQ ID NO: 86)
5'-gtaaatgcccctttggacc-3'
```

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, 11 clones out of the 60 clones were found to be positive for all primer sets, and the following analysis was performed by using those 11 clones.

[A. 2. 2] Two-Color FISH Analysis

Figure 50:
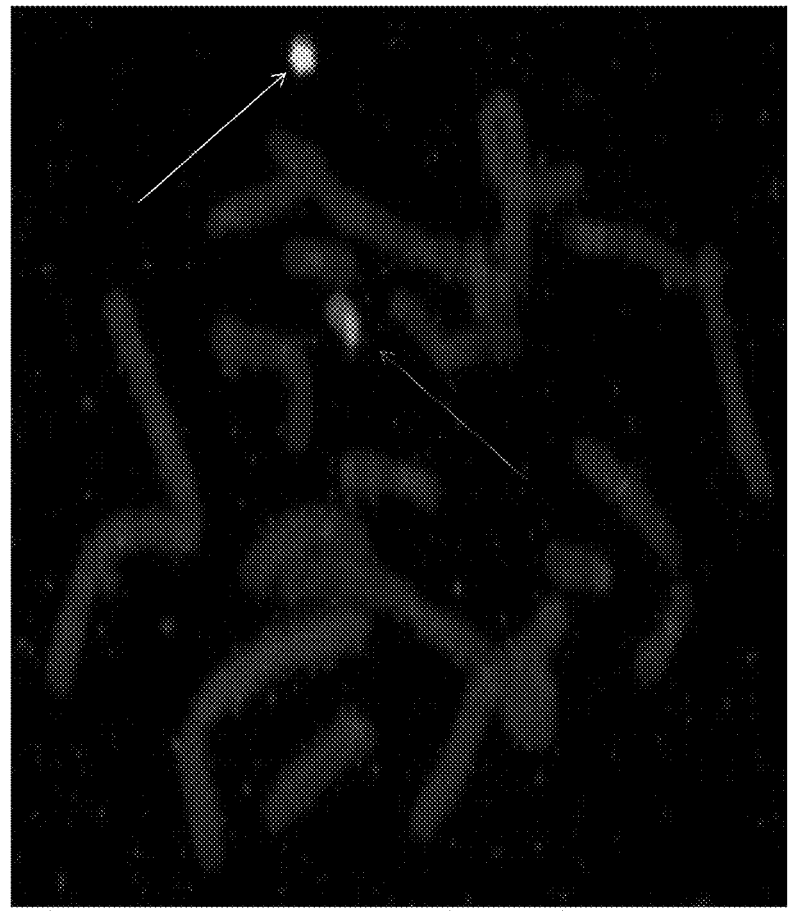
FIG. 50 shows the results of the two-color FISH analysis of CHO (HPRT⁻; MAC1, hChr21-loxP) in which mouse Cot-1 DNA and human Cot-1 DNA probes were used.

With six clones out of the 11 clones of CHO (HPRT⁻; MAC1, hChr21-loxP) obtained from the above, FISH analysis was carried out by using mouse Cot-1 DNA and human Cot-1 DNA as probes according to the method described by Shinohara et al. (Human Molecular Genetics, 10: 1163-1175, 2001). As a result, it was confirmed that a single copy of MAC1 and hChr21-loxP has introduced into CHO cells at a rate of 70% in one clone out of the six clones (FIG. 50).

From these results, it was concluded that hChr21-loxP could be introduced into CHO cells containing the mouse artificial chromosome vector MAC1.

Figure 51:
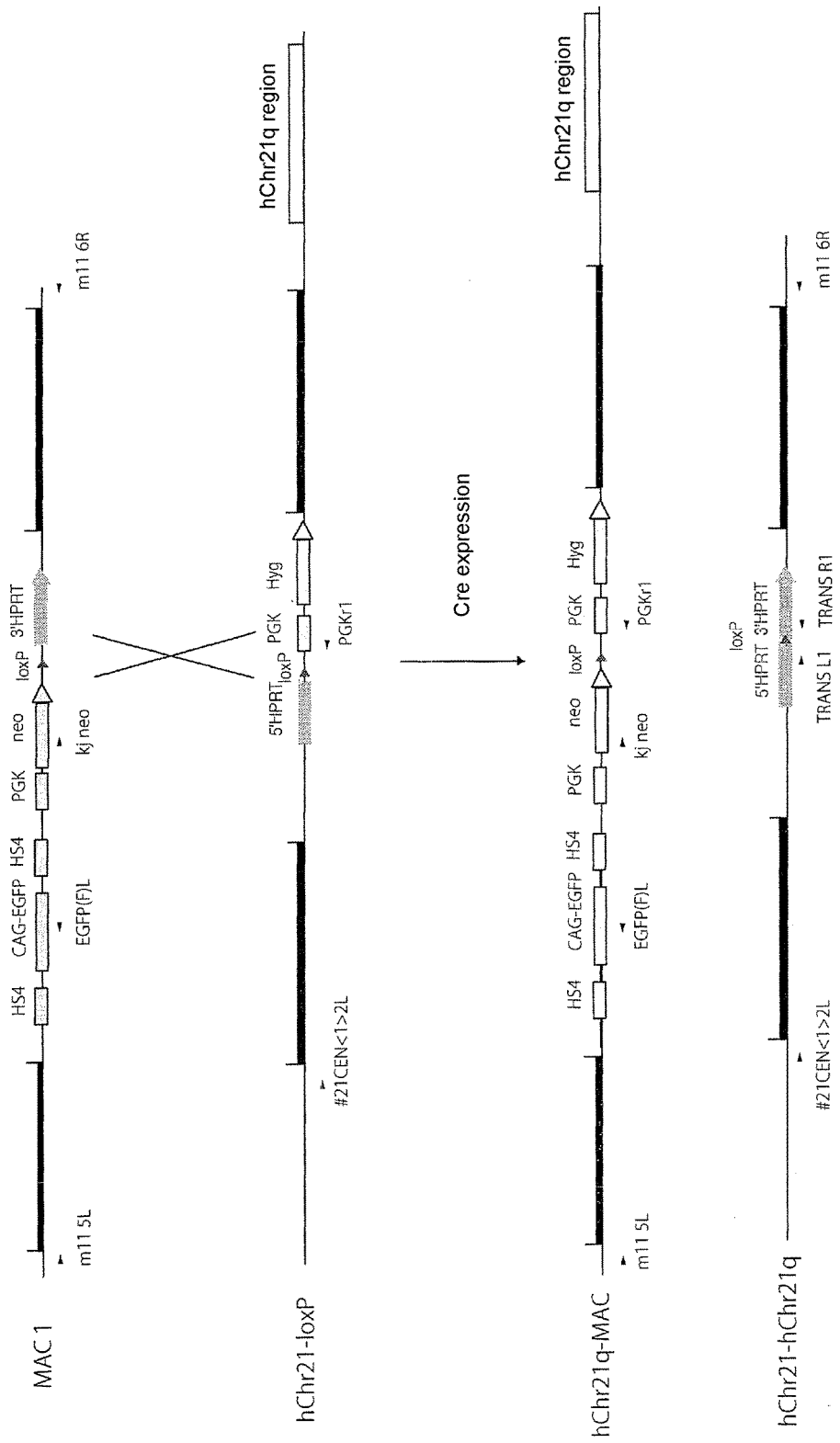
FIG. 51 shows the construction of mouse artificial chromosome hChr21q-MAC in which approximately 33 Mb hChr21q region was translocation-cloned into MAC1.

[B] Site Specific Translocation of 33 Mb Region Distal from AP001657 of Long Arm of Human Chromosome 21 into MAC1 Vector in CHO (HPRT⁻; MAC1, hChr21-loxP) Clone To stably keep a region distal from AP001657 of long arm of human chromosome 21, which is a DNA having 33 Mb size, in a mouse individual, translocation insertion into the mouse artificial chromosome vector MAC1 was performed (FIG. 51).

[B. 1] Transfection and Isolation of HAT Resistant Clone

Gene transfer was carried out by lipofection for the CHO (HPRT⁻; MAC1, hChr21-loxP)-37 obtained from the above. To cells in 6 wells with 90% confluency, 3 μg of Cre was added according to the commercially available protocol (Invitrogen). After 2-weeks culture conducted under HAT selection culture, a resistant colony was generated and total two colonies obtained by two gene transfers were isolated, amplified, and subjected to the following analysis (clone name: CHO (hChr21q-MAC, hChr21-hChr21q)).

[B. 2] Selection of Drug Resistant Clone

[B. 2. 1] PCR Analysis

For extracting genomic DNA from HAT resistant cell line and using it as a template for selecting a clone with reciprocal translocation, PCR was carried out by using the following primers and it was confirmed whether or not reciprocal chromosomal translocation has occurred on human chromosome 21 fragment and MAC1. The primer sequences are given below.

kj neo (described above)
PGKr1 (described above)
D21S265-L (described above)
D21S265-R (described above)
D21S261-L (described above)
D21S261-R (described above)
D21S268-L (described above)
D21S268-R (described above)
D21S266-L (described above)
D21S266-R (described above)
D21S1259-L (described above)
D21S1259-R (described above)
CBR-L (described above)
CBR-R (described above)
TRANS L1 (described above)
TRANS R1 (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, all two clones were found to be positive for all primer sets and the following analysis was performed by using those two clones.

[B. 2. 2] Two-Color FISH Analysis

Figure 52:
FIG. 52 shows the results of the two-color FISH analysis of CHO (hChr21q-MAC, hChr21-hChr21q) clone in which human Cot-1 DNA and mouse Cot-1 DNA were used as probes.

With the two clones of CHO (hChr21q-MAC, hChr21-hChr21q) obtained from the above, FISH analysis was carried out by using mouse Cot-1 DNA and human Cot-1 DNA as probes according to the method described by Shinohara et al. (Human Molecular Genetics, 10: 1163-1175, 2001). As a result, it was confirmed that the signal derived from human chromosome 21 was observed on MAC1 at a rate of 90% or more in two clones out of the two clones (FIG. 52).

From these results, it was concluded that cloning of 33 Mb region distal from AP001657 of long arm of human chromosome 21 into the mouse artificial chromosome vector MAC1 could be achieved by reciprocal translocation.

[C] Transfer of hChr21q-MAC from CHO Cell to Mouse ES Cell

Figure 53:
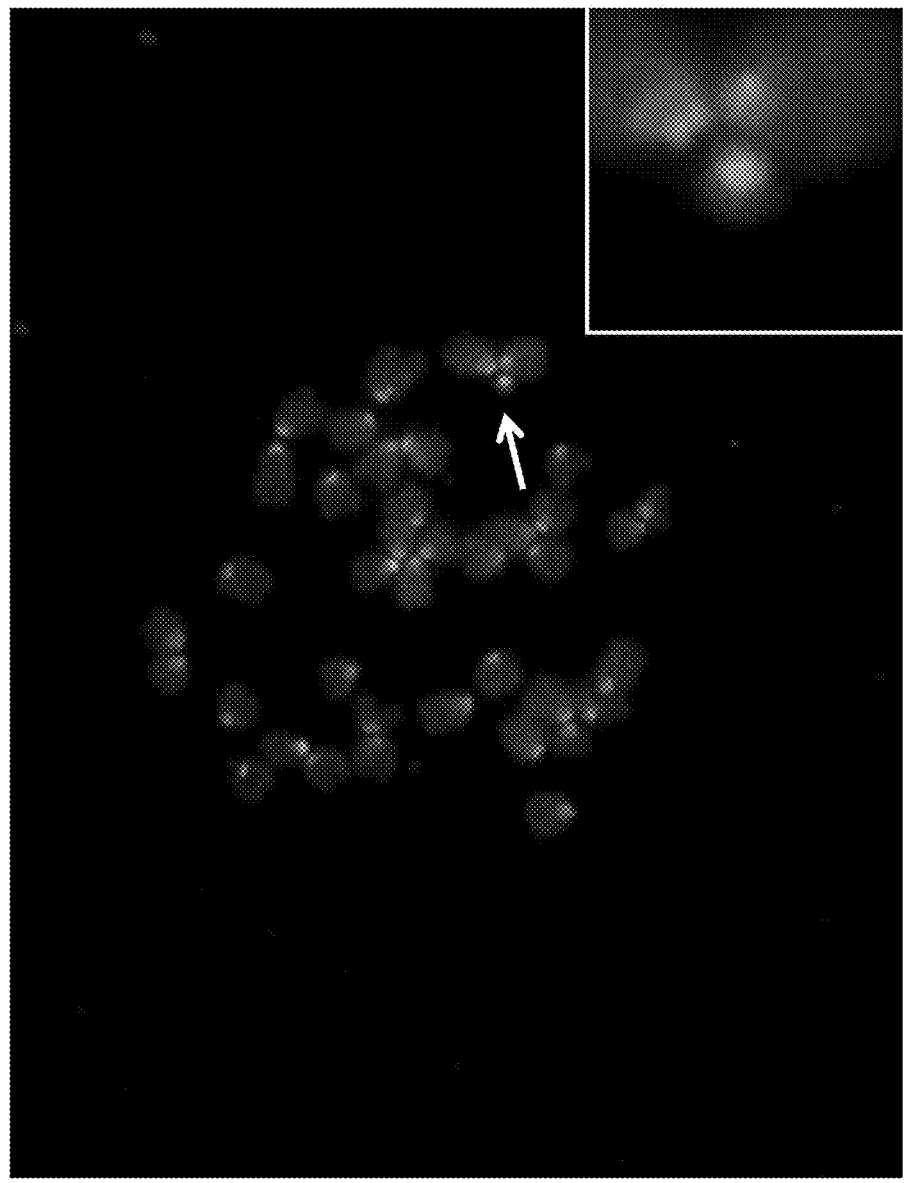
FIG. 53 shows the results of the two-color FISH analysis of TT2F (hChr21q-MAC) clone in which human Cot-1 DNA and mouse minor satellite DNA probes were used.

To prepare a chimeric mouse retaining hChr21q-MAC, transfer was carried out from CHO cells retaining hChr21q-MAC obtained from the above [B] to mouse ES cells (wild type TT2F) by microcell fusion. According to the method of Tomizuka et al. (Nature Genet. 16: 133, 1997), microcells were purified from approximately $10^8$ cells of CHO retaining hChr21q-MAC (CHO (hChr21q-MAC, hChr21-hChr21q) 1, 2)) and suspended in 5 ml of DMEM. Approximately $10^7$ mouse ES cells TT2F were detached by trypsin treatment, washed three times with DMEM, suspended in 5 ml of DMEM, and added to the microcells obtained by centrifugation. After centrifugation for 10 min at 1250 rpm, the supernatant was completely removed. The precipitates were resolved fully by tapping and added with 0.5 ml of 1:1.4 PEG solution [5 g of PEG1000 (Wako Pure Chemical Industries, Ltd.) and 1 ml of DMSO (Sigma) are dissolved in 6 ml of DMEM], and fully stirred for about 1 min and 30 sec. After that, 10 ml of DMEM was slowly added, centrifuged for 10 min at 1250 rpm, and suspended in 30 ml of ES culture medium. Thereafter, the cells were dispensed into three petri dishes with a diameter of 100 mm (Corning Incorporated) to which feeder cells have been previously added and then cultured. 24 hours later, the culture medium was exchanged with culture medium containing 300 μg/ml G418 and then subjected to selection culture for about 1 week. As a result, total 24 colonies were isolated, amplified, and subjected to the following analysis. Two clones from CHO (hChr21q-MAC, hChr21-hChr21q) 1 and six clones from CHO (hChr21q-MAC, hChr21-hChr21q) 2 were determined to be positive by PCR using the primers described before for detecting the hChr21q-MAC region only. In addition, for eight clones among the above, FISH analysis (Tomizuka et al., Nature Genet. 16: 133, 1997) was carried out by using human Cot-1 DNA and mouse minor satellite DNA. As a result, the clones that were specifically detected with the probes and had normal mouse nuclear type were found to be two clones (FIG. 53). From the above, it was concluded that two clones of TT2F cells retaining hChr21q-MAC were obtained.

[D] Stability of hChr21q-MAC in Mouse ES Cell

Figure 54:
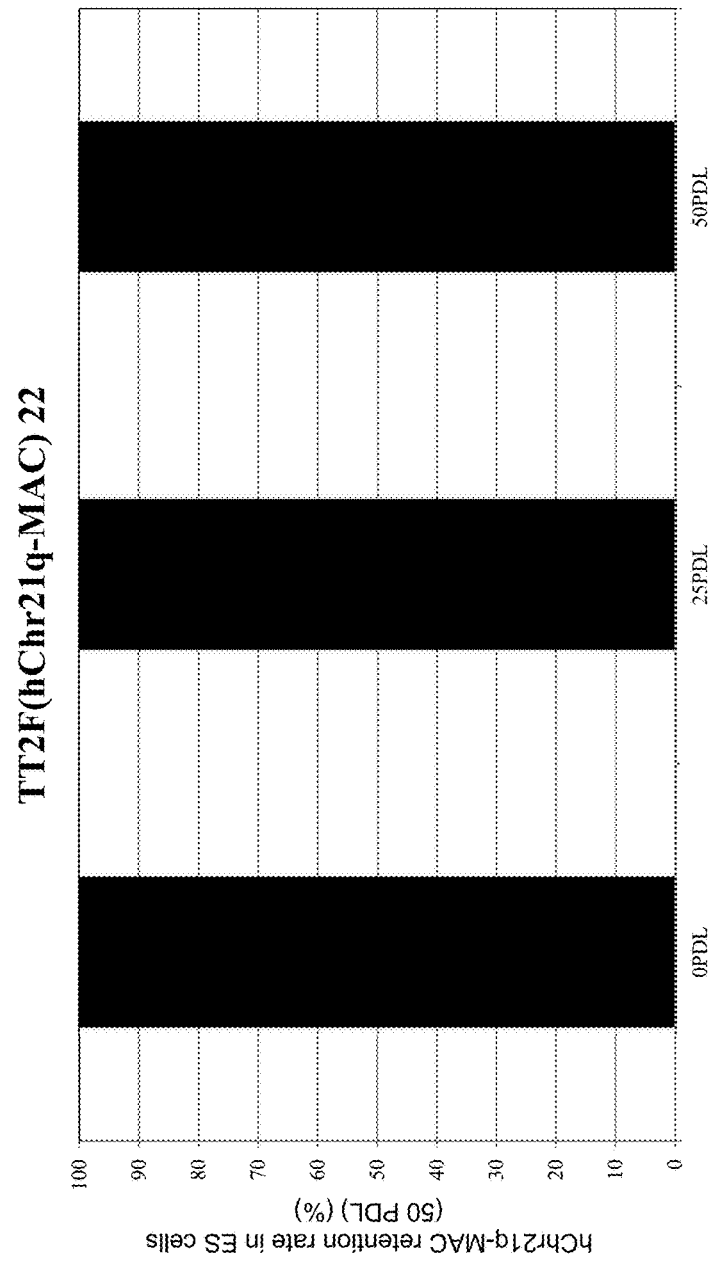
FIG. 54 shows the retention rate of hChr21q-MAC in ES cells after long-term culture (50 PDL).

Under non-selection culture of 0 to 50 PDL for the mouse ES clones obtained from the above (for example, TT2F (hChr21q-MAC) 22, obtained from the above [C]), the rate of cells retaining hChr21q-MAC after long-term culture was measured by FISH analysis. As a result, the retention rate of 95% or more was obtained even for 50 PDL (FIG. 54).

[E] Preparation of Chimeric Mouse Retaining hChr21q-MAC

Figure 55:
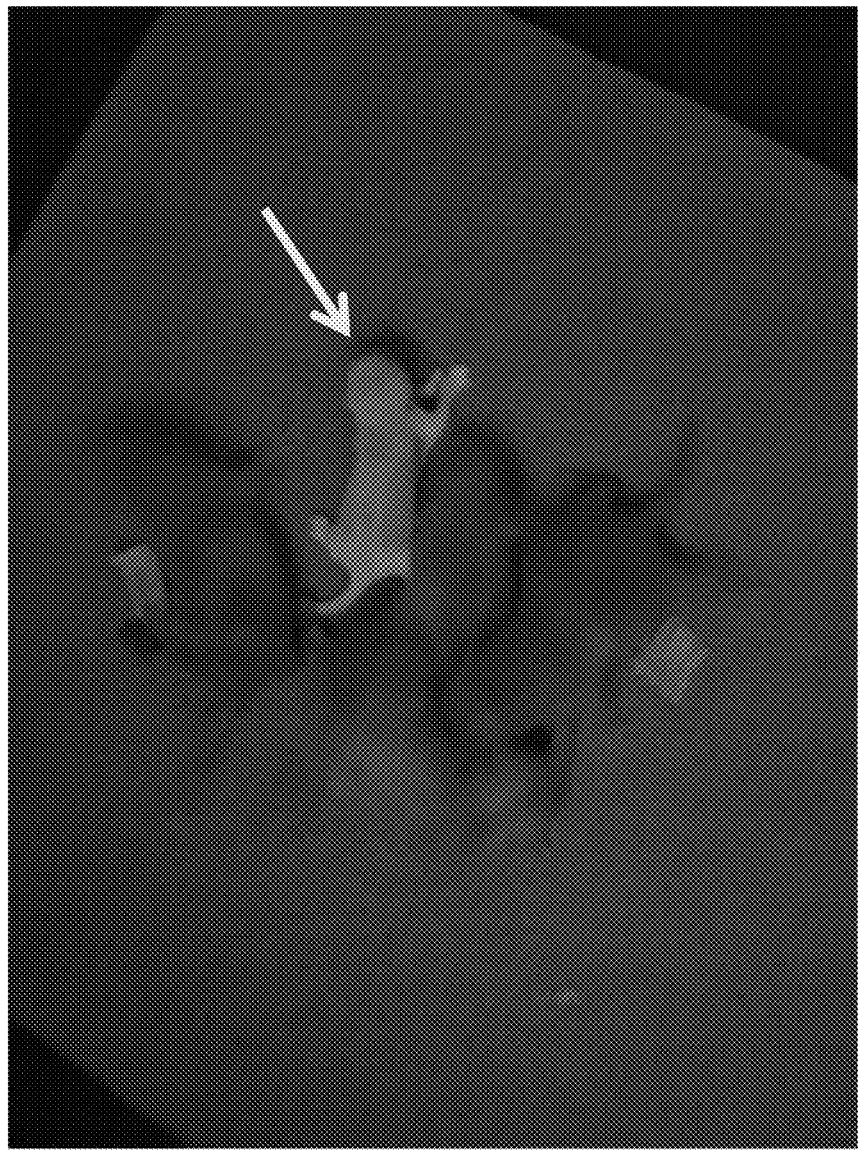
FIG. 55 shows the fluorescence picture of a chimeric mouse retaining hChr21q-MAC.

By using the ES cell clones retaining hChr21q-MAC obtained from the above [C], a chimeric mouse was prepared according to the method of Tomizuka et al. (Nature Genet. 16: 133, 1997). As a host cell, eight-cell stage embryos obtained by sexual crossbreeding of MCH (ICR) (white, purchased from CLEA Japan, Inc.) were used. Injected embryo was transplanted into a foster mother, and coat color of the new born mouse was examined to see whether or not it is a chimera. As the result that 220 embryos injected with ES clone retaining MAC1 (for example, TT2F (hChr21q-MAC) 20, 22, or the like obtained from the above [C]) were transplanted into foster mothers, 18 chimeric mice (in which dark brown color area was observed in coat color) were born. Among them, two animals were individuals having a chimeric rate of about 100% from which almost no white color area was observed. Further, one of them was a GFP-positive individual (FIG. 55). In other words, it was shown that ES cell line (TT2F) retaining the mouse artificial chromosome vector hChr21q-MAC retained a chimera forming ability, that is, an ability of differentiating into normal tissue of a mouse individual.

[F] As described in Example 8, mouse line-based TC (hChr21q-MAC) in which hChr21q-MAC is transmitted to a progeny can be prepared from the chimeric mouse retaining the mouse artificial chromosome vector hChr21q-MAC. Further, by using the TC (hChr21q-MAC) mouse line, stability of hChr21q-MAC in somatic cells can be examined. Still further, the TC (hChr21q-MAC) line can be used as a model mouse for Down's syndrome, and it can be advantageously used for elucidating the mechanism for onset of Down's syndrome or developing a therapeutic agent for alleviating the symptom.

Example 12

Construction of the Mouse Artificial Chromosome Vector hChr21q22.12-MAC

In order to prepare a mouse for also presenting Down's syndrome, translocation cloning of a DNA sequence containing a region distal from AP00172 of long arm of human chromosome 21 into the mouse artificial chromosome vector MAC1 is performed by using Cre/loxP system to construct hChr21q22.12-MAC in the same manner as in Example 3.

[A] Site Specific Insertion of loxP Sequence into AP001721 in Human Chromosome 21

For translocation insertion into the mouse artificial chromosome vector MAC1 via loxP sequence, loxP sequence is inserted into AP001721 proximal to DSCR (Down's syndrome critical region cluster) of human chromosome 21 (hChr21) in DT40 cells.

[A. 1] Preparation of Targeting Vector pCKloxPHyg

Targeting vector pCKloxPHyg for inserting loxP, which is a recognition sequence for Cre recombinase, into Down's syndrome causative gene region (DSCR), which is located extremely close to AP001721 of human chromosome 21 and on the centromere side (i.e., locating on the centromere side by approximately 50 Kb from AP001721) was prepared as follows. First, the AP001721 genome region was amplified by PCR using the following primers.

AML5' .L1;
(SEQ ID NO: 87)
5'-TAGAATTCGTAGGCTTGGAAGCAGTGAGAGAGAA-3'

AML5' .R2;
(SEQ ID NO: 88)
5'-GAAGACTGGTAAATCTGGTGGCTGTC-3'

AML5' .L4;
(SEQ ID NO: 89)
5'-ATTAGATCTCCTGCTGTTATCTCATGCACTCTCA-3'

AML5' .R4;
(SEQ ID NO: 90)
5'-ATTAGATCTATGATGCCTGATACATGGTCTGTGA-3'

Figure 56:
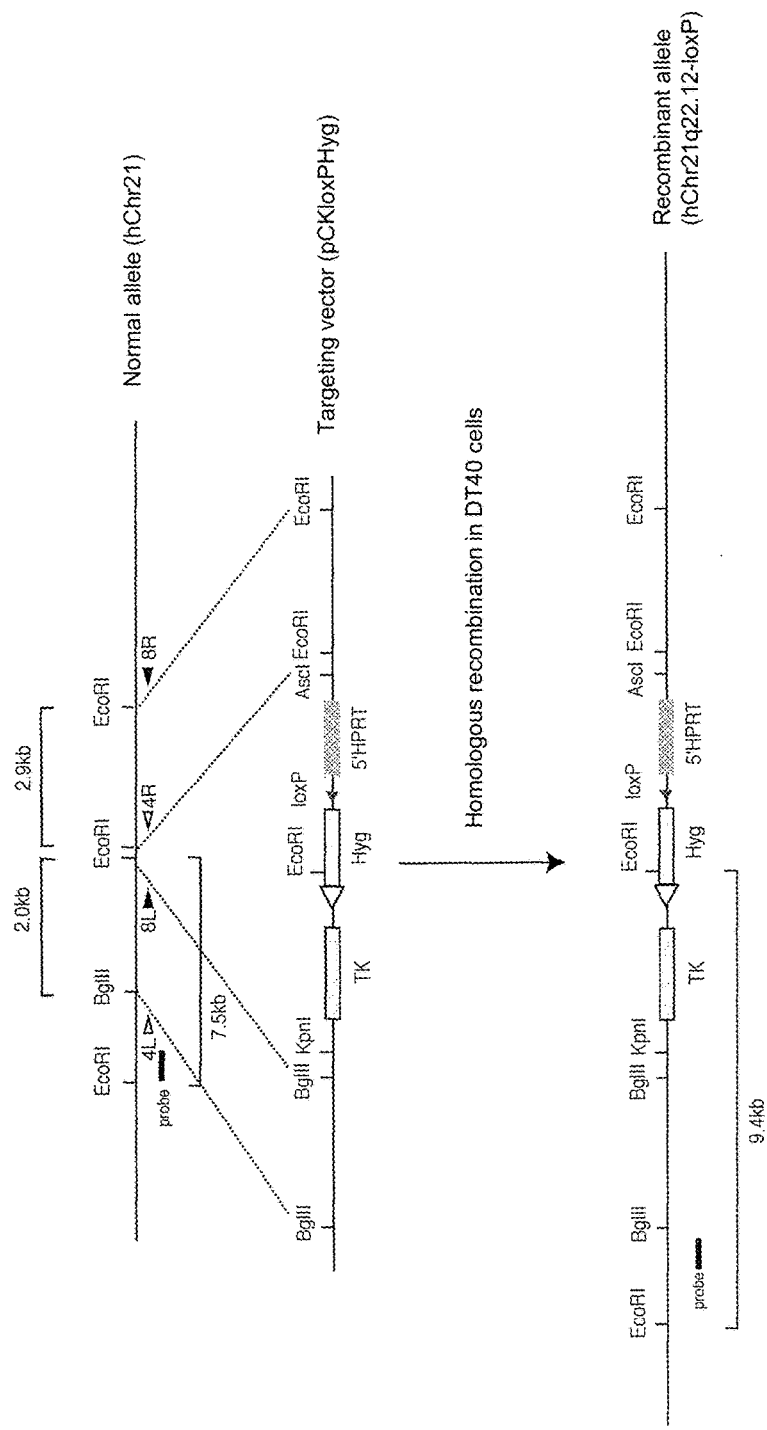
FIG. 56 shows the targeting vector (pCKloxPHyg) for inserting loxP sequence into the AP001721 proximal to DSCR (Down's syndrome causative region cluster) of human chromosome 21 (hChr21), a target sequence, and a chromosome allele produced by homologous recombination.

As a basic plasmid for inserting loxP sequence, V901 (Lexicon genetics) was used. For PCR, GeneAmp 9600 manufactured by PerkinElmer, Inc. was used as a thermal cycler and LA Taq (TAKARA SHUZO CO., LTD.) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 5 min were carried out. PCR product was treated with proteinase K (Gibco) and the PCR fragments (2.9 kb and 2.0 kb) were subjected to gel filtration by using CHROMASPIN-TE400 (Clontech). After that, the product was cleaved with the restriction enzymes EcoRI (NIPPON GENE CO., LTD.) and BglII (NIPPON GENE CO., LTD.) and subjected to gel filtration by using CHROMASPIN-TE1000 (Clontech). Thereafter, the MC1-TK sequence was cut out from V830 (Lexicon genetics) by using RsrII (NEB) and cloned into the recognition site for restriction enzyme HindIII in V901 plasmid (V901T-1). The PCR fragments (2.9 kb and 2.0 kb) were cloned into the EcoRI and BglII sites of V901T-1 plasmid (V901T-1HR2). Next, by using KpnI and AscI, the 5'-HPRT-loxP-Hyg was cut out from 5'-HPRT-loxP-Hyg-TK vector described by Kazuki et al. (Gene Therapy: PMID: 21085194, 2010), and then cloned into the AscI and KpnI sites of V901T-1HR2 (pCKloxPHyg). Size of the final construct inserted with loxP was 11.2 kb. The targeting vector, target sequence, and chromosome allele obtained by homologous recombination are shown in FIG. 56.

[A. 2] Transfection and Isolation of Hygromycin Resistant Clone

As described above, the targeting vector pCKloxPHyg prepared above was linearized with the restriction enzyme NotI (TAKARA), and used for transfection of the DT40 hybrid cells retaining human chromosome 21 (Kazuki et al. BBRC 2004, DT40 (21-2-3)). After exchanging the culture medium for culture medium containing hygromycin B (1.5 mg/ml), the cells were dispensed into three 96-well culture plates and then subjected to selection culture for about 2 weeks. Total 178 resistant colonies obtained from four transfections were isolated, amplified, and subjected to the following analysis (clone name: DT40 (hChr21q22.12-loxP)).

[A. 3] Selection of Homologous Recombinant
[A. 3. 1] PCR Analysis

Genomic DNA was extracted from the hygromycin resistant clone by using Puregene DNA Isolation Kit (Gentra Systems, Inc.) and identification of the homologous recombinant was carried out by PCR using the following two sets of primers.

Identification of the homologous recombinant was carried out by PCR using the following two sets of primers.

(SEQ ID NO: 91)
AML1oxP-4L; 5'-AGAAAGGCAGGTGAGTGTGGAGGTAGA-3'

(SEQ ID NO: 92)
AML1oxP-4R; 5'-GAAGTGGGCTCACAGGAATTTTCCAA-3'

(SEQ ID NO: 93)
AML1oxP-8L; 5'-GGGCCTCTTTATTTGGCAGAATATCACC-3'

(SEQ ID NO: 94)
AML1oxP-8R; 5'-TTACACTGAGATTCAGGGCACGATGA-3'

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 10 sec and 68° C. for 4 min were carried out. As a result of screening 178 clones, 71 clones were identified as a homologous recombinant.

[A. 3. 2] Southern Blot Analysis

For the ten clones which have been confirmed to have recombination by PCR analysis above, Southern blot analysis was carried out as follows. The genomic DNA was treated with the restriction enzyme EcoRI (TAKARA), electrophoresed on 0.8% agarose gel, and subjected to alkali blotting using a GeneScreen Plus™ hybridization transfer membrane (NEN™ Life Science Products, Inc.). The filter was then subjected to Southern hybridization by using SP7 probe, which has been obtained by amplification of the gene sequence in AP001721 by PCR, to identify the homologous recombinant. For preparing SP7 probe, PCR was carried out by using genomic DNA of DT40 (21-2-3) as a template and using the primers described below, and $^{32}$P labeled DNA probe was prepared by random priming using the PCR product as a template (according to Amersham's attached protocols).

Primers for Preparing SP7 Probe are:

(SEQ ID NO: 95)
SP7L; 5'- CAGCTGGGAAACACTGAGCAAGATTATG -3'

(SEQ ID NO: 96)
SP7R; 5'- CTGCTAGACTGAAAATGCGTTTCCTCTG -3'

Figure 57:
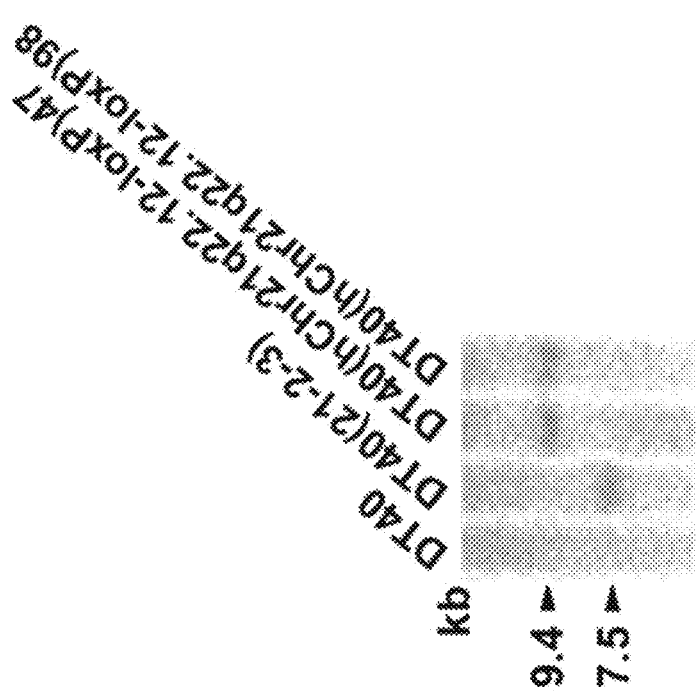
FIG. 57 shows the results of the Southern blot analysis of DT40 (hChr21q22.12-loxP).

For PCR, GeneAmp 9600 manufactured by PerkinElmer, Inc. was used as a thermal cycler and EX Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 93° C. for 5 min, 35 cycles of 93° C. for 1 min, 54° C. for 1 min, and 72° C. for 1 min as one cycle were carried out. Based on Southern hybridization, it was expected that a band at approximately 7.5 kb was detected from the non-homologous recombinant while a band at approximately 9.4 kb was detected from the homologous recombinant (FIG. 56). As a result of Southern hybridization, it was found that all ten clones out of the ten clones were the desired homologous recombinant. The representative results are given in FIG. 57.

[A. 3. 3] Two-Color FISH Analysis

Figure 58:
FIG. 58 shows the results of the two-color FISH analysis of DT40 (hChr21q22.12-loxP) clone in which human Cot-1 DNA and hygromycin DNA were used as probes.

FISH analysis was carried out according to Matsubara et al. (FISH test protocol, Shujunsha Co., Ltd., 1994). FISH analysis was carried out for ten clones out of the clones which have been confirmed to have recombination in the above by using human cot-1 DNA and hygromycin as probes. As a result, it was confirmed that human chromosome 21 was not translocated to the host chromosome in any clone, and based on the fact that hygromycin-derived signal was detected near 21q22, recombination has site-specifically occurred (FIG. 58). From these results, it was concluded that the loxP sequence as a gene introduction site was site-specifically inserted into human chromosome 21 fragment.
[B] Transfer of hChr21q22.12-loxP from DT40 Containing hChr21q22.12-loxP to CHO Cell Containing MAC1

For translocation insertion of a region distal from AP001721 of long arm of human chromosome 21 into the mouse artificial chromosome vector MAC1 via loxP sequence in CHO cells, hChr21q22.12-loxP which was obtained by inserting loxP sequence into AP001721 in human chromosome 21 was introduced into CHO cells containing the mouse artificial chromosome vector MAC1.
[B. 1] Microcell Fusion and Isolation of Drug Resistant Clone By using DT40 cell containing hChr21q22.12-loxP, i.e. DT40 (hChr21q22.12-loxP) 47, as a recipient cell, microcell fusion was carried out for CHO (HPRT⁻; MAC1), that is, CHO hprt depleted cells containing MAC1 (obtained from the Health Science Research Resources Bank, registration number: JCRB0218), in the same manner as above. Total 140 resistant colonies obtained by 15 microcell fusions were isolated, amplified, and subjected to the following analysis (clone name: CHO (HPRT⁻; MAC1, hChr21q22.12-loxP)).
[B. 2] Selection of Drug Resistant Clone
[B. 2. 1] PCR Analysis For extracting genomic DNA from hygromycin resistant cell line and using it as a template for selecting a recombinant, PCR was carried out for 20 clones out of the 140 clones above by using the following primers, and it was confirmed whether or not human chromosome 21 fragment has been introduced into the CHO cells containing MAC1. The primer sequences are given below.
m11 5L (described above)
EGFP (F) L (described above)
kj neo (described above)
m11 6R (described above)

```
D21S265-L:    gggtaagaaggtgcttaatgctc        (SEQ ID NO: 97)

D21S265-R:    tgaatatgggttctggatgtagtg       (SEQ ID NO: 98)

D21S261-L:    gaggggactgggacaagccctttgctggaagaga  (SEQ ID NO: 99)

D21S261-R:    acattaggaaaaatcaaaaggtccaattattaagg  (SEQ ID NO: 100)

D21S268-L:    CAACAGAGTGAGACAGGCTC           (SEQ ID NO: 101)

D21S268-R:    TTCCAGGAACCACTACACTG           (SEQ ID NO: 102)

D21S266-L:    ggcttggggacattgagtcatcacaatgtagatgt  (SEQ ID NO: 103)

D21S266-R:    gaagaaaggcaaatgaagacctgaacatgtaagtt  (SEQ ID NO: 104)

D21S1259-L:   GGGACTGTAATAAATATTCTGTTGG      (SEQ ID NO: 105)

D21S1259-R:   CACTGGCTCTCCTGACC              (SEQ ID NO: 106)

CBR-L:        gatcctcctgaatgcctg             (SEQ ID NO: 107)

CBR-R:        gtaaatgcctttggacc              (SEQ ID NO: 108)
```

Figure 59:
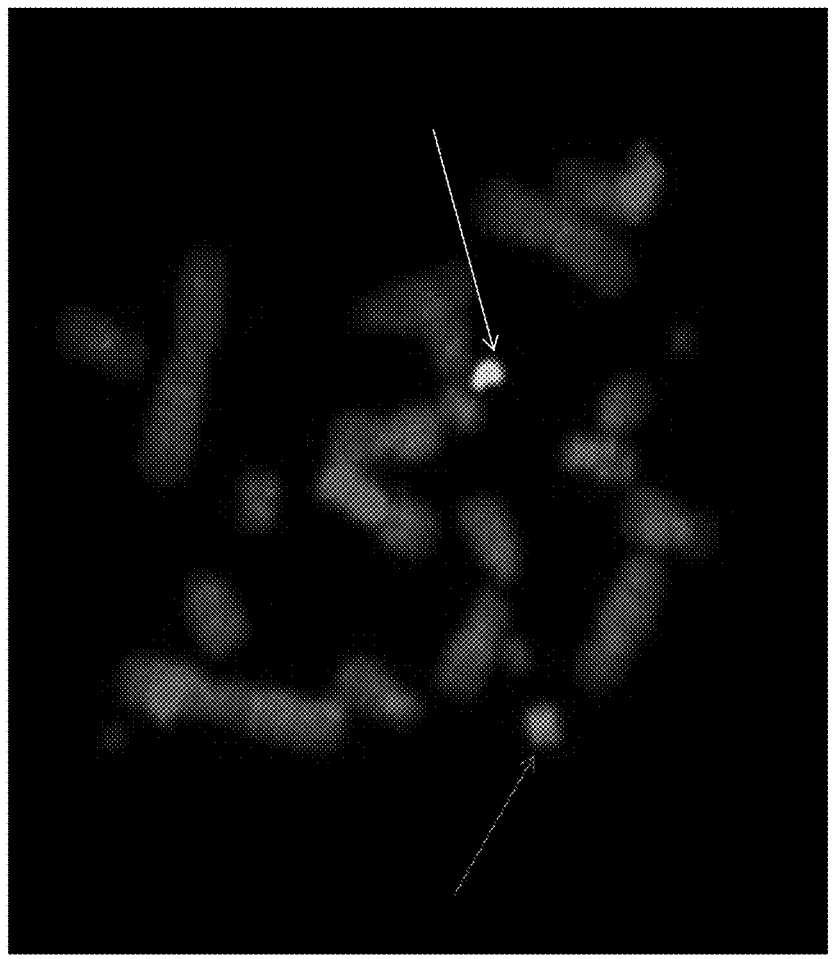
FIG. 59 shows the results of the two-color FISH analysis of CHO (HPRT⁻; MAC1, hChr21q22.12-loxP) clone in which human Cot-1 DNA and mouse Cot-1 DNA were used as probes.

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, 13 clones out of the 20 clones were found to be positive for all primer sets and the following analysis was performed by using those 13 clones.
[B. 2. 2] Two-Color FISH Analysis With six clones out of the 13 clones of CHO (HPRT⁻; MAC1, hChr21q22.12-loxP) obtained from the above, FISH analysis was carried out by using mouse Cot-1 DNA and human Cot-1 DNA as probes according to the method described by Shinohara et al. (Human Molecular Genetics, 10: 1163-1175, 2001). As a result, it was confirmed that singly copy of MAC1 and hChr21q22.12-loxP have been introduced into CHO cells at a rate of 75% in two clones out of the six clones (FIG. 59).

Figure 60:
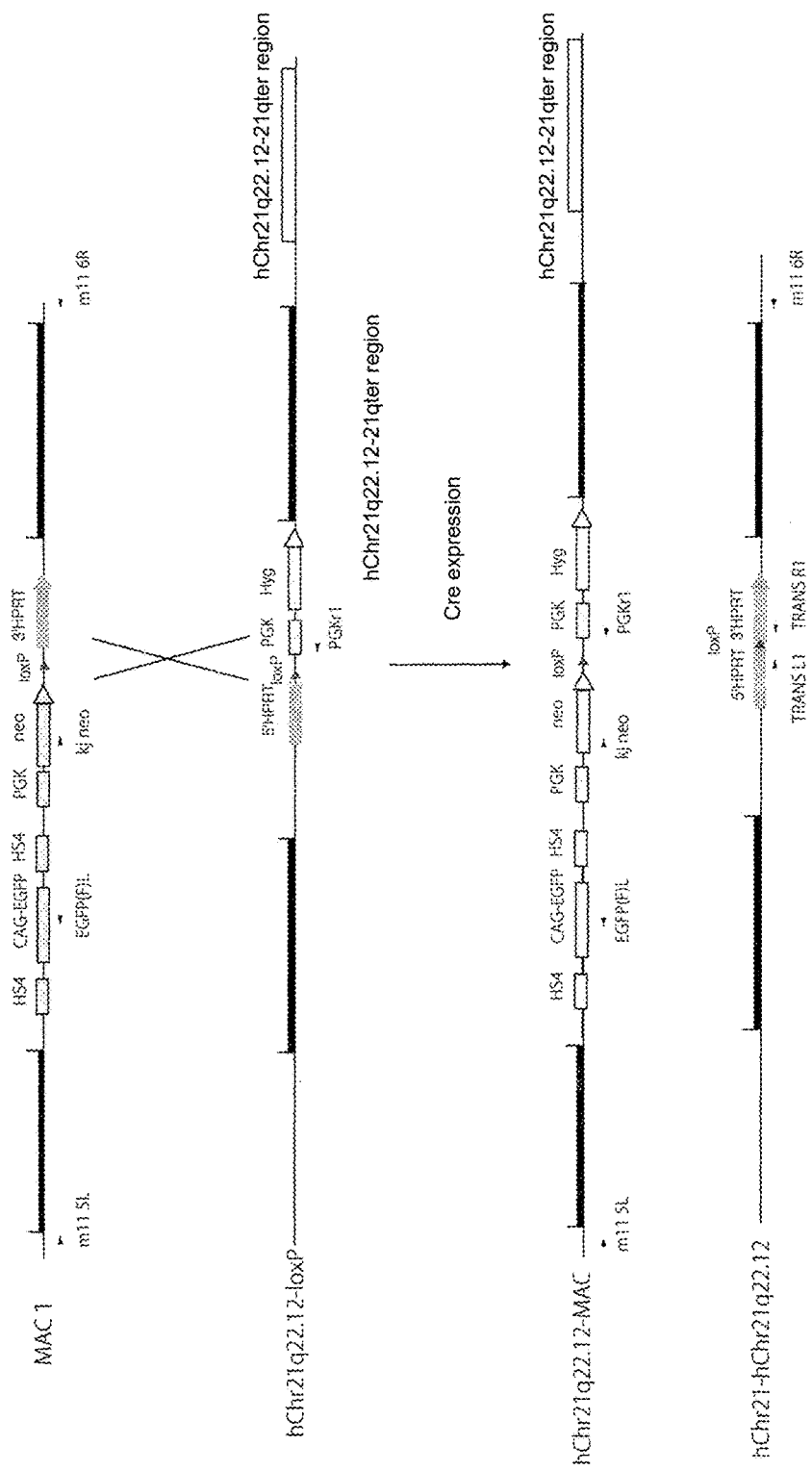
FIG. 60 shows the construction of mouse artificial chromosome hChr21q22.12-MAC in which approximately 12 Mb hChr21q22.12-qter region is translocation-cloned into MAC1.

From these results, it was concluded that hChr21q22.12-loxP could be introduced into CHO cells containing the mouse artificial chromosome vector MAC1.
[C] Site Specific Translocation of 12 Mb Region Distal from AP001721 of Long Arm of Human Chromosome 21 in CHO (HPRT⁻; MAC1, hChr21q22.12-loxP) Clone To stably keep a region distal from AP001721 of long arm of human chromosome 21, which is a DNA having 12 Mb size, in a mouse individual, translocation insertion into the mouse artificial chromosome vector MAC1 was performed (FIG. 60).
[C. 1] Transfection and Isolation of HAT Resistant Clone Gene introduction was carried out by lipofection for the CHO (HPRT⁻; MAC1, hChr21q22.12-loxP)-12 and -13 obtained from the above. To cells in 6 wells with 90% confluency, 3 μg of Cre was added according to the commercially available protocol (Invitrogen). After culture for 2 weeks under HAT selection culture, a resistant colony was generated and total 19 colonies obtained by two introductions were isolated, amplified, and subjected to the following analysis (clone name: CHO (hChr21q22.12-MAC, hChr21-hChr21q22.12)).
[C. 2] Selection of Drug Resistant Clone
[C. 2. 1] PCR Analysis For extracting genomic DNA from HAT resistant cell line and using it as a template for selecting a clone with reciprocal translocation, PCR was carried out by using the following primers and it was confirmed whether or not reciprocal chromosomal translocation has occurred on human chromosome 21 fragment and MAC1. The primer sequences are given below.
kj neo (described above)
PGKr1 (described above)
D21S265-L (described above)
D21S265-R (described above)
D21S261-L (described above)
D21S261-R (described above)
D21S268-L (described above)
D21S268-R (described above)

D21S266-L (described above)
D21S266-R (described above)
D21S1259-L (described above)
D21S1259-R (described above)
CBR-L (described above)
CBR-R (described above)
TRANS L1 (described above)
TRANS R1 (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, eight clones out of the 19 clones were found to be positive for all primer sets, and the following analysis was performed by using those 8 clones.

[C. 2. 2] Two-Color FISH Analysis

Figure 61:
FIG. 61 shows the results of the two-color FISH analysis of CHO (hChr21q22.12-MAC, hChr21-hChr21q22.12) clone in which human Cot-1 DNA and mouse Cot-1 DNA were used as probes.

For 8 clones of CHO (hChr21q22.12-MAC, hChr21-hChr21q22.12) obtained above, FISH analysis was carried out by using mouse Cot-1 DNA and human Cot-1 DNA as probes according to the method described by Shinohara et al. (Human Molecular Genetics, 10: 1163-1175, 2001). As a result, it was confirmed that the signal derived from human chromosome 21 was observed on MAC1 at a rate of 85% or more in all clones out of the eight clones (FIG. 61).

From these results, it was concluded that cloning of 12 Mb region distal from AP001721 of long arm of human chromosome 21 into the mouse artificial chromosome vector MAC1 could be achieved by reciprocal translocation.

[D] Transfer of hChr21q22.12-MAC from CHO Cell to Mouse ES Cell

Figure 62:
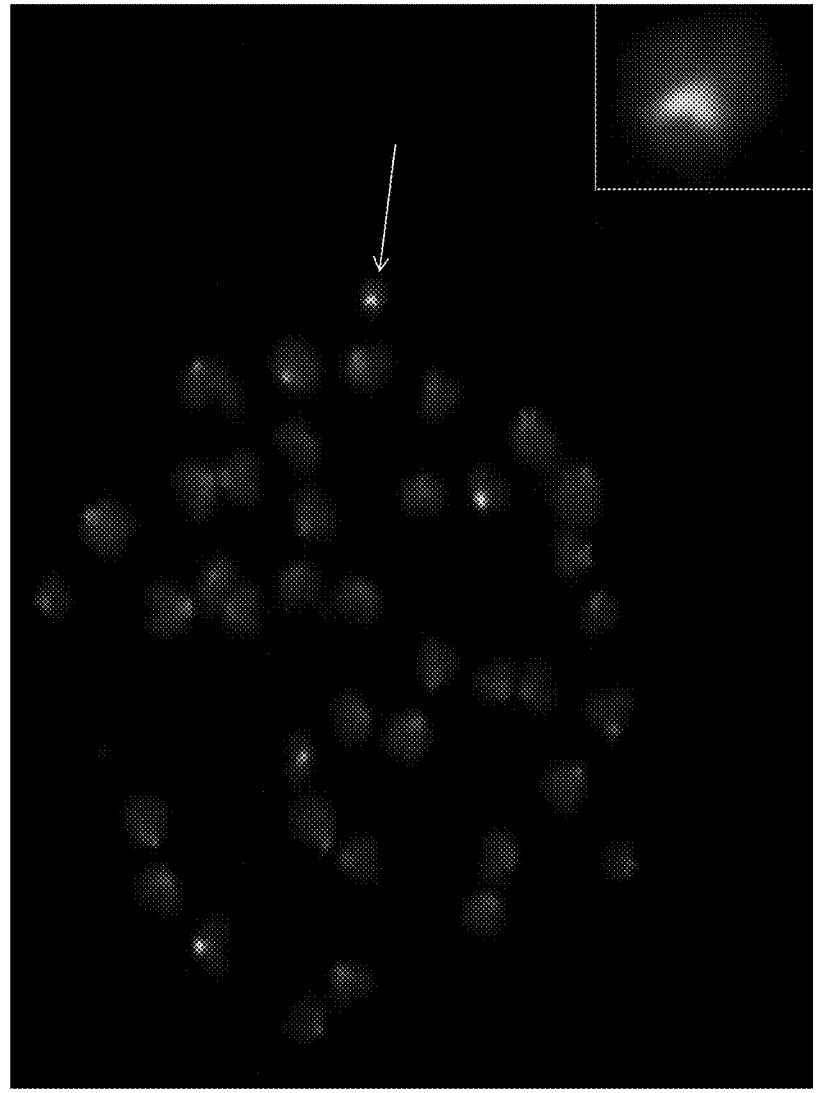
FIG. 62 shows the results of the two-color FISH analysis of TT2F (hChr21q22.12-MAC) clone in which human Cot-1 DNA and mouse minor satellite DNA probes were used.

To prepare a chimeric mouse retaining hChr21q22.12-MAC, transfer was carried out from CHO cells retaining hChr21q22.12-MAC obtained from the above [C] to mouse ES cells (wild type TT2F) by microcell fusion. According to the method of Tomizuka et al. (Nature Genet. 16: 133, 1997), microcells were purified from approximately $10^8$ cells of CHO retaining hChr21q-MAC (CHO (hChr21q22.12-MAC, hChr21-hChr21q22.12) 1, 12, or the liked) and suspended in 5 ml of DMEM. Approximately $10^7$ mouse ES cells of TT2F were detached by trypsin treatment, washed three times with DMEM, suspended in 5 ml of DMEM, and added to the microcells obtained by centrifugation. After centrifugation for 10 min at 1250 rpm, the supernatant was completely removed. The precipitates were resolved fully by tapping and added with 0.5 ml of 1:1.4 PEG solution [5 g of PEG1000 (Wako Pure Chemical Industries, Ltd.), and 1 ml of DMSO (SIGMA) were dissolved in 6 ml of DMEM], and fully stirred for about 1 min and 30 sec. After that, 10 ml of DMEM was slowly added, centrifuged for 10 min at 1250 rpm, and suspended in 30 ml of ES culture medium. Thereafter, the cells were dispensed into three petri dishes with a diameter of 100 mm (Corning Incorporated) to which feeder cells have been previously added and then cultured. 24 hours later, the culture medium was exchanged with culture medium containing 300 µg/ml G418 and then subjected to selection culture for about 1 week. As a result, total 13 colonies were isolated, amplified, and subjected to the following analysis. One clone from CHO (hChr21q22.12-MAC, hChr21-hChr21q22.12) 1 and one clone from CHO (hChr21q22.12-MAC, hChr21-hChr21q22.12) 12 were positive in PCR using the primers described above for detecting the hChr21q22.12-MAC region only. In addition, for two clones among the above, FISH analysis (Tomizuka et al., Nature Genet. 16: 133, 1997) was carried out by using human Cot-1 DNA and mouse minor satellite DNA. As a result, the clones that were specifically detected with the probes and had normal mouse nuclear type were found to be one clone (FIG. 62). From the above, it was concluded that one clone of TT2F cells retaining hChr21q22.12-MAC was obtained.

[E] Stability of hChr21q22.12-MAC in Mouse ES Cell

Figure 63:
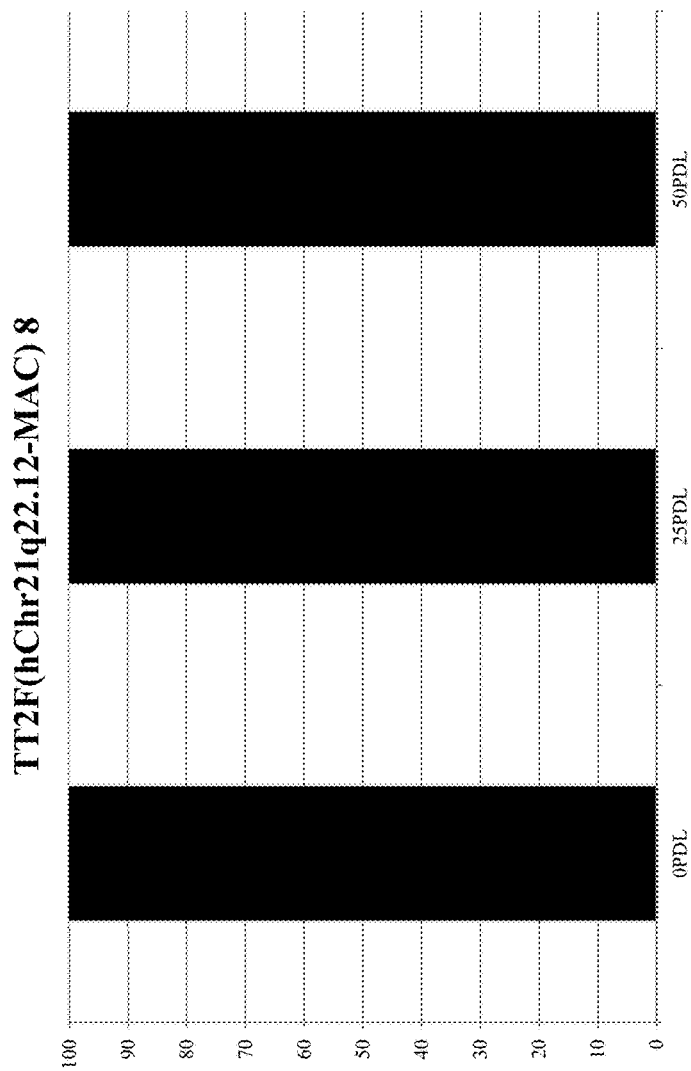
FIG. 63 shows the retention rate of hChr21q22.12-MAC in ES cells after long-term culture (50 PDL).

Under non-selection culture of 0 to 50 PDL for the mouse ES clones obtained from the above (for example, TT2F (hChr21q22.12-MAC) 8, obtained from the above [D]), the rate of cells retaining hChr21q22.12-MAC after long-term culture was measured by FISH analysis. As a result, the retention rate of 95% or more was obtained even for 50 PDL (FIG. 63).

[F] Preparation of Chimeric Mouse Retaining hChr21q22.12-MAC

By using the ES cell clones retaining hChr21q22.12-MAC obtained from the above [D], a chimeric mouse was prepared according to the method of Tomizuka et al. (Nature Genet. 16: 133, 1997). As a host cell, eight-cell stage embryos obtained by sexual crossbreeding of MCH (ICR) (white, purchased from CLEA Japan, Inc.) were used. Injected embryo was transplanted into a foster mother, and coat color of the new-born mouse was examined to see whether or not it was a chimera. As the result that 80 embryos injected with ES clone retaining hChr21q22.12-MAC (for example, TT2F (hChr21q22.12-MAC) 8, obtained from the above [D]) were transplanted into foster mothers, 43 chimeric mice (in which dark brown color area was observed in coat color) were born. Among them, three animals were individuals having a chimeric rate of about 100% from which almost no white color area was observed. In other words, it was shown that ES cell line (TT2F) retaining the mouse artificial chromosome vector hChr21q22.12-MAC retained a chimera forming ability, that is, an ability of differentiating into normal tissue of a mouse individual.

[G] As described in Example 8, mouse lineage-based TC (hChr21q22.12-MAC) in which hChr21q22.12-MAC has been transmitted to a progeny can be prepared from the chimeric mouse retaining the mouse artificial chromosome vector hChr21q22.12-MAC. Further, by using the TC (hChr21q22.12-MAC) mouse line, stability of hChr21q22.12-MAC in somatic cells can be examined. Further, the hChr21q22.12-MAC line can be used as a model mouse for Down's syndrome, and it can be advantageously used for elucidating the mechanism for onset of Down's syndrome or developing a therapeutic agent for alleviating the symptom. Still further, by comparing the phenotypes between TC (hChr21q-MAC) mouse line and TC (hChr21q22.12-MAC) mouse line, Down's syndrome critical gene region can be identified.

Example 13

Stability of the Mouse Artificial Chromosome Vector MAC2

[A] Stability of the Mouse Artificial Chromosome Vector MAC2 in CHO Cell

Figure 64:
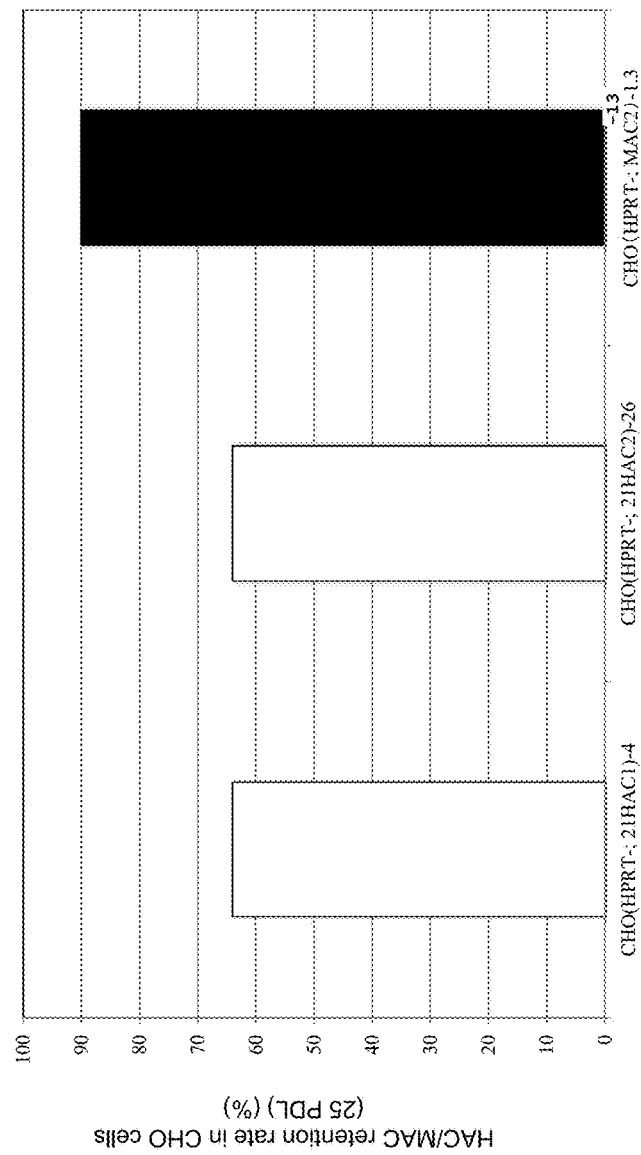
FIG. 64 shows the retention rate of 21HAC1 or 21HAC2 and MAC2 in CHO cells after long-term culture (25 PDL).

Under non-selection culture of 0 to 25 PDL for the CHO clones obtained from the above (for example, CHO (HPRT$^-$; MAC2)-13 and -18, obtained from Example 4 above), the rate of cells retaining MAC2 after long-term culture was measured by FISH analysis. As a result, the retention rate of 90% or more was obtained even for 25 PDL. In contrast, in the CHO cells retaining HAC vector (21HAC2) carrying GFP derived from chromosome 21 described by Kazuki et al. (Gene Therapy: PMID: 21085194, 2010), the retention rate was 70% or less for 25 PDL. The representative results are given in FIG. 64.

Example 14

Construction of the Mouse Artificial Chromosome Vector FVIII-MAC

As an example of gene encoding a useful protein, Factor VIII (FVIII) gene, which is a causative gene of hemophilia A, is inserted into the mouse artificial chromosome vector MAC2 by using Cre/loxP system, and expression and long-term stability of functional protein are examined
[A] Insertion of Gene Encoding Certain Useful Protein (for Example, FVIII) into the Mouse Artificial Chromosome Vector MAC2 by Using Cre/loxP System in CHO Cell Containing the Mouse Artificial Chromosome Vector MAC2 Vector.

Figure 65:
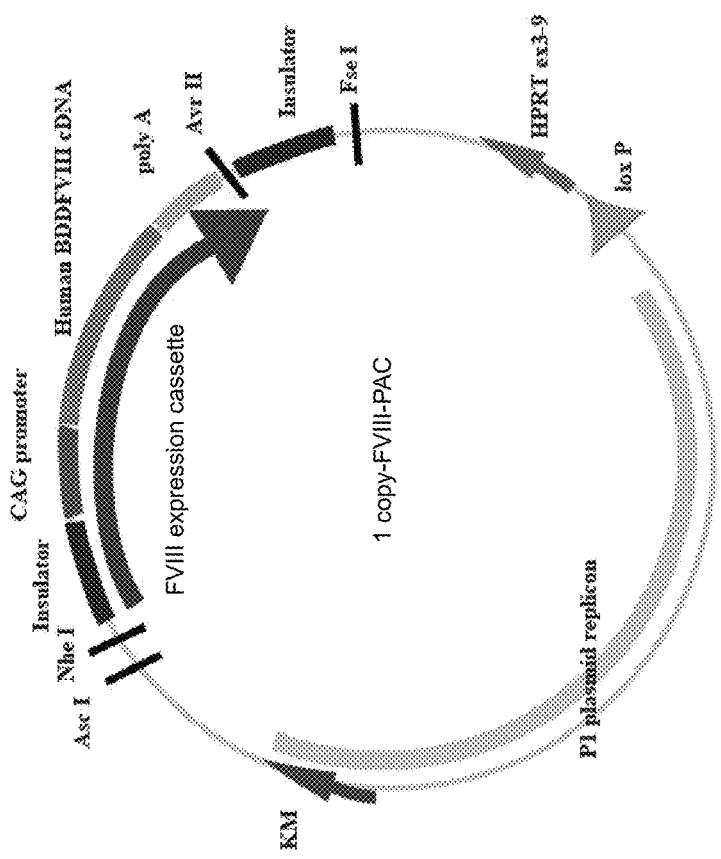
FIG. 65 shows the structure of one (1) copy-of FVIII-PAC.
Figure 66:
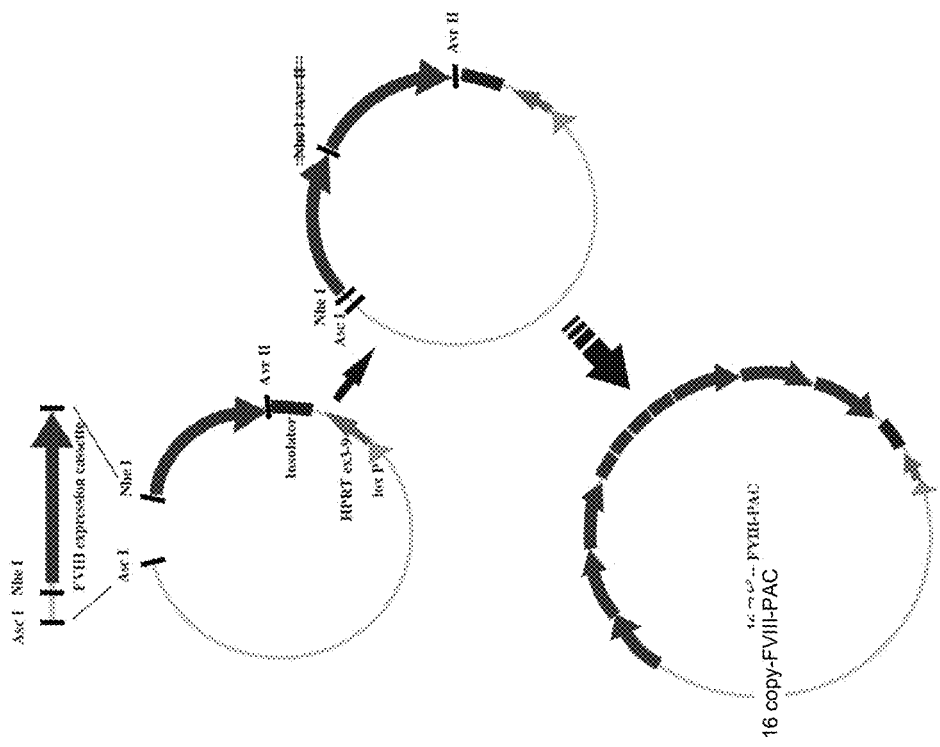
FIG. 66 shows the method of constructing 1-16 copies of FVIII-PAC.

It is examined whether or not loxP is operated and cyclic DNA can be site-specifically inserted into the mouse artificial chromosome vector MAC2 obtained by inserting 5' HPRT-loxP-PGKhyg type loxP sequence, as a DNA insertion sequence, into the mouse artificial chromosome vector MAC.
[A. 1] Preparation of Vector Inserted with FVIII The promoter and poly A region of pCAGGS (provided by Dr. Okabe at Osaka University) were cleaved at SalI and PstI sites, and cloned into SalI and PstI sites of pB3 obtained by modifying the multicloning site of pBluescript KS (−) (Stratagene) (pB-CAG). B domain depleted FVIII cDNA in pKF17K plasmid (provided by Professor Sakata at Jichi Medical University) was cleaved at XhoI and SalI sites, and cloned into EcoRI site located between the promoter and poly A of pB-CAG (pB-CAGF8). CAG-F8-pA region in pB-CAGF8 was isolated at SalI and AvrII sites, and cloned into SalI and AvrII sites so that it could be inserted into two HS4 insulator sequences on pB3ins2 (pB3-F8ins2). Next, pPAC4 (Children's Hospital Oakland Research Institute (CHORI), BAC/PAC Resources) was introduced into the vector incorporated with 3' HPRT-loxP sequence. FVIII expression cassette (HS4-CAG-F8-pA-HS4) as AscI and FseI region on pB3-F8ins2 was cloned into AscI and FseI sites of pPAC4 to give a single copy of FVIII insertion construct of HPRT re-construction system (vector name: pPAC4 F8ins2 H3-9 (single copy FVIII-PAC)) (FIG. 65). By utilizing the characteristics of compatible cohesive end of AvrII site and NheI site, first cassette region from AscI to AvrIl1 of a single copy of FVIII-PAC was re-cloned into the region from AscI to NheI sites of the same vector to obtain two copies of FVIII-PAC containing two expression cassettes. Similarly, the insertion cassette was re-cloned into AscI and AvrII and the vector side was re-cloned into AscI and NheI sites to prepare 2, 4, 8, or 16 copies of PAC vector having FVIII expression cassette (FIG. 66).
[A. 2] Transfection and Isolation of HAT Resistant Clone Gene introduction was carried out by lipofection. With regard to the cells in 6 wells with 90% confluency, 1 μg of Cre and 10 μg of a single copy of FVIII-PAC vector were introduced into CHO (HPRT−; MAC2)-13 described above and CHO (HPRT−; 21HAC2) described by Kazuki et al. (Gene Therapy: PMID: 21085194, 2010), according to the commercially available protocol (Invitrogen) (clone name: CHO (FVIIIx1-MAC) and CHO (FVIIIx1-HAC)). Further, 1 μg of Cre and 10 μg of 16 copies of FVIII-PAC vector were introduced into CHO (HPRT−; MAC2)-13 described above according to the commercially available protocol (Invitrogen) (clone name: CHO (FVIIIx16-MAC)). After culture for 2 weeks under HAT selection culture, resistant colony was generated, and total 83 colonies obtained by four introductions, that is, 46 clones for CHO (FVIIIx1-MAC), 18 clones for CHO (FVIIIx16-MAC), and 19 clones for CHO (FVIIIx 1-HAC), were isolated, amplified, and subjected to the following analysis.
[A. 3] Selection of Drug Resistant Clone
[A. 3. 1] PCR Analysis In order to select a recombinant by using as a template genomic DNA of HAT resistance cell line, PCR was carried out by using the following primers and it was confirmed whether or not site specific insertion of FVIII gene has occurred. The primer sequences are given below.
TRANS L1 (described above)
TRANS R1 (described above)

```
                                             (SEQ ID NO: 109)
        FVIII F: 5'-ATACAACGCTTTCTCCCCAA-3'

(SEQ ID NO: 110)
        FVIII R: 5'-TCTTGAACTGAGGGACACTG-3'
```

For PCR, GeneAmp 9600 manufactured by PerkinElmer, Inc. was used as a thermal cycler and Ex Taq (Applied Biosystems) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 10 min, 35 cycles of 94° C. for 30 sec, 60° C. for 30 sec, and 72° C. for 1 min were carried out. As a result of PCR, four clones derived from CHO (FVIIIx 1-MAC), 17 clones derived from CHO (FVIIIxl-HAC), and three clones derived from CHO (FVIIIx16-MAC) were found to be positive, and the following analysis was performed by using those 24 clones.
[A. 3. 2] Mono-Color FISH Analysis Based on the results above, for seven clones, mono-color FISH analysis was carried out according to Matsubara et al. (FISH test protocol, Shujunsha Co., Ltd., 1994). FISH analysis was carried out by using mouse cot-1 DNA or human cot-1 DNA as a probe. As a result, it was found that one clone derived from CHO (FVIIIx1-MAC) retained FVIII-MAC at a rate of 90% or more, two clones derived from CHO (FVIIIx1-HAC) retained FVIII-HAC at a rate of 90% or more, and one clone derived from CHO (FVIIIx16-MAC) retained FVIII-HAC at a rate of 90% or more.
[B] Gene Expression Analysis of FVIII Gene in CHO Cell By using CHO (FVIIIx1-MAC) 1-3 in which FVIIIx1-MAC was retained, CHO (FVIIIx1-HAC) 1-2 in which FVIIIx1-HAC was retained, and CHO (FVIIIx16-MAC) 16-1, 16-2, 16-3 in which FVIIIx16-MAC was retained, expression of FVIII mRNA was examined Specifically, as described above, RNA was extracted, cDNA was synthesized by using the RNA as a template, and PCR was carried out by using the following primers (described above). Temperature and cycle conditions were as follows: after heat denaturation at 94° C. for 10 min, 25 cycles of 94° C. for 30 sec, 60° C. for 30 sec, and 72° C. for 1 min were carried out.
FVIII F: (described above)
FVIII R: (described above)
GAPDH F: (described above)
GAPDH R: (described above)

As a result, it was found that FVIII mRNA was expressed at the same level in CHO (FVIII×1-MAC) and CHO (FVIII×1-HAC) while it was expressed more in CHO (FVIII×16-MAC) compared to the CHO (FVIII×1-MAC) and CHO (FVIII×1-HAC).

[C] Gene Function Analysis of FVIII Gene in CHO Cell

Figure 67:
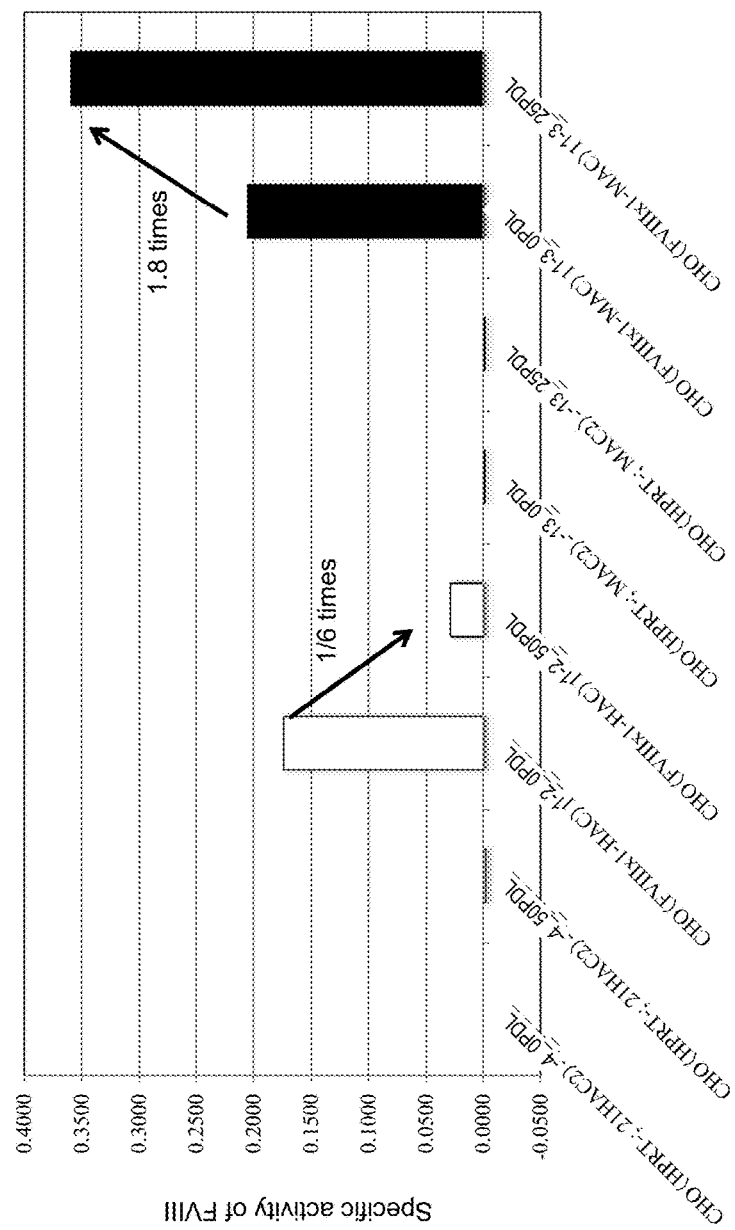
FIG. 67 shows the results of the clotting assay (comparison of FVIII activity) after long-term culture of CHO (FVIII×1-MAC)1-3 and CHO (FVIII×1-HAC)1-2.
Figure 68:
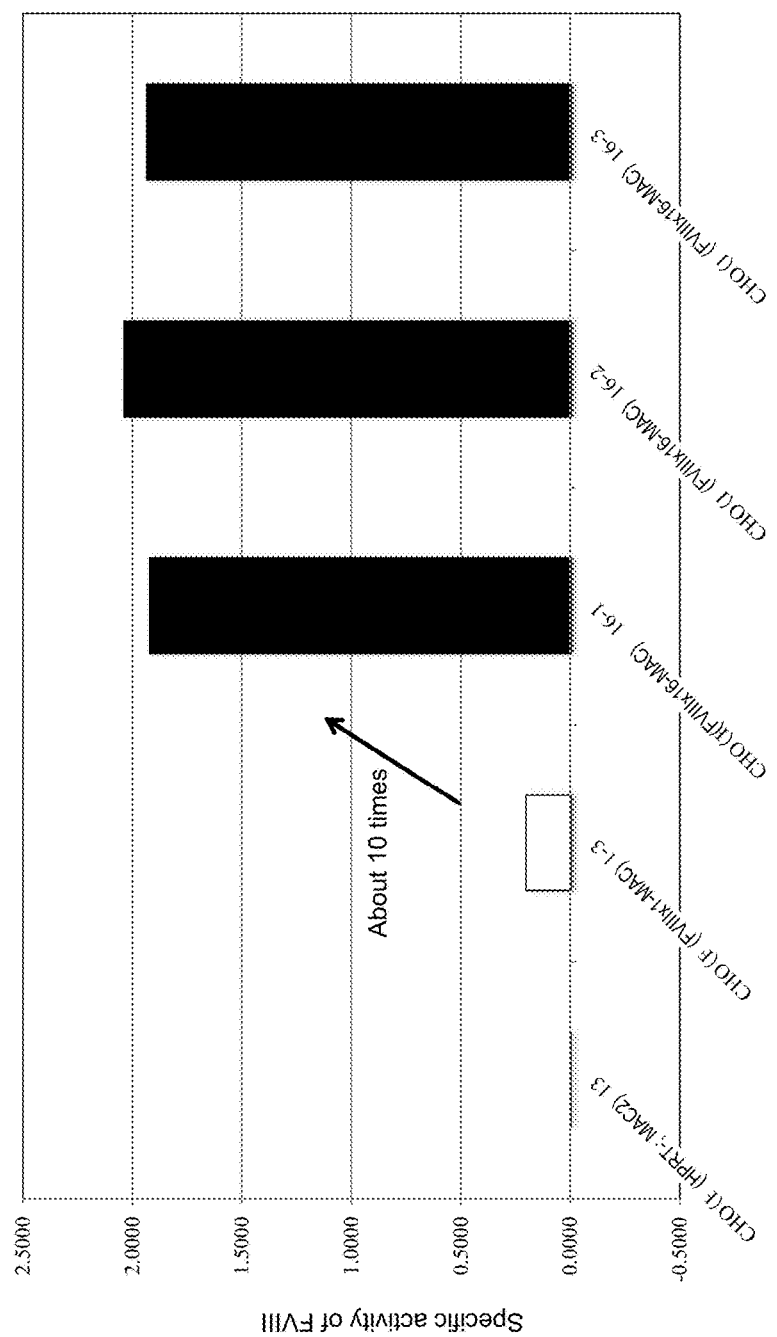
FIG. 68 shows the results of the clotting assay (comparison of FVIII activity) of CHO (FVIII×1-MAC) and CHO (FVIII×16-MAC).

To examine whether or not the FVIII protein expression was functional in the CHO (FVIII×1-MAC) 1-3 and CHO (FVIII×1-HAC) 1-2 from which expression of FVIII mRNA was confirmed, clotting assay (COSMO BIO CO., LTD.) was performed according to the protocol attached thereto. Cells were cultured under non-selection culture of 0 to 25 PDL, and cultured to a 6-well dish. At 100% confluency, the medium was exchanged with the fresh medium. 24 hours later, the culture supernatant was recovered and the activation degree of FVIII was measured based upon the FVIII activity. As a result, for 0 PDL, almost no difference was found in activity between CHO (FVIII×1-MAC) 1-3 and CHO (FVIII×1-HAC) 1-2. In contrast, the activity was increased as much as 1.8 times in CHO (FVIII×1-MAC) 1-3 even for 25 PDL, but it was decreased by 6 times in CHO (FVIII×1-HAC) 1-2 for 25 PDL (FIG. 67). Further, compared to CHO (FVIII×1-MAC) 1-3, the activity of CHO (FVIII×16-MAC) 16-1, 16-2, 16-3 was increased as much as about 10 times, from which it was confirmed that the activity increased in copy number dependent manner (FIG. 68).

From the above experiments, it was confirmed that, by carrying FVIII gene on mouse artificial chromosome MAC2 vector, functional expression of FVIII gene was observed and functional expression was more stably observed for a longer period of time in CHO retaining FVIII-MAC compared to CHO retaining FVIII-HAC. In addition, by using PAC vector, a DNA of not more than 200 kb which encodes a useful protein could be inserted.

Example 15

Construction of the Mouse Artificial Chromosome Vector MI-MAC Allowing Multiple-Gene Introduction As an example for describing the mouse artificial chromosome vector MAC2 carrying multiple genes, multi-integrase platform having five recognition sites for site specific recombinase (ΦC31 attP, R4 attP, TP901-1 attP, Bxb1 attP, FRT) was inserted by using Cre/loxP system to examine the introduction and expression of multiple genes.

[A. 1] Preparation of Multi-Integrase Platform Cassette

A cassette having multi-integrase platform for introducing multiple genes to a mouse artificial chromosome vector was prepared as follows by using Multisite-Gateway kit (Invitrogen). First, by using PGK-hyg (Clontech) as a template, (1)C31 attP site, R4 attP site, TP901-1 attP site, Bxb1 attP site, and FRT site, which are the sites for gene introduction, were added to PGK promoter sequence by first PCR (each primer pair F1-R1 given below). For PCR, GeneAmp 9600 manufactured by PerkinElmer, Inc. was used as a thermal cycler and KOD plus (Toyobo) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 2 min, 20 cycles of 94° C. for 15 sec, 68° C. for 30 sec, and 72° C. for 90 sec were carried out. The PCR product was treated with proteinase K (Gibco) and purified by CHROMASPIN-TE400 (Clontech).

B1-FRT-PGK-ΦC31 attP-B5r F1:
(SEQ ID NO: 111)
5'- GAAGTTCCTATACTTTCTAGAGAATAGGAACTTCATTCTACCGGG
TAGGGGAGGCGCTTTTCCC-3'

B1-FRT-PGK-ΦC31 attP-B5r R1:
(SEQ ID NO: 112)
5'-CAACTGAGAGAACTCAAAGGTTACCCCAGTTGGGGCACTACGGTCGA
AAGGCCCGGAGATGAGGAAGAGGA-3'

B5-PGK-R4 attP-B4 F1:
(SEQ ID NO: 113)
5'- GGGGACAACTTTGTATACAAAAGTTGATATTCTACCGGGTAGGGGA
GGCGCTTTTCCC-3'

B5-PGK-R4 attP-B4 R1:
(SEQ ID NO: 114)
5'-CACAAGCAGTACCACTGCTTCAAGTGGTATCGCTTTGGGGAACATGC
GGTCGAAAGGCCCGGAGATGAGGAAGAGGA-3'

B4r-PGK-TP901 attP-B3r F1:
(SEQ ID NO: 115)
5'- GGGGACAACTTTTCTATACAAAGTTGATATTCTACCGGGTAGGGG
AGGCGCTTTTCCC-3'

B4r-PGK-TP901 attP-B3r R1:
(SEQ ID NO: 116)
5'-CTTAATTGAAATAAACGAAATAAAAACTCGCAATTAAGCGAGTTGGA
AGGTCGAAAGGCCCGGAGATGAGGAAGAGGA-3'

B3-PGK-Bxb1 attP-B2 F1:
(SEQ ID NO: 117)
5'- GGGGACAACTTTGTATAATAAAGTTGGTATTCTACCGGGTAGGGGA
GGCGCTTTTCCC-3'

B3-PGK-Bxb1 attP-B2 R1:
(SEQ ID NO: 118)
5'-AGACCGCGGTGGTTGACCAGACAAACCACGAAGACACAGGTCATCAC
GGCCATAGGTCGAAAGGCCCGGAGATGAGGAAGAGGA-3'

By using the first PCR fragment thus obtained as a template, second PCR (each primer pair F1-R2, and F2-R2 for (1)C31 only) for adding gateway attB sequence which is required for Multisite-Gateway BP reaction was performed. The PCR conditions and the like were the same as above except that the cycle number was changed to 25 cycles. The primer F1 sequence is the same as those described above.

B1-FRT-PGK-ΦC31 attP-B5r F2:
(SEQ ID NO: 119)
5'- GGGGACAAGTTTGTACAAAAAAGCAGGCTTGGAAGTTCCTAT
ACTTTCTAGAGAATAGGAA-3'

B1-FRT-PGK-ΦC31 attP-B5r R2:
(SEQ ID NO: 120)
5'-GGGGACAACTTTTGTATACAAAGTTGTGACCCTACGCCCCCAACTGA
GAGAACTCAAAGGTTACCCCAGT-3'

B5-PGK-R4 attP-B4 R2:
(SEQ ID NO: 121)
5'-GGGGACAACTTTGTATAGAAAAGTTGGGTGCACCCGCAGAGTGTACC
CACAAGCAGTACCACTGCTTCAAGTGGTAT-3'

```
B4r-PGK-TP901 attP-B3r R2:
                                       (SEQ ID NO: 122)
5'-GGGGACAACTTTATTATACAAAGTTGTTAAAAGGAGTTTTTTAGTTA

CCTTAATTGAAATAAACGAAATAAAAACTCG-3'

B3-PGK-Bxb1 attP-B2 R2:
                                       (SEQ ID NO: 123)
5'-GGGGACCACTTTGTACAAGAAAGCTGGGTATGGGTTTGTACCGTACA

CCACTGAGACCGCGGTGGTTGACCAGACAAACCACG-3'
```

Figure 69:
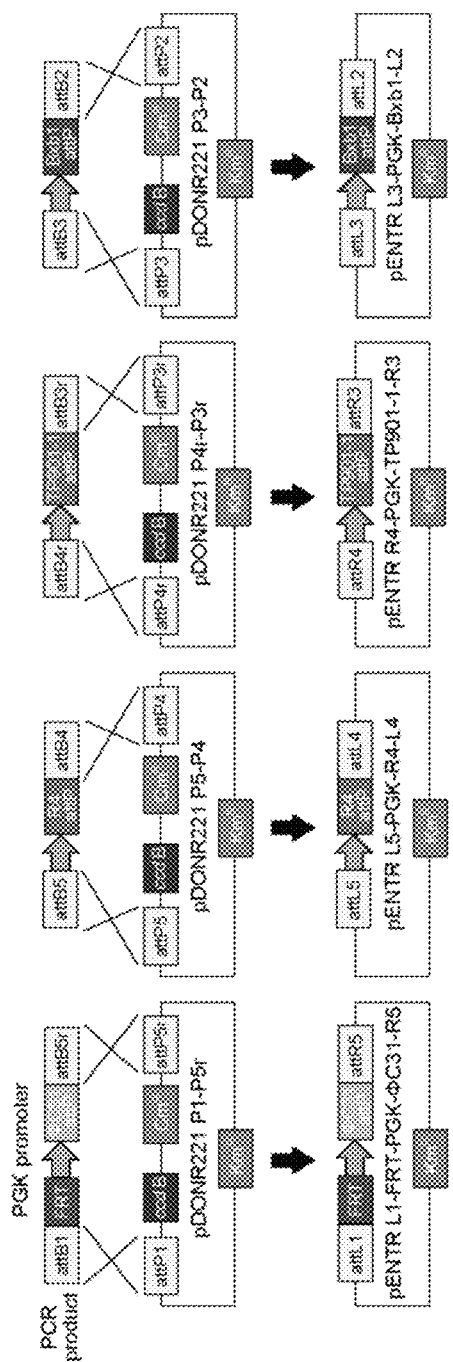
FIG. 69 shows the methods of constructing an entry vector for constructing a multi-integrase platform cassette.

The PCR fragments and the donor vector (Invitrogen: pDONR221 P1-P5r, pDONR221 P5-P4, pDONR221 P4r-P3r, pDONR221 P3-P2) having a corresponding gateway attP sequence were mixed with each other, and based on in vitro recombination reaction using BP clonase (BP reaction), entry vectors (pENTR L1-FRT-PGK-ΦC31-R5, pENTR L5-PGK-R4-L4, pENTR R4-PGK-TP901-1-R3, pENTR L3-PGK-Bxb1-L2) were prepared (FIG. 69). BP reaction was performed according to the conditions as recommended.

Next, the plasmid incorporated with 3' HPRT-loxP sequence, which is required for inserting the above gene insertion site into a mouse artificial chromosome vector, was prepared by the following procedure. The X3.1 was used as a template and amplification was carried out by using the following primers. The PCR conditions are the same as the conditions described above (cycle number: 25).

```
PGK2362:
                                       (SEQ ID NO: 124)
5'- TGATTGTTCAGGAGGAGGAAGCCGGTGGCG -3' loxP4548:
                                       (SEQ ID NO: 125)
5'- AGAGCCTTCAACCCAGTCAGCTCCTTCGAA -3'
```

Figure 70:
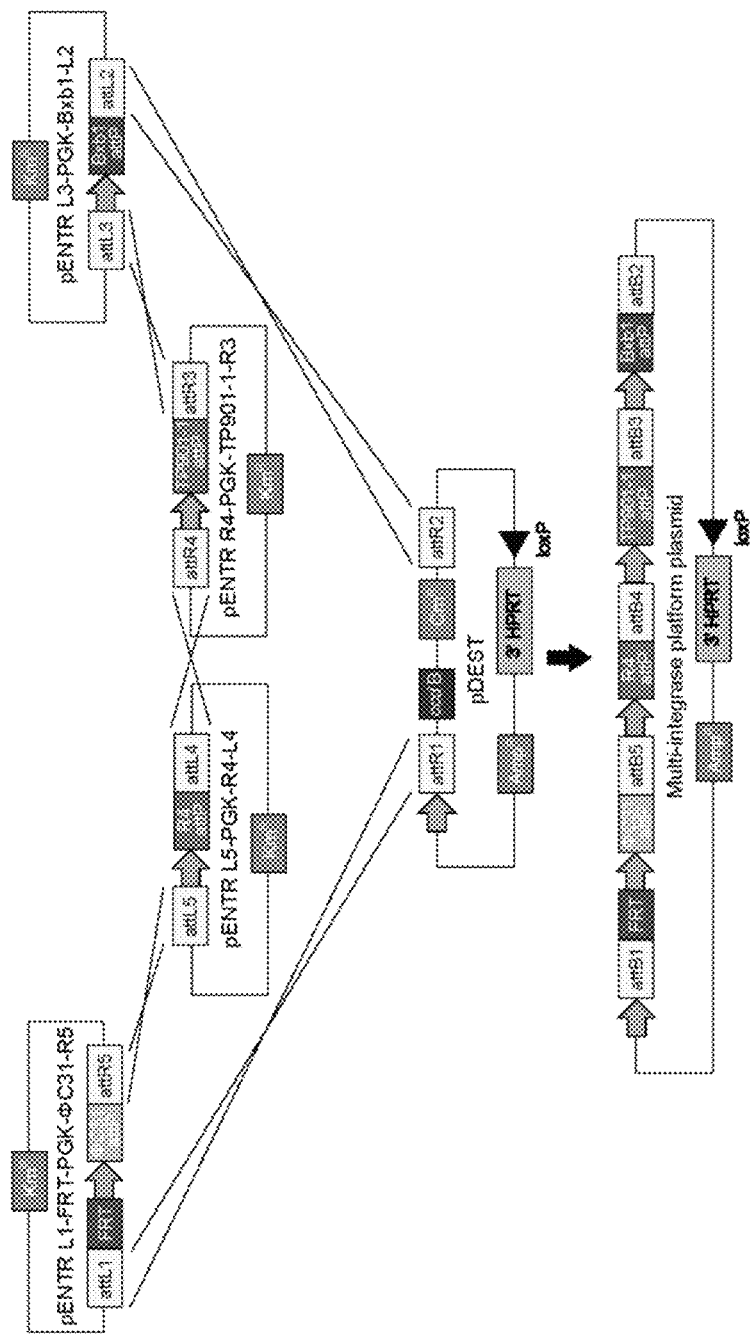
FIG. 70 shows the method of constructing a multi-integrase platform cassette.

The PCR fragment and DEST cassette (Invitrogen: R1-ccdB-Cm-R2) were subjected to blunt ligation to yield pDEST. Next, the pDEST and the entry vector (pENTR L1-FRT-PGK-ΦC31-R5, pENTR L5-PGK-R4-L4, pENTR R4-PGK-TP901-1-R3, pENTR L3-PGK-Bxb1-L2) prepared above were mixed with each other, and based on in vitro recombination reaction using LR clonase (LR reaction), the multi-integrase platform cassette was prepared (FIG. 70). The LR reaction was performed according to the conditions as recommended.

Figure 71:
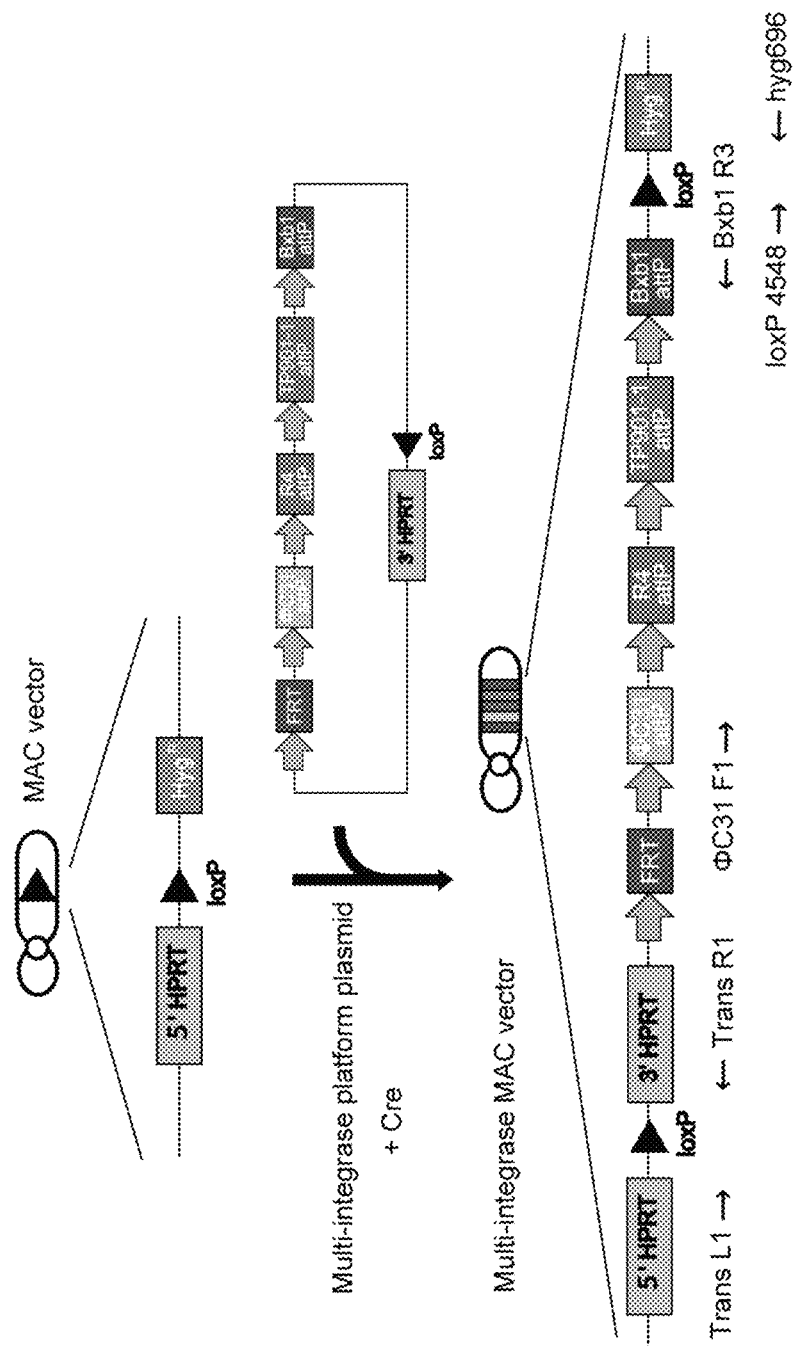
FIG. 71 shows the method of constructing MI-MAC vector.

[A. 2] Carrying Multi-Integrase Platform Cassette on the Mouse Artificial Chromosome Vector By Cre-loxP recombination into the above-described CHO (HPRT⁻; MAC2) or below-described CHO (HPRT⁻; MAC4) and attaining the HAT resistant clone, the multi-integrase platform cassette can be inserted into the mouse artificial chromosome vector MAC2 or MAC4 (referred to as MI-MAC) (FIG. 71).

[A. 3] Preparation of Cassette for Gene Introduction

A cassette vector for introducing an exogenous gene to multi-integrase platform was prepared as follows. First, the promoterless neomycin-resistant gene required for drug selection was amplified by using the following primers and pIRES Neo2 (Clontech) as a template. The PCR conditions are the same as the conditions described above (cycle number: 25).

```
NeoF:
                                       (SEQ ID NO: 126)
5'- AAAGATATCAACTCGAGATGGGATCGGCCATTGAACAAGATGGATT

G -3'

NeoR:
                                       (SEQ ID NO: 127)
5'- TTTGCTAGCCCCCAGCTGGTTCTTTCCGCCTCAGAAGCC -3'
```

Figure 72:
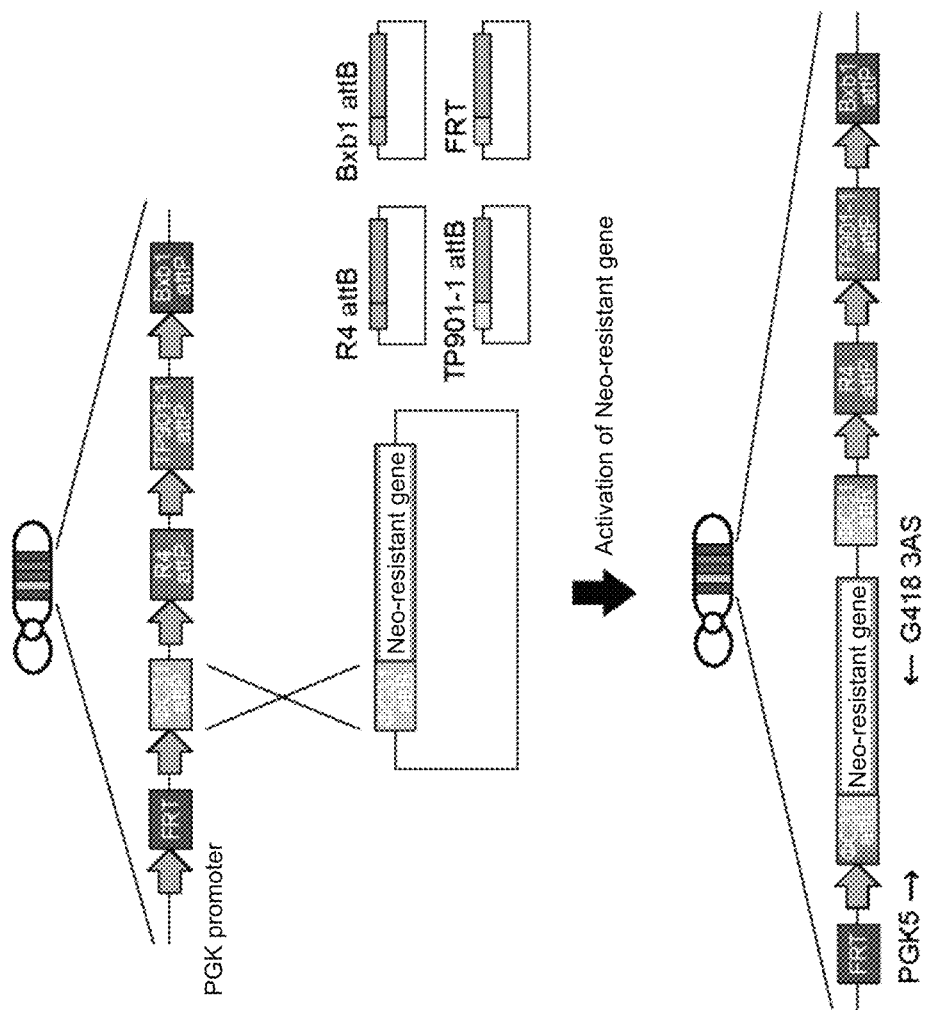
FIG. 72 shows the method of inserting a gene into MI-MAC vector.

After that, the PCR fragment was blunt-cloned into SLR test (Toyobo) which has been cleaved with the restriction enzyme EcoRV and at SmaI site to prepare pNeo. Then, the recombination sequence (ΦC31 attB, R4 attB, TP901-1 attB, Bxb1 attB, FRT) corresponding to each attP site or FRT site was prepared by de novo synthesis (ΦC31, Bxb1, FRT: Integrated DNA technologies Inc., R4, TP901-1: Invitrogen). pNeo was cleaved with the restriction enzyme SalI, and the DNA fragment containing ΦC31 attB or R4 attB was cut from the vector synthesized above by using the restriction enzyme SalI before ligation (pNeo-ΦC31 attB, pNeo-R4 attB). Similarly, pNeo was cleaved with the restriction enzyme ClaI, the DNA fragment containing TP901-1 attB or FRT was cut out from the vector synthesized above by using the restriction enzyme ClaI and ligated thereto to prepare pNeo-TP901-1 attB or pNeo-FRT, or pNeo was cleaved with the restriction enzyme NheI, and the DNA fragment containing Bxb1 attB was cut from the vector synthesized above by using the restriction enzyme NheI and ligated thereto to prepare pNeo-Bxb1 attB. These vectors allow insertions of any exogenous gene into BamHI site, and it is a cassette vector which can be carried on a mouse artificial chromosome having multi-integrase platform (FIG. 72).

[A. 4] Preparation of Vector for Expression of Site Specific Recombinase

Site specific recombinases ΦC31 integrase, R4 integrase, TP901-1 integrase, Bxb1 integrase) (GenBank accession numbers: φC31, CAA07153; R4, BAA07372; TP901-1, CAA59475; Bxb1, AAG59740), each of which can cause recombination between corresponding attB and attP, were prepared by de novo synthesis (ΦC31: Codon device, others: Invitrogen). These integrases were synthesized according to codon usage optimization for mammals to have high expression in mammalian cells. From the vector synthesized, the DNA fragment containing ΦC31 integrase was cut out by using restriction enzymes KpnI-XbaI and ligated to pVAX1 (Invitrogen) prepared by restriction with the restriction enzymes KpnI-XbaI to prepare pCMV-ΦC31, or the DNA fragment containing R4 integrase or TP901-1 integrase, Bxb1 integrase was cut out by using restriction enzymes NheI-XhoI and ligated to pVAX1 (Invitrogen) prepared by restriction with the restriction enzymes NheI-XhoI to prepare pCMV-R4, pCMV-TP901-1, pCMV-Bxb1 (FIG. 72).

[A. 5] Gene transfer to MI-MAC vector

By introducing the vector for expressing various site specific recombinases described above instead of Cre expression vector and introducing cassette for gene introduction instead of FVIII insertion vector, multiple (1 to 5) genes can be inserted to the mouse artificial chromosome vector MI-MAC vector. Further, as it is also possible to carry multiple multi-integrase platform cassettes on mouse artificial chromosome MAC vector, gene can be inserted without any limitation (FIG. 72).

Example 16

Construction of the Mouse Artificial Chromosome Vector PXR-MAC

Human PXR as a nuclear receptor is inserted into the mouse artificial chromosome vector MAC3 by using Cre/loxP system to construct PXR-MAC.

[A. 1] Preparation of Human PXR Insertion Vector

As a basic BAC vector for inserting human PXR gene and loxP sequence, RP11-169N13 (CHORI) containing full length human PXR gene was used. According to the method by Yamada et al. (J Hum Genet. 2008; 53 (5): 447-53), Amp-5' HPRT-loxP sequence for inserting the mouse artificial chromosome vector MAC3 was inserted into kanamycin resistant gene region of BAC vector based on homologous recombination (vector name: PXR-loxP).

Figure 73:
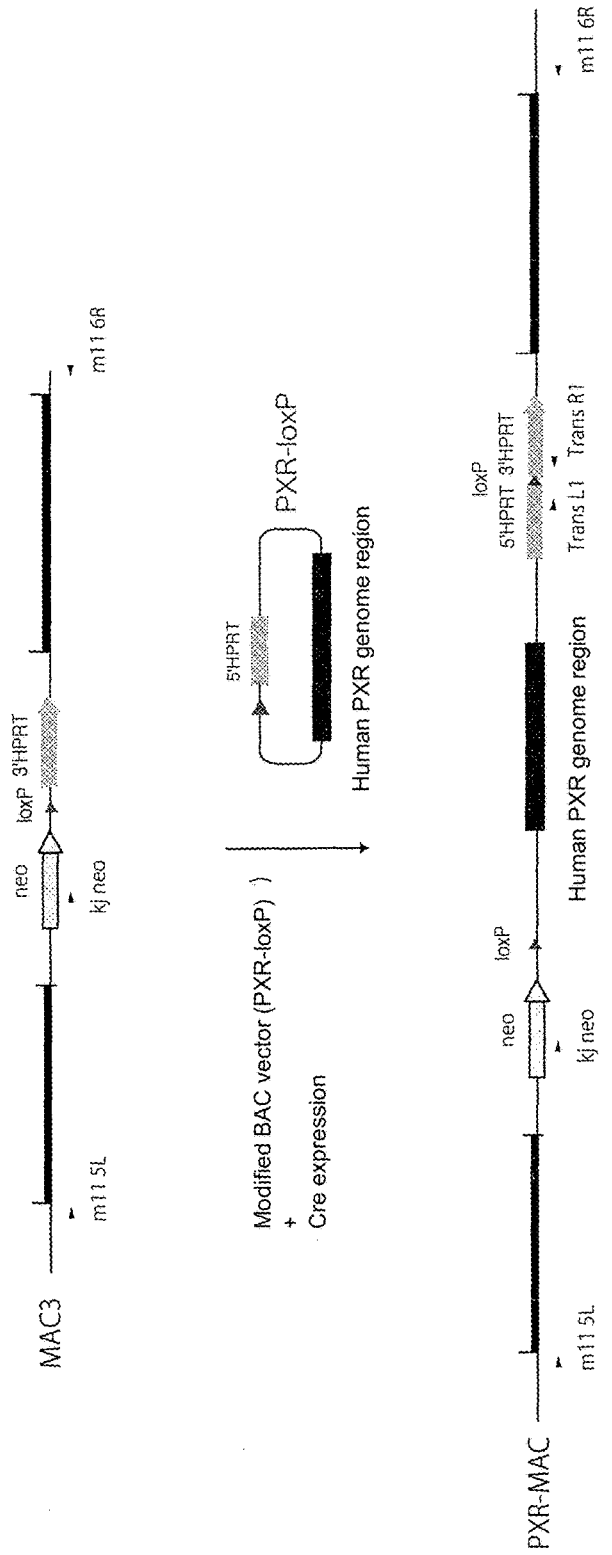
FIG. 73 shows the method of constructing PXR-MAC.

Site specific DNA insertion obtained by insertion of human PXS based on HPRT reconstruction system using Cre/loxP system is given in FIG. 73.

[A. 2] Transfection and Isolation of HAT Resistant Clone

Gene introduction was carried out by lipofection. To cells in 6 wells with 90% confluency, 1 µg of Cre and 2 µg of PXR-loxP vector were introduced according to the commercially available protocol (Invitrogen). After culture for 2 weeks under HAT selection culture, resistant colony was generated, and total 11 colonies obtained by two introductions were isolated, amplified, and subjected to the following analysis (clone name: CHO (PXR-MAC)).

[A. 3] Selection of Drug Resistant Clone

[A. 3. 1] PCR Analysis

In order to select a recombinant by using as a template genomic DNA of HAT resistance cell line, PCR was carried out by using the following primers and it was confirmed whether or not site specific insertion of PXR gene has occurred. The primer sequences are given below.

TRANS L1 (described above)
TRANS R1 (described above)

```
                                    (SEQ ID NO: 128)
hPXR1L:  5'-aaacagcaaggcaagcatcca-3'

(SEQ ID NO: 129)
hPXR1R:  5'-tgctttaatccagccctggtg-3'

(SEQ ID NO: 130)
hPXR2L:  5'-tgtttgctcaatcgtggtctcc-3'

(SEQ ID NO: 131)
hPXR2R:  5'-acaaaagccgaatgtggtgga-3'

(SEQ ID NO: 132)
hPXR3L:  5'-ccaagaggcccagaagcaaa-3'

(SEQ ID NO: 133)
hPXR3R:  5'-tccccacatacacggcagatt-3'

(SEQ ID NO: 134)
hPXR4L:  5'-acactgccaagagccgacaat-3'

(SEQ ID NO: 135)
hPXR4R:  5'-gcaaccttgcctctctgatggt-3'

(SEQ ID NO: 136)
hPXR5L:  5'-tcaaggtgtggaagggaccaa-3'

(SEQ ID NO: 137)
hPXR5R:  5'-acaaagcagctcggaagagga-3'

(SEQ ID NO: 138)
hPXR6L:  5'-gtttgttcctggggctggaat-3'

(SEQ ID NO: 139)
hPXR6R:  5'-caaggcaggcactttcataccc-3'
``` kj neo (described above)
m11 6R (described above)

For PCR, GeneAmp 9600 manufactured by PerkinElmer, Inc. was used as a thermal cycler and Ampli Taq Gold (Applied Biosystems) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 10 min, 35 cycles of 94° C. for 30 sec, 60° C. for 30 sec, and 72° C. for 30 sec were carried out. As a result of PCR, six clones out of the 11 clones were found to be positive for all primer sets, and the following analysis was performed by using those six clones.

[A. 3. 3] Two-Color FISH Analysis

Figure 74:
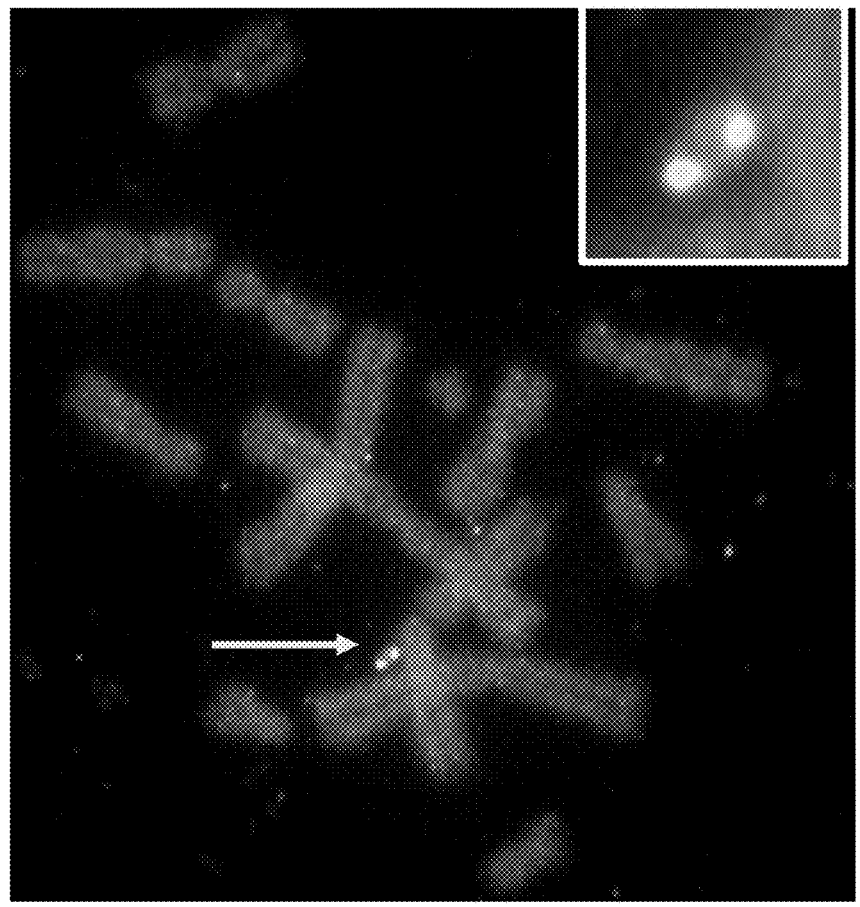
FIG. 74 shows the results of the two-color FISH analysis of CHO (PXR-MAC) clone in which mouse cot-1 DNA and human PXR-BAC-derived DNA (RP11-169N13) (CHORI) were used as probes.

With six clones selected from the above result, two-color FISH analysis was carried out according to Matsubara et al. (FISH test protocol, Shujunsha Co., Ltd., 1994). FISH analysis was carried out by using mouse cot-1 DNA and DNA (RP11-169N13) (CHORI) derived from human PXR-BAC as probes. As a result, it was found that, in five clones out of the six clones, PXR-MAC was retained at a rate of 60% or more and the signal derived from PXR-BAC was generated. Further, since no signal was detected from MAC3 before site specific insertion of PXR-BAC as a negative control, it was confirmed that human PXR gene was site-specifically inserted (FIG. 74).

From the experiments above, it was possible to confirm that, by carrying the human PXR gene on mouse artificial chromosome MAC3, CHO cells retaining the mouse artificial chromosome vector PXR-MAC was obtained.

Figure 75:
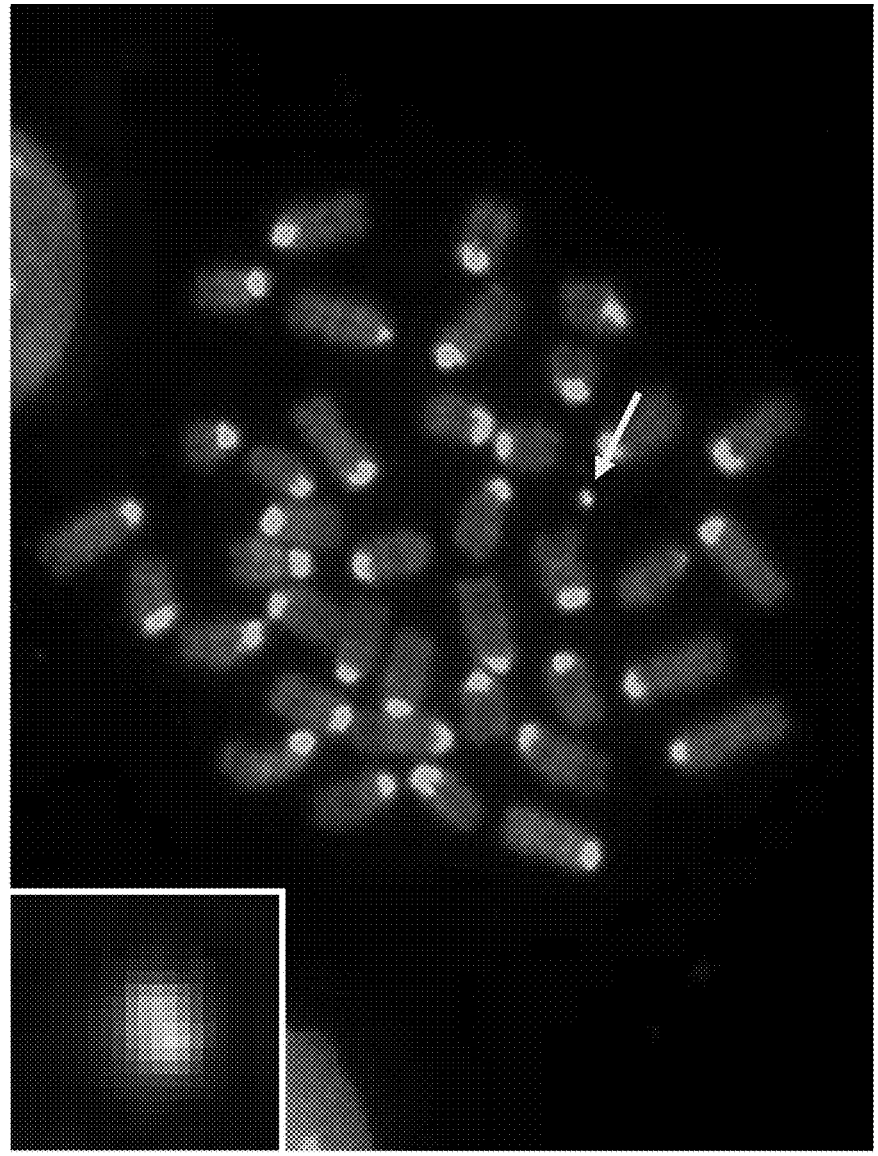
FIG. 75 shows the results of the mono-color FISH analysis of TT2F (PXR-MAC) clone in which human PXR-BAC-derived DNA (RP11-169N13) (CHORI) was used as a probe.

[B] Transfer of the Mouse Artificial Chromosome Vector PXR-MAC from CHO Cell Containing the Mouse Artificial Chromosome Vector PXR-MAC to Mouse ES Cell To prepare a chimeric mouse retaining PXR-MAC, introduction was carried out from CHO cells retaining PXR-MAC obtained from the above [A] to mouse ES cells (wild type TT2F) by microcell fusion. According to the method by Tomizuka et al. (Nature Genet. 16: 133, 1997), microcells were purified from approximately $10^8$ cells of CHO retaining PXR-MAC (CHO (PXR-MAC) 7, 9, 10, or the like) and suspended in 5 ml of DMEM. Approximately $10^7$ mouse ES cells of TT2F were detached by trypsin treatment, washed three times with DMEM, suspended in 5 ml of DMEM, and added to the microcells obtained by centrifugation. After centrifugation for 10 min at 1250 rpm, the supernatant was completely removed. The precipitates were resolved fully by tapping and added with 0.5 ml of 1:1.4 PEG solution [5 g of PEG1000 (Wako Pure Chemical Industries, Ltd.), 1 ml DMSO (SIGMA) dissolved in 6 ml of DMEM], and fully stirred for about 1 min and 30 sec. After that, 10 ml of DMEM was slowly added, centrifuged for 10 min at 1250 rpm, and suspended in 30 ml of ES culture medium. Thereafter, the cells were dispensed into three petri dishes with a diameter of 100 mm (Corning Incorporated) onto which feeder cells have been previously plated and then cultured. 24 hours later, the culture medium was exchanged with culture medium containing 300 µg/ml G418 and then subjected to selection culture for about 1 week. As a result, total 34 colonies were isolated, amplified, and subjected to the following analysis. Two clones from CHO (PXR-MAC) 7, two clones from CHO (PXR-MAC) 9, and 12 clones from CHO (PXR-MAC) 10 were determined to be positive by PCR using the primers described before for detecting the PXR-MAC region only. In addition, with the 16 clones, FISH analysis (Tomizuka et al., Nature Genet. 16: 133, 1997) was carried out by using DNA (RP11-169N13) (CHORI) derived from human PXR-BAC. As a result, the clones that were specifically detected with the probe were found to be four clones out of the 16 clones. From the above, it was concluded that four clones of TT2F cells retaining PXR-MAC are obtained (FIG. 75).

[C] As described in Example 8, by preparing a chimeric mouse using the mouse ES ells retaining the mouse artificial chromosome vector PXR-MAC, mouse line-based TC (PXR-MAC) in which PXR-MAC is transferred to a progeny can be prepared. Further, by using the TC (PXR-MAC) mouse line, stability of PXR-MAC in somatic cells can be examined. Further, the TC (PXR-MAC) mouse line allows reproduction of drug-induced CYP gene expression in human. Still further, by crossbreeding with the TC (CYP3A-MAC) mouse line, TC (CYP3A-MAC/PXR-MAC) can be prepared, and it may be also used as a model mouse for in vivo test that is used for testing a pharmacological effect and toxicity for development of a pharmaceutical product.

Example 17

Construction of the Mouse Artificial Chromosome Vector MAC4

The mouse artificial chromosome vector MAC4 is constructed in which GFP-5' HPRT-loxP-PGKhyg type loxP sequence as a DNA insertion sequence is inserted into the mouse artificial chromosome MAC. The 5' HPRT-loxP-PGKhyg type loxP sequence is inserted into HAC vector carrying GFP (21HAC2) derived from chromosome 21 described by Kazuki et al. (Gene Therapy: PMID: 21085194, 2010), and expression of HAC and MAC genes can be compared to each other in the same vector. Further, the vector for gene introduction that is used for insertion into 21HAC2 may be used as it is without undergoing a step for preparing a vector.

[A] Insertion of GFP-5' HPRT-loxP-Hyg Type loxP Sequence into Mouse Artificial chromosome MAC

[A. 1] Preparation of GFP-5' HPRT-loxP-Hyg Type loxP Targeting Vector

Figure 76:
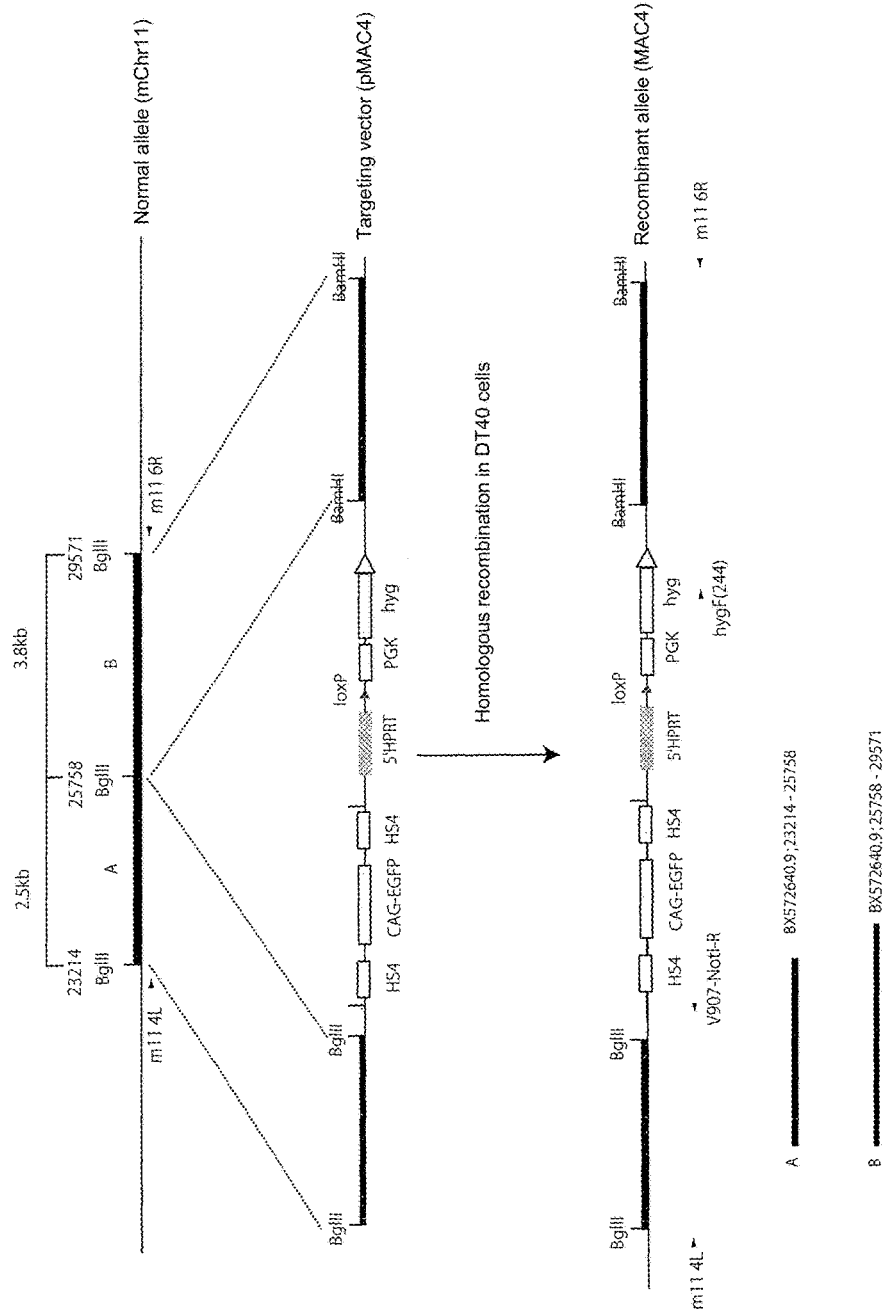
FIG. 76 shows a GFP-5' HPRT-loxP-hyg type of loxP targeting vector (pMAC4) and a partial structure of mouse artificial chromosome MAC4 allele in which homologous recombination was carried out by using the vector.

As a basic plasmid for inserting loxP sequence, pMAC2 prepared above was used. HS4-CAG-EGFP-HS4 (provided by Dr. Okabe at Osaka University and Dr. Felsenfeld at NIH), which is obtained by cutting out by using NotI and SalI, is blunted, and pMAC2 was cloned after it was cleaved with XhoI and blunting (vector name: pMAC4). The targeting vector, target sequence, and chromosome allele obtained by homologous recombination are shown in FIG. 76.

[A. 2] Transfection and Isolation of Drug Resistant Clone

As described above, targeting vector pMAC4 prepared above was linearized with the restriction enzyme NotI (TAKARA), and used for transfection of clone DT40 (MAC) prepared above. After exchanging the culture medium for culture medium containing hygromycin (1.5 mg/ml), the cells were dispensed into two 96-well culture plates and then subjected to selection culture for about 2 weeks. Total 36 resistant colonies obtained by one transfection were isolated, amplified, and subjected to the following analysis (clone name: DT40 (MAC4)).

[A. 3] Selection of Homologous Recombinant

[A. 3. 1] PCR Analysis

For extracting genomic DNA from hygromycin resistant cell line and using it as a template for selecting a recombinant, PCR was carried out by using the following primers and it was confirmed whether or not site specific recombination has occurred on the mouse chromosome vector MAC. The primer sequences are given below.

m11 4L: (described above)

V907-NotI-R:
    (SEQ ID NO: 140)
5'-AGATCTCGGCTAGAGGTACCCTAGAAGATC-3' hygF (244): (described above)

m11 6R (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 10 sec and 68° C. for 7 min were carried out. As a result of PCR, five clones out of the 36 clones were found to be positive for all primer sets, and therefore the following analysis was performed by using those 5 clones.

[A. 3. 2] Two-Color FISH Analysis

Figure 77:
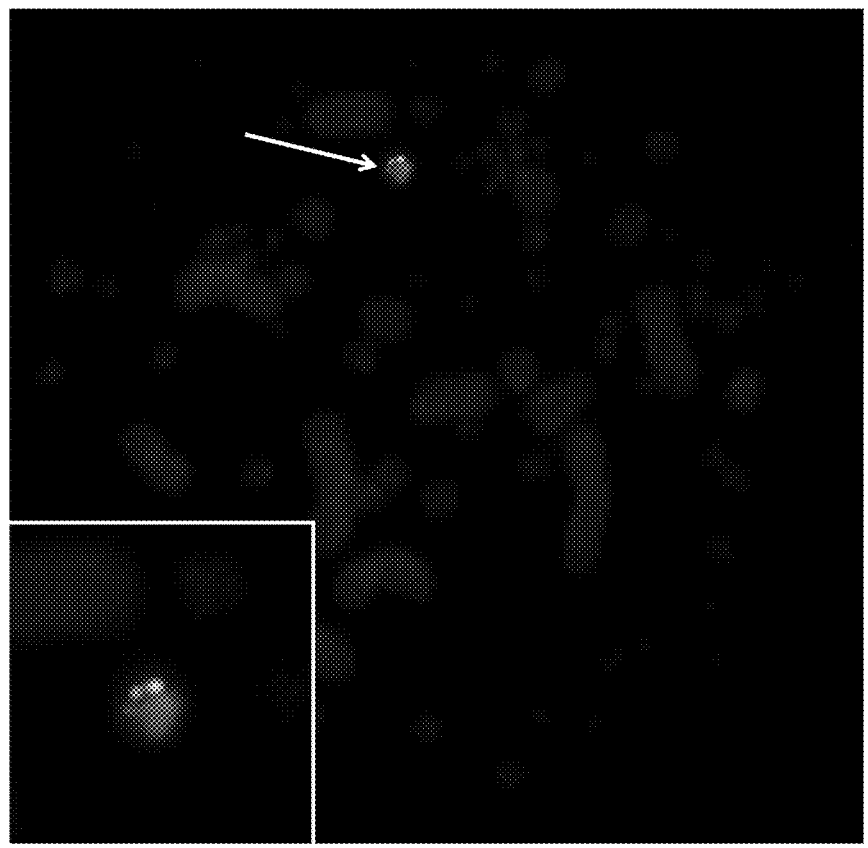
FIG. 77 shows the results of the two-color FISH analysis of DT40 (MAC4) clone in which mouse cot-1 DNA and GFP-5' HPRT-loxP-hyg cassette were used as probes.

With the five clones of DT40 (MAC4) obtained from above, two-color FISH analysis was carried out according to Matsubara et al. (FISH test protocol, Shujunsha Co., Ltd., 1994). FISH analysis was carried out by using mouse cot-1 DNA and GFP-5' HPRT-loxP-hyg cassette as probes. As a result, it was found that no signal derived from probe is detected in the mouse artificial chromosome vector MAC before targeting as a negative control, while the signal derived from probe is detected at a rate of 65% or more in five clones of DT40 (MAC4). Thus, it was visually confirmed that site specific recombination has occurred in the five clones (FIG. 77). From these results, it was possible to conclude that DT40 cell clones retaining the mouse artificial chromosome vector MAC4 are obtained.

[B] Introduction of MAC4 from Chicken DT40 Cell Containing the Mouse Artificial Chromosome Vector MAC4 to CHO Cell

[B. 1] Microcell Fusion and Isolation of Drug Resistant Clone

By using DT40 (MAC4)-B1-5, B1-74, B2-3, and B2-4 as recipient cells, microcell fusion was carried out for CHO (HPRT$^-$), which is a CHO hprt depleted cell (obtained from the Health Science Research Resources Bank, registration number: JCRB0218), in the same manner as above. Total 23 resistant colonies obtained by four microcell fusions were isolated, amplified, and subjected to the following analysis (clone name: CHO (HPRT$^-$; MAC4)).

[B. 2] Selection of Drug Resistant Clone

[B. 2. 1] PCR Analysis

For extracting genomic DNA from hygromycin resistant cell line and using it as a template for selecting a recombinant, PCR was carried out by using the following primers and it was confirmed whether or not mouse artificial chromosome MAC4 can be introduced into CHO cells. The primer sequences are given below.

m11 4L: (described above)
V907-NotI-R: (described above)
hygF (244): (described above)
m11 6R (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, seven clones out of the 23 clones were found to be positive for all primer sets, and the following analysis was performed by using those 7 clones.

[B. 2. 2] Mono-Color FISH Analysis

Figure 78:
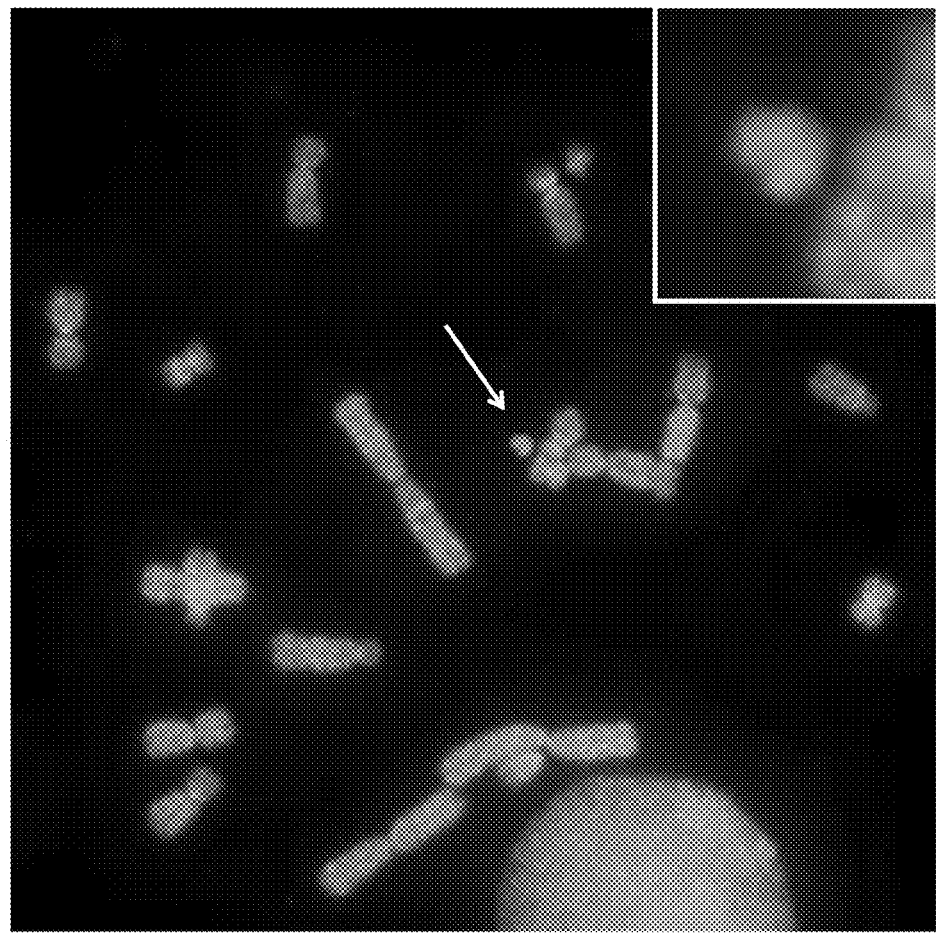
FIG. 78 shows the results of the mono-color FISH analysis of CHO (HPRT⁻; MAC4) clone in which mouse Cot-1 DNA was used as a probe.

With the seven clones of CHO (HPRT−; MAC4) obtained from the above, FISH analysis was carried out by using mouse Cot-1 DNA as a probe according to the method described by Shinohara et al. (Human Molecular Genetics, 10: 1163-1175, 2001). As a result, it was confirmed that MAC4 is introduced into CHO cells at a rate of 95% or more in four clones out of the seven clones (FIG. 78).

From these results, it was concluded that the mouse artificial chromosome vector MAC4 can be introduced into CHO cells.

[C] As described in Example 8, in vitro stability can be examined by preparing mouse ES cells retaining the mouse artificial chromosome vector MAC4 and using it. Further, by preparing a chimeric mouse using the ES cells, mouse line-based TC (MAC4) in which MAC4 is transmitted to a progeny can be prepared. Still further, by using the TC (MAC4) mouse line, stability of MAC4 in somatic cells can be examined.

Example 18

Construction of the Mouse Artificial Chromosome Vector UGT2-MAC

UGT2 cluster which is a group of human drug metabolizing enzyme genes is subjected to translocation cloning into the mouse artificial chromosome vector MAC4 by using Cre/loxP system to construct UGT2-MAC in the same manner as in Example 3. Further, stability of UGT2-MAC in the mouse ES cells is examined

[A] Site Specific Cleavage at AC125239 on Human Chromosome 4

To delete the gene at the distal side from UGT2 gene cluster of human chromosome 4, telomere truncation, which is site specific deletion of a chromosome, is performed.

[A. 1] Preparation of Targeting Vector pTELpuro-UGT2

Targeting vector pTELpuro-UGT2 for inserting human telomere sequence into AC125239 region, which is located extremely close to UGT2 gene locus of human chromosome 4 and on the telomere side (i.e., locating on the telomere side by approximately 150 Kb from UGT2 gene locus), was prepared as follows. First, the AC125239 genome region was amplified by PCR using the following primers.

```
                                       (SEQ ID NO: 141)
UGT2tel4L; 5'- ttctggcaagccttgaagggacaatact-3'

(SEQ ID NO: 142)
UGT2tel4R; 5'- gcctattttgcctcataacccactgctc-3'
```

Figure 79:
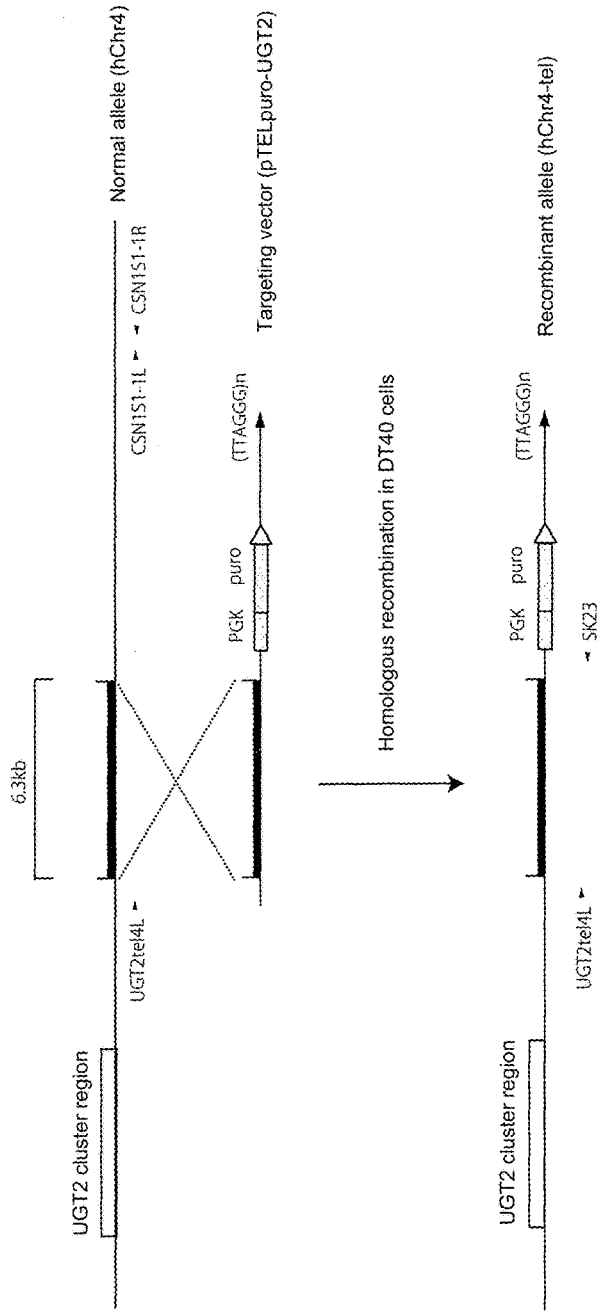
FIG. 79 shows the targeting vector (pTELpuro-UGT2) for inserting human telomere sequence into the AC1252392 region, which locates extremely close to UGT2 gene locus of human chromosome 4 and on the telomere side (i.e., locating on the telomere side by approximately 150 Kb from UGT2 gene locus), and a partial structure of the human chromosome 4 allele in which homologous recombination was carried out by using the vector.

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 8 min were carried out. PCR product was treated with proteinase K (Gibco) and subjected to gel filtration by using CHROMASPIN-TE400 (Clontech). After that, the product was cleaved with the restriction enzyme PstI (NIPPON GENE CO., LTD.) and BglII (NIPPON GENE CO., LTD.) and subjected to gel filtration by using CHROMASPIN-TE1000 (Clontech). The PCR fragment was cloned into the PstI and BamHI sites of plasmid pTELpuro (Kuroiwa et al., Nature Biotech., 20: 88, 2002). Since the genome sequence of AC125239 was in direction of centromere→telomere, the resultant in which cloned AC125239 genome fragment was in the same direction as the human telomere sequence was taken as desired targeting vector pTELpuro-UGT2. The size of the final construct for long-arm proximal region specific cleavage was 11.9 kb. The targeting vector, target sequence, and chromosome allele obtained by homologous recombination are shown in FIG. 79.

[A. 2] Transfection and Isolation of Drug Resistant Clone

According to the method described by Kazuki et al. BBRC 2004, chicken DT40 cells retaining human chromosome 4 were prepared from A9 (KM64-4) retaining human chromosome 4 (Kugoh et al. DNA research 1999) (clone name: DT40 (hChr4)). Next, as described above, the targeting vector pTELpuro-UGT2 prepared above was linearized with the restriction enzyme PstI (NIPPON GENE CO., LTD.), and used for transfection of the clone DT40 (hChr4) 1 prepared above. After exchanging the culture medium for culture medium containing puromycin (0.3 ug/ml), the cells were dispensed into ten 96-well culture plates and then subjected to selection culture for about 2 weeks. Total 96 resistant colonies obtained by four transfections were isolated, amplified, and subjected to the following analysis (clone name: DT40 (hChr4-tel)).

[A. 3] Selection of Homologous Recombinant
[A. 3. 1] PCR Analysis

In order to select a recombinant by using genomic DNA of puromycin resistant cell line as a template, as a primary screening, PCR was carried out by using the following primers that are located closer to the telomere side than the restriction sites, and it was confirmed whether or not site specific cleavage has occurred. The primer sequences are given below.

```
                                       (SEQ ID NO: 143)
CSN1S1-1L; 5'-tttctcctctcaaggaaaacca-3'

(SEQ ID NO: 144)
CSN1S1-1R; 5'-gccctccatatggcaagaca-3'
```

For PCR, GeneAmp 9600 manufactured by PerkinElmer, Inc. was used as a thermal cycler and Ampli Taq Gold (Applied Biosystems) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 95° C. for 10 min, 30 cycles of 95° C. for 20 sec, 55° C. for 30 sec, and 72° C. for 30 sec were carried out. Next, for two clones that were not detected with the above primers, it was confirmed, by PCR using the following primers, whether or not site specific homologous recombination has occurred. Sequences are as follows.
UGT2tel4L; (described above)

|  |  |
|---|---|
| SK23: | (SEQ ID NO: 145)<br>5'- ggccgctctagaactagtggatc-3' |
| UGT2A1-1L: | (SEQ ID NO: 146)<br>5'-tcttctgcatcaagccacatca-3' |
| UGT2A1-1R: | (SEQ ID NO: 147)<br>5'-agccaatgactaccttccattg-3' |
| UGT2A1-2L: | (SEQ ID NO: 148)<br>5'-atcagggagccaccgtagga-3' |
| UGT2A1-2R: | (SEQ ID NO: 149)<br>5'-gcaggcaagttatgccgtga-3' |
| UGT2A3-1L: | (SEQ ID NO: 150)<br>5'-tgcgcccaaacacatggata-3' |
| UGT2A3-1R: | (SEQ ID NO: 151)<br>5'-tggcagaaatgtaggccatga-3' |
| UGT2B4-1L: | (SEQ ID NO: 152)<br>5'-aggctggaagctgggaaacc-3' |
| UGT2B4-1R: | (SEQ ID NO: 153)<br>5'-cctgcatgaaatggatccaaag-3' |
| UGT2B7-1L: | (SEQ ID NO: 154)<br>5'-ccagcaagaaagattgtgatgc-3' |
| UGT2B7-1R: | (SEQ ID NO: 155)<br>5'-ttctaaccatgaactgggtggt-3' |
| UGT2B11-1L: | (SEQ ID NO: 156)<br>5'-gggtttctgctggcctgtgt-3' |
| UGT2B11-1R: | (SEQ ID NO: 157)<br>5'-tctggttttccagcttcaaatg-3' |
| UGT2B15-1L: | (SEQ ID NO: 158)<br>5'-ggtctccttggcatgcacct-3' |
| UGT2B15-1R: | (SEQ ID NO: 159)<br>5'-tgcaatgcttcttttccagttg-3' |
| UGT2B15-2L: | (SEQ ID NO: 160)<br>5'-cagcatggagggttttaaatgg-3' |
| UGT2B15-2R: | (SEQ ID NO: 161)<br>5'-atgttggcgtgctgcatcc-3' |
| UGT2B28-1L: | (SEQ ID NO: 162)<br>5'-catttgaagctggaaaaccaga-3' |
| UGT2B28-1R: | (SEQ ID NO: 163)<br>5'-cctgggtggtaaatctctgaaa-3' |

For PCR, LA Taq (TAKARA SHUZO CO., LTD.) was used with the above primers. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 8 min were carried out. Only in two clones having site specific recombination, a band at approximately 8 kb was detected. In DT40 and DT40 (hChr4) 1 as a negative control, no band was detected.

[A. 3. 2] Two-Color FISH Analysis

Figure 80:
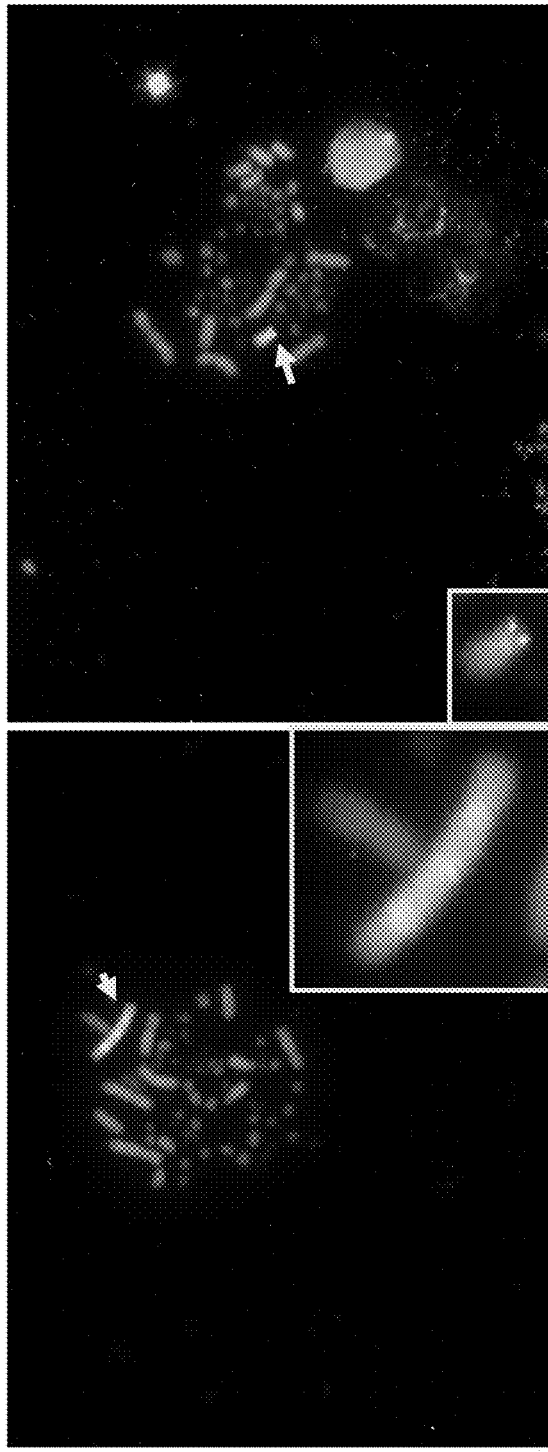
FIG. 80 shows the results of the two-color FISH analysis of DT40 (hChr4-tel) in which human cot-1 DNA and puromycin DNA were used as probes. Left panel represents DT40 (hChr4) before modification, and right panel represents DT40 (hChr40-tel) after modification.

FISH analysis was carried out according to Matsubara et al. (FISH test protocol, Shujunsha Co., Ltd., 1994). FISH analysis was carried out for two clones out of the clones which have been confirmed to have recombination in the above by using human cot-1 DNA and puromycin DNA as probes. As a result, it was found that human chromosome 4 was not translocated to the host chromosome in any clone, and based on the fact that puromycin-derived signal was detected at the terminal of human chromosome 4 fragment and restriction occurred on the desired site, it was confirmed that recombination has site-specifically occurred (FIG. 80).

From these results, it was concluded that, in clone DT40 (hChr4-tel) 35 and 73, cleavage can be made at a region distal from AC125239 which is closer to the telomere side than UGT2 gene cluster region.

[B] Site Specific Insertion of loxP Sequence into AC074378 of Human Chromosome 4

For translocation insertion into the mouse artificial chromosome vector MAC4 via loxP sequence, loxP sequence is inserted into AC074378 proximal to UGT2 gene cluster of hChr4-tel in DT40 cells.

[B. 1] Preparation of Targeting Vector pUGT2loxPneo

Targeting vector pUGT2loxPneo for inserting loxP, which is a recognition sequence for Cre recombinase, into AC074378 region, which is located extremely close to UGT2 gene locus of human chromosome 4 and on the centromere side (i.e., locating on the centromere side by approximately 300 Kb from UGT2 gene locus), was prepared as follows. First, the AC074378 genome region was amplified by PCR using the following primers.

|  |  |
|---|---|
| UGT2loxP3L: | (SEQ ID NO: 164)<br>5'- ggaacaatcccaatcaaaacctcagtgc-3' |
| UGT2loxP4R: | (SEQ ID NO: 165)<br>5'- cgaggattcaagccacatccctaactct-3' |

Figure 81:
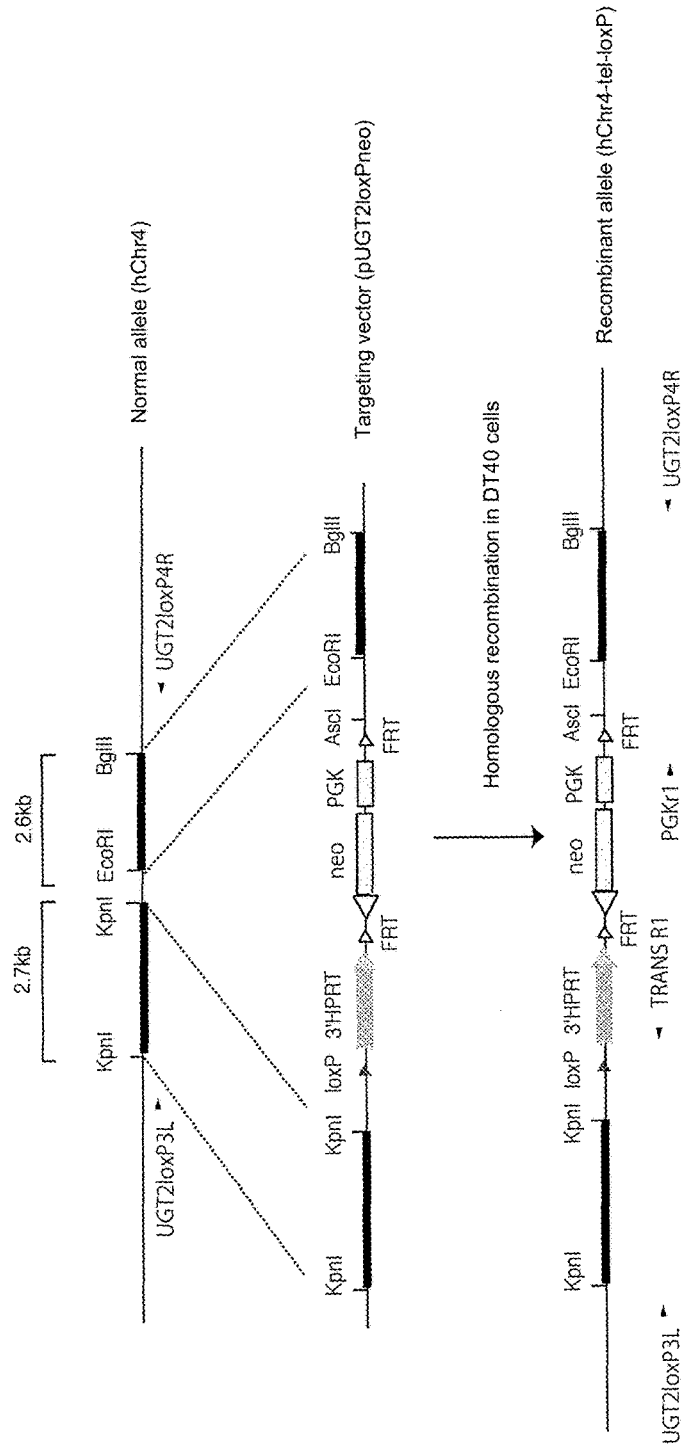
FIG. 81 shows a targeting vector (pUGT2loxPneo) for inserting loxP sequence into the AC074378 of human chromosome 4, a target sequence, and a chromosome allele produced by homologous recombination.

As a basic plasmid for inserting loxP sequence, V907 (Lexicon genetics) was used. For PCR, GeneAmp 9600 manufactured by PerkinElmer, Inc. was used as a thermal cycler and LA Taq (TAKARA SHUZO CO., LTD.) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 7 min were carried out. PCR product was treated with proteinase K (Gibco) and subjected to gel filtration by using CHROMASPIN-TE400 (Clontech). After that, the product was cleaved with the restriction enzymes KpnI (NIPPON GENE CO., LTD.), EcoRI (NIPPON GENE CO., LTD.), and BglII (NIPPON GENE CO., LTD.) and subjected to gel filtration by using CHROMASPIN-TE1000 (Clontech). The PCR fragments (2.7 kb and 2.6 kb) were cloned into the KpnI or EcoRI and BglII sites of V907 plasmid (vector name: V907-UGT2HR2). Next, FRT-pGKneo-FRT was cleaved from pNT1.1, which is loxP-FRT-pGKneo-FRT-loxP cassette (obtained from Genome Information Research Center, Osaka University), with EcoRI and BamHI and cloned into BglII site of the X3.1 (vector name: X3.1-FRT-pGKneo-FRT). Thereafter, V907-UGT2HR2 was cleaved with the restriction enzyme EcoRI and the DNA fragment containing loxP was cut out from X3.1-FRT-pGKneo-FRT by using the restriction enzyme EcoRI, and then they were ligated to each other. The resultant product having the loxP sequence in the same direction as the cloned AC074378 genome fragment was taken as targeting vector pUGT2loxPneo. Size of the final construct inserted with loxP was 11.1 kb. The targeting vector, target sequence, and chromosome allele obtained by homologous recombination are shown in FIG. 81.

[B. 2] Transfection and Isolation of Drug Resistant Clone

As described above, the targeting vector pUGT2loxPneo prepared above was linearized with the restriction enzyme NotI (TAKARA), and used for transfection of the chicken DT40 cells retaining human chromosome 4 (clone DT40 (hChr4-tel) 35. After exchanging the culture medium with a culture medium containing neomycin (1.5 mg/ml), the cells were dispensed into three 96-well culture plates and then subjected to selection culture for about 2 weeks. Total 12 resistant colonies obtained by two transfections were isolated, amplified, and subjected to the following analysis (clone name: DT40 (hChr4-tel-loxP)).

[B. 3] Selection of Homologous Recombinant

[B. 3. 1] PCR Analysis

Genomic DNA was extracted from the neomycin resistant clones by using Puregene DNA Isolation Kit (Gentra Systems, Inc.) and identification of the homologous recombinant was carried out by PCR using the following two sets of primer.

Identification of the homologous recombinants was carried out by PCR using the following two sets of primer.
UGT2loxP3L (described above)
TRANS R1 (described above)
PGKr1 (described above)
UGT2loxP4R (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 10 sec and 68° C. for 4 min were carried out. As a result of screening 12 clones, five clones were identified as a homologous recombinant.

[B. 3. 2] Two-Color FISH Analysis

Figure 82:
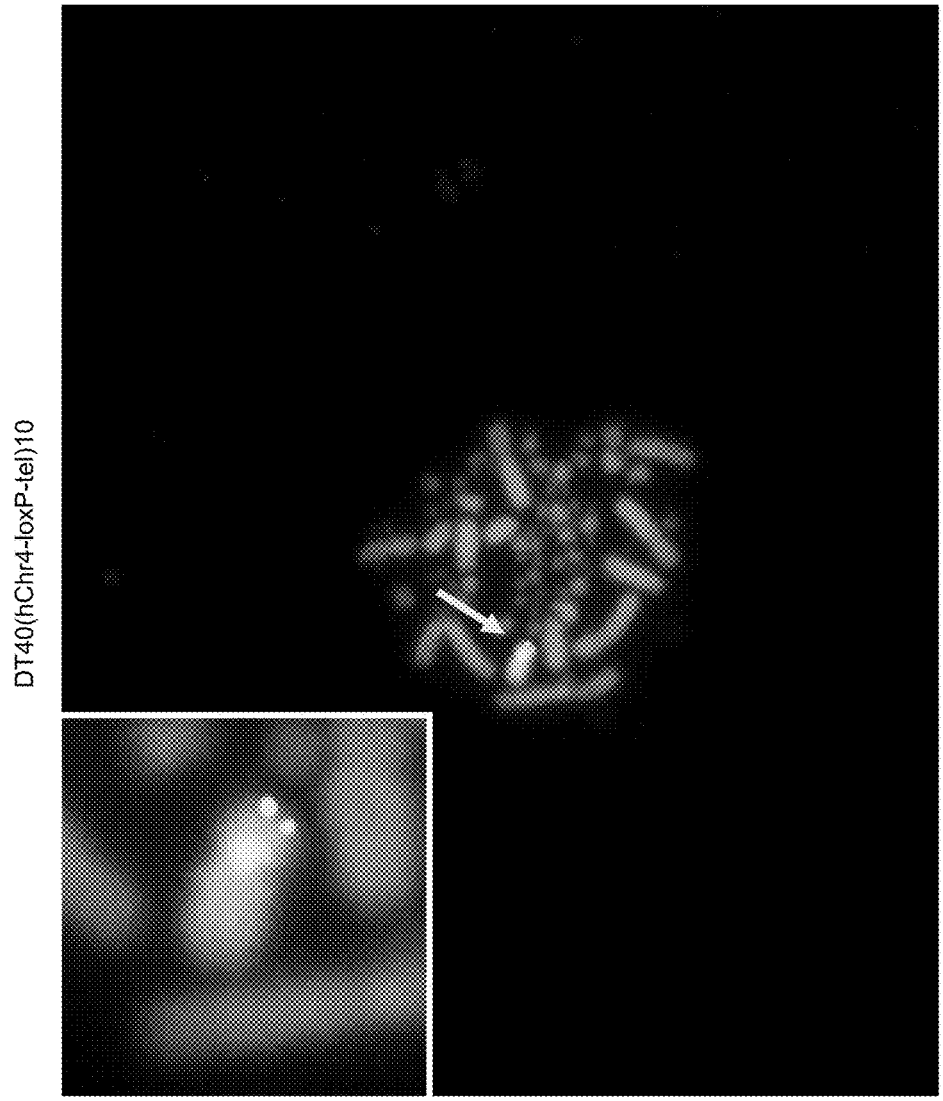
FIG. 82 shows the results of the two-color FISH analysis of DT40 (hChr4-loxP-tel) in which human cot-1 DNA and neomycin DNA were used as probes.

FISH analysis was carried out according to Matsubara et al. (FISH test protocol, Shujunsha Co., Ltd., 1994). FISH analysis was carried out for four clones out of the clones which have been confirmed to have recombination in the above by using human cot-1 DNA and neomycin DNA as probes. As a result, it was found that human chromosome 4 was not translocated to the host chromosome in any clone, and based on the fact that neomycin-derived signal was detected near 4q13, it was confirmed that recombination has site-specifically occurred (FIG. 82). From these results, it was concluded that loxP sequence as a gene introduction site is site-specifically inserted into AC074378 of human chromosome 4.

[C] Introduction of hChr4-loxP-Tel from DT40 Containing hChr4-loxP-Tel to CHO Cells Containing MAC4

For translocation insertion of human UGT2 gene cluster region into the mouse artificial chromosome vector MAC4 via loxP sequence in CHO cells, hChr4-loxP-tel is introduced into CHO cells containing the mouse artificial chromosome vector MAC4.

[C. 1] Microcell Fusion and Isolation of Drug Resistant Clone

By using DT40 (hChr4-loxP-tel) 5 and 10 as a recipient cell, microcell fusion was carried out for CHO (HPRT−; MAC4), which is a CHO hprt depleted cell containing MAC4 (obtained from the Health Science Research Resources Bank, registration number: JCRB0218), in the same manner as above. Total 22 resistant colonies obtained by three microcell fusions were isolated, amplified, and subjected to the following analysis (clone name: CHO (HPRT−; MAC4, hChr4-loxP-tel)).

[C. 2] Selection of Drug Resistant Clone

[C. 2. 1] PCR Analysis

For extracting genomic DNA from neomycin resistant cell line and using it as a template for selecting a recombinant, PCR was carried out by using the following primers and it was confirmed whether or not human chromosome 4 fragment is introduced into CHO cells containing MAC4. The primer sequences are given below.
m11 4L: (described above)
V907-NotI-R: (described above)
hygF (244): (described above)
m11 6R (described above)
UGT2tel4L; (described above)
SK23 (described above)
UGT2A1-1L (described above)
UGT2A1-1R (described above)
UGT2A1-2L (described above)
UGT2A1-2R (described above)
UGT2A3-1L (described above)
UGT2A3-1R (described above)
UGT2B4-1L (described above)
UGT2B4-1R (described above)
UGT2B7-1L (described above)
UGT2B7-1R (described above)
UGT2B11-1L (described above)
UGT2B11-1R (described above)
UGT2B15-1L (described above)
UGT2B15-1R (described above)
UGT2B15-2L (described above)
UGT2B15-2R (described above)
UGT2B28-1L (described above)
UGT2B28-1R (described above)
UGT2loxP3L (described above)
TRANS R1 (described above)
PGKr1 (described above)
UGT2loxP4R (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, five clones out of the 22 clones were found to be positive for all primer sets, and the following analysis was performed by using those five clones.

[C. 2. 2] Two-Color FISH Analysis

Figure 83:
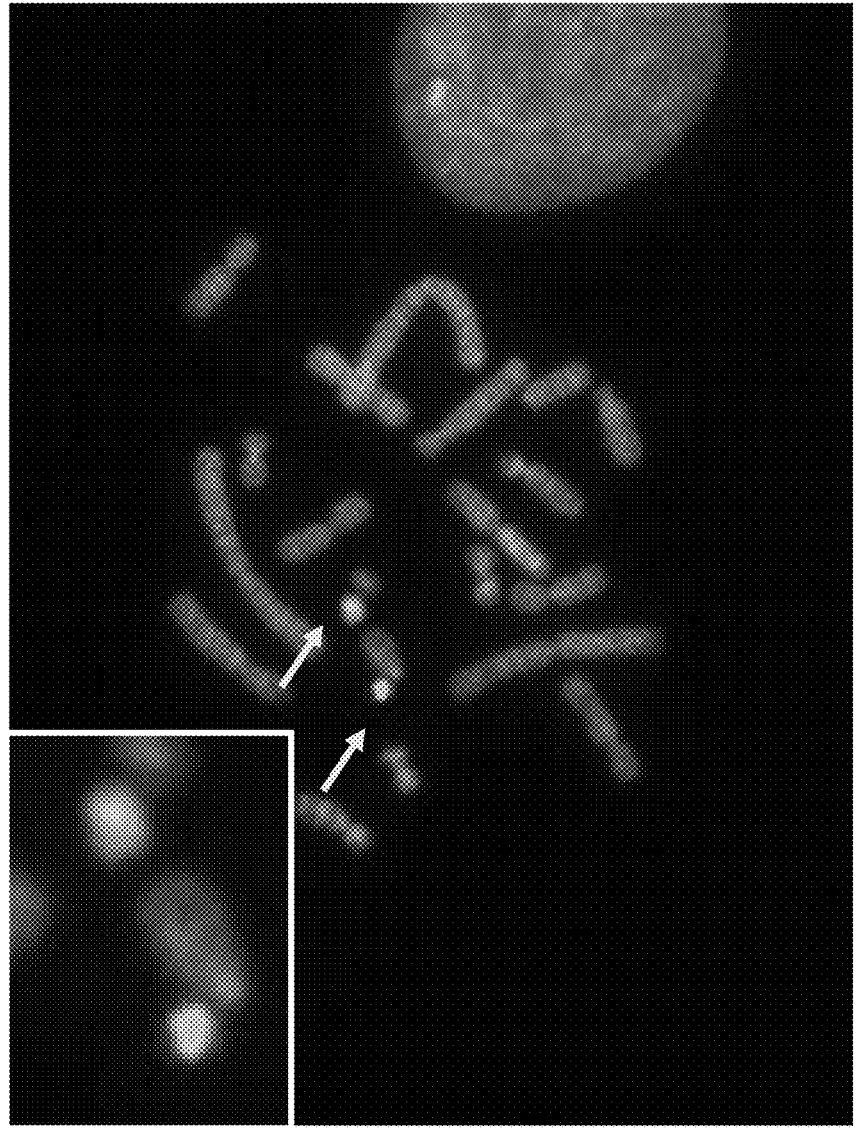
FIG. 83 shows the results of the two-color FISH analysis of CHO (HPRT⁻; MAC4, hChr4-loxP-tel) clone in which human Cot-1 DNA and mouse Cot-1 DNA were used as probes.

For the five clones of CHO (HPRT−; MAC4, hChr4-loxP-tel) obtained from the above, FISH analysis was carried out by using mouse Cot-1 DNA and human Cot-1 DNA as probes according to the method described by Shinohara et al. (Human Molecular Genetics, 10: 1163-1175, 2001). As a result, it was confirmed that one copy or two copies of MAC1 and hChr4-loxP-tel were introduced into CHO cells with a rate of 90% or more in one clone (FIG. 83).

From these results, it was concluded that hChr4-loxP-tel could be introduced into the CHO cells containing the mouse artificial chromosome vector MAC4.

Figure 84:
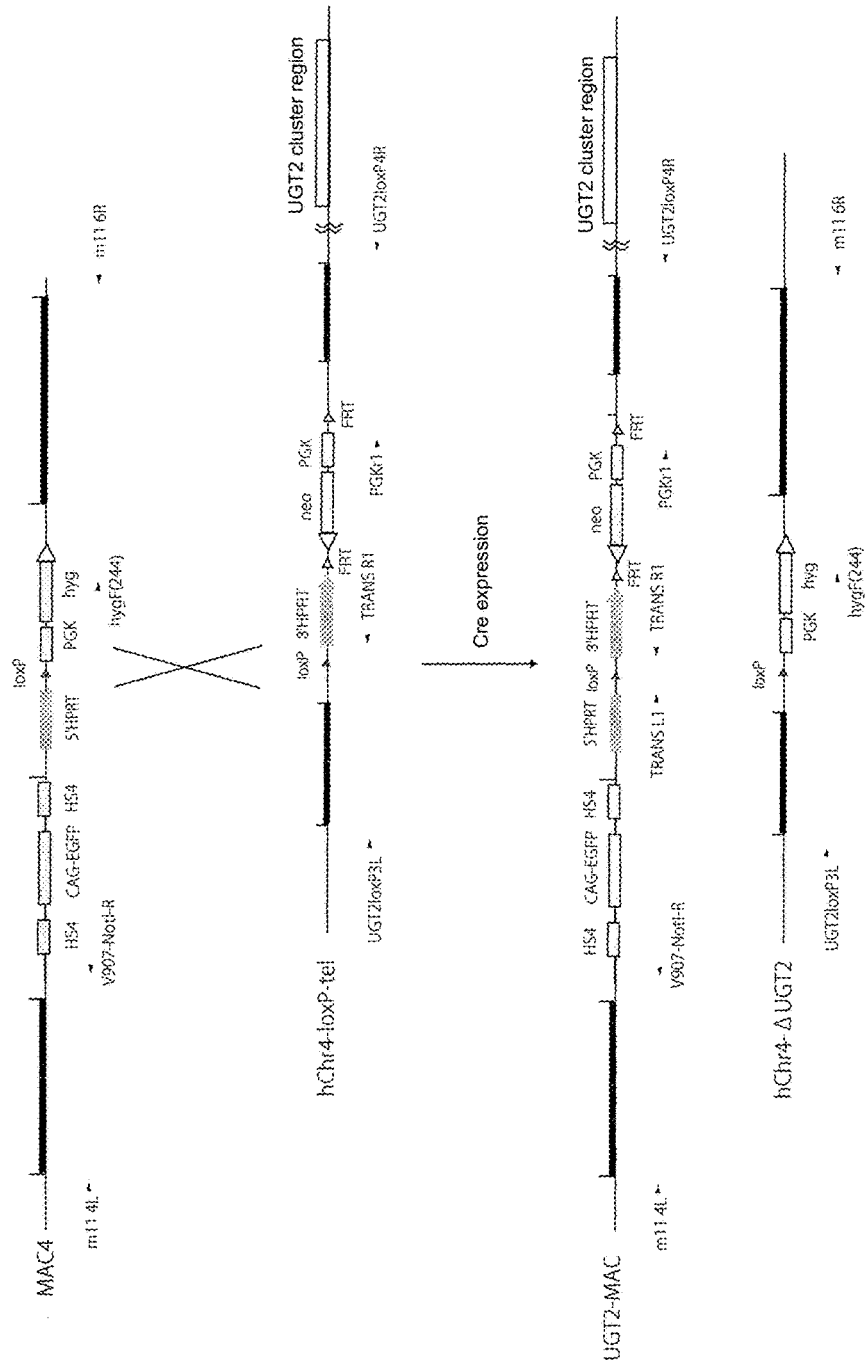
FIG. 84 shows the construction of mouse artificial chromosome UGT2-MAC in which 2 Mb human UGT2 gene cluster region (i.e., AC074378-human UGT2 gene cluster-AC125239) was translocation-cloned into MAC4.

[D] Site Specific Translocation of 2 Mb Human UGT2 Gene Cluster Region (i.e., AC074378-Human UGT2 Gene Cluster-AC125239) to MAC4 Vector in CHO (HPRT−; MAC4, hChr4-loxP-Tel) Clone To stably keep the human UGT2 gene cluster, which is a DNA with 2 Mb size, in a mouse individual, translocation insertion into the mouse artificial chromosome vector MAC4 is performed (FIG. 84).

[D. 1] Transfection and Isolation of HAT Resistant Clone

Gene introduction was carried out by lipofection for CHO (HPRT⁻; MAC4, hChr4-loxP-tel) 8 obtained from the above. To cells in 6 wells with 90% confluency, 3 μg of Cre was introduced according to the commercially available protocol (Invitrogen). After culture for 2 weeks under HAT selection culture, a resistant colony was generated and total six colonies obtained by two introductions were isolated, amplified, and subjected to the following analysis (clone name: CHO (UGT2-MAC, hChr4-ΔUGT2)).

[D. 2] Selection of Drug Resistant Clone

[D. 2. 1] PCR Analysis

For extracting genomic DNA from HAT resistant cell line and using it as a template for selecting a clone with reciprocal translocation, PCR was carried out by using the following primers and it was confirmed whether or not reciprocal chromosomal translocation has occurred on human chromosome 4 fragment and MAC4. The primer sequences are given below.

m11 4L: (described above)
V907-NotI-R: (described above)
hygF (244): (described above)
m11 6R (described above)
UGT2tel4L; (described above)
SK23 (described above)
UGT2A1-1L (described above)
UGT2A1-1R (described above)
UGT2A1-2L (described above)
UGT2A1-2R (described above)
UGT2A3-1L (described above)
UGT2A3-1R (described above)
UGT2B4-1L (described above)
UGT2B4-1R (described above)
UGT2B7-1L (described above)
UGT2B7-1R (described above)
UGT2B11-1L (described above)
UGT2B11-1R (described above)
UGT2B15-1L (described above)
UGT2B15-1R (described above)
UGT2B15-2L (described above)
UGT2B15-2R (described above)
UGT2B28-1L (described above)
UGT2B28-1R (described above)
UGT2loxP3L (described above)
TRANS R1 (described above)
PGKr1 (described above)
UGT2loxP4R (described above)
TRANS L1 (described above)
TRANS R1 (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, all six clones out of the six clones were found to be positive for all primer sets, and the following analysis was performed by using those six clones.

[D. 2. 2] Two-Color FISH Analysis

Figure 85:
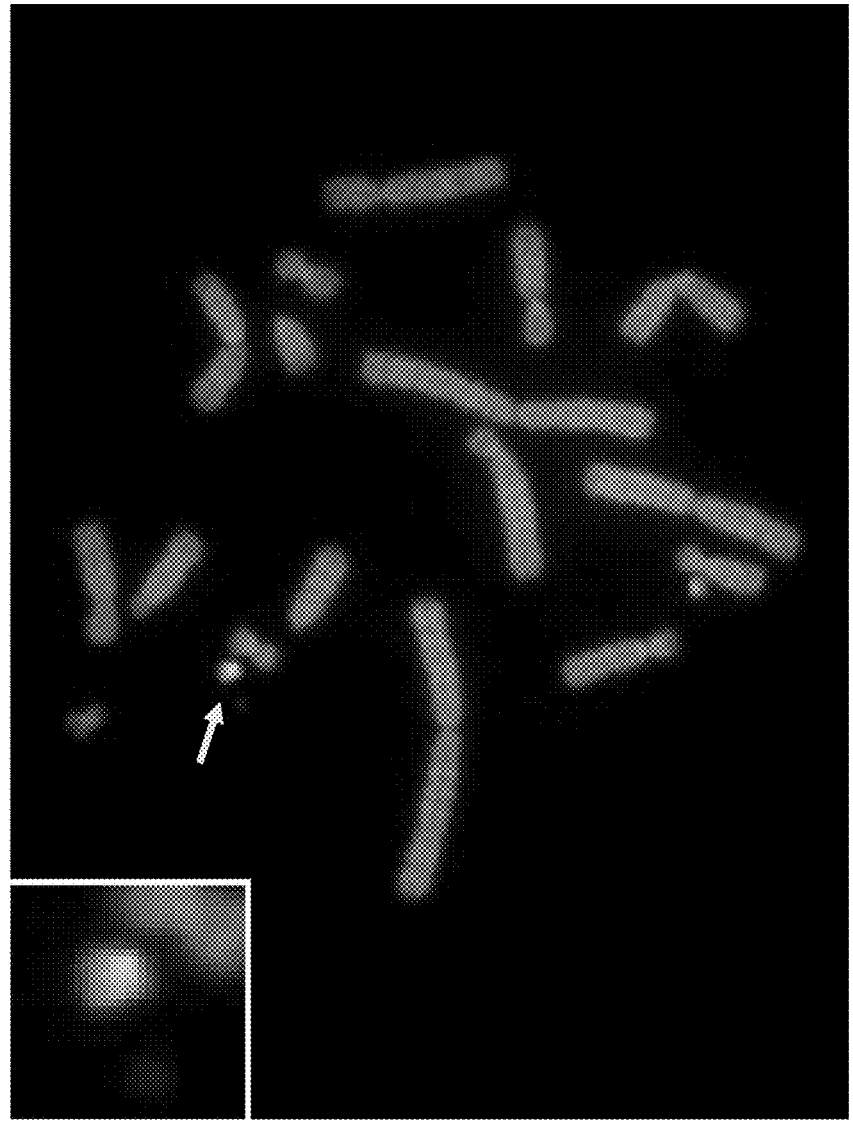
FIG. 85 shows the results of the two-color FISH analysis of CHO (UGT2-MAC, hChr4-ΔUGT2) clone in which UGT2-BAC (RP11-643N16) (CHORI) DNA and mouse Cot-1 DNA were used as probes.

With the six clones of CHO (UGT2-MAC, hChr4-ΔUGT2) obtained from the above, FISH analysis was carried out by using UGT2-BAC (RP11-643N16) (CHORI) DNA and mouse Cot-1 DNA as probes according to the method described by Shinohara et al. (Human Molecular Genetics, 10: 1163-1175, 2001). As a result, it was confirmed that the signal derived from human UGT2 was observed on MAC4 at a rate of 50% or more in two clones out of the six clones (FIG. 85).

From these results, it was concluded that 2 Mb of UGT2 cluster on human chromosome 4 fragment could be cloned into the mouse artificial chromosome vector MAC4 by reciprocal translocation.

[E] Transfer of UGT2-MAC from CHO Cell to Mouse A9 Cell

Figure 86:
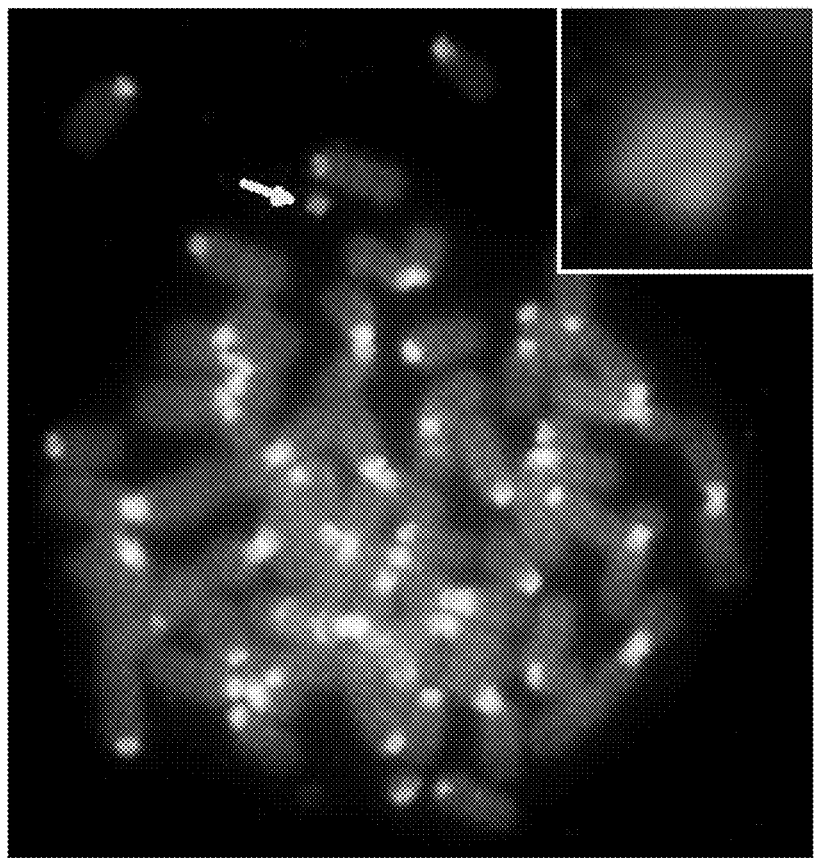
FIG. 86 shows the results of the two-color FISH analysis of A9 (UGT2-MAC) clone in which UGT2-BAC (RP11-643N16) (CHORI) and mouse minor satellite DNA were used as probes.

To prepare mouse ES cells retaining UGT2-MAC, transfer was carried out from CHO cells retaining UGT2-MAC (CHO (UGT2-MAC, hChr4-ΔUGT2) 4, 5) obtained from the above [D] to, as a mouse A9 cell, mouse A9 cells having high microcell forming ability by microcell fusion. Total 16 resistant colonies obtained by four microcell fusions were isolated, amplified, and subjected to the following analysis (clone name: A9 (UGT2-MAC)). As a result, there were five clones which were determined to be positive by PCR using the primers described above for detecting the UGT2-MAC region only. In addition, FISH analysis (Tomizuka et al., Nature Genet. 16: 133, 1997) was carried out by using UGT2-BAC (RP11-643N16) (CHORI) and mouse minor satellite DNA as probes. As a result, the presence of UGT2-MAC, which is specifically detected with the probes, was confirmed in all five clones out of the five clones (FIG. 86). From the above, it was concluded that five clones of A9 cells retaining UGT2-MAC were obtained.

[F] Transfer of UGT2-MAC from A9 Cell to Mouse ES Cell

Figure 87:
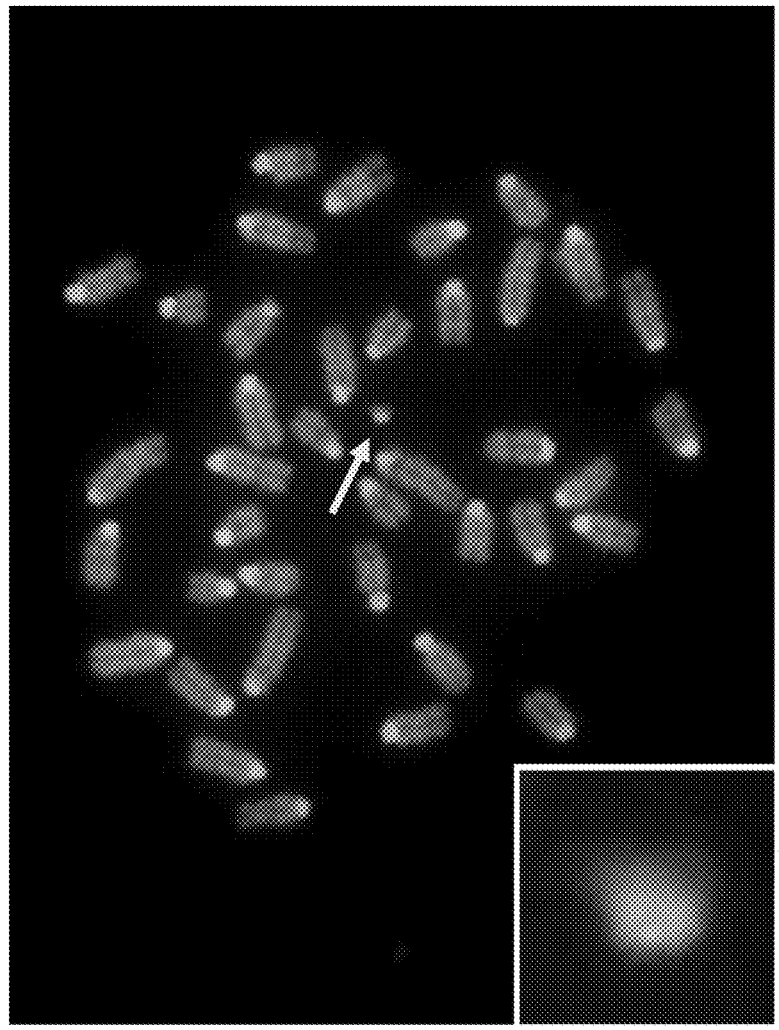
FIG. 87 shows the results of the mono-color FISH analysis of TT2F (UGT2-MAC) clone in which UGT2-BAC (RP11-643N16) (CHORI) DNA was used as a probe.

To prepare a chimeric mouse retaining UGT2-MAC, introduction was carried out from A9 cells retaining UGT2-MAC obtained from the above [E] to mouse ES cells (wild type TT2F) by microcell fusion. According to the method of Tomizuka et al. (Nature Genet. 16: 133, 1997), microcells were purified from approximately $10^8$ cells of A9 retaining UGT2-MAC (A9 (UGT2-MAC) 13, 15, or the like) and suspended in 5 ml of DMEM. Approximately $10^7$ mouse ES cells were removed by trypsin treatment, washed three times with DMEM, suspended in 5 ml of DMEM, and added to the microcells obtained by centrifugation. After centrifugation for 10 min at 1250 rpm, the supernatant was completely removed. The precipitates were resolved fully by tapping and added with 0.5 ml of 1:1.4 PEG solution [5 g of PEG1000 (Wako Pure Chemical Industries, Ltd.) and 1 ml of DMSO (Sigma) are dissolved in 6 ml of DMEM], and fully stirred for about 1 min and 30 sec. After that, 10 ml of DMEM was slowly added, centrifuged for 10 min at 1250 rpm, and suspended in 30 ml of ES culture medium. Thereafter, the cells were dispensed into three petri dishes with a diameter of 100 mm (Corning Incorporated) onto which feeder cells have been previously plated and then cultured. 24 hours later, the culture medium was exchanged with culture medium containing 300 μg/ml G418 and then subjected to selection culture for about 1 week. As a result, total 25 colonies were isolated, amplified, and subjected to the following analysis. Five clones from A9 (UGT2-MAC) 13 and four clones from A9 (UGT2-MAC) 15 were positive in PCR using the primers described before for detecting the UGT2-MAC region only. In addition, with nine clones among the above, FISH analysis (Tomizuka et al., Nature Genet. 16: 133, 1997) was carried out by using UGT2-BAC (RP11-643N16) (CHORI) and mouse minor satellite DNA. As a result, the clones that are specifically detected with the probes and have normal mouse nuclear type were found to be seven clones (FIG. 87). From the above, it was concluded that seven clones of TT2F cells retaining UGT2-MAC were obtained.

[G] Stability of UGT2-MAC in Mouse ES Cells

Figure 88:
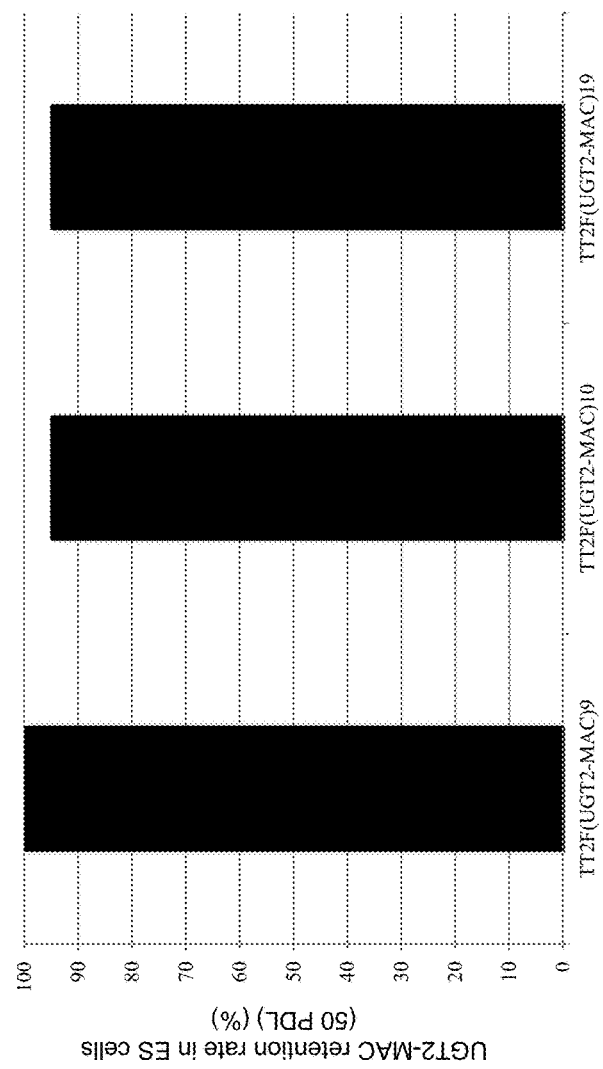
FIG. 88 shows the retention rate of UGT2-MAC in ES cells after long-term culture (75 PDL).

Under non-selection culture of 0 to 50 PDL for the mouse ES clones obtained from the above (for example, TT2F (UGT2-MAC) 9, 10, 19, obtained from the above [F]), a rate of cells retaining UGT2-MAC after long-term culture was measured by FISH analysis. As a result, the retention rate of 95% or more was obtained even for 50 PDL (FIG. 88).

[H] As described in Example 8, by preparing the chimeric mouse using the mouse ES cells retaining the mouse artificial chromosome vector UGT2-MAC, mouse line-based TC (UGT2-MAC) in which UGT2-MAC has been transmitted to a progeny can be prepared. Further, by using the TC (UGT2-MAC) mouse line, stability of UGT2-MAC in somatic cells can be examined Still further, since human drug metabolism can be reproduced by the TC (UGT2-MAC) mouse line, it can be used as a model mouse for in vivo test that is used for testing a pharmacological effect and toxicity in the phase II reaction for development of a pharmaceutical product.

Example 19

Construction of the Mouse Artificial Chromosome Vector CYP2C-MAC

Translocation cloning of CYP2C cluster, which is a human drug metabolizing enzyme gene group into the mouse artificial chromosome vector MAC4 is performed by using Cre/loxP system to construct CYP2C-MAC in the same manner as in Example 3.

[A] Site Specific Cleavage at AL157834 on Human Chromosome 10

To delete genes existing on the distal side from CYP2C gene cluster of human chromosome 10, telomere truncation, which is site specific deletion of a chromosome, is performed.

[A. 1] Preparation of Targeting Vector pTELpuro-CYP2C

Targeting vector pTELpuro-CYP2C for inserting human telomere sequence to AL157834 region, which is located extremely close to CYP2C gene locus of human chromosome 10 and on the telomere side (i.e., locating on the telomere side by approximately 150 Kb from CYP2C gene locus), was prepared as follows. First, the AL157834 genome region was amplified by PCR using the following primers.

```
                                      (SEQ ID NO: 166)
2Ctel2L;  5'- GCTATGAGACACAGGGCAGCTGAAAGTC-3'

(SEQ ID NO: 167)
2Ctel2R;  5'- TTGTGAACCACCATGCCTAGCTGAAAGT-3'
```

Figure 89:
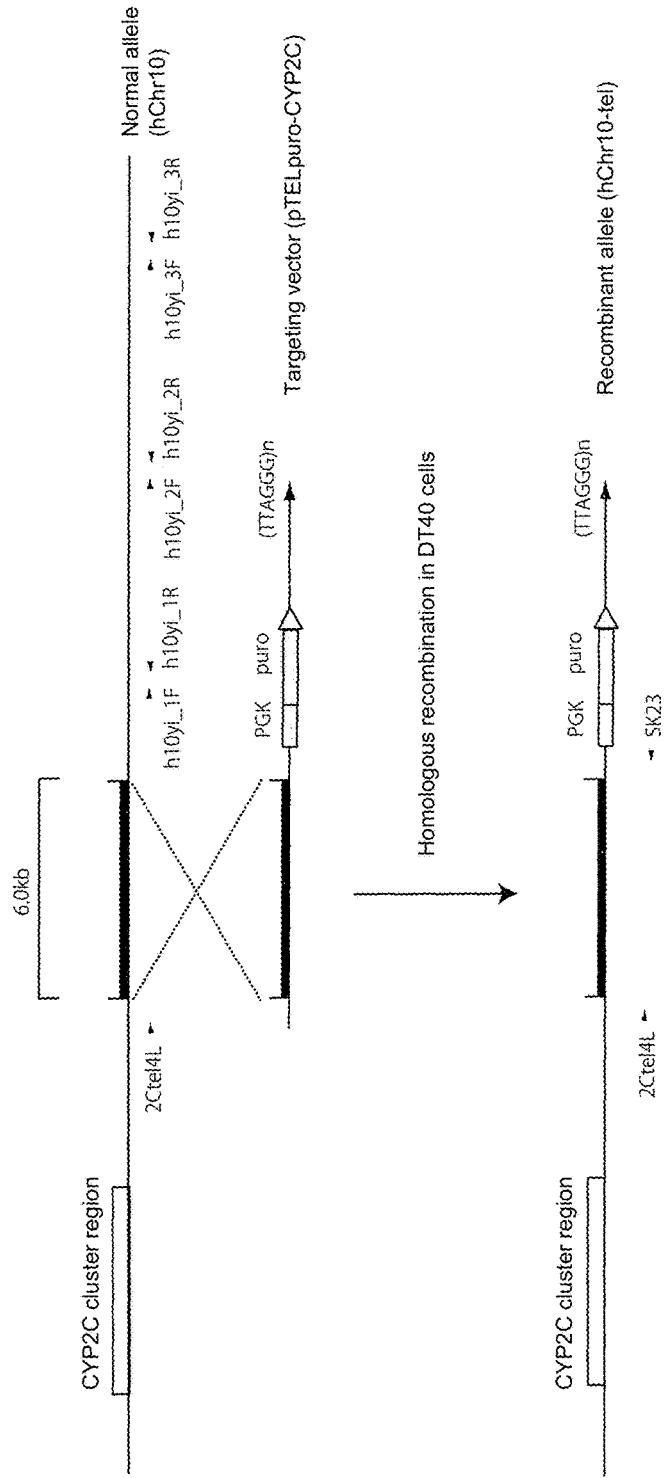
FIG. 89 shows a targeting vector (pTELpuro-CYP2C) for inserting a human telomere sequence into the AL157834 region, which is located extremely close to CYP2C gene locus of human chromosome 10 and on the telomere side (i.e., locating on the telomere side by approximately 150 Kb from CYP2C gene locus), and a partial structure of the human chromosome 10 allele in which homologous recombination was carried out by using the vector.

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 8 min were carried out. PCR product was treated with proteinase K (Gibco) and subjected to gel filtration by using CHROMASPIN-TE400 (Clontech). After that, the product was cleaved with the restriction enzymes BamHI (NIPPON GENE CO., LTD.) and BglII (NIPPON GENE CO., LTD.) and subjected to gel filtration by using CHROMASPIN-TE1000 (Clontech). The PCR fragment was cloned into the BamHI site of plasmid pTELpuro (Kuroiwa et al., Nature Biotech., 20: 88, 2002). Since the genome sequence of AL157834 is in the direction of centromere→telomere, the resultant in which cloned AL157834 genome fragment is in the same direction as the human telomere sequence was taken as desired targeting vector pTELpuro-CYP2C. Size of the final construct for long-arm proximal region specific restriction was 11.6 kb. The targeting vector, target sequence, and chromosome allele obtained by homologous recombination are shown in FIG. 89.

[A. 2] Transfection and Isolation of Drug Resistant Clone

According to the method described by Kazuki et al. BBRC 2004, chicken DT40 cells retaining human chromosome 10 were prepared from A9 (KM32-2) and A9 (KM26-3) (Kugoh et al. DNA research 1999) retaining human chromosome 10 (clone name: DT40 (hChr10)). Next, as described above, the targeting vector pTELpuro-CYP2C prepared above was linearized with the restriction enzyme PstI (NIPPON GENE CO., LTD.), and used for transfection of the clone DT40 (hChr10) 1, 42 prepared above. After exchanging the culture medium for culture medium containing puromycin (0.3 μg/ml), the cells were dispensed into ten 96-well culture plates and then subjected to selection culture for about 2 weeks. Total 96 resistant colonies obtained by four transfections were isolated, amplified, and subjected to the following analysis (clone name: DT40 (hChr10-tel)).

[A. 3] Selection of Homologous Recombinant

[A. 3. 1] PCR Analysis

In order to select a recombinant by using as a template the genomic DNA of puromycin resistant cell line, as a primary screening, PCR was carried out by using the following primers that are located closer to the telomere side than the restriction sites, and it was confirmed whether or not site specific cleavage has occurred. The primer sequences are given below.

```
                                      (SEQ ID NO: 168)
h10yi_1F;  5'- ACGGGGCTCCTACTCTTGTC-3'

(SEQ ID NO: 169)
h10yi_1R;  5'- GCTTCCACCTGCATCTCAC-3'

(SEQ ID NO: 170)
h10yi_2F;  5'- CAATGCCTTATGCATGTTGTG-3'

(SEQ ID NO: 171)
h10yi_2R;  5'- TCCACAGCATACTGCTGACC-3'

(SEQ ID NO: 172)
h10yi_3F;  5'- AAGGAAGGTGACCGCCTACT-3'

(SEQ ID NO: 173)
h10yi_3R;  5'- CATCCGAGGACATCTTTGGT-3'
```

For PCR, GeneAmp 9600 manufactured by PerkinElmer, Inc. was used as a thermal cycler and Ampli Taq Gold (Applied Biosystems) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 95° C. for 10 min, 30 cycles of 95° C. for 20 sec, 55° C. for 30 sec, and 72° C. for 30 sec were carried out.

Next, for three clones that are not detected with the above primers, it was confirmed, by PCR using the following primers, whether or not site specific homologous recombination has occurred. Sequences are as follows.

```
2Ctel4L;
                                   (SEQ ID NO: 174)
5'- ATCTGCAGGGAAGGGATCCAGTTTCAGCTTCCTAC-3'
```

SK23 (described above)

```
                                   (SEQ ID NO: 175)
CYP2C8-1F:    5'-ACATGTCAAAGAGACACACA-3'

(SEQ ID NO: 176)
CYP2C8-1R:    5'-TAGCATATTTCCAATAATAGGA-3'

(SEQ ID NO: 177)
CYP2C9-1F:    5'-AGAAGGCTTCAATGGATTCTC-3'

(SEQ ID NO: 178)
CYP2C9-1R:    5'-TGTCCTTAATACCTATCTGTAGG-3'

(SEQ ID NO: 179)
CYP2C18-1F:   5'-ACAGCTGGATCCATTGAAGG-3'

(SEQ ID NO: 180)
CYP2C19-1F:   5'-ACACACACTTAATTAGCATGGA-3'

(SEQ ID NO: 181)
CYP2C19-1R:   5'-TTGGTTAAGGATTTGCTGACA-3'
```

For PCR, LA Taq (TAKARA SHUZO CO., LTD.) was used with the above primers. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 8 min were carried out. Only in two clones having site specific recombination, a band at approximately 8 kb was detected. In DT40 and DT40 (hChr10) 1, 42 as a negative control, no band was detected.

[B. 3. 2] Two-Color FISH Analysis

Figure 90:
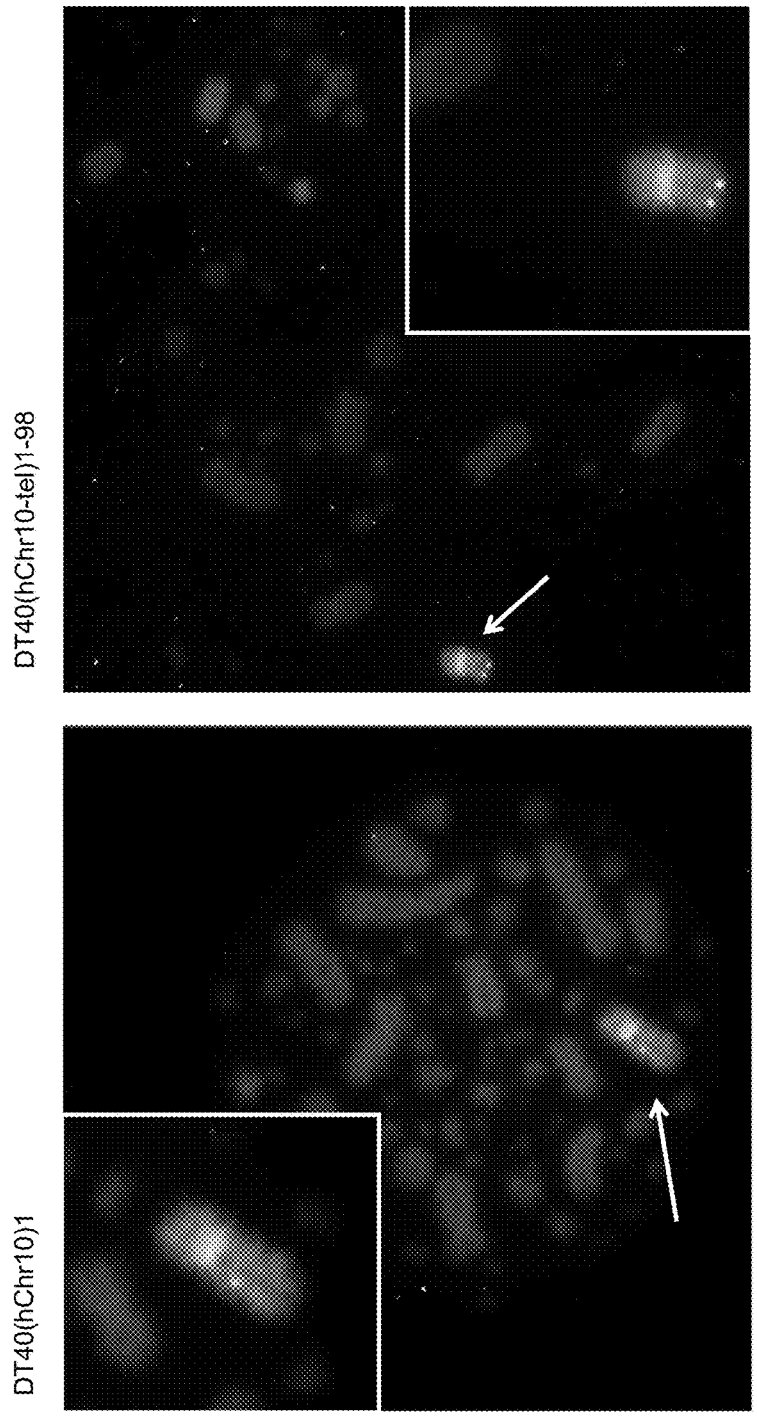
FIG. 90 shows the results of the two-color FISH analysis of DT40 (hChr10-tel) in which human cot-1 DNA and puromycin DNA were used as probes. Left panel represents DT40 (hChr10) before modification, and right panel represents DT40 (hChr10-tel) after modification.

FISH analysis was carried out according to Matsubara et al. (FISH test protocol, Shujunsha Co., Ltd., 1994). With three clones which have been confirmed to have recombination in the above, FISH analysis was carried out by using human cot-1 DNA and puromycin DNA as probes. As a result, it was found that human chromosome 10 was not translocated to the host chromosome in any clone, and based on the fact that puromycin-derived signal was detected at the terminal of human chromosome 10 fragment and restrictions occurred at desired sites, it was confirmed that recombination has site-specifically occurred (FIG. 90).

From these results, it was concluded that, in clone DT40 (hChr10-tel) 5, 98, and 101, cleavage can be made at a region distal from AL157834 which is closer to the telomere side than CYP2C gene cluster region.

[B] Site Specific Insertion of loxP Sequence to AL138759 of Human Chromosome 10

For translocation insertion into the mouse artificial chromosome vector MAC4 via loxP sequence, loxP sequence is inserted into AL138759 proximal to CYP2C gene cluster of hChr10-tel in DT40 cells.

[B. 1] Preparation of Targeting Vector pCYP2CloxPneo

Targeting vector pCYP2CloxPneo for inserting loxP as a recognition sequence for Cre recombinase into AL138759 region, which is located extremely close to CYP2C gene locus of human chromosome 10 and on the centromere side (i.e., locating on the centromere side by approximately 300 Kb from CYP2C gene locus), was prepared as follows. First, the AL138759 genome region was amplified by PCR using the following primers.

```
hloxP-SacII-EcoRI-F:
                                   (SEQ ID NO: 182)
5'- TCCCCGCGGATCTGCTCCATACTCTGTACC-3' hloxP-1R:
                                   (SEQ ID NO: 183)
5'-CATTCAAGGGGTTCTGGGTCTGTAAACT-3'
```

Figure 91:
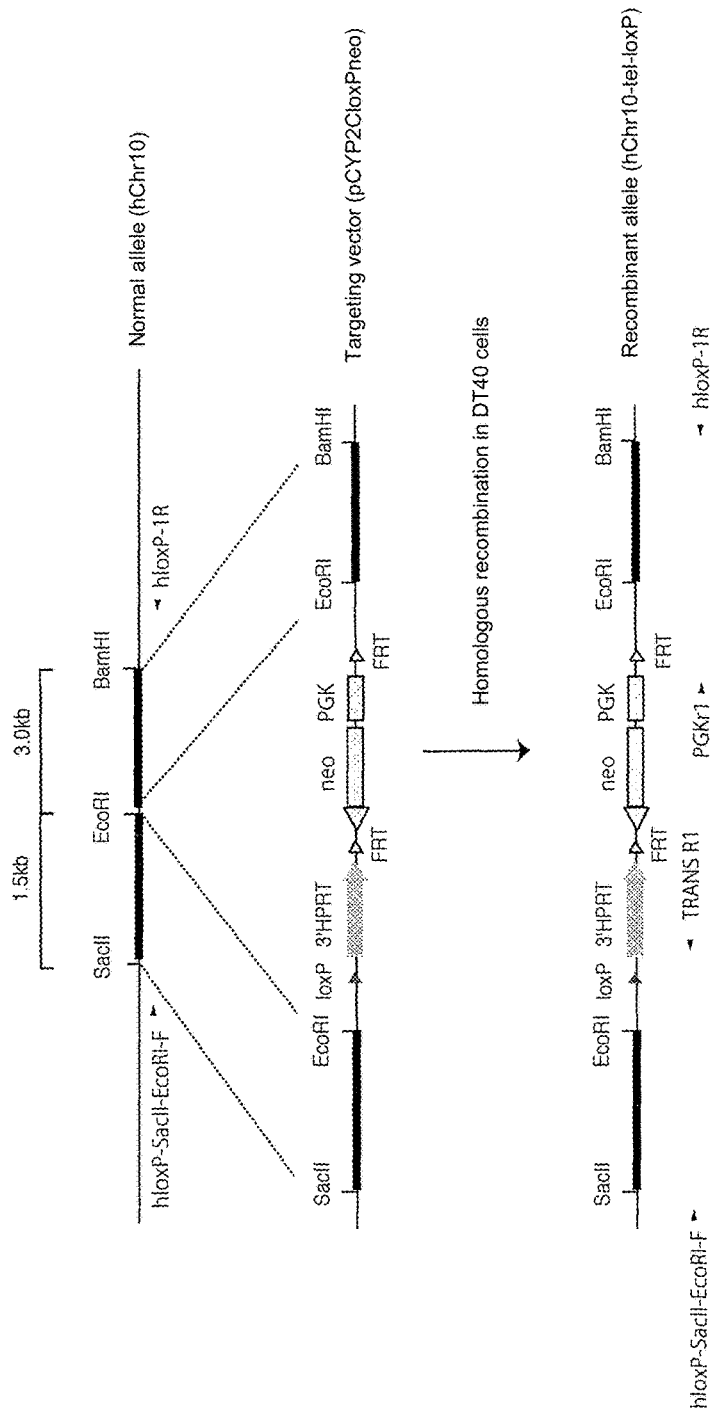
FIG. 91 shows the targeting vector (pCYP2CloxPneo) for inserting loxP sequence into the AL138759 of human chromosome 10, a target sequence, and a chromosome allele produced by homologous recombination.

As a basic plasmid for inserting loxP sequence, V907 (Lexicon genetics) was used. For PCR, GeneAmp 9600 manufactured by PerkinElmer, Inc. was used as a thermal cycler and LA Taq (TAKARA SHUZO CO., LTD.) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 7 min were carried out. PCR product was treated with proteinase K (Gibco) and subjected to gel filtration by using CHROMASPIN-TE400 (Clontech). After that, the product was cleaved with the restriction enzymes SacII (NIPPON GENE CO., LTD.), EcoRI (NIPPON GENE CO., LTD.), and BamHI (NIPPON GENE CO., LTD.) and subjected to gel filtration by using CHROMASPIN-TE1000 (Clontech). The PCR fragments (1.5 kb and 3.0 kb) were cloned into the SacII and EcoRI or EcoRI and BamHI sites of V907 plasmid (vector name: V907-CYP2CHR2). Next, V907-CYP2CHR2 was cleaved with the restriction enzyme EcoRI, and the DNA fragment containing loxP was cut out from the X3.1-FRT-pGKneo-FRT by using the restriction enzyme EcoRI, and then they were ligated to each other. The resultant having the loxP sequence in the same direction as the cloned AL138759 genome fragment was taken as targeting vector pCYP2CloxPneo. Size of the final construct inserted with loxP is 10.3 kb. The targeting vector, target sequence, and chromosome allele obtained by homologous recombination are shown in FIG. 91.

[B. 2] Transfection and Isolation of Drug Resistant Clone

As described above, the targeting vector pCYP2CloxPneo prepared above was linearized with the restriction enzyme NotI (TAKARA), and used for transfection of the chicken DT40 cells (clone DT40 (hChr10-tel) 1-98 retaining human chromosome 10. After exchanging the culture medium for culture medium containing neomycin (1.5 mg/ml), the cells were dispensed into three 96-well culture plates and then subjected to selection culture for about 2 weeks. Total 15 resistant colonies obtained by two transfections were isolated, amplified, and subjected to the following analysis (clone name: DT40 (hChr10-tel-loxP)).

[B. 3] Selection of Homologous Recombinant

[B. 3. 1] PCR Analysis

Genomic DNA was extracted from the neomycin resistant clone by using Puregene DNA Isolation Kit (Gentra Systems, Inc.) and identification of the homologous recombinants was carried out by PCR using the following two sets of primer.

Identification of the homologous recombinants was carried out by PCR using the following two sets of primer.

hloxP-SacII-EcoRI-F (described above)

TRANS R1 (described above)

PGKr 1 (described above)

hloxP-1R (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 10 sec and 68° C. for 4 min were carried out. As a result of screening 15 clones, one clone was identified as a homologous recombinant.

[B. 3. 2] Two-Color FISH Analysis

FISH analysis was carried out according to Matsubara et al. (FISH test protocol, Shujunsha Co., Ltd., 1994). With one clone which have been confirmed to have recombination in the above, FISH analysis was carried out by using human cot-1 DNA and neomycin as probes. As a result, it was found that human chromosome 10 was not translocated to the host chromosome in any clone, and based on the fact that neomycin-derived signal was detected near 10q24, it was confirmed that recombination has site-specifically occurred. From these results, it was concluded that loxP sequence as a gene introduction site was inserted site-specifically into AL138759 of human chromosome 10.

[C] Introduction of hChr10-loxP-Tel from DT40 Containing hChr10-loxP-Tel to CHO Cell Containing MAC4

For translocation insertion of human CYP2C gene cluster region into the mouse artificial chromosome vector MAC4 via loxP sequence in CHO cells, hChr10-loxP-tel is introduced into CHO cells containing the mouse artificial chromosome vector MAC4.

[C. 1] Microcell Fusion and Isolation of Drug Resistant Clone

By using DT40 (hChr10-loxP-tel) 7 as a recipient cell, microcell fusion was carried out for CHO (HPRT$^-$; MAC4), which is CHO hprt depleted cells containing MAC4 (obtained from the Health Science Research Resources Bank, registration number: JCRB0218), in the same manner as above. Total eight resistant colonies obtained by three microcell fusions were isolated, amplified, and subjected to the following analysis (clone name: CHO (HPRT$^-$; MAC4, hChr10-loxP-tel)).

[C. 2] Selection of Drug Resistant Clone
[C. 2. 1] PCR Analysis

For extracting genomic DNA from neomycin resistant cell line and using it as a template for selecting a recombinant, PCR was carried out by using the following primers and it was confirmed whether or not human chromosome 10 fragment is introduced into CHO cells containing MAC4. The primer sequences are given below.
m11 4L: (described above)
V907-NotI-R: (described above)
hygF (244): (described above)
m11 6R (described above)
2Cte14L (described above)
SK23 (described above)
CYP2C8-1F (described above)
CYP2C8-1R (described above)
CYP2C9-1F (described above)
CYP2C9-1R (described above)
CYP2C18-1F (described above)
CYP2C19-1F (described above)
CYP2C19-1R (described above)
hloxP-SacII-EcoRI-F (described above)
TRANS R1 (described above)
PGKr1 (described above)
hloxP-1R (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, all eight clones out of the eight clones were found to be positive for all primer sets, and the following analysis was performed by using those eight clones.

[C. 2. 2] Two-Color FISH Analysis

Figure 92:
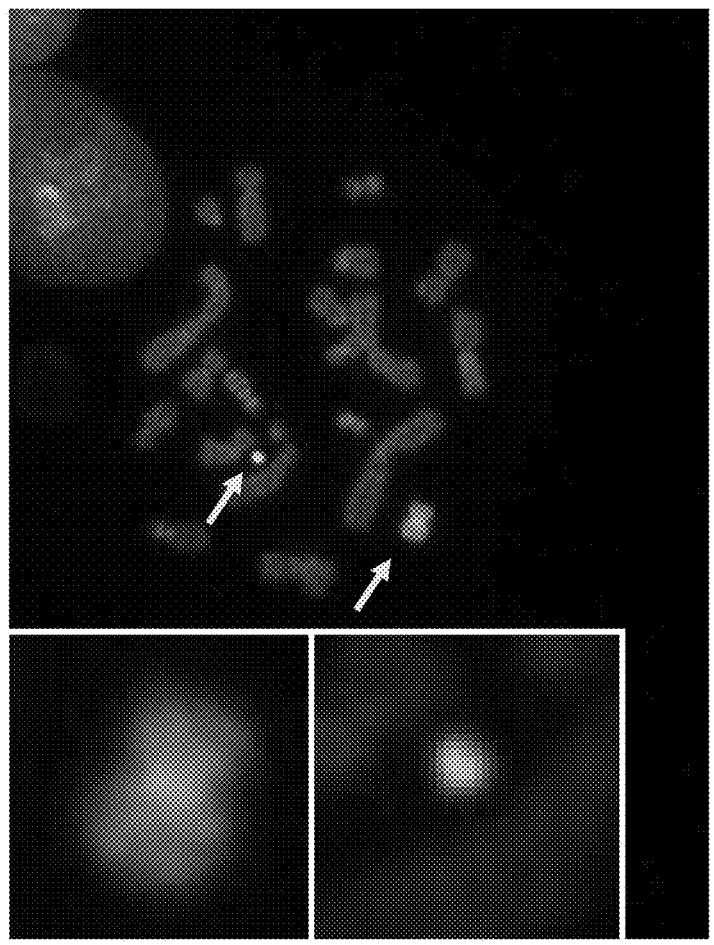
FIG. 92 shows the results of the two-color FISH analysis of (HPRT$^-$; MAC4, hChr10-loxP-tel) clone in which mouse Cot-1 DNA and human Cot-1 DNA were used as probes.

With the eight clones of CHO (HPRT$^-$; MAC4, hChr10-loxP-tel) obtained from the above, FISH analysis was carried out by using mouse Cot-1 DNA and human Cot-1 DNA as probes according to the method described by Shinohara et al. (Human Molecular Genetics, 10: 1163-1175, 2001). As a result, it was confirmed that one or two copies of MAC1 and hChr10-loxP-tel are introduced into CHO cells with a rate of 90% or more in two clones (FIG. 92).

From these results, it was concluded that hChr10-loxP-tel can be introduced into CHO cells containing the mouse artificial chromosome vector MAC4.

Figure 93:
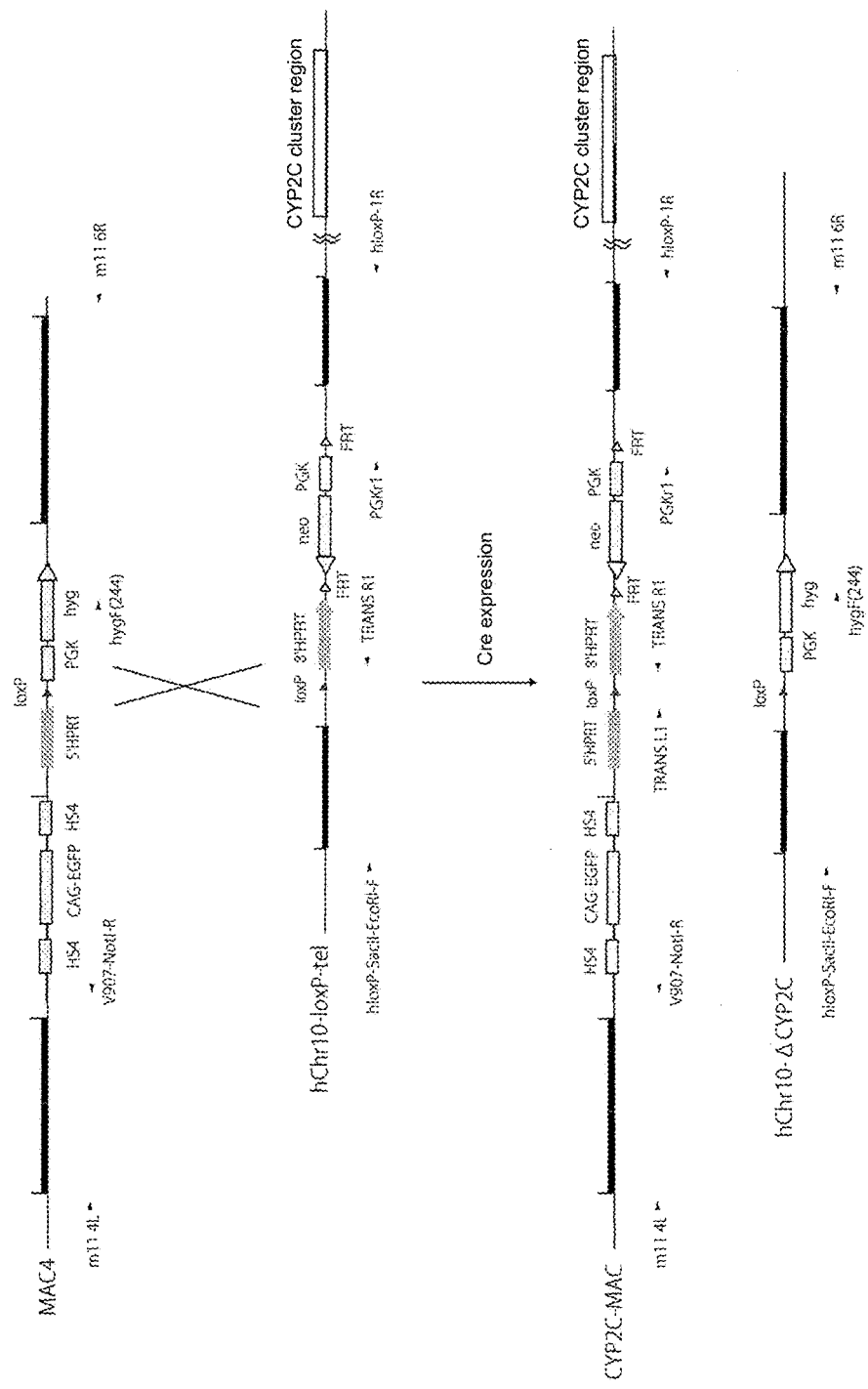
FIG. 93 shows the construction of mouse artificial chromosome CYP2C-MAC in which 380 kb human CYP2C gene cluster region (i.e., AL138759-human CYP2C gene cluster-AL157834) was translocation-cloned into MAC4.

[D] Site Specific Translocation of 380 kb Human CYP2C Gene Cluster Region (i.e., AL138759-Human CYP2C Gene Cluster-AL157834) to MAC4 Vector in CHO (HPRT$^-$; MAC4, hChr10-loxP-Tel) Clone To stably keep the human 2CYP2C gene cluster, which is a 380 kb DNA, in a mouse individual, translocation insertion into the mouse artificial chromosome vector MAC4 is performed (FIG. 93).

[D. 1] Transfection and Isolation of HAT Resistant Clone

Gene introduction was carried out by lipofection for CHO (HPRT$^-$; MAC4, hChr10-loxP-tel) 1 and 5 obtained from the above. To cells in 6 wells with 90% confluency, 3 µg of Cre was introduced according to the commercially available protocol (Invitrogen). After culture for 2 weeks under HAT selection culture, a resistant colony was generated and total 11 colonies obtained by two introductions were isolated, amplified, and subjected to the following analysis (clone name: CHO (CYP2C-MAC, hChr10-ΔCYP2C)).

[D. 2] Selection of Drug Resistant Clone
[D. 2. 1] PCR Analysis

For extracting genomic DNA from HAT resistant cell line and using it as a template for selecting a clone with reciprocal translocation, PCR was carried out by using the following primers and it was confirmed whether or not reciprocal chromosomal translocation has occurred on human chromosome 10 fragment and MAC4. The primer sequences are given below.
m11 4L: (described above)
V907-NotI-R: (described above)
hygF (244): (described above)
m11 6R (described above)
2Cte14L (described above)
SK23 (described above)
CYP2C8-1F (described above)
CYP2C8-1R (described above)
CYP2C9-1F (described above)
CYP2C9-1R (described above)
CYP2C18-1F (described above)
CYP2C19-1F (described above)
CYP2C19-1R (described above)
hloxP-SacII-EcoRI-F (described above)
PGKr1 (described above)
hloxP-1R (described above)
TRANS L1 (described above)
TRANS R1 (described above)

For PCR, GeneAmp 9600 manufactured by PerkinElmer, Inc. was used as a thermal cycler and LA Taq (TAKARA)

was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, nine clones out of the 11 clones were found to be positive for all primer sets, and the following analysis was carried out by using those nine clones.

[D. 2. 2] Two-Color FISH Analysis

Figure 94:
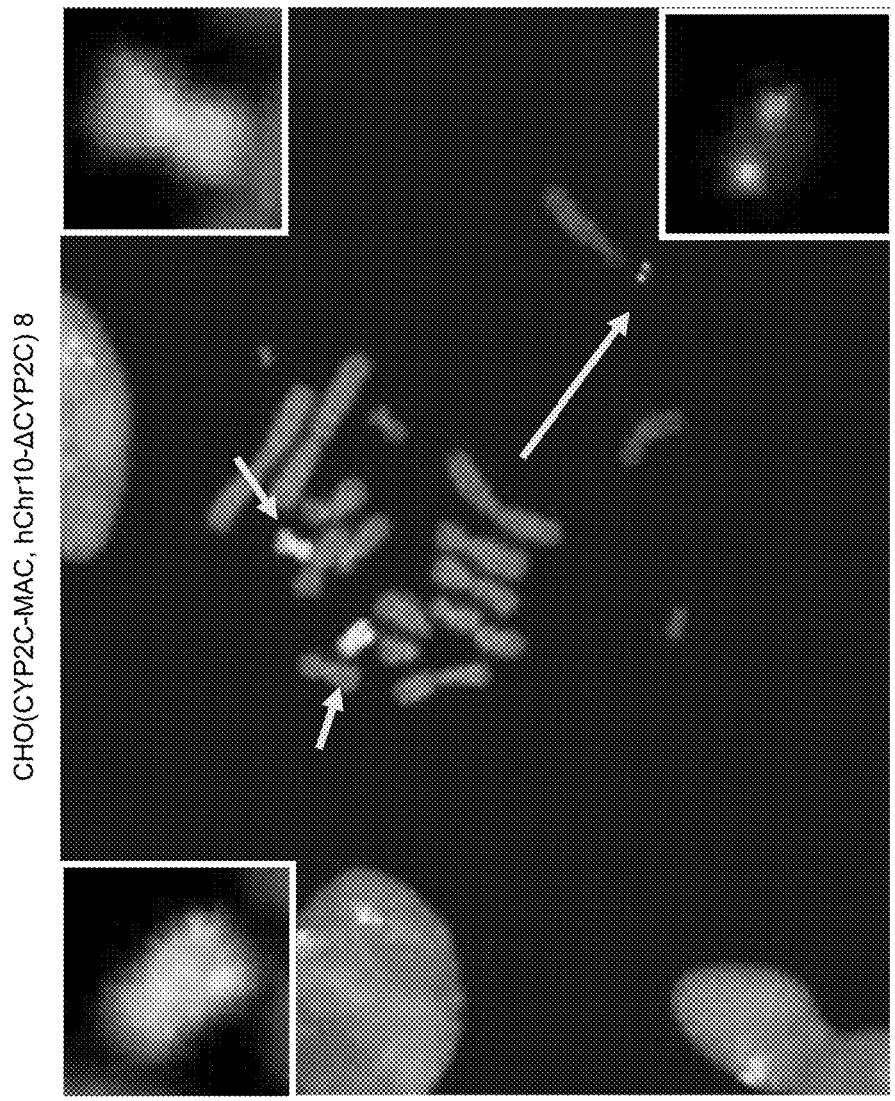
FIG. 94 shows the results of the two-color FISH analysis of CHO (CYP2C-MAC, hChr10-ΔCYP2C) clone in which CYP2C-BAC (RP11-466J14) (CHORI) DNA and mouse Cot-1 DNA were used as probes.

With the nine clones of CHO (CYP2C-MAC, hChr10-ΔCYP2C) obtained from the above, FISH analysis was carried out by using CYP2C-BAC (RP11-466J14) (CHORI) DNA and mouse Cot-1 DNA as probes according to the method described by Shinohara et al. (Human Molecular Genetics, 10: 1163-1175, 2001). As a result, it was confirmed that the signal derived from human CYP2C was observed on MAC4 at a rate of 50% or more in three clones out of the nine clones (FIG. 94).

From these results, it was concluded that 380 kb of CYP2C cluster on human chromosome 10 fragment can be cloned into the mouse artificial chromosome vector MAC4 by reciprocal translocation.

[E] Transfer of CYP2C-MAC from CHO Cell to Mouse A9 Cell

To prepare mouse ES cells retaining CYP2C-MAC, introduction was carried out from CHO cells (CHO (CYP2C-MAC, hChr10-ΔCYP2C) 2, 8, 10) retaining CYP2C-MAC obtained from the above [D] to, as a mouse A9 cell, mouse A9 cells having high microcell forming ability by microcell fusion. Total four resistant colonies obtained by four microcell fusions were isolated, amplified, and subjected to the following analysis (clone name: A9 (CYP2C-MAC)). As a result, there were four clones which are positive in PCR using the primers described before for detecting the CYP2C-MAC region only. In addition, FISH analysis (Tomizuka et al., Nature Genet. 16: 133, 1997) was carried out by using CYP2C-BAC (RP11-466J14) (CHORI) and mouse minor satellite DNA as probes. As a result, the presence of CYP2C-MAC, which is specifically detected with the probes, was confirmed in two clones out of the four clones. From the above, it was concluded that two clones of A9 cells retaining CYP2C-MAC are obtained.

[F] As described in Example 8, in vitro stability can be examined by preparing mouse ES cells retaining the mouse artificial chromosome vector CYP2C-MAC and using it. Further, by preparing a chimeric mouse using the ES cells, the mouse lineage-based TC (CYP2C-MAC) in which CYP2C-MAC is transferred to a progeny can be prepared. Further, by using the TC (CYP2C-MAC) mouse line, stability of CYP2C-MAC in somatic cells can be examined Still further, the liver microsome derived from TC (CYP2C-MAC) mouse line may be used as a sample for testing a pharmacological effect and toxicity in the phase I reaction for development of a pharmaceutical product. Further, because human drug metabolism can be reproduced by TC (CYP2C-MAC) mouse line, it may be also used as a model mouse for in vivo test that is used for testing a pharmacological effect and toxicity in the phase I reaction for development of a pharmaceutical product.

Example 20

Construction of the Mouse Artificial Chromosome Vector MDR1-MAC

Translocation cloning of MDR1 gene, which is a human drug metabolizing enzyme gene group, into the mouse artificial chromosome vector MAC4 is performed by using Cre/loxP system to construct MDR1-MAC in the same manner as in Example 3.

[A] Site Specific Insertion of loxP Sequence into AC005045 on Human Chromosome 7

For translocation insertion to the mouse artificial chromosome vector MAC4 via loxP sequence, loxP sequence is inserted into AC005045 proximal to MDR1 gene of human chromosome 7 (hChr7) in DT40 cells.

[A. 1] Preparation of Targeting Vector pMDR1loxPbs

Targeting vector pMDR1loxPbs for inserting loxP as a recognition sequence for Cre recombinase into AC005045 region, which is located extremely close to MDR1 gene locus of human chromosome 7 and on the centromere side (i.e., locating on the centromere side by approximately 50 Kb from MDR1 gene locus), was prepared as follows. First, the AC005045 genome region was amplified by PCR using the following primers.

(SEQ ID NO: 184)
MDR1loxP2L: 5'- gccaagtgtagctggagaatgattcgtg -3'

(SEQ ID NO: 185)
MDR1loxP1R: 5'- acaaggcacttcaggataccaagcttcc -3'

Figure 95:
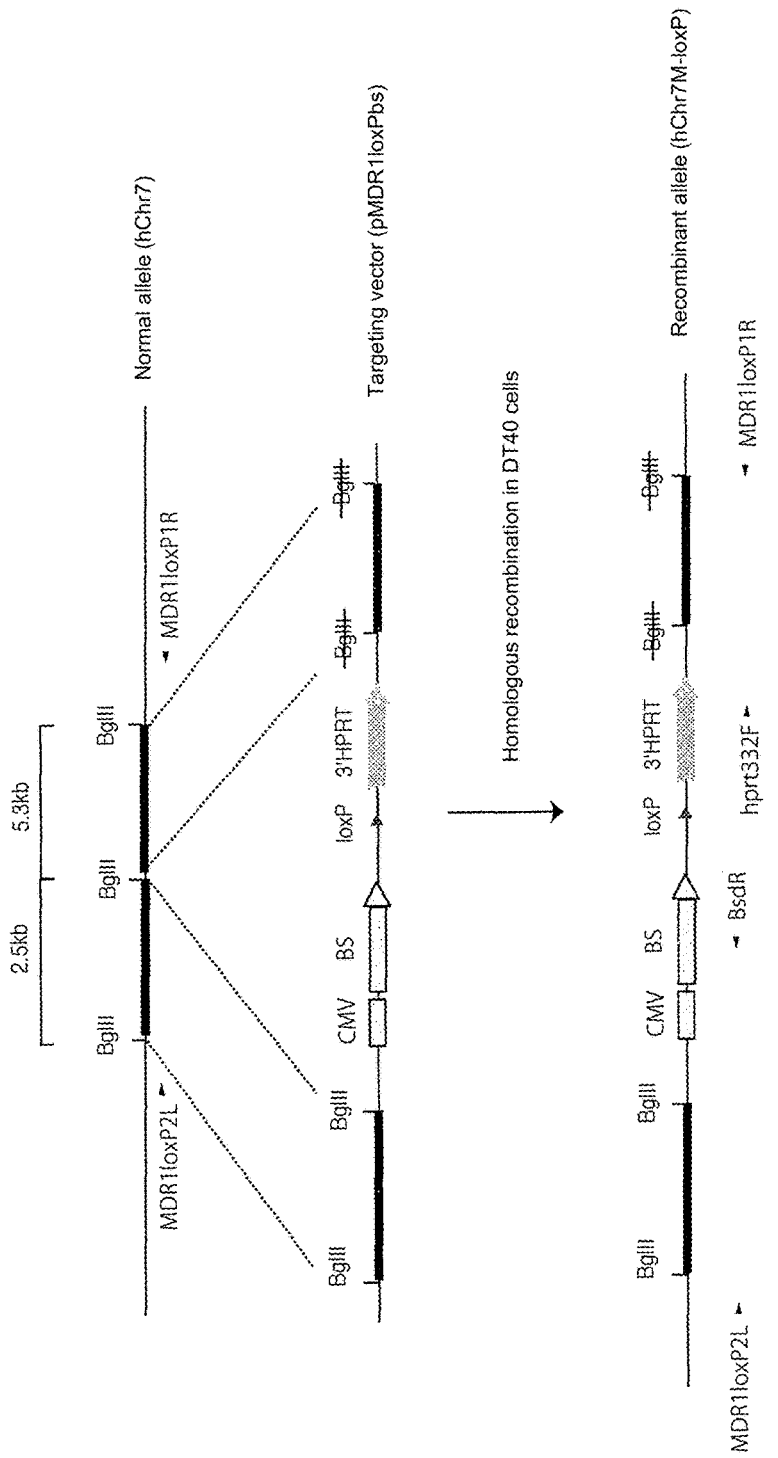
FIG. 95 shows the targeting vector (pMDR1loxPbs) for inserting loxP sequence into the AC005045 of human chromosome 7, a target sequence, and a chromosome allele produced by homologous recombination.

As a basic plasmid for inserting loxP sequence, V901 (Lexicon genetics) was used. For PCR, GeneAmp 9600 manufactured by PerkinElmer, Inc. was used as a thermal cycler and LA Taq (TAKARA SHUZO CO., LTD.) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 7 min were carried out. PCR product was treated with proteinase K (Gibco) and subjected to gel filtration by using CHROMASPIN-TE400 (Clontech). After that, the product was cleaved with the restriction enzyme BglII (NIPPON GENE CO., LTD.) and subjected to gel filtration by using CHROMASPIN-TE1000 (Clontech). The PCR fragments (2.5 kb and 5.3 kb) were cloned into the BglII and BamHI sites of V901 plasmid (vector name: V901-MDR1HR2). Next, V901-MDR1HR2 was cleaved with the restriction enzymes AscI (NEB) and KpnI and the DNA fragment containing loxP was cut out from the cassette vector Bs-loxP-3' HPRT (Hoshiya et al., Mol Ther. 2009; 17(2): 309-17) by using the restriction enzymes AscI and KpnI, and then they were ligated to each other. The resultant product having the loxP sequence in the same direction as the cloned AC005045 genome fragment was taken as targeting vector pMDR1loxPbs. Size of the final construct inserted with loxP is 13.0 kb. The targeting vector, target sequence, and chromosome allele obtained by homologous recombination are shown in FIG. 95.

[A. 2] Transfection and Isolation of Drug Resistant Clone

As described above, the targeting vector pMDR1loxPbs prepared above was linearized with the restriction enzyme NotI (TAKARA), and used for transfection of chicken DT40 cells (cloneDT40-#7) retaining human chromosome 7, which is prepared according to the method described in WO 01/011951. After exchanging the culture medium for culture medium containing blasticidin S (15 µg/ml), the cells were dispensed into three 96-well culture plates and then subjected to selection culture for about 2 weeks. Total nine resistant colonies obtained by two transfections were isolated, amplified, and subjected to the following analysis (clone name: DT40 (hChr7M-loxP)).

[A. 3] Selection of Homologous Recombinant
[A. 3. 1] PCR Analysis

Genomic DNA was extracted from the blasticidin S resistant clones by using Puregene DNA Isolation Kit (Gentra Systems, Inc.) and identification of homologous recombinant was carried out by PCR using the following two sets of primer.

Identification of homologous recombinant was carried out by PCR using the following two sets of primers.
MDR1loxP2L (described above)

```
                                    (SEQ ID NO: 186)
BsdR:         5'-gctcaagatgcccctgttct-3'

(SEQ ID NO: 187)
hprt332F:     5'-aaagatggtcaaggtcgcaa-3'
```

MDR1loxP1R (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 10 sec and 68° C. for 4 min were carried out. As a result of screening nine clones, three clones were identified as a homologous recombinant.

[A. 3. 3] Two-Color FISH Analysis

FISH analysis was carried out according to Matsubara et al. (FISH test protocol, Shujunsha Co., Ltd., 1994). With the three clones which have been confirmed to have recombination in the above, FISH analysis was carried out by using human cot-1 DNA and blasticidin DNA as probes. As a result, it was found that human chromosome 7 was not translocated to the host chromosome in any clone, and based on the fact that neomycin-derived signal was detected near 7q21, it was confirmed that recombination has site-specifically occurred. From these results, it was concluded that loxP sequence as a gene introduction site was site-specifically inserted into AC005045 of human chromosome 7.

[B] Site Specific Cleavage at AC003083 on Human Chromosome 7

To delete the gene at the distal side from MDR1 gene of human chromosome 7, telomere truncation as site specific deletion of chromosome is performed.

[B. 1] Preparation of Targeting Vector pTELpuro-MDR1

Targeting vector pTELpuro-MDR1 for inserting human telomere sequence into AC003083 region, which was located extremely close to MDR1 gene locus of human chromosome 7 and on the telomere side (i.e., locating on the telomere side by approximately 50 Kb from MDR1 gene locus), was prepared as follows. First, the AC003083 genome region was amplified by PCR using the following primers.

```
                                         (SEQ ID NO: 188)
MDR1tel5L; 5'- ctattctaaaaagctgccttggcccaca-3'

(SEQ ID NO: 189)
MDR1tel5R; 5'- tgtagcccagttcctaatgggacacaga-3'
```

Figure 96:
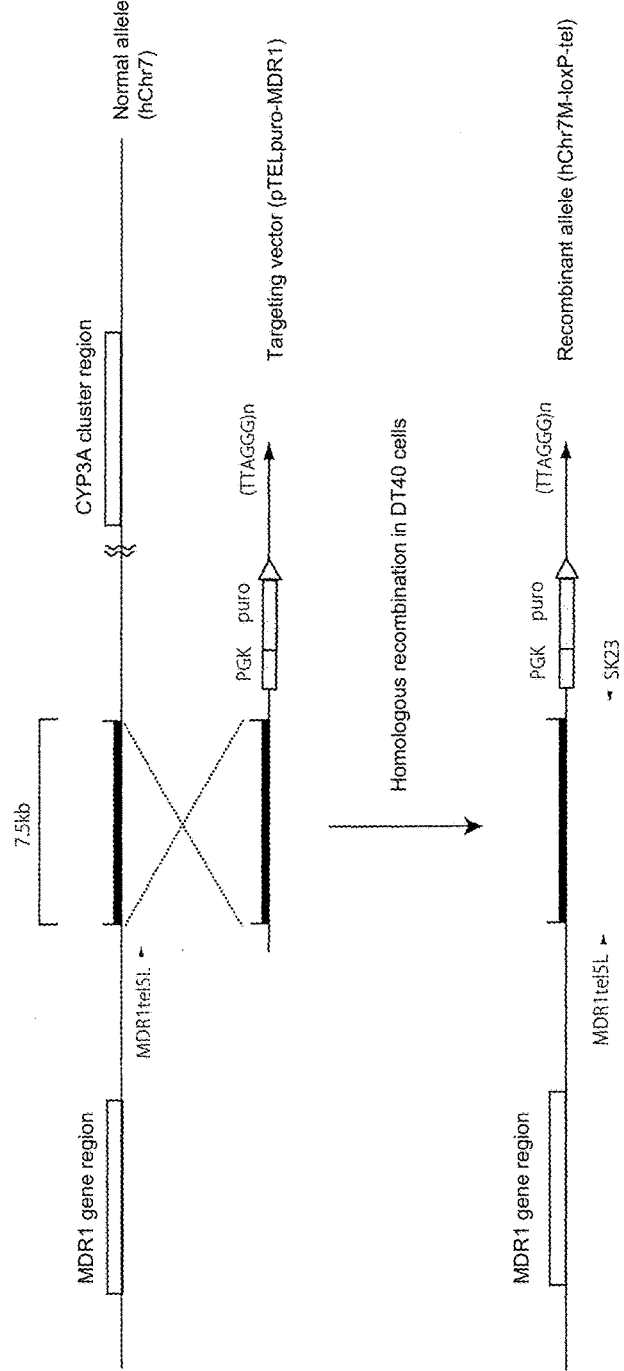
FIG. 96 shows a targeting vector (pTELpuro-MDR1) for inserting a human telomere sequence into the AC003083 region, which is located extremely close to MDR1 gene locus of human chromosome 7 and on the telomere side (i.e., locating on the telomere side by approximately 50 Kb from MDR1 gene locus), and a partial structure of the human chromosome 7 allele in which homologous recombination was carried out by using the vector.

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 8 min were carried out. PCR product was treated with proteinase K (Gibco) and subjected to gel filtration by using CHROMASPIN-TE400 (Clontech). After that, the product was cleaved with the restriction enzymes EcoRI (NIPPON GENE CO., LTD.) and PstI (NIPPON GENE CO., LTD.) and subjected to gel filtration by using CHROMASPIN-TE1000 (Clontech). The PCR fragment was cloned into the EcoRI and PstI sites of plasmid pTELpuro (Kuroiwa et al., Nature Biotech., 20: 88, 2002). Since the genome sequence of AC003083 is in the direction of centromere→telomere, the resultant in which cloned AC003083 genome fragment is in the same direction as the human telomere sequence was taken as desired targeting vector pTELpuro-MDR1. Size of the final construct for long-arm proximal region specific restriction was 13.1 kb. The targeting vector, target sequence, and chromosome allele obtained by homologous recombination are shown (FIG. 96).

[B. 2] Transfection and Isolation of Drug Resistant Clone

As described above, the targeting vector pTELpuro-MDR1 prepared above was linearized with the restriction enzyme EcoRI (NIPPON GENE CO., LTD.), and used for transfection of the clone DT40 (hChr7M-loxP) 8, 9 prepared above. After exchanging the culture medium for culture medium containing puromycin (0.3 μg/ml), the cells were dispensed into ten 96-well culture plates and then subjected to selection culture for about 2 weeks. Total 96 resistant colonies obtained by four transfections were isolated, amplified, and subjected to the following analysis (clone name: DT40 (hChr7M-loxP-tel)).

[B. 3] Selection of Homologous Recombinant
[B. 3. 1] PCR Analysis

In order to select a recombinant by using as a template the genomic DNA of puromycin resistant cell line, as a primary screening, PCR was carried out by using the following primers that are located closer to the telomere side than the restriction sites, and occurrence of site specific cleavage was examined. The primer sequences are given below.

CYP3A4 R (described above)
CYP3A4 F (described above)
CYP3A5 R (described above)
CYP3A5 F (described above)
CYP3A7 R (described above)
CYP3A7 F (described above)

For PCR, GeneAmp 9600 manufactured by PerkinElmer, Inc. was used as a thermal cycler and Ampli Taq Gold (Applied Biosystems) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 95° C. for 10 min, 30 cycles of 95° C. for 20 sec, 55° C. for 30 sec, and 72° C. for 30 sec were carried out.

Next, for three clones that are not detected with the above primers, it was confirmed, by PCR using the following primers, whether or not site specific homologous recombination has occurred. Sequences are as follows.

```
MDR1tel5L;
                                         (SEQ ID NO: 190)
5'- ATCTGCAGGGAAGGGATCCAGTTTCAGCTTCCTAC-3'
```

SK23 (described above)

```
                                         (SEQ ID NO: 191)
MDR1-1L:  5'- ctcctaggagtactcacttc-3'
```

-continued

```
                                     (SEQ ID NO: 192)
MDR1-1R:   5'-aacagaaacatggcttggcg-3'

(SEQ ID NO: 193)
MDR1-2L:   5'-cgccaagccatgtttctgttt-3'

(SEQ ID NO: 194)
MDR1-2R:   5'-aaggaaatgctttctgccttg-3'

(SEQ ID NO: 195)
MDR1-3L:   5'-gtgcaacggaagccagaaca-3'

(SEQ ID NO: 196)
MDR1-3R:   5'-agcggcctctgcttctttga-3'

(SEQ ID NO: 197)
MDR1-4L:   5'-ctgattggctgggcaggaac-3'

(SEQ ID NO: 198)
MDR1-4R:   5'-cttggaacggccaccaagac-3'

(SEQ ID NO: 199)
MDR1-5L:   5'-ggtgctggttgctgcttaca-3'

(SEQ ID NO: 200)
MDR1-5R:   5'-cccaacatcgtgcacatcaa-3'

(SEQ ID NO: 201)
MDR1-6L:   5'-gtcagtgttgatggacagga-3'

(SEQ ID NO: 202)
MDR1-6R:   5'-gcattggcttccttgacagc-3'

(SEQ ID NO: 203)
MDR1-7L:   5'-ggttccaggcttgctgtaat-3'

(SEQ ID NO: 204)
MDR1-7R:   5'-tctttcagtgcttgtccaga-3'

(SEQ ID NO: 205)
MDR1-8L:   5'-ggcaaagaaataaagcgactg-3'

(SEQ ID NO: 206)
MDR1-8R:   5'-cctcctttgctgccctcaca-3'

(SEQ ID NO: 207)
MDR1-9L:   5'-tcttgtccaaactgcctgtga-3'

(SEQ ID NO: 208)
MDR1-9R:   5'-tgcaagaatcagcaggatcaa-3'
```

For PCR, LA Taq (TAKARA SHUZO CO., LTD.) was used with the above primers. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 35 cycles of 98° C. for 20 sec and 68° C. for 8 min were carried out. Only in three clones having site specific recombination, a band at approximately 8 kb was detected. In DT40 and DT40 (hChr7M-loxP) 8, 9 as negative controls, no band was detected.

[B. 3. 2] Two-Color FISH Analysis

Figure 97:
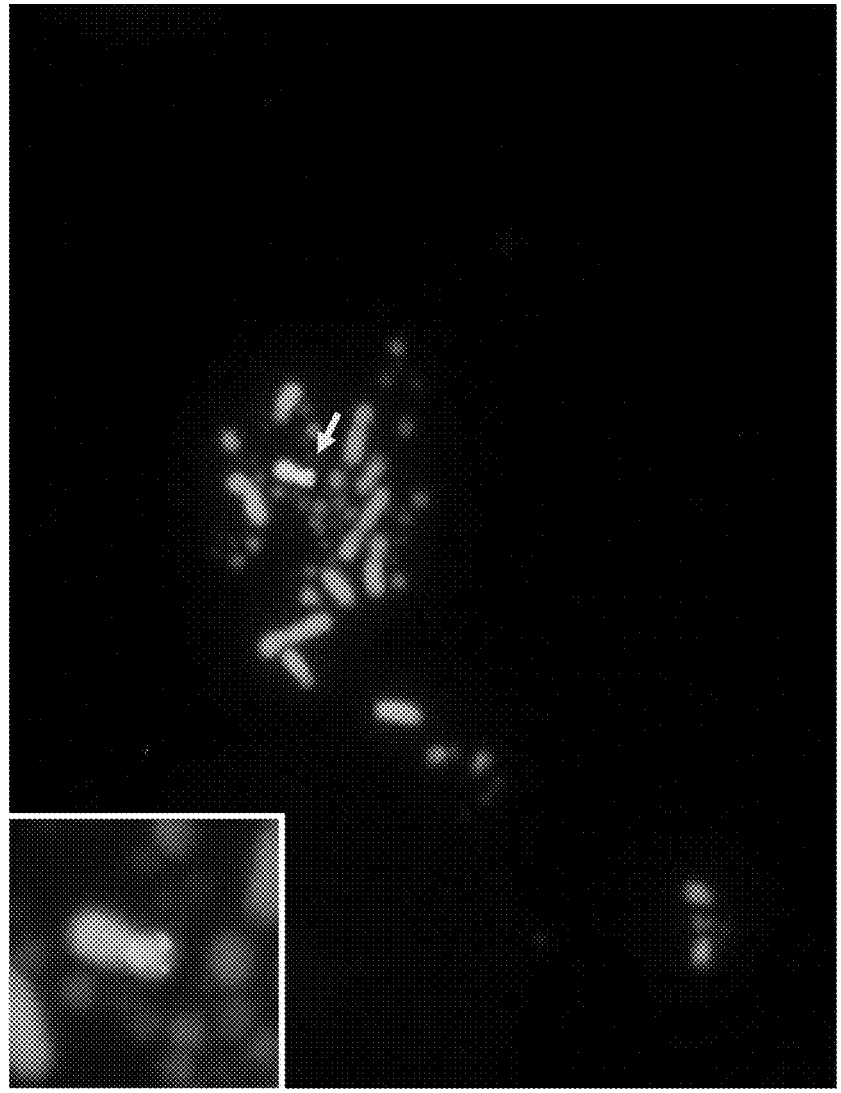
FIG. 97 shows the results of the two-color FISH analysis of DT40 (hChr7M-loxP-tel) in which human cot-1 DNA and puromycin DNA were used as probes.

FISH analysis was carried out according to Matsubara et al. (FISH test protocol, Shujunsha Co., Ltd., 1994). With the three clones which have been confirmed to have recombination in the above, FISH analysis was carried out by using human cot-1 DNA and puromycin DNA as probes. As a result, it was found that human chromosome 7 was not translocated to the host chromosome in any clone, and based on the fact that puromycin-derived signal was detected at terminal of human chromosome 7 fragment and restrictions occurred at desired sites, it was confirmed that recombination has site-specifically occurred (FIG. 97).

From these results, it was concluded that, in clone DT40 (hChr7M-loxP-tel) 10, 12, and 70, cleavage could be made at distal region from AC003083 which was closer to the telomere side than MDR1 gene region.

[C] Transfer of hChr7M-loxP-Tel from DT40 Containing hChr7M-loxP-Tel to CHO Cell Containing MAC4

For translocation insertion of human MDR1 gene region into the mouse artificial chromosome vector MAC4 via loxP sequence in CHO cells, hChr7M-loxP-tel is introduced into CHO cells containing the mouse artificial chromosome vector MAC4.

[C. 1] Microcell Fusion and Isolation of Drug Resistant Clone

By using DT40 (hChr7M-loxP-tel) 10 and 70 as recipient cells, microcell fusion was carried out for CHO (HPRT$^-$; MAC4), which is a CHO hprt depleted cell containing MAC4 (obtained from the Health Science Research Resources Bank, registration number: JCRB0218), in the same manner as above. Total 15 resistant colonies obtained by four microcell fusions were isolated, amplified, and subjected to the following analysis (clone name: CHO (HPRT$^-$; MAC4, hChr7M-loxP-tel)).

[C. 2] Selection of Drug Resistant Clone

[C. 2. 1] PCR Analysis

For extracting genomic DNA from blasticidin S resistant cell line and using it as a template for selecting a recombinant, PCR was carried out by using the following primers and it was confirmed whether or not human chromosome 7 fragment was introduced into CHO cells containing MAC4. The primer sequences are given below.

m11 4L: (described above)
V907-NotI-R: (described above)
hygF (244): (described above)
m11 6R (described above)
MDR1loxP2L (described above)

```
                                     (SEQ ID NO: 209)
BsdR:         5'-gctcaagatgcccctgttct-3'

(SEQ ID NO: 210)
hprt332F:     5'-aaagatggtcaaggtcgcaa-3'
```

MDR1loxP 1R (described above)
MDR1te15L (described above)
SK23 (described above)
MDR1-1L (described above)
MDR1-1R (described above)
MDR1-2L (described above)
MDR1-2R (described above)
MDR1-3L (described above)
MDR1-3R (described above)
MDR1-4L (described above)
MDR1-4R (described above)
MDR1-5L (described above)
MDR1-5R (described above)
MDR1-6L (described above)
MDR1-6R (described above)
MDR1-7L (described above)
MDR1-7R (described above)
MDR1-8L (described above)
MDR1-8R (described above)
MDR1-9L (described above)
MDR1-9R (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, six clones out of the 15 clones were found to be positive for all primer sets, and the following analysis was performed by using those 6 clones.

[C. 2. 2] Two-Color FISH Analysis

Figure 98:
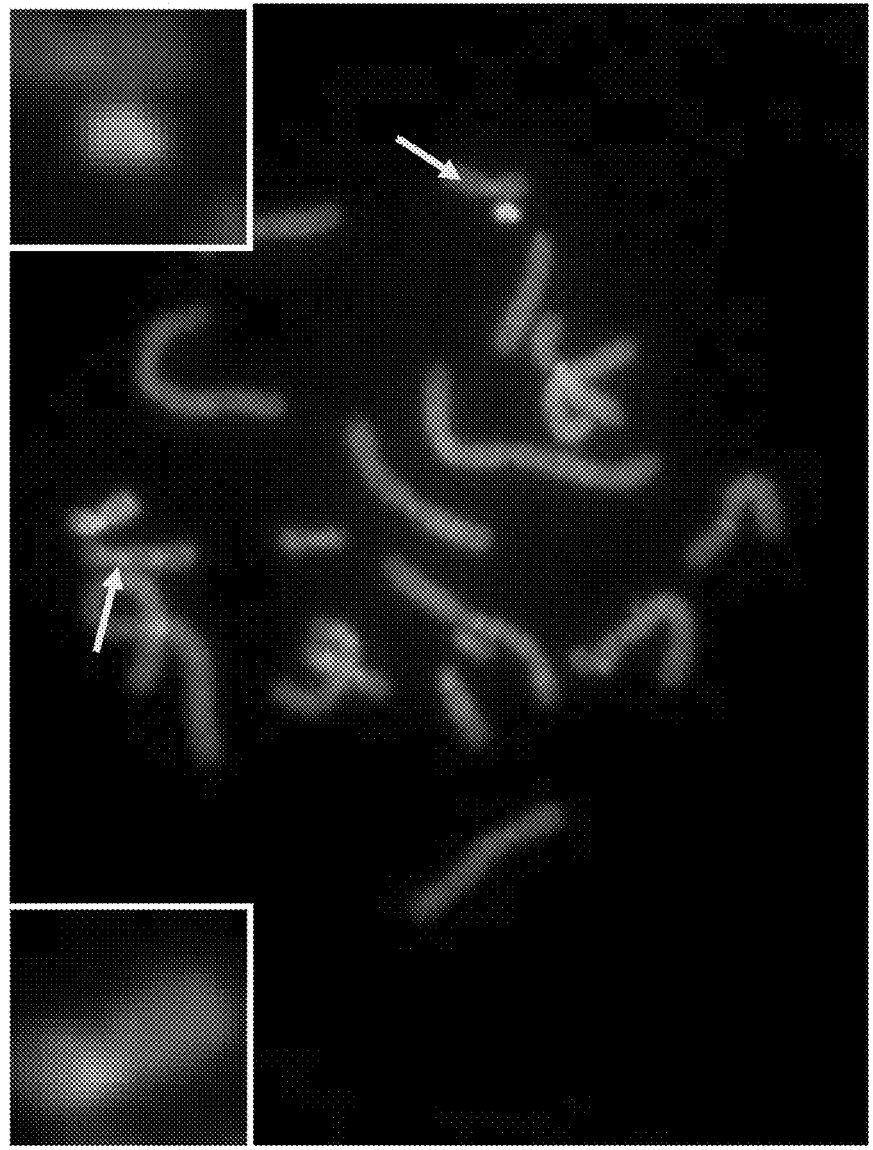
FIG. 98 shows the results of the two-color FISH analysis of CHO (HPRT$^-$; MAC4, hChr7M-loxP-tel) clone in which mouse Cot-1 DNA and human Cot-1 DNA were used as probes.

With the six clones of CHO (HPRT⁻; MAC4, hChr7M-loxP-tel) obtained from the above, FISH analysis was carried out by using mouse Cot-1 DNA and human Cot-1 DNA as probes according to the method described by Shinohara et al. (Human Molecular Genetics, 10: 1163-1175, 2001). As a result, it was confirmed that one or two copies of MAC1 and hChr7M-loxP-tel were introduced into CHO cells at a rate of 80% or more in two clones (FIG. 98).

From these results, it was concluded that hChr7M-loxP-tel could be introduced into CHO cells containing the mouse artificial chromosome vector MAC4.

Figure 99:
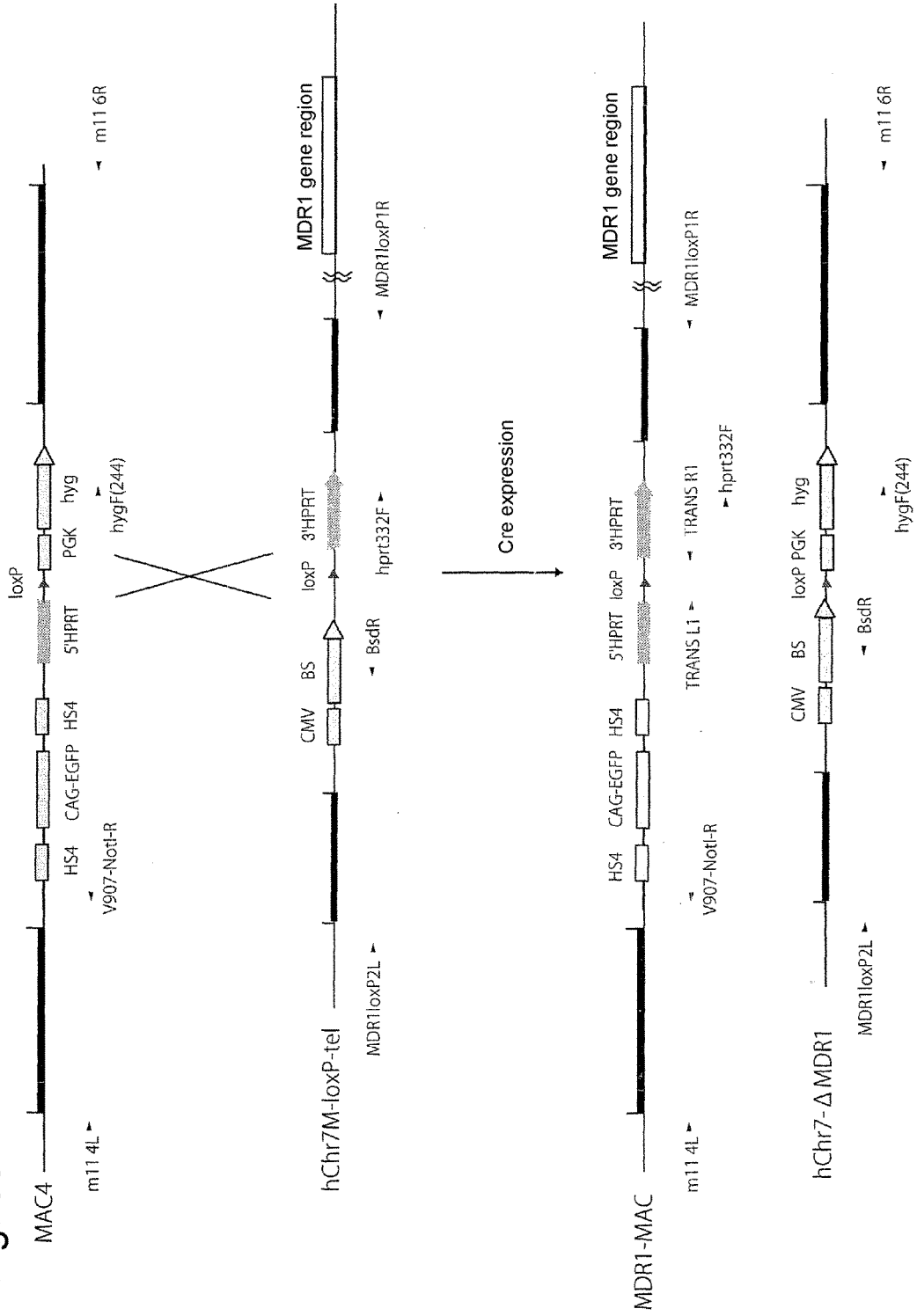
FIG. 99 shows the construction of mouse artificial chromosome MDR1-MAC in which 210 kb human MDR1 gene region (i.e., AC005045-human MDR1 gene-AC003083) was translocation-cloned into MAC4 vector.

[D] Site Specific Translocation of 210 kb Human MDR1 Gene Region (i.e., AC005045-Human MDR1 Gene-AC003083) to MAC4 Vector in CHO (HPRT⁻; MAC4, hChr7M-loxP-Tel) Clone To stably keep the human MDR1 gene, which is a 210 kb DNA, in a mouse individual, translocation insertion into the mouse artificial chromosome vector MAC4 is performed (FIG. 99).

[D. 1] Transfection and Isolation of HAT Resistant Clone

Gene introduction was carried out by lipofection for CHO (HPRT⁻; MAC4, hChr7M-loxP-tel) 7 and 15 obtained from the above. To cells in 6 wells with 90% confluency, 3 µg of Cre was introduced according to the commercially available protocol (Invitrogen). After culture for 2 weeks under HAT selection culture, a resistant colony was generated and total ten colonies obtained by two introductions were isolated, amplified, and subjected to the following analysis (clone name: CHO (MDR1-MAC, hChr7-ΔMDR1)).

[D. 2] Selection of Drug Resistant Clone

[D. 2. 1] PCR Analysis

For extracting genomic DNA from HAT resistant cell line and using it as a template for selecting a clone with reciprocal translocation, PCR was carried out by using the following primers and it was confirmed whether or not reciprocal chromosomal translocation has occurred on human chromosome 7 fragment and MAC4. The primer sequences are given below.

m11 4L: (described above)
V907-NotI-R: (described above)
hygF (244): (described above)
m11 6R (described above)
MDR1loxP2L (described above)

```
                                        (SEQ ID NO: 211)
    BsdR:        5'-gctcaagatgcccctgttct-3'

(SEQ ID NO: 212)
    hprt332F:    5'-aaagatggtcaaggtcgcaa-3'
```

MDR1loxP1R (described above)
MDR1te15L (described above)
SK23 (described above)
MDR1-1L (described above)
MDR1-1R (described above)
MDR1-2L (described above)
MDR1-2R (described above)
MDR1-3L (described above)
MDR1-3R (described above)
MDR1-4L (described above)
MDR1-4R (described above)
MDR1-5L (described above)
MDR1-5R (described above)
MDR1-6L (described above)
MDR1-6R (described above)
MDR1-7L (described above)
MDR1-7R (described above)
MDR1-8L (described above)
MDR1-8R (described above)
MDR1-9L (described above)
MDR1-9R (described above)
TRANS L1 (described above)
TRANS R1 (described above)

For PCR, GeneAmp 9600 manufactured by PerkinElmer, Inc. was used as a thermal cycler and LA Taq (TAKARA) was used as Taq polymerase. Buffers and dNTPs (dATP, dCTP, dGTP, dTTP) used were those included in the product and they were used under the conditions described by manufacturer's instruction. Temperature and cycle conditions were as follows: after heat denaturation at 94° C. for 1 min, 30 cycles of 98° C. for 10 sec and 68° C. for 7 min were carried out. As a result of PCR, six clones out of ten clones were found to be positive for all primer sets, and the following analysis was performed by using those six clones.

[D. 2. 2] Two-Color FISH Analysis

Figure 100:
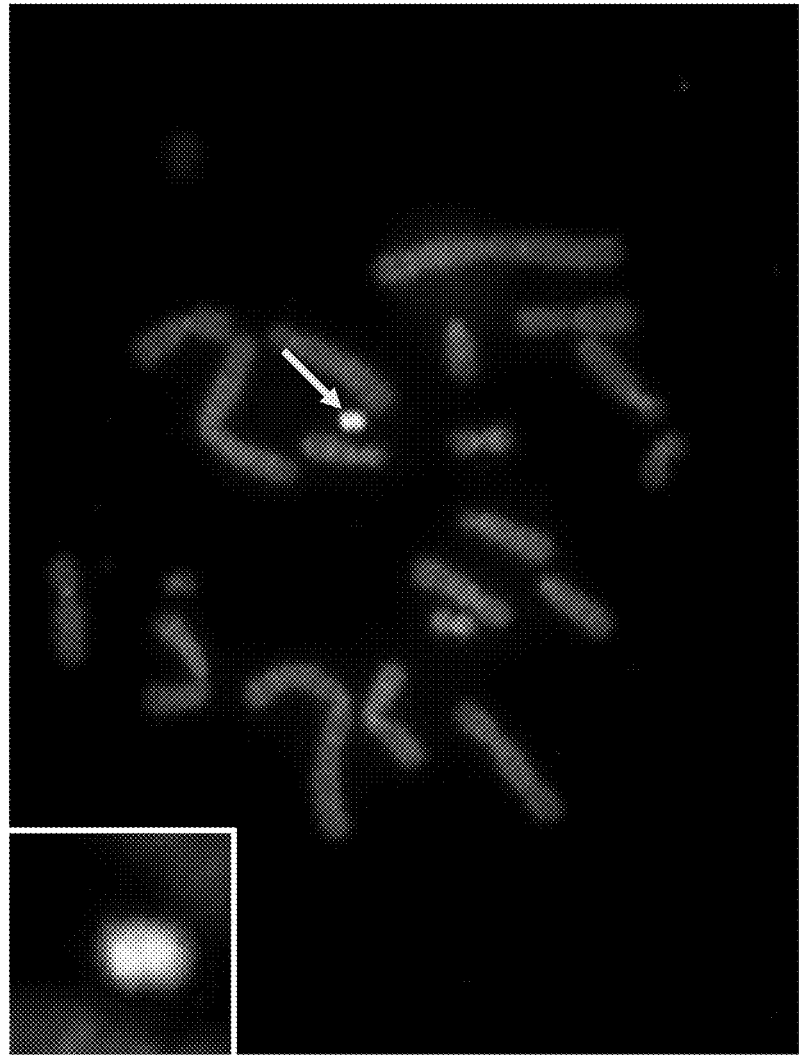
FIG. 100 shows the results of the two-color FISH analysis of CHO (MDR1-MAC, hChr7-ΔMDR1) clone in which MDR1-BAC (RP11-784L5) (CHORI) DNA and mouse Cot-1 DNA were used as probes.

With the six clones of CHO (MDR1-MAC, hChr7-ΔMDR1) obtained from the above, FISH analysis was carried out by using MDR1-BAC (RP11-784L5) (CHORI) DNA and mouse Cot-1 DNA as probes according to the method described by Shinohara et al. (Human Molecular Genetics, 10: 1163-1175, 2001). As a result, it was confirmed that the signal derived from human MDR1 was observed on MAC4 at a rate of 60% or more in three clones out of the six clones (FIG. 100).

From these results, it was concluded that 210 kb of MDR1 gene of human chromosome 7 fragment could be cloned into the mouse artificial chromosome vector MAC4 by reciprocal translocation.

[E] Transfer of MDR1-MAC from CHO Cells to Mouse A9 Cells

To prepare mouse ES cells retaining MDR1-MAC, transfer was carried out from CHO cells retaining MDR1-MAC obtained from the above [D] (CHO (MDR1-MAC, hChr7-ΔMDR1) 1, 2, 4) to, as mouse A9 cells, mouse A9 cells having high microcell forming ability by microcell fusion. Total seven resistant colonies obtained by four microcell fusions were isolated, amplified, and subjected to the following analysis (clone name: A9 (MDR1-MAC)). As a result, there were five clones which are positive in PCR using the primers described before for detecting the MDR1-MAC region only. In addition, FISH analysis (Tomizuka et al., Nature Genet. 16: 133, 1997) was carried out by using MDR1-BAC (RP11-784L5) (CHORI) and mouse minor satellite DNA as probes. As a result, the presence of MDR1-MAC region, which is specifically detected with the probes, was confirmed in three clones out of the five clones. From these results, it was concluded that three clones of A9 cells retaining MDR1-MAC were obtained.

[F] As described in Example 8, in vitro stability can be examined by preparing mouse ES cells retaining the mouse artificial chromosome vector MDR1-MAC. Further, by preparing a chimeric mouse using the ES cells, the mouse line-based TC (MDR1-MAC) in which MDR1-MAC is transferred to a progeny can be prepared. Further, by using the TC (MDR1-MAC) mouse line, stability of MDR1-MAC in somatic cells can be examined. Further, TC (MDR1-MAC) mouse line allows reproduction of drug transport in human or the like. Still further, since TC (CYP3A-MAC/

MDR1-MAC) line can be prepared by crossbreeding with the TC (CYP3A-MAC) mouse line, it may be used as a model mouse for in vivo test that is used for testing a pharmacological effect and toxicity for development of a pharmaceutical product.

INDUSTRIAL APPLICABILITY

The mouse artificial chromosome vector of the invention has the same usefulness as the human artificial chromosome described in WO 2009/063722. Further, having enhanced retention rate in rodent cells or individuals, it can be stably retained in rodent cells to retain stably the target gene (group) for a long period of time. Still further, as there is no deviation in amount of introduced gene among individuals or tissues of rodents like a mouse, more accurate analysis of introduced gene can be achieved among individuals or tissues. The mouse artificial chromosome vector of the invention can be used for various purposes and uses like introduction of an exogenous gene to a recipient cell, establishment of iPS cells or use for regenerative medicine, preparation of cells for expressing exogenous genes or useful non-human animals, protein production, and analysis of gene function.

Accession Number of Deposit:
Accession number of DT40 B6bT-1: FERM BP-11128
Free Text of Sequence Listings
SEQ ID NO: 1 to 212: Primer All publications, patents, and patent applications cited herein are incorporated herein by reference in their entirety.

The invention claimed is:

1. A non-human animal comprising a mouse artificial chromosome vector, wherein the mouse artificial chromosome vector comprises: a natural centromere derived from a mouse chromosome 11; a mouse-chromosome-derived long-arm fragment formed by deleting at least about 99% of all endogenous genes from the long arm of the mouse chromosome 11; and a telomere sequence so as to form the mouse artificial chromosome vector contained in the deposited cell line DT40 B6bT-1 (FERM BP-11128) wherein the vector is stably retained in cells and tissues of the non-human animal at a retention rate of about 90% or more, and wherein the non-human animal is a rodent selected from the group consisting of a mouse and a rat.

2. The non-human animal according to claim 1, wherein the mouse-chromosome-derived long-arm fragment is formed by deleting at least 99.5% of all endogenous genes from the long arm of the mouse chromosome 11.

3. The non-human animal according to claim 1, further comprising one or more DNA sequence insertion sites.

4. The non-human animal according to claim 3, wherein the DNA sequence insertion site is a recognition site for a site-specific recombinase.

5. The non-human animal according to claim 3, wherein the DNA sequence insertion site is a loxP sequence, an FRT sequence, φC31 attB and φC31 attP sequences, R4 attB and R4 attP sequences, TP901-1 attB and TP901-1 attP sequences, or Bxb1 attB and Bxb1 attP sequences.

6. The non-human animal according to claim 1, further comprising a reporter gene, a selection marker gene, or both.

7. The non-human animal according to claim 1, further comprising an exogenous DNA sequence.

8. The non-human animal according to claim 1, wherein the exogenous DNA sequence has a size of 200 kb or more.

9. The non-human animal according to claim 7, wherein the exogenous DNA sequence is a human DNA sequence.

10. The non-human animal according to claim 7, wherein the exogenous DNA sequence is a DNA sequence of a drug-metabolism-related gene.

11. The non-human animal according to claim 10, wherein the drug-metabolism-related gene is a gene encoding an enzyme involved in a phase I reaction or a phase II reaction.

12. The non-human animal according to claim 11, wherein the enzyme gene involved in a phase I reaction encodes at least one enzyme selected from the group consisting of CYPs of CYP1A, CYP1B, CYP2A, CYP2B, CYP2C, CYP2D, CYP2E, CYP2J, CYP3A, CYP4A, CYP4B and subfamilies thereof, and CESs.

13. The non-human animal according to claim 11, wherein the enzyme gene involved in the phase II reaction encodes at least one enzyme selected from the group consisting of UGT1 and UGT2.

14. The non-human animal according to claim 10, wherein the drug-metabolism-related gene is a gene encoding a transporter.

15. The non-human animal according to claim 14, wherein the gene encoding the transporter is at least one gene selected from the group consisting of MDR1, MDR2, MRP2, OAT, OATP, OCT, and BCRP.

16. The non-human animal according to claim 10, wherein the drug-metabolism-related gene is a gene encoding a nuclear receptor.

17. The non-human animal according to claim 16, wherein the gene encoding the nuclear receptor is at least one gene selected from the group consisting of PXR, AhR, CAR, and PPARα.

18. The non-human animal according to claim 7, wherein the exogenous DNA sequence is a DNA sequence of a human-chromosome-derived long arm or short arm.

19. The non-human animal according to claim 7, wherein the exogenous DNA sequence comprises at least two genes selected from the group consisting of genes encoding an enzyme involved in a phase I reaction, genes encoding an enzyme involved in a phase II reaction, genes encoding a transporter, and genes encoding a nuclear receptor.

20. The non-human animal according to claim 18, wherein the DNA sequence of the human-chromosome-derived long arm or short arm comprises a human chromosome region responsible for a disease gene.

21. The non-human animal according to claim 7, wherein the exogenous DNA sequence is a gene or DNA sequence encoding a polypeptide selected from the group consisting of cytokines, hormones, growth factors, nutritional factors, hematopoietic factors, coagulation or hemolysis factors, immunoglobulins, G protein-coupled receptors, or enzymes, or a gene or DNA sequence used for treatment involved in a disease.

22. The non-human animal according to claim 1, wherein the cell is a hepatocyte, enterocyte, renal cell, splenocyte, lung cell, cardiac cell, skeletal muscle cell, brain cell, bone marrow cell, lymphocyte, megakaryocyte, sperm, or ovum.

23. The non-human animal according to claim 1, wherein the tissue is from a liver, intestine, kidney, spleen, lung, heart, skeletal muscle, brain, bone marrow, testis, or ovary.

24. The non-human animal according to claim 21, wherein the disease is muscular dystrophy, hemophilia, neurodegenerative disease, autoimmune disease, allergic disease, or genetic disease.

* * * * *

```
                        SEQUENCE LISTING

<160> NUMBER OF SEQ ID NOS: 212

<210> SEQ ID NO 1
    <211> LENGTH: 19
    <212> TYPE: DNA
    <213> ORGANISM: Artificial
    <220> FEATURE:
    <223> OTHER INFORMATION: primer

<400> SEQUENCE: 1
catgtgggag cggcaattc                                                   19

<210> SEQ ID NO 2
    <211> LENGTH: 25
    <212> TYPE: DNA
    <213> ORGANISM: Artificial
    <220> FEATURE:
    <223> OTHER INFORMATION: primer

<400> SEQUENCE: 2
ttgagtggaa tgagttcttc aatcg                                            25

<210> SEQ ID NO 3
    <211> LENGTH: 37
    <212> TYPE: DNA
    <213> ORGANISM: Artificial
    <220> FEATURE:
    <223> OTHER INFORMATION: primer

<400> SEQUENCE: 3
cgaggatccc acattggtag tcttttcact gccatca                               37

<210> SEQ ID NO 4
    <211> LENGTH: 37
    <212> TYPE: DNA
    <213> ORGANISM: Artificial
    <220> FEATURE:
    <223> OTHER INFORMATION: primer

<400> SEQUENCE: 4
cgaggatccc cacttaactt ttccaggctt acggaga                               37

<210> SEQ ID NO 5
    <211> LENGTH: 28
    <212> TYPE: DNA
    <213> ORGANISM: Artificial
    <220> FEATURE:
    <223> OTHER INFORMATION: primer

<400> SEQUENCE: 5
```
tgacagagag cttcctcctg cctctgta                                               28

<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
ctaaagaccc tcatgctcct gtgtggaa                                               28

<210> SEQ ID NO 7
<211> LENGTH: 27
<212> TYPE: DNA
<213> ORGANISM: Artificial
<220> FEATURE:
<223> OTHER INFORMATION: primer

<400> SEQUENCE: 7
gttcaacctg agctccacat catgctc                                                27

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
cactctttac ccctcaccgc taaccttg                                               28

<210> SEQ ID NO 9
<211> LENGTH: 26
<212> TYPE: DNA
<213> ORGANISM: Artificial
<220> FEATURE:
<223> OTHER INFORMATION: primer

<400> SEQUENCE: 9
catcgccttc tatcgccttc ttgacg                                                 26

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
cctgaagttc atctgcacca                                                        20

<210> SEQ ID NO 11
<211> LENGTH: 28
<212> TYPE: DNA
<213> ORGANISM: Artificial
<220> FEATURE:
<223> OTHER INFORMATION: primer

<400> SEQUENCE: 11
ggcctagagc ctggactcat tcattcaa                                               28

<210> SEQ ID NO 12
<211> LENGTH: 28
<212> TYPE: DNA

<210> SEQ ID NO 12
<211> LENGTH: 28
<212> TYPE: DNA
<213> ORGANISM: Artificial
<220> FEATURE:
<223> OTHER INFORMATION: primer

<400> SEQUENCE: 12
gacagatgtc atgccccagg taggtatg            28

<210> SEQ ID NO 13
<211> LENGTH: 28
<212> TYPE: DNA
<213> ORGANISM: Artificial
<220> FEATURE:
<223> OTHER INFORMATION: primer

<400> SEQUENCE: 13
agttcttttg agggcctaga gcctggac            28

<210> SEQ ID NO 14
<211> LENGTH: 28
<212> TYPE: DNA
<213> ORGANISM: Artificial
<220> FEATURE:
<223> OTHER INFORMATION: primer

<400> SEQUENCE: 14
aaaggacaga aggagggagc aacaggat            28

<210> SEQ ID NO 15
<211> LENGTH: 28
<212> TYPE: DNA
<213> ORGANISM: Artificial
<220> FEATURE:
<223> OTHER INFORMATION: primer

<400> SEQUENCE: 15
tctgggcatc agtgtcctct ccagtaaa            28

<210> SEQ ID NO 16
<211> LENGTH: 28
<212> TYPE: DNA
<213> ORGANISM: Artificial
<220> FEATURE:
<223> OTHER INFORMATION: primer

<400> SEQUENCE: 16
ttggcgacat ccaatgctag tgctattc            28

<210> SEQ ID NO 17
<211> LENGTH: 28
<212> TYPE: DNA
<213> ORGANISM: Artificial
<220> FEATURE:
<223> OTHER INFORMATION: primer

<400> SEQUENCE: 17
tggagacgtt gtttagcctc tcctcctc            28

<210> SEQ ID NO 18
<211> LENGTH: 28
<212> TYPE: DNA
<213> ORGANISM: Artificial
<220> FEATURE:
<223> OTHER INFORMATION: primer

<400> SEQUENCE: 18
cacagcttag aggccattcc catagtcc            28

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19
tgcggtgaag gtccaaggag atagattt                                    28

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
tctagcagag agatggtggc aggattca                                    28

<210> SEQ ID NO 21
<211> LENGTH: 23
<212> TYPE: DNA
<213> ORGANISM: Artificial
<220> FEATURE:
<223> OTHER INFORMATION: primer

<400> SEQUENCE: 21
tgagggtact tgaagggctg atg                                         23

<210> SEQ ID NO 22
<211> LENGTH: 23
<212> TYPE: DNA
<213> ORGANISM: Artificial
<220> FEATURE:
<223> OTHER INFORMATION: primer

<400> SEQUENCE: 22
caggggctgc tcccctttta tta                                         23

<210> SEQ ID NO 23
<211> LENGTH: 22
<212> TYPE: DNA
<213> ORGANISM: Artificial
<220> FEATURE:
<223> OTHER INFORMATION: primer

<400> SEQUENCE: 23
cctaacatcg tgtcccagct ca                                          22

<210> SEQ ID NO 24
<211> LENGTH: 24
<212> TYPE: DNA
<213> ORGANISM: Artificial
<220> FEATURE:
<223> OTHER INFORMATION: primer

<400> SEQUENCE: 24
tcctttcaga ccccttcatc ttag                                        24

<210> SEQ ID NO 25
<211> LENGTH: 23
<212> TYPE: DNA
<213> ORGANISM: Artificial
<220> FEATURE:

<223> OTHER INFORMATION: primer

<400> SEQUENCE: 25
ttcagcccca accaaagaca cta                                    23

<210> SEQ ID NO 26
<211> LENGTH: 24
<212> TYPE: DNA
<213> ORGANISM: Artificial
<220> FEATURE:
<223> OTHER INFORMATION: primer

<400> SEQUENCE: 26
gccccgaacc cctacaaata taga                                   24

<210> SEQ ID NO 27
<211> LENGTH: 23
<212> TYPE: DNA
<213> ORGANISM: Artificial
<220> FEATURE:
<223> OTHER INFORMATION: primer

<400> SEQUENCE: 27
gggcctccaa taagtgtccc ata                                    23

<210> SEQ ID NO 28
<211> LENGTH: 23
<212> TYPE: DNA
<213> ORGANISM: Artificial
<220> FEATURE:
<223> OTHER INFORMATION: primer

<400> SEQUENCE: 28
ttgctgactt agttgcagca gga                                    23

<210> SEQ ID NO 29
<211> LENGTH: 23
<212> TYPE: DNA
<213> ORGANISM: Artificial
<220> FEATURE:
<223> OTHER INFORMATION: primer

<400> SEQUENCE: 29
cccattggca agatacatgg aga                                    23

<210> SEQ ID NO 30
<211> LENGTH: 23
<212> TYPE: DNA
<213> ORGANISM: Artificial
<220> FEATURE:
<223> OTHER INFORMATION: primer

<400> SEQUENCE: 30
agtgtggatg ctcctggatg aag                                    23

<210> SEQ ID NO 31
<211> LENGTH: 27
<212> TYPE: DNA
<213> ORGANISM: Artificial
<220> FEATURE:
<223> OTHER INFORMATION: primer

<400> SEQUENCE: 31
gtaaacgccc tcaaggagca agcatga                                27

<210> SEQ ID NO 32
<211> LENGTH: 27
<212> TYPE: DNA
<213> ORGANISM: Artificial
<220> FEATURE:
<223> OTHER INFORMATION: primer

<400> SEQUENCE: 32
tgtgaccaaa gatttagcgc agtgcgt                                   27

<210> SEQ ID NO 33
<211> LENGTH: 27
<212> TYPE: DNA
<213> ORGANISM: Artificial
<220> FEATURE:
<223> OTHER INFORMATION: primer

<400> SEQUENCE: 33
cccaggaatc agtcaggaag gctgtaa                                   27

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
gaattcagcg agagcctgac                                           20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
gatgttggcg acctcgtatt                                           20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
ggctgcatca gcatcatcta                                           20

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
gcaagactgt gagccagtga                                           20

<210> SEQ ID NO 38
<211> LENGTH: 22
<212> TYPE: DNA
<213> ORGANISM: Artificial
<220> FEATURE:
<223> OTHER INFORMATION: primer

<400> SEQUENCE: 38
tcagctgtgt gctgttgttt gc                                              22

<210> SEQ ID NO 39
<211> LENGTH: 22
<212> TYPE: DNA
<213> ORGANISM: Artificial
<220> FEATURE:
<223> OTHER INFORMATION: primer

<400> SEQUENCE: 39
atagaagggt ctgtctggct gg                                              22

<210> SEQ ID NO 40
<211> LENGTH: 22
<212> TYPE: DNA
<213> ORGANISM: Artificial
<220> FEATURE:
<223> OTHER INFORMATION: primer

<400> SEQUENCE: 40
gagttaatgg tgctaactgg gg                                              22

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
accctgaaat gaagacgggc                                                 20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
tccccctgaa attaagctta                                                 20

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
tgaggtctct ggtgttctca                                                 20

<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
tccccctgaa attacgcttt                                                 20

<210> SEQ ID NO 45
<211> LENGTH: 20

```
<212> TYPE: DNA
<213> ORGANISM: Artificial
<220> FEATURE:
<223> OTHER INFORMATION: primer

<400> SEQUENCE: 45
catttcaggg ttctatttgt                                              20

<210> SEQ ID NO 46
<211> LENGTH: 28
<212> TYPE: DNA
<213> ORGANISM: Artificial
<220> FEATURE:
<223> OTHER INFORMATION: primer

<400> SEQUENCE: 46
gtattggtca ccacggccga gtttccgc                                     28

<210> SEQ ID NO 47
<211> LENGTH: 22
<212> TYPE: DNA
<213> ORGANISM: Artificial
<220> FEATURE:
<223> OTHER INFORMATION: primer

<400> SEQUENCE: 47
tggaggccat aaacaagaag ac                                           22

<210> SEQ ID NO 48
<211> LENGTH: 21
<212> TYPE: DNA
<213> ORGANISM: Artificial
<220> FEATURE:
<223> OTHER INFORMATION: primer

<400> SEQUENCE: 48 cccctttgacc cagaaattcc a                                           21

<210> SEQ ID NO 49
<211> LENGTH: 28
<212> TYPE: DNA
<213> ORGANISM: Artificial
<220> FEATURE:
<223> OTHER INFORMATION: primer

<400> SEQUENCE: 49
actcctaagg gagttggtgc tgttggtg                                     28

<210> SEQ ID NO 50
<211> LENGTH: 24
<212> TYPE: DNA
<213> ORGANISM: Artificial
<220> FEATURE:
<223> OTHER INFORMATION: primer

<400> SEQUENCE: 50
gagctgcaag aactcttcct cacg                                         24

<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
```
gtatggaaaa gtgtggggct                                           20

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
atacttcaag aattgggatg                                           20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
ccaagctatg ctcttcaccg                                           20

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
tgaagaagtc ctcctaagct                                           20

<210> SEQ ID NO 55
<211> LENGTH: 20
<212> TYPE: DNA
<213> ORGANISM: Artificial
<220> FEATURE:
<223> OTHER INFORMATION: primer

<400> SEQUENCE: 55
ctctgtttcc aaaagatacc                                           20

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
tcaacatctt tcttgcaagt                                           20

<210> SEQ ID NO 57
<211> LENGTH: 20
<212> TYPE: DNA
<213> ORGANISM: Artificial
<220> FEATURE:
<223> OTHER INFORMATION: primer

<400> SEQUENCE: 57
agcttttaag atttaatcca                                           20

<210> SEQ ID NO 58
<211> LENGTH: 20
<212> TYPE: DNA
<213> ORGANISM: Artificial

<220> FEATURE:
<223> OTHER INFORMATION: primer

<400> SEQUENCE: 58
gagctttgtg ggtctcagag                                       20

<210> SEQ ID NO 59
<211> LENGTH: 20
<212> TYPE: DNA
<213> ORGANISM: Artificial
<220> FEATURE:
<223> OTHER INFORMATION: primer

<400> SEQUENCE: 59
ctctcagaat tcaaaagact                                       20

<210> SEQ ID NO 60
<211> LENGTH: 20
<212> TYPE: DNA
<213> ORGANISM: Artificial
<220> FEATURE:
<223> OTHER INFORMATION: primer

<400> SEQUENCE: 60
agaagaagtc ctccaaagcg                                       20

<210> SEQ ID NO 61
<211> LENGTH: 20
<212> TYPE: DNA
<213> ORGANISM: Artificial
<220> FEATURE:
<223> OTHER INFORMATION: primer

<400> SEQUENCE: 61
tatgacacaa ctagcaccac                                       20

<210> SEQ ID NO 62
<211> LENGTH: 20
<212> TYPE: DNA
<213> ORGANISM: Artificial
<220> FEATURE:
<223> OTHER INFORMATION: primer

<400> SEQUENCE: 62
agtgtctagt gttctgggat                                       20

<210> SEQ ID NO 63
<211> LENGTH: 20
<212> TYPE: DNA
<213> ORGANISM: Artificial
<220> FEATURE:
<223> OTHER INFORMATION: primer

<400> SEQUENCE: 63
tcaaacgcct ctccttgctg                                       20

<210> SEQ ID NO 64
<211> LENGTH: 20
<212> TYPE: DNA
<213> ORGANISM: Artificial
<220> FEATURE:
<223> OTHER INFORMATION: primer

<400> SEQUENCE: 64
gcttgccttt ctttgccttc                                       20

<210> SEQ ID NO 65
<211> LENGTH: 20
<212> TYPE: DNA
<213> ORGANISM: Artificial
<220> FEATURE:
<223> OTHER INFORMATION: primer

<400> SEQUENCE: 65
ggtaaagtac ttgaggcaga                                           20

<210> SEQ ID NO 66
<211> LENGTH: 20
<212> TYPE: DNA
<213> ORGANISM: Artificial
<220> FEATURE:
<223> OTHER INFORMATION: primer

<400> SEQUENCE: 66
agaaagggct ttatgagaga                                           20

<210> SEQ ID NO 67
<211> LENGTH: 20
<212> TYPE: DNA
<213> ORGANISM: Artificial
<220> FEATURE:
<223> OTHER INFORMATION: primer

<400> SEQUENCE: 67
agaaacatga ggcagggatt                                           20

<210> SEQ ID NO 68
<211> LENGTH: 20
<212> TYPE: DNA
<213> ORGANISM: Artificial
<220> FEATURE:
<223> OTHER INFORMATION: primer

<400> SEQUENCE: 68
acaaggagac atttagtgca                                           20

<210> SEQ ID NO 69
<211> LENGTH: 20
<212> TYPE: DNA
<213> ORGANISM: Artificial
<220> FEATURE:
<223> OTHER INFORMATION: primer

<400> SEQUENCE: 69
taccccagta tttgatgcac                                           20

<210> SEQ ID NO 70
<211> LENGTH: 20
<212> TYPE: DNA
<213> ORGANISM: Artificial
<220> FEATURE:
<223> OTHER INFORMATION: primer

<400> SEQUENCE: 70
agataactga ctgagccaca                                           20

<210> SEQ ID NO 71
<211> LENGTH: 19
<212> TYPE: DNA
<213> ORGANISM: Artificial
<220> FEATURE:
<223> OTHER INFORMATION: primer

<400> SEQUENCE: 71
ccatcttcca ggagcgaga                                                19

<210> SEQ ID NO 72
<211> LENGTH: 20
<212> TYPE: DNA
<213> ORGANISM: Artificial
<220> FEATURE:
<223> OTHER INFORMATION: primer

<400> SEQUENCE: 72
tgtcatacca ggaaatgagc                                               20

<210> SEQ ID NO 73
<211> LENGTH: 28
<212> TYPE: DNA
<213> ORGANISM: Artificial
<220> FEATURE:
<223> OTHER INFORMATION: primer

<400> SEQUENCE: 73
aaatgcatca ccattctccc agttaccc                                      28

<210> SEQ ID NO 74
<211> LENGTH: 22
<212> TYPE: DNA
<213> ORGANISM: Artificial
<220> FEATURE:
<223> OTHER INFORMATION: primer

<400> SEQUENCE: 74
ggagatgagg aagaggagaa ca                                            22

<210> SEQ ID NO 75
<211> LENGTH: 23
<212> TYPE: DNA
<213> ORGANISM: Artificial
<220> FEATURE:
<223> OTHER INFORMATION: primer

<400> SEQUENCE: 75
gggtaagaag gtgcttaatg ctc                                           23

<210> SEQ ID NO 76
<211> LENGTH: 24
<212> TYPE: DNA
<213> ORGANISM: Artificial
<220> FEATURE:
<223> OTHER INFORMATION: primer

<400> SEQUENCE: 76
tgaatatggg ttctggatgt agtg                                          24

<210> SEQ ID NO 77
<211> LENGTH: 35
<212> TYPE: DNA
<213> ORGANISM: Artificial
<220> FEATURE:
<223> OTHER INFORMATION: primer

<400> SEQUENCE: 77 gaggggact gggacaagcc ctttgctgga agaga                               35

<210> SEQ ID NO 78

```
<211> LENGTH: 35
<212> TYPE: DNA
<213> ORGANISM: Artificial
<220> FEATURE:
<223> OTHER INFORMATION: primer

<400> SEQUENCE: 78
acattaggaa aaatcaaaag gtccaattat taagg                           35

<210> SEQ ID NO 79
<211> LENGTH: 20
<212> TYPE: DNA
<213> ORGANISM: Artificial
<220> FEATURE:
<223> OTHER INFORMATION: primer

<400> SEQUENCE: 79
caacagagtg agacaggctc                                            20

<210> SEQ ID NO 80
<211> LENGTH: 20
<212> TYPE: DNA
<213> ORGANISM: Artificial
<220> FEATURE:
<223> OTHER INFORMATION: primer

<400> SEQUENCE: 80
ttccaggaac cactacactg                                            20

<210> SEQ ID NO 81
<211> LENGTH: 35
<212> TYPE: DNA
<213> ORGANISM: Artificial
<220> FEATURE:
<223> OTHER INFORMATION: primer

<400> SEQUENCE: 81
ggcttgggga cattgagtca tcacaatgta gatgt                           35

<210> SEQ ID NO 82
<211> LENGTH: 35
<212> TYPE: DNA
<213> ORGANISM: Artificial
<220> FEATURE:
<223> OTHER INFORMATION: primer

<400> SEQUENCE: 82
gaagaaaggc aaatgaagac ctgaacatgt aagtt                           35

<210> SEQ ID NO 83
<211> LENGTH: 25
<212> TYPE: DNA
<213> ORGANISM: Artificial
<220> FEATURE:
<223> OTHER INFORMATION: primer

<400> SEQUENCE: 83
gggactgtaa taaatattct gttgg                                      25

<210> SEQ ID NO 84
<211> LENGTH: 17
<212> TYPE: DNA
<213> ORGANISM: Artificial
<220> FEATURE:
<223> OTHER INFORMATION: primer

<400> SEQUENCE: 84
```

-continued

```
cactggctct cctgacc                                              17

<210> SEQ ID NO 85
<211> LENGTH: 18
<212> TYPE: DNA
<213> ORGANISM: Artificial
<220> FEATURE:
<223> OTHER INFORMATION: primer

<400> SEQUENCE: 85
gatcctcctg aatgcctg                                             18

<210> SEQ ID NO 86
<211> LENGTH: 18
<212> TYPE: DNA
<213> ORGANISM: Artificial
<220> FEATURE:
<223> OTHER INFORMATION: primer

<400> SEQUENCE: 86
gtaaatgccc tttggacc                                             18

<210> SEQ ID NO 87
<211> LENGTH: 34
<212> TYPE: DNA
<213> ORGANISM: Artificial
<220> FEATURE:
<223> OTHER INFORMATION: primer

<400> SEQUENCE: 87
tagaattcgt aggcttggaa gcagtgagag agaa                           34

<210> SEQ ID NO 88
<211> LENGTH: 26
<212> TYPE: DNA
<213> ORGANISM: Artificial
<220> FEATURE:
<223> OTHER INFORMATION: primer

<400> SEQUENCE: 88
gaagactggt aaatctggtg gctgtc                                    26

<210> SEQ ID NO 89
<211> LENGTH: 34
<212> TYPE: DNA
<213> ORGANISM: Artificial
<220> FEATURE:
<223> OTHER INFORMATION: primer

<400> SEQUENCE: 89
attagatctc ctgctgttat ctcatgcact ctca                           34

<210> SEQ ID NO 90
<211> LENGTH: 34
<212> TYPE: DNA
<213> ORGANISM: Artificial
<220> FEATURE:
<223> OTHER INFORMATION: primer

<400> SEQUENCE: 90
attagatcta tgatgcctga tacatggtct gtga                           34

<210> SEQ ID NO 91
<211> LENGTH: 27
<212> TYPE: DNA
```

```
<213> ORGANISM: Artificial
<220> FEATURE:
<223> OTHER INFORMATION: primer

<400> SEQUENCE: 91
agaaaggcag gtgagtgtgg aggtaga                                              27

<210> SEQ ID NO 92
<211> LENGTH: 26
<212> TYPE: DNA
<213> ORGANISM: Artificial
<220> FEATURE:
<223> OTHER INFORMATION: primer

<400> SEQUENCE: 92
gaagtgggct cacaggaatt ttccaa                                               26

<210> SEQ ID NO 93
<211> LENGTH: 28
<212> TYPE: DNA
<213> ORGANISM: Artificial
<220> FEATURE:
<223> OTHER INFORMATION: primer

<400> SEQUENCE: 93
gggcctcttt atttggcaga atatcacc                                             28

<210> SEQ ID NO 94
<211> LENGTH: 26
<212> TYPE: DNA
<213> ORGANISM: Artificial
<220> FEATURE:
<223> OTHER INFORMATION: primer

<400> SEQUENCE: 94
ttacactgag attcagggca cgatga                                               26

<210> SEQ ID NO 95
<211> LENGTH: 28
<212> TYPE: DNA
<213> ORGANISM: Artificial
<220> FEATURE:
<223> OTHER INFORMATION: primer

<400> SEQUENCE: 95
cagctgggaa acactgagca agattatg                                             28

<210> SEQ ID NO 96
<211> LENGTH: 28
<212> TYPE: DNA
<213> ORGANISM: Artificial
<220> FEATURE:
<223> OTHER INFORMATION: primer

<400> SEQUENCE: 96
ctgctagact gaaaatgcgt ttcctctg                                             28

<210> SEQ ID NO 97
<211> LENGTH: 23
<212> TYPE: DNA
<213> ORGANISM: Artificial
<220> FEATURE:
<223> OTHER INFORMATION: primer

<400> SEQUENCE: 97
gggtaagaag gtgcttaatg ctc                                                  23
```

```
<210> SEQ ID NO 98
<211> LENGTH: 24
<212> TYPE: DNA
<213> ORGANISM: Artificial
<220> FEATURE:
<223> OTHER INFORMATION: primer

<400> SEQUENCE: 98
tgaatatggg ttctggatgt agtg                                           24

<210> SEQ ID NO 99
<211> LENGTH: 35
<212> TYPE: DNA
<213> ORGANISM: Artificial
<220> FEATURE:
<223> OTHER INFORMATION: primer

<400> SEQUENCE: 99 gaggggggact gggacaagcc ctttgctgga agaga                              35

<210> SEQ ID NO 100
<211> LENGTH: 35
<212> TYPE: DNA
<213> ORGANISM: Artificial
<220> FEATURE:
<223> OTHER INFORMATION: primer

<400> SEQUENCE: 100
acattaggaa aaatcaaaag gtccaattat taagg                               35

<210> SEQ ID NO 101
<211> LENGTH: 20
<212> TYPE: DNA
<213> ORGANISM: Artificial
<220> FEATURE:
<223> OTHER INFORMATION: primer

<400> SEQUENCE: 101
caacagagtg agacaggctc                                                20

<210> SEQ ID NO 102
<211> LENGTH: 20
<212> TYPE: DNA
<213> ORGANISM: Artificial
<220> FEATURE:
<223> OTHER INFORMATION: primer

<400> SEQUENCE: 102
ttccaggaac cactacactg                                                20

<210> SEQ ID NO 103
<211> LENGTH: 35
<212> TYPE: DNA
<213> ORGANISM: Artificial
<220> FEATURE:
<223> OTHER INFORMATION: primer

<400> SEQUENCE: 103
ggcttgggga cattgagtca tcacaatgta gatgt                               35

<210> SEQ ID NO 104
<211> LENGTH: 35
<212> TYPE: DNA
<213> ORGANISM: Artificial
<220> FEATURE:
```

<223> OTHER INFORMATION: primer

<400> SEQUENCE: 104
gaagaaaggc aaatgaagac ctgaacatgt aagtt                                    35

<210> SEQ ID NO 105
<211> LENGTH: 25
<212> TYPE: DNA
<213> ORGANISM: Artificial
<220> FEATURE:
<223> OTHER INFORMATION: primer

<400> SEQUENCE: 105
gggactgtaa taaatattct gttgg                                              25

<210> SEQ ID NO 106
<211> LENGTH: 17
<212> TYPE: DNA
<213> ORGANISM: Artificial
<220> FEATURE:
<223> OTHER INFORMATION: primer

<400> SEQUENCE: 106
cactggctct cctgacc                                                       17

<210> SEQ ID NO 107
<211> LENGTH: 18
<212> TYPE: DNA
<213> ORGANISM: Artificial
<220> FEATURE:
<223> OTHER INFORMATION: primer

<400> SEQUENCE: 107
gatcctcctg aatgcctg                                                      18

<210> SEQ ID NO 108
<211> LENGTH: 18
<212> TYPE: DNA
<213> ORGANISM: Artificial
<220> FEATURE:
<223> OTHER INFORMATION: primer

<400> SEQUENCE: 108
gtaaatgccc tttggacc                                                      18

<210> SEQ ID NO 109
<211> LENGTH: 20
<212> TYPE: DNA
<213> ORGANISM: Artificial
<220> FEATURE:
<223> OTHER INFORMATION: primer

<400> SEQUENCE: 109
atacaacgct ttctccccaa                                                    20

<210> SEQ ID NO 110
<211> LENGTH: 20
<212> TYPE: DNA
<213> ORGANISM: Artificial
<220> FEATURE:
<223> OTHER INFORMATION: primer

<400> SEQUENCE: 110
tcttgaactg agggacactg                                                    20

```
<210> SEQ ID NO 111
<211> LENGTH: 64
<212> TYPE: DNA
<213> ORGANISM: Artificial
<220> FEATURE:
<223> OTHER INFORMATION: primer

<400> SEQUENCE: 111
gaagttccta tactttctag agaataggaa cttcattcta ccgggtaggg gaggcgcttt      60
tccc                                                                  64

<210> SEQ ID NO 112
<211> LENGTH: 71
<212> TYPE: DNA
<213> ORGANISM: Artificial
<220> FEATURE:
<223> OTHER INFORMATION: primer

<400> SEQUENCE: 112
caactgagag aactcaaagg ttaccccagt tggggcacta cggtcgaaag gcccggagat      60
gaggaagagg a                                                          71

<210> SEQ ID NO 113
<211> LENGTH: 58
<212> TYPE: DNA
<213> ORGANISM: Artificial
<220> FEATURE:
<223> OTHER INFORMATION: primer

<400> SEQUENCE: 113
ggggacaact tgtatacaa aagttgatat tctaccgggt aggggaggcg cttttccc         58

<210> SEQ ID NO 114
<211> LENGTH: 77
<212> TYPE: DNA
<213> ORGANISM: Artificial
<220> FEATURE:
<223> OTHER INFORMATION: primer

<400> SEQUENCE: 114
cacaagcagt accactgctt caagtggtat cgctttgggg aacatgcggt cgaaaggccc      60
ggagatgagg aagagga                                                    77

<210> SEQ ID NO 115
<211> LENGTH: 58
<212> TYPE: DNA
<213> ORGANISM: Artificial
<220> FEATURE:
<223> OTHER INFORMATION: primer

<400> SEQUENCE: 115
ggggacaact tttctataca aagttgatat tctaccgggt aggggaggcg cttttccc        58

<210> SEQ ID NO 116
<211> LENGTH: 78
<212> TYPE: DNA
<213> ORGANISM: Artificial
<220> FEATURE:
<223> OTHER INFORMATION: primer

<400> SEQUENCE: 116
cttaattgaa ataaacgaaa taaaaactcg caattaagcg agttggaagg tcgaaaggcc      60
cggagatgag gaagagga                                                   78
```

```
<210> SEQ ID NO 117
<211> LENGTH: 58
<212> TYPE: DNA
<213> ORGANISM: Artificial
<220> FEATURE:
<223> OTHER INFORMATION: primer

<400> SEQUENCE: 117
ggggacaact tgtataata aagttggtat tctaccgggt aggggaggcg ctttccc         58

<210> SEQ ID NO 118
<211> LENGTH: 84
<212> TYPE: DNA
<213> ORGANISM: Artificial
<220> FEATURE:
<223> OTHER INFORMATION: primer

<400> SEQUENCE: 118
agaccgcggt ggttgaccag acaaaccacg aagacacagg tcatcacggc cataggtcga    60
aaggcccgga gatgaggaag agga                                          84

<210> SEQ ID NO 119
<211> LENGTH: 61
<212> TYPE: DNA
<213> ORGANISM: Artificial
<220> FEATURE:
<223> OTHER INFORMATION: primer

<400> SEQUENCE: 119
ggggacaagt tgtacaaaa aagcaggctt ggaagttcct atactttcta gagaatagga    60
a                                                                   61

<210> SEQ ID NO 120
<211> LENGTH: 70
<212> TYPE: DNA
<213> ORGANISM: Artificial
<220> FEATURE:
<223> OTHER INFORMATION: primer

<400> SEQUENCE: 120
ggggacaact tttgtataca aagttgtgac cctacgcccc caactgagag aactcaaagg    60
ttaccccagt                                                          70

<210> SEQ ID NO 121
<211> LENGTH: 77
<212> TYPE: DNA
<213> ORGANISM: Artificial
<220> FEATURE:
<223> OTHER INFORMATION: primer

<400> SEQUENCE: 121
ggggacaact tgtatagaa aagttgggtg cacccgcaga gtgtacccac aagcagtacc    60
actgcttcaa gtggtat                                                  77

<210> SEQ ID NO 122
<211> LENGTH: 78
<212> TYPE: DNA
<213> ORGANISM: Artificial
<220> FEATURE:
<223> OTHER INFORMATION: primer

<400> SEQUENCE: 122
ggggacaact ttattataca aagttgttaa aaggagtttt ttagttacct taattgaaat    60
```

```
aaacgaaata aaaactcg                                                   78

<210> SEQ ID NO 123
<211> LENGTH: 83
<212> TYPE: DNA
<213> ORGANISM: Artificial
<220> FEATURE:
<223> OTHER INFORMATION: primer

<400> SEQUENCE: 123
ggggaccact ttgtacaaga aagctgggta tgggtttgta ccgtacacca ctgagaccgc     60
ggtggttgac cagacaaacc acg                                             83

<210> SEQ ID NO 124
<211> LENGTH: 30
<212> TYPE: DNA
<213> ORGANISM: Artificial
<220> FEATURE:
<223> OTHER INFORMATION: primer

<400> SEQUENCE: 124
tgattgttca ggaggaggaa gccggtggcg                                      30

<210> SEQ ID NO 125
<211> LENGTH: 30
<212> TYPE: DNA
<213> ORGANISM: Artificial
<220> FEATURE:
<223> OTHER INFORMATION: primer

<400> SEQUENCE: 125
agagccttca acccagtcag ctccttcgaa                                      30

<210> SEQ ID NO 126
<211> LENGTH: 47
<212> TYPE: DNA
<213> ORGANISM: Artificial
<220> FEATURE:
<223> OTHER INFORMATION: primer

<400> SEQUENCE: 126
aaagatatca actcgagatg ggatcggcca ttgaacaaga tggattg                   47

<210> SEQ ID NO 127
<211> LENGTH: 39
<212> TYPE: DNA
<213> ORGANISM: Artificial
<220> FEATURE:
<223> OTHER INFORMATION: primer

<400> SEQUENCE: 127
tttgctagcc cccagctggt tctttccgcc tcagaagcc                            39

<210> SEQ ID NO 128
<211> LENGTH: 21
<212> TYPE: DNA
<213> ORGANISM: Artificial
<220> FEATURE:
<223> OTHER INFORMATION: primer

<400> SEQUENCE: 128
aaacagcaag gcaagcatcc a                                               21

<210> SEQ ID NO 129
```

```
<211> LENGTH: 21
<212> TYPE: DNA
<213> ORGANISM: Artificial
<220> FEATURE:
<223> OTHER INFORMATION: primer

<400> SEQUENCE: 129
tgctttaatc agccctggt g                                                  21

<210> SEQ ID NO 130
<211> LENGTH: 22
<212> TYPE: DNA
<213> ORGANISM: Artificial
<220> FEATURE:
<223> OTHER INFORMATION: primer

<400> SEQUENCE: 130
tgtttgctca atcgtggtct cc                                                22

<210> SEQ ID NO 131
<211> LENGTH: 21
<212> TYPE: DNA
<213> ORGANISM: Artificial
<220> FEATURE:
<223> OTHER INFORMATION: primer

<400> SEQUENCE: 131
acaaaagccg aatgtggtgg a                                                 21

<210> SEQ ID NO 132
<211> LENGTH: 20
<212> TYPE: DNA
<213> ORGANISM: Artificial
<220> FEATURE:
<223> OTHER INFORMATION: primer

<400> SEQUENCE: 132
ccaagaggcc cagaagcaaa                                                   20

<210> SEQ ID NO 133
<211> LENGTH: 21
<212> TYPE: DNA
<213> ORGANISM: Artificial
<220> FEATURE:
<223> OTHER INFORMATION: primer

<400> SEQUENCE: 133
tccccacata cacggcagat t                                                 21

<210> SEQ ID NO 134
<211> LENGTH: 21
<212> TYPE: DNA
<213> ORGANISM: Artificial
<220> FEATURE:
<223> OTHER INFORMATION: primer

<400> SEQUENCE: 134
acactgccaa gagccgacaa t                                                 21

<210> SEQ ID NO 135
<211> LENGTH: 22
<212> TYPE: DNA
<213> ORGANISM: Artificial
<220> FEATURE:
<223> OTHER INFORMATION: primer

<400> SEQUENCE: 135
```
gcaaccttgc ctctctgatg gt                                              22

<210> SEQ ID NO 136
<211> LENGTH: 21
<212> TYPE: DNA
<213> ORGANISM: Artificial
<220> FEATURE:
<223> OTHER INFORMATION: primer

<400> SEQUENCE: 136
tcaaggtgtg aagggacca a                                                21

<210> SEQ ID NO 137
<211> LENGTH: 21
<212> TYPE: DNA
<213> ORGANISM: Artificial
<220> FEATURE:
<223> OTHER INFORMATION: primer

<400> SEQUENCE: 137
acaaagcagc tcggaagagg a                                               21

<210> SEQ ID NO 138
<211> LENGTH: 21
<212> TYPE: DNA
<213> ORGANISM: Artificial
<220> FEATURE:
<223> OTHER INFORMATION: primer

<400> SEQUENCE: 138
gtttgttcct ggggctggaa t                                               21

<210> SEQ ID NO 139
<211> LENGTH: 22
<212> TYPE: DNA
<213> ORGANISM: Artificial
<220> FEATURE:
<223> OTHER INFORMATION: primer

<400> SEQUENCE: 139
caaggcaggc actttcatac cc                                              22

<210> SEQ ID NO 140
<211> LENGTH: 30
<212> TYPE: DNA
<213> ORGANISM: Artificial
<220> FEATURE:
<223> OTHER INFORMATION: primer

<400> SEQUENCE: 140
agatctcggc tagaggtacc ctagaagatc                                      30

<210> SEQ ID NO 141
<211> LENGTH: 28
<212> TYPE: DNA
<213> ORGANISM: Artificial
<220> FEATURE:
<223> OTHER INFORMATION: primer

<400> SEQUENCE: 141
ttctggcaag ccttgaaggg acaatact                                        28

<210> SEQ ID NO 142
<211> LENGTH: 28
<212> TYPE: DNA

<213> ORGANISM: Artificial
<220> FEATURE:
<223> OTHER INFORMATION: primer

<400> SEQUENCE: 142
gcctattttg cctcataacc cactgctc                    28

<210> SEQ ID NO 143
<211> LENGTH: 22
<212> TYPE: DNA
<213> ORGANISM: Artificial
<220> FEATURE:
<223> OTHER INFORMATION: primer

<400> SEQUENCE: 143
tttctcctct caaggaaaac ca                          22

<210> SEQ ID NO 144
<211> LENGTH: 20
<212> TYPE: DNA
<213> ORGANISM: Artificial
<220> FEATURE:
<223> OTHER INFORMATION: primer

<400> SEQUENCE: 144
gccctccata tggcaagaca                             20

<210> SEQ ID NO 145
<211> LENGTH: 23
<212> TYPE: DNA
<213> ORGANISM: Artificial
<220> FEATURE:
<223> OTHER INFORMATION: primer

<400> SEQUENCE: 145
ggccgctcta gaactagtgg atc                         23

<210> SEQ ID NO 146
<211> LENGTH: 22
<212> TYPE: DNA
<213> ORGANISM: Artificial
<220> FEATURE:
<223> OTHER INFORMATION: primer

<400> SEQUENCE: 146
tcttctgcat caagccacat ca                          22

<210> SEQ ID NO 147
<211> LENGTH: 22
<212> TYPE: DNA
<213> ORGANISM: Artificial
<220> FEATURE:
<223> OTHER INFORMATION: primer

<400> SEQUENCE: 147
agccaatgac taccttccat tg                          22

<210> SEQ ID NO 148
<211> LENGTH: 20
<212> TYPE: DNA
<213> ORGANISM: Artificial
<220> FEATURE:
<223> OTHER INFORMATION: primer

<400> SEQUENCE: 148
atcagggagc caccgtagga                             20

<210> SEQ ID NO 149
<211> LENGTH: 20
<212> TYPE: DNA
<213> ORGANISM: Artificial
<220> FEATURE:
<223> OTHER INFORMATION: primer

<400> SEQUENCE: 149
gcaggcaagt tatgccgtga                                              20

<210> SEQ ID NO 150
<211> LENGTH: 20
<212> TYPE: DNA
<213> ORGANISM: Artificial
<220> FEATURE:
<223> OTHER INFORMATION: primer

<400> SEQUENCE: 150
tgcgcccaaa cacatggata                                              20

<210> SEQ ID NO 151
<211> LENGTH: 21
<212> TYPE: DNA
<213> ORGANISM: Artificial
<220> FEATURE:
<223> OTHER INFORMATION: primer

<400> SEQUENCE: 151
tggcagaaat gtaggccatg a                                            21

<210> SEQ ID NO 152
<211> LENGTH: 20
<212> TYPE: DNA
<213> ORGANISM: Artificial
<220> FEATURE:
<223> OTHER INFORMATION: primer

<400> SEQUENCE: 152
aggctggaag ctgggaaacc                                              20

<210> SEQ ID NO 153
<211> LENGTH: 22
<212> TYPE: DNA
<213> ORGANISM: Artificial
<220> FEATURE:
<223> OTHER INFORMATION: primer

<400> SEQUENCE: 153
cctgcatgaa atggatccaa ag                                           22

<210> SEQ ID NO 154
<211> LENGTH: 22
<212> TYPE: DNA
<213> ORGANISM: Artificial
<220> FEATURE:
<223> OTHER INFORMATION: primer

<400> SEQUENCE: 154
ccagcaagaa agattgtgat gc                                           22

<210> SEQ ID NO 155
<211> LENGTH: 22
<212> TYPE: DNA
<213> ORGANISM: Artificial
<220> FEATURE:

<223> OTHER INFORMATION: primer

<400> SEQUENCE: 155
ttctaaccat gaactgggtg gt                                    22

<210> SEQ ID NO 156
<211> LENGTH: 20
<212> TYPE: DNA
<213> ORGANISM: Artificial
<220> FEATURE:
<223> OTHER INFORMATION: primer

<400> SEQUENCE: 156
gggtttctgc tggcctgtgt                                       20

<210> SEQ ID NO 157
<211> LENGTH: 22
<212> TYPE: DNA
<213> ORGANISM: Artificial
<220> FEATURE:
<223> OTHER INFORMATION: primer

<400> SEQUENCE: 157
tctggttttc cagcttcaaa tg                                    22

<210> SEQ ID NO 158
<211> LENGTH: 20
<212> TYPE: DNA
<213> ORGANISM: Artificial
<220> FEATURE:
<223> OTHER INFORMATION: primer

<400> SEQUENCE: 158
ggtctccttg gcatgcacct                                       20

<210> SEQ ID NO 159
<211> LENGTH: 22
<212> TYPE: DNA
<213> ORGANISM: Artificial
<220> FEATURE:
<223> OTHER INFORMATION: primer

<400> SEQUENCE: 159
tgcaatgctt cttttccagt tg                                    22

<210> SEQ ID NO 160
<211> LENGTH: 22
<212> TYPE: DNA
<213> ORGANISM: Artificial
<220> FEATURE:
<223> OTHER INFORMATION: primer

<400> SEQUENCE: 160
cagcatggag ggttttaaat gg                                    22

<210> SEQ ID NO 161
<211> LENGTH: 19
<212> TYPE: DNA
<213> ORGANISM: Artificial
<220> FEATURE:
<223> OTHER INFORMATION: primer

<400> SEQUENCE: 161
atgttggcgt gctgcatcc                                        19

```
<210> SEQ ID NO 162
<211> LENGTH: 22
<212> TYPE: DNA
<213> ORGANISM: Artificial
<220> FEATURE:
<223> OTHER INFORMATION: primer

<400> SEQUENCE: 162
catttgaagc tggaaaacca ga                                              22

<210> SEQ ID NO 163
<211> LENGTH: 22
<212> TYPE: DNA
<213> ORGANISM: Artificial
<220> FEATURE:
<223> OTHER INFORMATION: primer

<400> SEQUENCE: 163
cctgggtggt aaatctctga aa                                              22

<210> SEQ ID NO 164
<211> LENGTH: 28
<212> TYPE: DNA
<213> ORGANISM: Artificial
<220> FEATURE:
<223> OTHER INFORMATION: primer

<400> SEQUENCE: 164
ggaacaatcc caatcaaaac ctcagtgc                                        28

<210> SEQ ID NO 165
<211> LENGTH: 28
<212> TYPE: DNA
<213> ORGANISM: Artificial
<220> FEATURE:
<223> OTHER INFORMATION: primer

<400> SEQUENCE: 165
cgaggattca agccacatcc ctaactct                                        28

<210> SEQ ID NO 166
<211> LENGTH: 28
<212> TYPE: DNA
<213> ORGANISM: Artificial
<220> FEATURE:
<223> OTHER INFORMATION: primer

<400> SEQUENCE: 166
gctatgagac acagggcagc tgaaagtc                                        28

<210> SEQ ID NO 167
<211> LENGTH: 28
<212> TYPE: DNA
<213> ORGANISM: Artificial
<220> FEATURE:
<223> OTHER INFORMATION: primer

<400> SEQUENCE: 167
ttgtgaacca ccatgcctag ctgaaagt                                        28

<210> SEQ ID NO 168
<211> LENGTH: 20
<212> TYPE: DNA
<213> ORGANISM: Artificial
<220> FEATURE:
<223> OTHER INFORMATION: primer
```

<400> SEQUENCE: 168
acggggctcc tactcttgtc						20

<210> SEQ ID NO 169
<211> LENGTH: 19
<212> TYPE: DNA
<213> ORGANISM: Artificial
<220> FEATURE:
<223> OTHER INFORMATION: primer

<400> SEQUENCE: 169
gcttccacct gcatctcac						19

<210> SEQ ID NO 170
<211> LENGTH: 21
<212> TYPE: DNA
<213> ORGANISM: Artificial
<220> FEATURE:
<223> OTHER INFORMATION: primer

<400> SEQUENCE: 170
caatgcctta tgcatgttgt g						21

<210> SEQ ID NO 171
<211> LENGTH: 20
<212> TYPE: DNA
<213> ORGANISM: Artificial
<220> FEATURE:
<223> OTHER INFORMATION: primer

<400> SEQUENCE: 171
tccacagcat actgctgacc						20

<210> SEQ ID NO 172
<211> LENGTH: 20
<212> TYPE: DNA
<213> ORGANISM: Artificial
<220> FEATURE:
<223> OTHER INFORMATION: primer

<400> SEQUENCE: 172
aaggaaggtg accgcctact						20

<210> SEQ ID NO 173
<211> LENGTH: 20
<212> TYPE: DNA
<213> ORGANISM: Artificial
<220> FEATURE:
<223> OTHER INFORMATION: primer

<400> SEQUENCE: 173
catccgagga catctttggt						20

<210> SEQ ID NO 174
<211> LENGTH: 35
<212> TYPE: DNA
<213> ORGANISM: Artificial
<220> FEATURE:
<223> OTHER INFORMATION: primer

<400> SEQUENCE: 174
atctgcaggg aagggatcca gtttcagctt cctac						35

<210> SEQ ID NO 175
<211> LENGTH: 20

```
<212> TYPE: DNA
<213> ORGANISM: Artificial
<220> FEATURE:
<223> OTHER INFORMATION: primer

<400> SEQUENCE: 175
acatgtcaaa gagacacaca                                           20

<210> SEQ ID NO 176
<211> LENGTH: 22
<212> TYPE: DNA
<213> ORGANISM: Artificial
<220> FEATURE:
<223> OTHER INFORMATION: primer

<400> SEQUENCE: 176
tagcatattt ccaataatag ga                                        22

<210> SEQ ID NO 177
<211> LENGTH: 21
<212> TYPE: DNA
<213> ORGANISM: Artificial
<220> FEATURE:
<223> OTHER INFORMATION: primer

<400> SEQUENCE: 177
agaaggcttc aatggattct c                                         21

<210> SEQ ID NO 178
<211> LENGTH: 23
<212> TYPE: DNA
<213> ORGANISM: Artificial
<220> FEATURE:
<223> OTHER INFORMATION: primer

<400> SEQUENCE: 178
tgtccttaat acctatctgt agg                                       23

<210> SEQ ID NO 179
<211> LENGTH: 20
<212> TYPE: DNA
<213> ORGANISM: Artificial
<220> FEATURE:
<223> OTHER INFORMATION: primer

<400> SEQUENCE: 179
acagctggat ccattgaagg                                           20

<210> SEQ ID NO 180
<211> LENGTH: 22
<212> TYPE: DNA
<213> ORGANISM: Artificial
<220> FEATURE:
<223> OTHER INFORMATION: primer

<400> SEQUENCE: 180
acacacactt aattagcatg ga                                        22

<210> SEQ ID NO 181
<211> LENGTH: 21
<212> TYPE: DNA
<213> ORGANISM: Artificial
<220> FEATURE:
<223> OTHER INFORMATION: primer

<400> SEQUENCE: 181
```
ttggttaagg atttgctgac a        21

<210> SEQ ID NO 182
<211> LENGTH: 30
<212> TYPE: DNA
<213> ORGANISM: Artificial
<220> FEATURE:
<223> OTHER INFORMATION: primer

<400> SEQUENCE: 182
tccccgcgga tctgctccat actctgtacc        30

<210> SEQ ID NO 183
<211> LENGTH: 28
<212> TYPE: DNA
<213> ORGANISM: Artificial
<220> FEATURE:
<223> OTHER INFORMATION: primer

<400> SEQUENCE: 183
cattcaaggg gttctgggtc tgtaaact        28

<210> SEQ ID NO 184
<211> LENGTH: 28
<212> TYPE: DNA
<213> ORGANISM: Artificial
<220> FEATURE:
<223> OTHER INFORMATION: primer

<400> SEQUENCE: 184
gccaagtgta gctggagaat gattcgtg        28

<210> SEQ ID NO 185
<211> LENGTH: 28
<212> TYPE: DNA
<213> ORGANISM: Artificial
<220> FEATURE:
<223> OTHER INFORMATION: primer

<400> SEQUENCE: 185
acaaggcact tcaggatacc aagcttcc        28

<210> SEQ ID NO 186
<211> LENGTH: 20
<212> TYPE: DNA
<213> ORGANISM: Artificial
<220> FEATURE:
<223> OTHER INFORMATION: primer

<400> SEQUENCE: 186
gctcaagatg cccctgttct        20

<210> SEQ ID NO 187
<211> LENGTH: 20
<212> TYPE: DNA
<213> ORGANISM: Artificial
<220> FEATURE:
<223> OTHER INFORMATION: primer

<400> SEQUENCE: 187
aaagatggtc aaggtcgcaa        20

<210> SEQ ID NO 188
<211> LENGTH: 28
<212> TYPE: DNA
<213> ORGANISM: Artificial

```
<220> FEATURE:
<223> OTHER INFORMATION: primer

<400> SEQUENCE: 188
ctattctaaa aagctgcctt ggcccaca                                        28

<210> SEQ ID NO 189
<211> LENGTH: 28
<212> TYPE: DNA
<213> ORGANISM: Artificial
<220> FEATURE:
<223> OTHER INFORMATION: primer

<400> SEQUENCE: 189
tgtagcccag ttcctaatgg gacacaga                                        28

<210> SEQ ID NO 190
<211> LENGTH: 35
<212> TYPE: DNA
<213> ORGANISM: Artificial
<220> FEATURE:
<223> OTHER INFORMATION: primer

<400> SEQUENCE: 190
atctgcaggg aagggatcca gtttcagctt cctac                                35

<210> SEQ ID NO 191
<211> LENGTH: 20
<212> TYPE: DNA
<213> ORGANISM: Artificial
<220> FEATURE:
<223> OTHER INFORMATION: primer

<400> SEQUENCE: 191
ctcctaggag tactcacttc                                                 20

<210> SEQ ID NO 192
<211> LENGTH: 20
<212> TYPE: DNA
<213> ORGANISM: Artificial
<220> FEATURE:
<223> OTHER INFORMATION: primer

<400> SEQUENCE: 192
aacagaaaca tggcttggcg                                                 20

<210> SEQ ID NO 193
<211> LENGTH: 21
<212> TYPE: DNA
<213> ORGANISM: Artificial
<220> FEATURE:
<223> OTHER INFORMATION: primer

<400> SEQUENCE: 193
cgccaagcca tgtttctgtt t                                               21

<210> SEQ ID NO 194
<211> LENGTH: 21
<212> TYPE: DNA
<213> ORGANISM: Artificial
<220> FEATURE:
<223> OTHER INFORMATION: primer

<400> SEQUENCE: 194
aaggaaatgc tttctgcctt g                                               21
```

<210> SEQ ID NO 195
<211> LENGTH: 20
<212> TYPE: DNA
<213> ORGANISM: Artificial
<220> FEATURE:
<223> OTHER INFORMATION: primer

<400> SEQUENCE: 195
gtgcaacgga agccagaaca                                                  20

<210> SEQ ID NO 196
<211> LENGTH: 20
<212> TYPE: DNA
<213> ORGANISM: Artificial
<220> FEATURE:
<223> OTHER INFORMATION: primer

<400> SEQUENCE: 196
agcggcctct gcttctttga                                                  20

<210> SEQ ID NO 197
<211> LENGTH: 20
<212> TYPE: DNA
<213> ORGANISM: Artificial
<220> FEATURE:
<223> OTHER INFORMATION: primer

<400> SEQUENCE: 197
ctgattggct gggcaggaac                                                  20

<210> SEQ ID NO 198
<211> LENGTH: 20
<212> TYPE: DNA
<213> ORGANISM: Artificial
<220> FEATURE:
<223> OTHER INFORMATION: primer

<400> SEQUENCE: 198
cttggaacgg ccaccaagac                                                  20

<210> SEQ ID NO 199
<211> LENGTH: 20
<212> TYPE: DNA
<213> ORGANISM: Artificial
<220> FEATURE:
<223> OTHER INFORMATION: primer

<400> SEQUENCE: 199
ggtgctggtt gctgcttaca                                                  20

<210> SEQ ID NO 200
<211> LENGTH: 20
<212> TYPE: DNA
<213> ORGANISM: Artificial
<220> FEATURE:
<223> OTHER INFORMATION: primer

<400> SEQUENCE: 200
cccaacatcg tgcacatcaa                                                  20

<210> SEQ ID NO 201
<211> LENGTH: 20
<212> TYPE: DNA
<213> ORGANISM: Artificial
<220> FEATURE:
<223> OTHER INFORMATION: primer

<400> SEQUENCE: 201
gtcagtgttg atggacagga                                               20

<210> SEQ ID NO 202
<211> LENGTH: 20
<212> TYPE: DNA
<213> ORGANISM: Artificial
<220> FEATURE:
<223> OTHER INFORMATION: primer

<400> SEQUENCE: 202
gcattggctt ccttgacagc                                               20

<210> SEQ ID NO 203
<211> LENGTH: 20
<212> TYPE: DNA
<213> ORGANISM: Artificial
<220> FEATURE:
<223> OTHER INFORMATION: primer

<400> SEQUENCE: 203
ggttccaggc ttgctgtaat                                               20

<210> SEQ ID NO 204
<211> LENGTH: 20
<212> TYPE: DNA
<213> ORGANISM: Artificial
<220> FEATURE:
<223> OTHER INFORMATION: primer

<400> SEQUENCE: 204
tctttcagtg cttgtccaga                                               20

<210> SEQ ID NO 205
<211> LENGTH: 21
<212> TYPE: DNA
<213> ORGANISM: Artificial
<220> FEATURE:
<223> OTHER INFORMATION: primer

<400> SEQUENCE: 205
ggcaaagaaa taaagcgact g                                             21

<210> SEQ ID NO 206
<211> LENGTH: 20
<212> TYPE: DNA
<213> ORGANISM: Artificial
<220> FEATURE:
<223> OTHER INFORMATION: primer

<400> SEQUENCE: 206
cctcctttgc tgccctcaca                                               20

<210> SEQ ID NO 207
<211> LENGTH: 21
<212> TYPE: DNA
<213> ORGANISM: Artificial
<220> FEATURE:
<223> OTHER INFORMATION: primer

<400> SEQUENCE: 207
tcttgtccaa actgcctgtg a                                             21

<210> SEQ ID NO 208

```
<211> LENGTH: 21
<212> TYPE: DNA
<213> ORGANISM: Artificial
<220> FEATURE:
<223> OTHER INFORMATION: primer

<400> SEQUENCE: 208
tgcaagaatc agcaggatca a                                              21

<210> SEQ ID NO 209
<211> LENGTH: 20
<212> TYPE: DNA
<213> ORGANISM: Artificial
<220> FEATURE:
<223> OTHER INFORMATION: primer

<400> SEQUENCE: 209
gctcaagatg cccctgttct                                                20

<210> SEQ ID NO 210
<211> LENGTH: 20
<212> TYPE: DNA
<213> ORGANISM: Artificial
<220> FEATURE:
<223> OTHER INFORMATION: primer

<400> SEQUENCE: 210
aaagatggtc aaggtcgcaa                                                20

<210> SEQ ID NO 211
<211> LENGTH: 20
<212> TYPE: DNA
<213> ORGANISM: Artificial
<220> FEATURE:
<223> OTHER INFORMATION: primer

<400> SEQUENCE: 211
gctcaagatg cccctgttct                                                20

<210> SEQ ID NO 212
<211> LENGTH: 20
<212> TYPE: DNA
<213> ORGANISM: Artificial
<220> FEATURE:
<223> OTHER INFORMATION: primer

<400> SEQUENCE: 212
aaagatggtc aaggtcgcaa                                                20
```